United States Patent
Romero et al.

[11] Patent Number: 5,866,589
[45] Date of Patent: Feb. 2, 1999

[54] ALKYL SUBSTITUTED PIPERADINYL AND PIPERAZINYL ANTI-AIDS COMPOUNDS

[75] Inventors: Donna L. Romero; Richard C. Thomas, both of Kalamazoo; Paul D. May, Richland; Toni-Jo Poel, Wayland, all of Mich.

[73] Assignee: Pharmacia & Upjohn Company, Kalamazoo, Mich.

[21] Appl. No.: 860,178

[22] PCT Filed: Nov. 28, 1995

[86] PCT No.: PCT/US95/14558

§ 371 Date: Jun. 9, 1997

§ 102(e) Date: Jun. 9, 1997

[87] PCT Pub. No.: WO96/18628

PCT Pub. Date: Jun. 20, 1996

Related U.S. Application Data

[63] Continuation of Ser. No. 400,095, Mar. 7, 1995, abandoned, which is a continuation-in-part of Ser. No. 354,925, Dec. 13, 1994, abandoned.

[51] Int. Cl.[6] ...................... A61K 31/445; C07D 401/12; C07D 401/14

[52] U.S. Cl. .......................... 514/318; 514/370; 514/321; 514/322; 514/323; 514/324; 514/326; 546/193; 546/196; 546/197; 546/198; 546/199; 546/201; 546/202; 546/208; 546/210

[58] Field of Search ....................... 546/193, 196, 546/197, 198, 199, 201, 202, 208, 210; 514/318, 320, 321, 322, 323, 324, 326

[56] References Cited

U.S. PATENT DOCUMENTS

| | | | |
|---|---|---|---|
| 3,686,188 | 8/1972 | Huebner | 546/196 |
| 5,489,593 | 2/1996 | Palmer et al. | 514/252 |
| 5,688,610 | 11/1997 | Palmer et al. | 544/360 |

FOREIGN PATENT DOCUMENTS

| | | | |
|---|---|---|---|
| 43 07 883 | 9/1993 | Germany | A61K 3/70 |
| WO92/18089 | 10/1992 | WIPO . | |
| WO94/09781 | 5/1994 | WIPO | A61K 3/495 |

*Primary Examiner*—Ceila Chang
*Attorney, Agent, or Firm*—Bruce Stein

[57] ABSTRACT

Anti-AIDS compounds of formula (I)

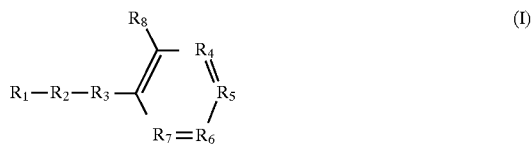

wherein $R_1$, $R_2$, $R_3$, $R_4$, $R_5$, $R_6$, and $R_7$ are as defined in the specification and $R_8$ is alkyl of substituted alkyl.

15 Claims, No Drawings

5,866,589

ALKYL SUBSTITUTED PIPERADINYL AND PIPERAZINYL ANTI-AIDS COMPOUNDS

This application is a continuation (national phase) of International Application No. PCT/US95/14558, International Filing Date 28 Nov. 1995, which was a continuation of U.S. patent application Ser. No. 08/400,095 filed 7 Mar. 1995, now abandoned, which was a continuation-in-part of U.S. patent application Ser. No. 08/354,925 filed 13 Dec. 1994 now abandoned.

BACKGROUND OF THE INVENTION

1. Field of the Invention

The Anti-AIDS Amines (I) are useful in treating individuals who have AIDS as well as those individuals who are HIV positive but do not as yet have AIDS.

2. Description of the Related Art

An estimated one to one and one-half million people in the United States are infected with a human retrovirus, the human immunodeficiency virus type I (HIV-1) which is the etiological agent of acquired immunodeficiency syndrome, AIDS, see Science, 661–662 (1986). Of those infected, an estimated two hundred and fifty thousands people will develop AIDS in the next five years, see Science, 1352–1357 (1985). On Mar. 20, 1987, the FDA approved the use of the compound, AZT (zidovudine), to treat AIDS patients with a recent initial episode of pneumocystis carinii pneumonia, AIDS patients with conditions other than pneumocystis carinii pneumonia or patients infected with the virus with an absolute CD4 lymphocyte count of less than 200/mm$^3$ in the peripheral blood. AZT is a known inhibitor of viral reverse transcriptase, an enzyme necessary for human immunodeficiency virus replication.

U.S. Pat. No. 4,724,232 claims a method of treating humans having acquired immunodeficiency syndrome utilizing 3'-azido-3'-deoxy-thymidine (azidothymidine, AZT).

Following the discovery of the anti-HIV activity of AZT, much effort has been focused on a wide variety of other dideoxynucleoside analogues in the search for superior agents. In the case of the 2',3'-dideoxy series, ddC and ddI have shown potent activity against HIV in vitro and have been evaluated in clinical trials, see Drug News & Perspectives, 5(3) 153–169 (1992) in particular page 160. The FDA has approved ddI for the treatment of HIV-1 infections in adults and pediatrics patients who are intolerant to, or whose health has significantly deteriorated while on, AZT treatment, see AIDS Research and Human Retroviruses, 8(6), 963–990, 1992 (1992) in particular page 966.

It is known in the art that certain antibiotics and polyanionic dyes inhibit retrovirus reverse transcriptase.

International Publication No. WO 88/08424 (U.S. Pat. No. 5,120,843) disclosed compounds which can be represented as aromatic-connector-piperazine-[substituted aromatic] or aromatic-connector-piperazine-[substituted heteroaromatic], in particular see the compounds of formulas (I) and (III). None of those compounds were disclosed as having the utility set forth in this invention. In U.S. Pat. No. 5,120,843 it was disclosed that the compounds of formula (I) of International Publication No. WO 88/08424 were useful against AIDS.

Many publications have reported the ability of various sulfated compounds to inhibit virus replication, including HIV.

Nature 343, 470 (1990) and Science 250, 1411 (1990) discloses potent benzodiazepin type reverse transcriptase inhibitors. The compounds of the present invention are not benzodiazepin type compounds.

U.S. Pat. Nos. 3,146,234 and 3,188,313 disclose a number of compounds which can be represented as:

(5-substituted)-(indol-2-yl)-linker-piperazinyl-(substituted phenyl), (5-substituted)-(indol-2-yl)-linker-piperazinyl-(unsubstituted heteroaryl).

The compounds of the present invention do not include phenyl (whether substituted or not) attached to the piperazinyl moiety. Further, the compounds of the present invention require that the heteroaryl group must be substituted.

VINITI, 3979–82 (1982) in Russian and Chem. Abst. 100(7) 51549b (1984) discloses a compound which can be represented as 5-methoxy(indol-2-yl)-carbonyl-piperazinyl-(2-quinolinyl)

which differs from the claimed compounds in that none of the claimed compounds have quinoline structure or any bicyclic structure attached to the piperazinyl, piperidinyl or aminopiperidinyl moiety.

JP 01132579 (1987) discloses compounds which can be represented as (optionally substituted)-[indol-2-yl]-CO-piperazinyl-(CH$_2$)$_n$-[pyridinyl]

which have very strong blood platelet agglutination inhibiting activity where n is 1–5 which differs from the claimed compounds in that the claimed compounds do not permit any linking group between the piperazinyl moiety and the heteroaryl group.

Indian J. Chem. Sect. B, 17B(3), 246–9 (1979) and Indian J. Med. Res., 63(10), 1418–25 (1975) disclose compounds which can be represented as:

(indol-2-yl)-carbonyl-piperazinyl-(CH$_2$)$_n$-(optionally substituted phenyl)

The Indian J. Chem. Sect. B, 17B(3), 246–9 (1979) reported on p. 247 that none of the compounds showed any noteworthy (CNS) biological activity. The Indian J. Med. Res., 63(10), 1418–25 (1975) reported some of the compounds they prepared had anti-viral activity against Semliki forest virus (SFV) in mice. One compound, a dihydroisoquinolin was tested and found to be inactive against new castle disease virus in chick embryo. These compounds differ from the claimed compounds in that the claimed compounds require a heteroaryl group not a phenyl group attached to the piperazinyl moiety.

International Publication EP 370 381 A2, published 5 May 90 discloses compounds which can be represented as

[heteroaryl]-CO-piperazinyl-[quinolinone]

where heteroaryl includes 2-indolyl which differ from the claimed compounds in that none of the claimed compounds have quinoline structure or any bicyclic structure attached to the piperazinyl moiety. The disclosed compounds possess cardiotonic and hypotensive activities and the capability of reducing the heart rate.

J. Med. Pharm. Chem., 5, 932–43 (1962) and U.S. Pat. No. 3,135,794 disclose CAS 100731-59-7 which can be represented as:

5,6-dimethoxy-(indol-3-yl)-ethylene-piperazinyl-(2-pyridinyl)

The compounds of the present invention do not include 3-indolyl type compounds nor to they include compounds where the "linker" is ethylene. Further, they require that the heteroaryl group (pyridinyl) be substituted.

U.S. Pat. No. 4,954,502 (Example 38) discloses a compound which can be represented as:

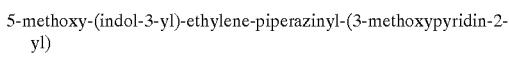
5-methoxy-(indol-3-yl)-ethylene-piperazinyl-(3-methoxypyridin-2-yl)

The compounds of the present invention do not include 3-indolyl type compounds nor to they include compounds where the "linker" is ethylene. While they require that the heteroaryl group (pyridinyl) be substituted methoxy and other alkoxy substitution is prohibited.

Other 3-indolyl compounds not believed to be as relevant as the ones cited above are disclosed in U.S. Pat. No. 3,751,417, *J. Org. Chem.*, 44(26), 4809–13 (1979), U.S. Pat. No. 4,302,589, U.S. Pat. No. 3,328,407, FR 1,551,082, *Arch. Pharm.* (Weinheim, Ger.), 321(7), 377–83 (1988) and *J. Med. Chem.*, 9(1), 140–2 (1966).

U.S. Pat. Nos. 5,032,598 and 5,215,989 discloses class III anti-arrhythmic compounds of the formula

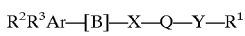
$R^2R^3Ar$—[B]—X—Q—Y—$R^1$ which if the appropriate substituents were selected generically encompasses some of the compounds of the present invention.

U.S. Pat. Nos. 3,472,855 and 3,562,278 disclose 3-indolinyl compounds which are useful as psychomotor depressants. The Anti-AIDS Amines (I) of the present invention are 2-indolyl not 3-indolyl compounds and are useful for a totally different purpose, inhibition of HIV-RT and treatment of AIDS.

U.S. Pat. No. 3,362,956 discloses compounds of the general formula

[3-quinolyl]-$(CH_2)_n$-[piperazinyl type]-[pyridinyl/phenyl].

The Anti-AIDS Amines (I) of the present invention differ from the prior art compounds in that they do not include 3-quinolyl type compounds.

U.S. Pat. No. 3,472,854 discloses compounds of the general formula

[2-benzimidazolyl]-$(CH_2)_n$-[piperazinyl type]-[pyridinyl/phenyl].

The Anti-AIDS Amines (I) of the present invention differ from the prior art compounds in that no methylene linker is permitted between the benzimidazolyl group and the piperazinyl group.

U.S. Pat. No. 3,491,098 discloses compounds of the general formula

[4(5)-imidazolyl]-$(CH_2)_n$-[piperazinyl type]-[pyridinyl/phenyl].

The Anti-AIDS Amines (I) of the present invention differ from the prior art compounds in that no methylene linker is permitted between the imidazolyl group and the piperazinyl group.

U.S. Pat. No. 3,511,841 discloses compounds of the general formula

[azaindolyl]-$(CH_2)_n$-[piperazinyl type]-[pyridinyl/phenyl]

[azaindolyl]-CO-[piperazinyl type]-[pyridinyl/phenyl]

The Anti-AIDS Amines (I) of the present invention differ from the prior art compounds in that they have substituted oxygen or substituted amino groups on the pyridinyl group.

International Publication No. WO 91/09849 discloses diaromatic substituted heterocyclic compounds of the type [aryl/heteroaryl]-connector-piperazine type-aryl/heteroaryl useful in treating individuals infected with the HIV virus. This document discloses compounds of the type (substituted)indole-CO-piperazinyl-(non-alkyl substituted) pyridinyl.

International Publication No. WO 93/01181 also discloses compounds of the type (substituted)indole-CO-piperazinyl-(non-alkyl substituted)pyridinyl useful in treating individuals infected with the HIV virus.

EP 0 154 969 and U.S. Pat. No. 4,613,598 disclose compounds of the formula

[substituted]-aromatic-CO—$(CH_2)_{3-5}$-[piperazinyl]-Ar

[substituted]-aromatic-CHOH—$(CH_2)_{3-5}$-[piperazinyl]-Ar where Ar is pyridinyl, —φ or substituted —φ which have the ability to lower blood pressure.

*Proceedings of the National Academy of Sciences* 88, 8806–10 (1991) discloses various bis(heteroaryl)piperazinyl non-nucleoside reverse transcriptase inhibitors which potently and specifically block human immunodeficiency virus type 1 replication.

There are a number of other chemically unrelated compounds which have been reported to inhibit HIV and/or be useful in the treatment of AIDS.

SUMMARY OF INVENTION

Disclosed are Anti-AIDS compounds of the formula:

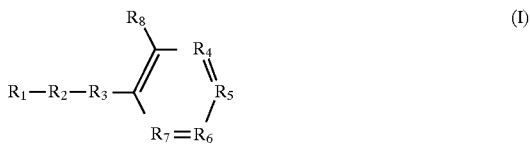
(I)

where (I) $R_1$ is:

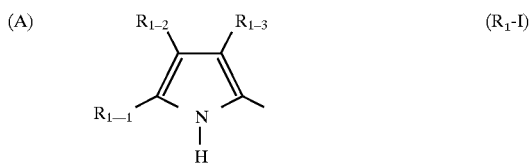
(A) ($R_1$-I)

where $R_{1-1}$ is:
(1) —H,
(2) —F,
(3) —Cl,
(4) —Br,
(5) $C_1$–$C_5$ alkyl,
(6) —CO—$CH_3$,
(7) —CO—OH,
(8) —CO—$OR_{1-1A}$ where $R_{1-1A}$ is $C_1$–$C_3$ alkyl,
(9) —CO—$NH_2$,
where $R_{1-2}$ is:
(1) —H,
(2) —F,
(3) —Cl,
(4) —Br,
(5) $C_1$–$C_5$ alkyl,
(6) —CO—$CH_3$,
(7) —CO—OH,
(8) —CO—$OR_{1-2A}$ where $R_{1-2A}$ is $C_1$–$C_3$ alkyl,
(9) —CO—$NH_2$, where $R_{1-3}$ is:
 (1) —H,
 (2) —F,
 (3) —Cl,
 (4) —Br,
 (5) $C_1$–$C_5$ alkyl,
 (6) —CO—$CH_3$,
 (7) —CO—OH,
 (8) —CO—$OR_{1-3A}$ where $R_{1-3A}$ is $C_1$–$C_3$ alkyl,
 (9) —CO—$NH_2$, (B)

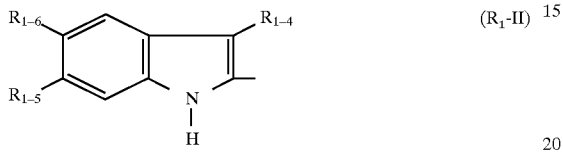

($R_1$-II)

where $R_{1-4}$ is:
 (1) —H,
 (2) —$CH_3$,
where $R_{1-5}$ is:
 (1) —H,
 (2) —F,
 (3) —Cl,
 (4) —Br,
 (5) —CN,
 (6) —CHO,
 (7) —$(CH_2)_{n1}$—OH where $n_1$ is 1 thru 5,
 (8) —$(CH_2)_{n1}$—$N(R_{1-5A})(R_{1-5B})$ where $n_1$ is as defined above and where $R_{1-5A}$ and $R_{1-5B}$ are the same or different and are:
  (a) —H,
  (b) $C_1$–$C_4$ alkyl or where $R_{1-5A}$ and $R_{1-5B}$ are taken together with the attached nitrogen atom to form a heterocyclic ring selected from the group consisting of
  (c) 1-pyrrolidinyl,
  (d) 1-piperidinyl,
  (e) 1-piperazinyl,
  (f) N-morpholinyl,
 (9) —CO—O—$R_{1-5C}$ where $R_{1-5C}$ is:
  (a) $C_1$–$C_6$ alkyl,
  (b) $C_3$–$C_7$ cycloalkyl,
  (c) —φ,
 (10) —CO—$N(R_{1-5D})(R_{1-5E})$ where $R_{1-5D}$ and $R_{1-5E}$ are the same or different and are:
  (a) $C_1$–$C_6$ alkyl,
  (b) $C_3$–$C_7$ cycloalkyl,
  (c) —φ, and where $R_{1-5A}$ and $R_{1-5B}$ are taken together with the attached nitrogen atom to form a heterocyclic ring selected from the group consisting of
  (d) 1-pyrrolidinyl,
  (e) 1-piperidinyl,
  (f) 1-piperazinyl,
  (g) N-morpholinyl,
 (11) —$(CH_2)_{n3}$—$N(R_{1-5M})(R_{1-5N})$ where $n_3$, $R_{1-5M}$, $R_{1-5N}$ and $R_{1-5O}$ are as defined below,
 (12) —$NO_2$,
 (13) —$NH_2$,
 (14) —$N_3$,
 (15) —NH—$CH_2$—φ,
 (16) —$NR_{1-5D}R_{1-5E}$ where $R_{1-5D}$ and $R_{1-5E}$ are the same or different and are:
  (a) —H,
  (b) $C_1$–$C_5$ alkyl or where $R_{1-5D}$ and $R_{1-5E}$ are taken together with the attached nitrogen atom to form a heterocyclic ring selected from the group consisting of
  (c) 1-pyrrolidinyl,
  (d) 1-piperidinyl,
  (e) 1-piperazinyl,
  (f) N-morpholinyl,
 (17) —$NR_{1-5F}(CH_2)_{n2}$—$N(R_{1-5G})(R_{1-5H})$ where $n_6$ is 2 thru 5, where $R_{1-5F}$ is:
  (a) —H,
  (b) $C_1$–$C_4$ alkyl, where $R_{1-5G}$ and $R_{1-5H}$ are the same or different and are:
   (a) —H,
   (b) $C_1$–$C_4$ alkyl and where $R_{1-5G}$ and $R_{1-5H}$ are taken together with the attached nitrogen atom to form a heterocyclic ring selected from the group consisting of:
   (c) 1-pyrrolidinyl,
   (d) 1-piperidinyl,
   (e) 1-piperazinyl,
   (f) N-morpholinyl,
 (18) —N=C($R_{1-5I}$)—$N(R_{1-5J})(R_{1-5K})$ where $R_{1-5I}$ is:
  (a) $R_{1-5I}$ is
   (i) —H,
   (ii) $C_1$–$C_4$ alkyl, where
  $R_{1-5J}$ and $R_{1-5K}$ are the same or different and are
   (i) $C_1$–$C_6$ alkyl,
   (ii) $C_3$–$C_7$ cycloalkyl,
   (iii) —φ,
  (b) $R_{1-5J}$ and $R_{1-5K}$ are taken together with the attached nitrogen atom to form a heterocyclic ring selected from the group consisting of
   (i) 1-pyrrolidinyl,
   (ii) 1-piperidinyl,
   (iii) 1-piperazinyl,
   (iv) N-morpholinyl,
  (c) $R_{1-5I}$ and $R_{1-5J}$ are taken together with the attached nitrogen atom to form a heterocyclic ring selected from the group consisting of
   (i) 1-pyrrolidinyl,
   (ii) 1-piperidinyl,
 (19) —NH—CO—$CF_3$,
 (20) —$N(R_{1-5F})$—CO—$R_{1-5L}$ where $R_{1-5L}$ is:
  (a) —H,
  (b) $C_1$–$C_4$ alkyl,
  (c) —φ and where $R_{1-5F}$ is defined above,
 (21) —NH—CO—$(CH_2)_{n3}$—$NR_{1-5M}R_{1-5N}$ where $n_3$ is 1 thru 3, where $R_{1-5M}$ and $R_{1-5N}$ are the same or different and are:
  (a) —H,
  (b) $C_1$–$C_6$ alkyl,
  (c) —φ,
  (d) 2-pyridinyl,
  (e) 3-pyridinyl,
  (f) 4-pyridinyl and where $R_{1-5M}$ and $R_{1-5N}$ are taken together with the attached nitrogen atom, and other heteroatom if necessary, to form a ring selected from the group consisting of:
  (g) 1-pyrrolidinyl,
  (h) 1-piperidinyl,
  (i) 1-piperazinyl optionally substituted in the
   (i) 4-position with $C_1$–$C_5$ alkyl,
   (ii) 3- and/or 5-position with $C_1$–$C_3$ alkyl and N-oxides thereof, (j) N-morpholinyl,
(22) —N($R_{1-5O}$)—CO—N($R_{1-5O}$)—($CH_2$)$_{n3}$—N($R_{1-5M}$)($R_{1-5N}$) where the $R_{1-5O}$'s are the same or different and are:
  (a) —H,
  (b) $C_1$–$C_3$ alkyl and where $n_3$, $R_{1-5M}$ and $R_{1-5N}$ are as defined above,
(23) —N($R_{1-5O}$)—CO—N($R_{1-5O}$)—($CH_2$)$_{n4}$—$R_{1-5P}$ where $n_4$ is 0 thru 3, where $R_{1-5P}$ is:
  (a) 2-pyridinyl,
  (b) 3-pyridinyl,
  (c) 4-pyridinyl and where $R_{1-5O}$ is as defined above,
(24) —N($R_{1-5O}$)—CO—N($R_{1-5M}$)($R_{1-5N}$) where $R_{1-5M}$, $R_{1-5N}$ and $R_{1-5O}$ are as defined above,
(25) —NH—CO-[4-(1-$R_{1-5M}$)piperidinyl] where $R_{1-5M}$ is as defined above,
(26) —N($R_{1-5O}$)—CO—O—$R_{1-5Q}$ where $R_{1-5Q}$ is:
  (a) $C_1$–$C_4$ alkyl,
(27) —NH—$SO_2$—$R_{1-5C}$ where $R_{1-5C}$ is as defined above,
(28) —NH—$SO_2$-[1-methyl-4-imidazolyl],
(29) —N($R_{1-5R}$)—$SO_2$—$R_{1-5S}$ where $R_{1-5R}$ is $C_1$–$C_3$ alkyl, where $R_{1-5S}$ is $C_1$–$C_4$ alkyl and where $R_{1-5R}$ and $R_{1-5S}$ are taken together with the attached nitrogen atom to form a heterocyclic ring of 5 or 6 atoms,
(30) —N($R_{1-5O}$)—$SO_2$—($CH_2$)$_{n4}$—$R_{1-5P}$ where $n_4$, $R_{1-5O}$ and $R_{1-5P}$ are as defined above,
(31) —N($R_{1-5O}$)—$SO_2$—($CH_2$)$_{n3}$—N($R_{1-5M}$)($R_{1-5N}$) where $n_3$, $R_{1-5M}$, $R_{1-5N}$ and $R_{1-5O}$ are as defined above,
(32) —NH—$SO_2$—$CF_3$,
(33) —N($R_{1-5O}$)—$SO_2$—N($R_{1-5M}$)($R_{1-5N}$) where $R_{1-5M}$, $R_{1-5N}$ and $R_{1-5O}$ are as defined above,
(34) —OH,
(35) —O—$R_{1-5T}$ where $R_{1-5T}$ is $C_1$–$C_4$ alkyl,
(36) —O—$CH_2$—φ,
(37) —O—$CF_3$,
(38) —O—$CH_2$—COO$R_{1-5U}$ where $R_{1-5U}$ is:
  (a) —H,
  (b) $C_1$–$C_4$ alkyl,
  (c) —φ,
  (d) —$CH_2$—φ,
  (e) —O—($CH_2CH_2$—O—)$_{n5}$—$R_{1-5V}$ where $n_5$ is 1 thru 4 and where $R_{1-5V}$ is:
    (i) —H,
    (ii) $C_1$–$C_4$ alkyl,
(39) —O—CO—($CH_2$)$_{n3}$—N$R_{1-5M}R_{1-5N}$ where $n_3$, $R_{1-5M}$ and $R_{1-5N}$ are as defined above,
(40) —O—$SO_2$—$CH_3$,
(41) —O—$SO_2$—$CH_2$—$CH_3$,
(42) —O—$SO_2$—$CH(CH_3)_2$,
(43) —O—$SO_2$—($CH_2$)$_{n3}$—N($R_{1-5M}$)($R_{1-5N}$) where n3, $R_{1-5M}$ and $R_{1-5N}$ are as defined above,
(44) —O—$SO_2$—($CH_2$)$_{n4}$—$R_{1-5P}$ where $n_4$ and $R_{1-5P}$ are as defined above,
(45) —O—$SO_2$—$CF_3$,
(46) —N$R_{1-5I}$-prodrug where $R_{1-5I}$ is as defined above and prodrug is:
  (a) —CO—$CH_2$—CO—NH—$CH_2$—$SO_2$—$O^-$ cation$^+$,
  (b) —CO—($CH_2$)$_{n10}$—$R_{1-5W}$ where $n_{10}$ is 1 thru 7 and $R_{1-5W}$ is:
    (i) —COO$^-$ cation$^+$,
    (ii) —N$R_{1-5X}R_{1-5Y}$ where $R_{1-5X}$ and $R_{1-5Y}$ are the same or different and are:
      (A) —H,
      (B) $C_1$–$C_3$ alkyl,
    (iii) —$N^+R_{1-5X}R_{1-5Y}R_{1-5Z}$ halide$^-$ where $R_{1-5Z}$ is:
      (A) —H,
      (B) $C_1$–$C_3$ alkyl, where halide is:
      (C) —Cl,
      (D) —Br, and where $R_{1-5X}$ and $R_{1-5Y}$ are as defined above,
  (c) —CO—CH(amino acid)-$NH_2$ where amino acid is:
    (i) —H,
    (ii) —$CH_3$,
    (iii) —$CH(CH_3)_2$,
    (iv) —$CH_2$—$CH(CH_3)_2$,
    (v) —$CH_2$—OH,
    (vi) —$CH(OH)(CH_3)$,
    (vii) —$CH_2$—φ,
    (viii) —$CH_2$-[p-hydroxyphenyl],
    (ix) —$CH_2$-[3-indolyl],
    (x) —$CH_2$—S—S—$CH_2$—$CH(NH_2)$—COOH,
    (xi) —$CH_2$—SH,
    (xii) —$CH_2CH_2$—S—$CH_3$,
    (xiii) —$CH_2$—COOH,
    (xiv) —$CH_2$—CO—$NH_2$,
    (xv) —$CH_2$—$CH_2$—COOH,
    (xvi) —$CH_2$—$CH_2$—CO—$NH_2$,
    (xvii) —$CH_2$-[2-histidyl],
    (xviii) —($CH_2$)$_3$—NH—C(NH)—$NH_2$,
    (xix) —($CH_2$)$_4$—$NH_2$,
    (xx) —$CH_2$—$CH_2$—CH(OH)—$CH_2$—$NH_2$,
    (xxi) —($CH_2$)$_3$—$NH_2$,
    (xxii) —($CH_2$)$_3$—NH—CO—$NH_2$,
    (xxiii) —$CH_2CH_2$—OH,
  (d) —CO—CH=CH—CO—$O^-$ cation$^+$,
  (e) —CO—N*—CH=CH—N=CH* where the atoms marked with an asterisk (*) are bonded to each other resulting in the formation of a ring,
  (f) —CO—C*=C[($CH_2$)$_{n11}$—$NH_2$]—CH=CH—CH=CH* where $n_{11}$ is 1 or 2 and where the atoms marked with an asterisk (*) are bonded to each other resulting in the formation of a ring,
  (g) —CO—C*=CH—CH=C(—N$R_{1-5X}$)—CH=CH* where $R_{1-5X}$ is as defined above and where the atoms marked with an asterisk (*) are bonded to each other resulting in the formation of a ring,
  (h) —CO—($CH_2$)$_{n10}$—CO—O—[$C_6H_{12}O_6$ sugars] where $n_{10}$ is as defined above,
  (i) —CO—O—CH($CH_2$—O—CO—$R_{1-5AA}$)$_2$ where the $R_{1-5AA}$'s are the same or different and are:
  (j) $C_1$–$C_{18}$ alkyl,
  (k) —CO—($CH_2$)$_6$—CO—N($CH_3$)—$CH_2$—$CH_2$—$SO_3^-$ cation$^+$,
  (l) —$CH_2$—O—CO—($CH_2$)$_{n10}$—N$R_{1-5X}R_{1-5Y}$ where $n_{10}$, $R_{1-5X}$ and $R_{1-5Y}$ are as defined above,
  (m) —CO—NH—$C_6H_4$—$R_{1-5BB}$ where $R_{1-5BB}$ is:
    (i) —H,
    (ii) $C_1$–$C_3$ alkyl,
    (iii) —$NO_2$,
  (n) —N$R_{1-5X}R_{1-5Y}$ where $R_{1-5X}$ and $R_{1-5Y}$ are as defined above, where $R_{1-6}$ is:
(1) —H,
(2) —F,
(3) —Cl,
(4) —Br,
(5) —CN, (6) —CHO, (7) —(CH$_2$)$_{n1}$—OH where n$_1$ is 1 thru 5, (8) —(CH$_2$)$_{n1}$—N(R$_{1-6A}$)(R$_{1-6B}$) where n$_1$ is as defined above and where R$_{1-6A}$ and R$_{1-6B}$ are the same or different and are:
  (a) —H,
  (b) C$_1$–C$_4$ alkyl or where R$_{1-6A}$ and R$_{1-6B}$ are taken together with the attached nitrogen atom to form a heterocyclic ring selected from the group consisting of
  (c) 1-pyrrolidinyl,
  (d) 1-piperidinyl,
  (e) 1-piperazinyl,
  (f) N-morpholinyl, (9) —CO—O—R$_{1-6C}$ where R$_{1-6C}$ is:
  (a) C$_1$–C$_6$ alkyl,
  (b) C$_3$–C$_7$ cycloalkyl,
  (c) —φ,

(10) —CO—N(R$_{1-6D}$)(R$_{1-6E}$) where R$_{1-6D}$ and R$_{1-6E}$ are the same or different and are:
  (a) C$_1$–C$_6$ alkyl,
  (b) C$_3$–C$_7$ cycloalkyl,
  (c) —φ, and where R$_{1-6A}$ and R$_{1-6B}$ are taken together with the attached nitrogen atom to form a heterocyclic ring selected from the group consisting of
  (d) 1-pyrrolidinyl,
  (e) 1-piperidinyl,
  (f) 1-piperazinyl,
  (g) N-morpholinyl,

(11) —(CH$_2$)$_{n3}$—N(R$_{1-6M}$)(R$_{1-6N}$) where n$_3$, R$_{1-6M}$, R$_{1-6N}$ and R$_{1-6O}$ are as defined below,

(12) —NO$_2$,

(13) —NH$_2$,

(14) —N$_3$,

(15) —NH—CH$_2$—φ,

(16) —NR$_{1-6D}$R$_{1-6E}$ where R$_{1-6D}$ and R$_{1-6E}$ are the same or different and are:
  (a) —H,
  (b) C$_1$–C$_5$ alkyl or where R$_{1-6D}$ and R$_{1-6E}$ are taken together with the attached nitrogen atom to form a heterocyclic ring selected from the group consisting of
  (c) 1-pyrrolidinyl,
  (d) 1-piperidinyl,
  (e) 1-piperazinyl,
  (f) N-morpholinyl,

(17) —NR$_{1-6F}$(CH$_2$)$_{n2}$—N(R$_{1-6G}$)(R$_{1-6H}$) where n$_6$ is 2 thru 5, where R$_{1-6F}$ is:
  (a) —H,
  (b) C$_1$–C$_4$ alkyl, where R$_{1-6G}$ and R$_{1-6H}$ are the same or different and are:
  (a) —H,
  (b) C$_1$–C$_4$ alkyl and where R$_{1-6G}$ and R$_{1-6H}$ are taken together with the attached nitrogen atom to form a heterocyclic ring selected from the group consisting of:
  (c) 1-pyrrolidinyl,
  (d) 1-piperidinyl,
  (e) 1-piperazinyl,
  (f) N-morpholinyl,

(18) —N=C(R$_{1-6I}$)—N(R$_{1-6J}$)(R$_{1-6K}$) where R$_{1-6I}$ is:
  (a) R$_{1-6I}$ is
    (i) —H,
    (ii) C$_1$–C$_4$ alkyl, where R$_{1-6J}$ and R$_{1-6K}$ are the same or different and are
    (i) C$_1$–C$_6$ alkyl,
    (ii) C$_3$–C$_7$ cycloalkyl,
    (iii) —φ,
  (b) R$_{1-6J}$ and R$_{1-6K}$ are taken together with the attached nitrogen atom to form a heterocyclic ring selected from the group consisting of
    (i) 1-pyrrolidinyl,
    (ii) 1-piperidinyl,
    (iii) 1-piperazinyl,
    (iv) N-morpholinyl,
  (c) R$_{1-6I}$ and R$_{1-6J}$ are taken together with the attached nitrogen atom to form a heterocyclic ring selected from the group consisting of
    (i) 1-pyrrolidinyl,
    (ii) 1-piperidinyl,

(19) —NH—CO—CF$_3$,

(20) —N(R$_{1-6F}$)—CO—R$_{1-6L}$ where R$_{1-6L}$ is:
  (a) —H,
  (b) C$_1$–C$_4$ alkyl,
  (c) —φ and where R$_{1-6F}$ is defined above,

(21) —NH—CO—(CH$_2$)$_{n3}$—NR$_{1-6M}$R$_{1-6N}$ where n$_3$ is 1 thru 3, where R$_{1-6M}$ and R$_{1-6N}$ are the same or different and are:
  (a) —H,
  (b) C$_1$–C$_6$ alkyl,
  (c) —φ,
  (d) 2-pyridinyl,
  (e) 3-pyridinyl,
  (f) 4-pyridinyl and where R$_{1-6M}$ and R$_{1-6N}$ are taken together with the attached nitrogen atom, and other heteroatom if necessary, to form a ring selected from the group consisting of:
  (g) 1-pyrrolidinyl,
  (h) 1-piperidinyl,
  (i) 1-piperazinyl optionally substituted in the
    (i) 4-position with C$_1$–C$_5$ alkyl,
    (ii) 3- and/or 5-position with C$_1$–C$_3$ alkyl and N-oxides thereof,
  (j) N-morpholinyl,

(22) —N(R$_{1-6O}$)—CO—N(R$_{1-6O}$)—(CH$_2$)$_{n3}$—N(R$_{1-6M}$)(R$_{1-6N}$) where the R$_{1-6O}$'s are the same or different and are:
  (a) —H,
  (b) C$_1$–C$_3$ alkyl and where n$_3$, R$_{1-6M}$ and R$_{1-6N}$ are as defined above,

(23) —N(R$_{1-6O}$)—CO—N(R$_{1-6O}$)—(CH$_2$)$_{n4}$—R$_{1-6P}$ where n$_4$ is 0 thru 3, where R$_{1-6P}$ is:
  (a) 2-pyridinyl,
  (b) 3-pyridinyl,
  (c) 4-pyridinyl and where R$_{1-6O}$ is as defined above,

(24) N(R$_{1-6O}$)—CO—N(R$_{1-6M}$)(R$_{1-6N}$) where R$_{1-6M}$, R$_{1-6N}$ and R$_{1-6O}$ are as defined above,

(25) —NH—CO—[4-(1-R$_{1-6M}$)piperidinyl] where R$_{1-6M}$ is as defined above,

(26) —N(R$_{1-6O}$)—CO—O—R$_{1-6Q}$ where R$_{1-6Q}$ is:
  (a) C$_1$–C$_4$ alkyl,

(27) —NH—SO$_2$—R$_{1-6C}$ where R$_{1-6C}$ is as defined above,

(28) —NH—SO$_2$-[1-methyl-4-imidazolyl],

(29) —N(R$_{1-6R}$)—SO$_2$—R$_{1-6S}$ where R$_{1-6R}$ is C$_1$–C$_3$ alkyl, where R$_{1-6S}$ is C$_1$–C$_4$ alkyl and where R$_{1-6R}$ and R$_{1-6S}$ are taken together with the attached nitrogen atom to form a heterocyclic ring of 5 or 6 atoms,

(30) —N(R$_{1-6O}$)—SO$_2$—(CH$_2$)$_{n4}$—R$_{1-6P}$ where n$_4$, R$_{1-6O}$ and R$_{1-6P}$ are as defined above,

(31) —N(R$_{1-6O}$)—SO$_2$—(CH$_2$)$_{n3}$—N(R$_{1-6M}$)(R$_{1-6N}$) where n$_3$, R$_{1-6M}$, R$_{1-6N}$ and R$_{1-6O}$ are as defined above,
(32) —NH—SO$_2$—CF$_3$,
(33) —N(R$_{1-6O}$)—SO$_2$—N(R$_{1-6M}$)(R$_{1-6N}$) where R$_{1-6M}$, R$_{1-6N}$ and R$_{1-6O}$ are as defined above,
(34) —OH,
(35) —O—R$_{1-6T}$ where R$_{1-6T}$ is C$_1$–C$_4$ alkyl,
(36) —O—CH$_2$—ϕ,
(37) —O—CF$_3$,
(38) —O—CH$_2$—COOR$_{1-6U}$ where R$_{1-6U}$ is:
  (a) —H,
  (b) C$_1$–C$_4$ alkyl,
  (c) —ϕ,
  (d) —CH$_2$—ϕ,
  (e) —O—(CH$_2$CH$_2$—O—)$_{n5}$—R$_{1-6V}$ where n$_5$ is 1 thru 4 and where R$_{1-6V}$ is:
    (i) —H,
    (ii) C$_1$–C$_4$ alkyl,
(39) —O—CO—(CH$_2$)$_{n3}$—NR$_{1-6M}$R$_{1-6N}$ where n$_3$, R$_{1-6M}$ and R$_{1-6N}$ are as defined above,
(40) —O—SO$_2$—CH$_3$,
(41) —O—SO$_2$—CH$_2$—CH$_3$,
(42) —O—SO$_2$—CH(CH$_3$)$_2$,
(43) —O—SO$_2$—(CH$_2$)$_{n3}$—N(R$_{1-6M}$)(R$_{1-6N}$) where n3, R$_{1-6M}$ and R$_{1-6N}$ are as defined above,
(44) —O—SO$_2$—(CH$_2$)$_{n4}$—R$_{1-6P}$ where n$_4$ and R$_{1-6P}$ are as defined above,
(45) —O—SO$_2$—CF$_3$,
(46) —NR$_{1-6I}$-prodrug where R$_{1-6I}$ is as defined above and prodrug is:
  (a) —CO—CH$_2$—CO—NH—CH$_2$—SO$_2$—O$^-$ cation$^+$,
  (b) —CO—(CH$_2$)$_{n10}$—R$_{1-6W}$ where n$_{10}$ is 1 thru 7 and R$_{1-6W}$ is:
    (i) —COO$^-$ cation$^+$,
    (ii) —NR$_{1-6X}$R$_{1-6Y}$ where R$_{1-6X}$ and R$_{1-6Y}$ are the same or different and are:
      (A) —H,
      (B) C$_1$–C$_3$ alkyl,
    (iii) —N$^+$R$_{1-6X}$R$_{1-6Y}$R$_{1-6Z}$ halide$^-$ where R$_{1-6Z}$ is:
      (A) —H,
      (B) C$_1$–C$_3$ alkyl, where halide is:
      (C) —Cl,
      (D) —Br, and where R$_{1-6X}$ and R$_{1-6Y}$ are as defined above,
  (c) —CO—CH(amino acid)-NH$_2$ where amino acid is:
    (i) —H,
    (ii) —CH$_3$,
    (iii) —CH(CH$_3$)$_2$,
    (iv) —CH$_2$—CH(CH$_3$)$_2$,
    (v) —CH$_2$—OH,
    (vi) —CH(OH)(CH$_3$),
    (vii) —CH$_2$—ϕ,
    (viii) —CH$_2$-[p-hydroxyphenyl],
    (ix) —CH$_2$-[3-indolyl],
    (x) —CH$_2$—S—S—CH$_2$—CH(NH$_2$)—COOH,
    (xi) —CH$_2$—SH,
    (xii) —CH$_2$CH$_2$—S—CH$_3$,
    (xiii) —CH$_2$—COOH,
    (xiv) —CH$_2$—CO—NH$_2$,
    (xv) —CH$_2$—CH$_2$—COOH,
    (xvi) —CH$_2$—CH$_2$—CO—NH$_2$,
    (xvii) —CH$_2$-[2-histidyl],
    (xviii) —(CH$_2$)$_3$—NH—C(NH)—NH$_2$,
    (xix) —(CH$_2$)$_4$—NH$_2$,
    (xx) —CH$_2$—CH$_2$—CH(OH)—CH$_2$—NH$_2$,
    (xxi) —(CH$_2$)$_3$—NH$_2$,
    (xxii) —(CH$_2$)$_3$—NH—CO—NH$_2$,
    (xxiii) —CH$_2$CH$_2$—OH,
  (d) —CO—CH=CH—CO—O$^-$ cation$^+$,
  (e) —CO—N*—CH=CH—N=CH* where the atoms marked with an asterisk (*) are bonded to each other resulting in the formation of a ring,
  (f) —CO—C*=C[(CH$_2$)$_{n11}$—NH$_2$]—CH=CH—CH=CH* where n$_{11}$ is 1 or 2 and where the atoms marked with an asterisk (*) are bonded to each other resulting in the formation of a ring,
  (g) —CO—C*=CH—CH=C(—NR$_{1-6X}$)—CH=CH* where R$_{1-6X}$ is as defined above and where the atoms marked with an asterisk (*) are bonded to each other resulting in the formation of a ring,
  (h) —CO—(CH$_2$)$_{n10}$—CO—O—[C$_6$H$_{12}$O$_6$ sugars] where n$_{10}$ is as defined above,
  (i) —CO—O—CH(CH$_2$—O—CO—R$_{1-6AA}$)$_2$ where the R$_{1-6AA}$'s are the same or different and are:
  (j) C$_1$–C$_{18}$ alkyl,
  (k) —CO—(CH$_2$)$_6$—CO—N(CH$_3$)—CH$_2$—CH$_2$—SO$_3^-$ cation$^+$,
  (l) —CH$_2$—O—CO—(CH$_2$)$_{n10}$—NR$_{1-6X}$R$_{1-6Y}$ where n$_{10}$, R$_{1-6X}$ and R$_{1-6Y}$ are as defined above,
  (m) —CO—NH—C$_6$H$_4$—R$_{1-6BB}$ where R$_{1-6BB}$ is:
    (i) —H,
    (ii) C$_1$–C$_3$ alkyl,
    (iii) —NO$_2$,
  (n) —NR$_{1-6X}$R$_{1-6Y}$ where R$_{1-6X}$ and R$_{1-6Y}$ are as defined above, with the proviso that only one of R$_{1-5}$ or R$_{1-6}$ is —NR$_{1-5I}$-prodrug or —NR$_{1-6I}$-prodrug;

(C)

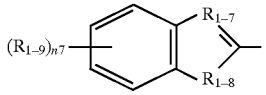

where R$_{1-7}$ is:
(1) —N= provided R$_2$ is not —CH$_2$—,
(2) —CR$_{1-7A}$ where R$_{1-7A}$ is:
  (a) —CO—O—R$_{1-7B}$ where R$_{1-7B}$ is:
    (i) —H,
    (ii) C$_1$–C$_4$ alkyl,
  (b) —CO—N(R$_{1-7C}$)(R$_{1-7D}$) where R$_{1-7C}$ and R$_{1-7D}$ are the same or different and are:
    (i) —H,
    (ii) C$_1$–C$_4$ alkyl and where R$_{1-7C}$ and R$_{1-7D}$ are taken together with the attached nitrogen atom to form a heterocyclic ring selected from the group consisting of:
    (iii) 1-pyrrolidinyl,
    (iv) 1-piperidinyl,
    (v) 1-piperazinyl,
    (vi) N-morpholinyl,
  (c) —CO—COO—R$_{1-7B}$ where R$_{1-7B}$ is as defined above,
  (d) C$_1$–C$_3$ alkyl,
  (e) —CO—ϕ,
  (f) —CO—R$_{1-7B}$ where R$_{1-7B}$ is as defined above,
  (g) —CO—CO—N(R$_{1-7C}$)(R$_{1-7D}$) where R$_{1-7C}$ and R$_{1-7D}$ are as defined above,
  (h) —(CH$_2$)$_{n6}$—OH where n$_6$ is 1 or 2;
where R$_{1-8}$ is:

(1) —NR$_{1-8A}$— where R$_{1-8A}$ is:
  (a) —H,
  (b) —SO$_2$—φ,
  (c) —SO$_2$—CH$_3$,
  (d) —CO—R$_{1-8B}$ where R$_{1-8B}$ is:
    (i) C$_1$–C$_4$ alkyl,
    (ii) —CF3,
    (iii) —φ;
where R$_{1-9}$ is:
(1) —H,
(2) —F,
(3) —Cl,
(4) —Br,
(5) C$_1$–C$_6$ alkyl,
(6) —CHO,
(7) C$_1$–C$_3$ alkoxy,
(8) —CO—OR$_{1-9A}$ where R$_{1-9A}$ is:
  (a) —H,
  (b) C$_1$–C$_4$ alkyl,
  (d) —CH$_2$—φ,
(9) —C≡N,
(10) —(CH$_2$)$_{n8}$—OH where n$_8$ is 1 thru 5,
(11) —(CH$_2$)$_{n8}$—N(R$_{1-9B}$)(R$_{1-9C}$) where R$_{1-9B}$ and R$_{1-9C}$ are the same or different and are:
  (a) —H,
  (b) C$_1$–C$_4$ alkyl and where R$_{1-9B}$ and R$_{1-9C}$ are taken together with the attached nitrogen atom to form a heterocyclic ring selected from the group consisting of:
  (c) 1-pyrrolidinyl,
  (d) 1-piperidinyl,
  (e) 1-piperazinyl,
  (f) N-morpholinyl and where n$_8$ is as defined above,
(12) —NO$_2$,
(13) —N$_3$,
(14) —NR$_{1-9D}$R$_{1-9E}$ where R$_{1-9D}$ and R$_{1-9E}$ are the same or different and are:
  (a) —H,
  (b) C$_1$–C$_5$ alkyl and where R$_{1-9D}$ and R$_{1-9E}$ are taken together with the attached nitrogen atom to form a heterocyclic ring selected from the group consisting of:
  (c) 1-pyrrolidinyl,
  (d) 1-piperidinyl,
  (e) 1-piperazinyl,
  (f) N-morpholinyl,
  (g) 1-aziridinyl,
(15) —N(R$_{1-9F}$)(CH$_2$)$_{n9}$—N(R$_{1-9G}$)(R$_{1-9H}$) where n$_9$ is 2 thru 5, where R$_{1-9F}$ is:
  (a) —H,
  (b) C$_{1-4}$ alkyl, where R$_{1-9G}$ and R$_{1-9H}$ are the same or different and are:
  (c) —H,
  (d) C$_{1-4}$ alkyl and where R$_{1-9G}$ and R$_{1-9H}$ are taken together with the attached nitrogen atom to form a heterocyclic ring selected from the group consisting of:
  (e) 1-pyrrolidinyl,
  (f) 1-piperidinyl,
  (g) 1-piperazinyl,
  (h) N-morpholinyl,
  (i) 1-aziridinyl,
(16) —NH—SO$_2$—R$_{1-9I}$ where R$_{1-9I}$ is:
  (a) C$_1$–C$_4$ alkyl,
  (b) C$_3$–C$_7$ cycloalkyl,
  (c) —φ,
  (d) —CH$_2$—φ,
(17) —N=C(R$_{1-9J}$)—N(R$_{1-9K}$)(R$_{1-9L}$) where
  (a) R$_{1-9J}$ is
    (i) —H,
    (ii) C$_1$–C$_4$ alkyl, where
  R$_{1-9K}$ and R$_{1-9L}$ are the same or different and are
    (iii) C$_1$–C$_6$ alkyl,
    (iv) C$_3$–C$_7$ cycloalkyl,
    (v) —φ,
  (b) R$_{1-9K}$ and R$_{1-9L}$ are taken together with the attached nitrogen atom to form a heterocyclic ring selected from the group consisting of
    (i) 1-pyrrolidinyl,
    (ii) 1-piperidinyl,
    (iii) 1-piperazinyl,
    (iv) N-morpholinyl,
  (c) R$_{1-9J}$ and R$_{1-9K}$ are taken together with the attached nitrogen atom to form a heterocyclic ring selected from the group consisting of
    (i) 1-pyrrolidinyl,
    (ii) 1-piperidinyl,
(18) —NR$_{1-9F}$—CO—R$_{1-9M}$ where R$_{1-6M}$ is:
  (a) —H,
  (b) C$_1$–C$_4$ alkyl,
  (c) —φ and where R$_{1-9F}$ is as defined above,
(19) —OH,
(20) —O—CH$_2$—φ,
(21) —O—CF$_3$,
(22) —O—CH$_2$—COOR$_{1-9A}$ where R$_{1-9A}$ is as defined above,
(23) —O—CO—R$_{1-9M}$ where R$_{1-9M}$ is as defined above,
(24) —O—SO$_2$—(C$_1$–C$_4$ alkyl),
(25) —O—CO—(CH$_2$)$_{n9}$—COOH, where n$_9$ is as defined above,
(26) —O—(CH$_2$)$_{n9}$—N(R$_{1-9G}$)(R$_{1-9H}$) where n$_9$, R$_{1-9G}$ and R$_{1-9H}$ are as defined above,
(27) —O-prodrug where prodrug is
  (a) —PO$_2$—O$^-$ cation$^+$ and as defined above,
(28) C$_1$–C$_3$ alkylthio, where n$_7$ is 1 thru 3, and
(1) when n$_7$ is 2 or 3, the R$_{1-9}$'s can be the same or different and
(2) when n$_7$ is 2 and the two R$_{1-9}$ groups are ortho to each other they can be taken together to form —O—CH$_2$—O—, with the proviso that if n$_7$ is 2 or 3, only one of the R$_{1-9}$ groups can be a prodrug;

(D)

(R$_1$-IV)

(E)

(R$_1$-V)

where n$_{12}$ is 0 thru 2 and where R$_{1-8}$ and R$_{1-9}$ are as defined above,
where R$_{1-10}$ is:
(1) —H,
(2) —F, (3) —Cl,
(4) —Br,
(5) $C_1$–$C_6$ alkyl,
(6) —C≡N,
(7) —CHO,
(8) —$(CH_2)_{n13}$—OH where $n_{13}$ is 1 thru 5,
(9) —$(CH_2)_{n13}$—$N(R_{1-10A})(R_{1-10B})$ where $n_{13}$ is as defined above and $R_{10-A}$ and $R_{10-B}$ are the same or different and are:
  (a) —H,
  (b) $C_1$–$C_4$ alkyl and where $R_{1-10A}$ and $R_{1-10B}$ are taken together with the attached nitrogen atom to form a heterocyclic ring selected from the group consisting of
  (c) 1-pyrrolidinyl,
  (d) 1-piperidinyl,
  (e) 1-piperazinyl,
  (f) N-morpholinyl,
(10) —CO—O—$R_{1-10C}$ where $R_{1-10C}$ is
  (a) $C_1$–$C_6$ alkyl,
  (b) $C_3$–$C_7$ cycloalkyl,
  (c) —φ,
(11) —CO—$N(R_{1-10D})(R_{1-10E})$ where $R_{1-10D}$ and $R_{1-10E}$ are the same or different and are
  (a) $C_1$–$C_6$ alkyl,
  (b) $C_3$–$C_7$ cycloalkyl,
  (c) —φ, and where $R_{1-10D}$ and $R_{1-10E}$ are taken together with the attached nitrogen atom to form a heterocyclic ring selected from the group consisting of
  (d) 1-pyrrolidinyl,
  (e) 1-piperidinyl,
  (f) 1-piperazinyl,
  (g) N-morpholinyl,
(12) —$NO_2$,
(13) —$NH_2$,
(14) —$N_3$,
(15) —NH—$CH_2$—φ,
(16) —NH—$SO_2$—$R_{1-10F}$ where $R_{1-10F}$ is
  (a) $C_1$–$C_6$ alkyl,
  (b) $C_3$–$C_7$ cycloalkyl,
  (c) —φ,
(17) —$NR_{1-10G}(CH_2)_{n14}$—$N(R_{1-10A})(R_{1-10B})$ where $n_{14}$ is 2 thru 5, where $R_{1-10G}$ is
  (a) —H,
  (b) $C_{1-4}$ alkyl, where $R_{1-10A}$ and $R_{1-10B}$ are as defined above,
(18) —$N(R_{1-10A})(R_{1-10B})$ where $R_{1-10A}$ and $R_{1-10B}$ are as defined above,
(19) —N=$C(R_{1-10H})$—$N(R_{1-10I})(R_{1-10J})$ where
  (a) $R_{1-10H}$ is
    (i) —H,
    (ii) $C_1$–$C_4$ alkyl, where $R_{1-10I}$ and $R_{1-10J}$ are
      (i) $C_1$–$C_6$ alkyl,
      (ii) $C_3$–$C_7$ cycloalkyl,
      (iii) —φ, and where
  (b) $R_{1-10I}$ and $R_{1-10J}$ are taken together with the attached nitrogen atom to form a heterocyclic ring selected from the group consisting of
    (i) 1-pyrrolidinyl,
    (ii) 1-piperidinyl,
    (iii) 1-piperazinyl,
    (iv) N-morpholinyl,
  (c) $R_{1-10H}$ and $R_{1-10J}$ are taken together with the attached nitrogen atom to form a heterocyclic ring selected from the group consisting of
    (v) 1-pyrrolidinyl,
    (vi) 1-piperidinyl,
(20) —$N(R_{1-10G})$—CO—$R_{1-10K}$ where $R_{1-10K}$ is
  (a) —H,
  (b) $C_1$–$C_4$ alkyl,
  (c) —φ and where $R_{1-10G}$ is defined above,
(21) —$N(R_{1-10G})$-prodrug, where $R_{1-10G}$ and prodrug is as defined above,
(22) —O—$CH_2$—φ,
(23) —O—$CF_3$,
(24) —O—$CH_2$—$COOR_{1-10L}$ where $R_{1-10L}$ is
  (a) —H,
  (b) $C_1$–$C_4$ alkyl,
  (c) —φ,
  (d) —$CH_2$—φ,
(25) —O—$SO_2$—($C_1$–$C_4$ alkyl);

(F)

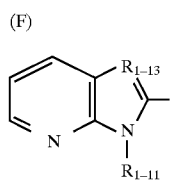

($R_1$-VI)

where $R_{1-11}$
  (1) —H,
and $R_{1-13}$ is
  (1) —CH=,
  (2) —$CR_{1-13A}$ where $R_{1-13A}$ is:
    (a) $C_1$–$C_3$ alkyl,
    (b) —$(CH_2)_{n15}$—OH where $n_{15}$ is 1 or 2;

(G)

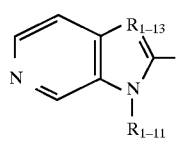

($R_1$-VII)

where $R_{1-11}$ and $R_{1-13}$ are as defined above;

(H)

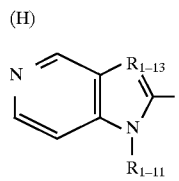

($R_1$-VIII)

where $R_{1-11}$ and $R_{1-13}$ are as defined above;

(I)

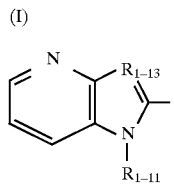

($R_1$-IX)

where $R_{1-11}$ and $R_{1-13}$ are as defined above;

(J) 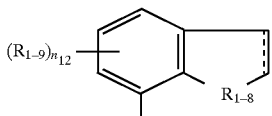 ($R_1$-X)

where $R_{1-8}$, $R_{1-9}$ and $n_{12}$ are as defined above;
where (II) $R_2$ is:
(A) —CO—,
(B) —CH$_2$—;
where (III) $R_3$ is:

(A) 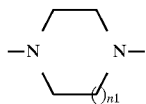 ($R_3$-I)

where $n_1$ is 1 or 2, (B) 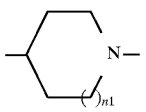 ($R_3$-II)

where $n_1$ is as defined above, (C) 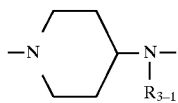 ($R_3$-III)

where $R_{3-1}$ is:
(1) $C_1$–$C_6$ alkyl,
(2) $C_3$–$C_7$ cycloalkyl;

(D) 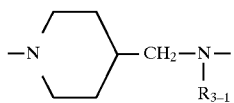 ($R_3$-IV)

where $R_{3-1}$ is as defined above;

(E) 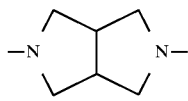 ($R_3$-V)

(F) —$R_{3-2}$—(CH$_2$)$_{n3}$—$R_{3-3}$—(CH$_2$)$_{n4}$—$R_{3-4}$— where $R_{3-2}$ is:
(1) —O—,
(2) —N(C$_1$–C$_4$alkyl)-,
(3) —C(R$_{3-2A}$)(R$_{3-2B}$)— where $R_{3-2A}$ and $R_{3-2B}$ are the same or different and are:
(a) —H,
(b) $C_1$–$C_4$ alkyl,
where $n_3$ is 1 thru 5,
where $R_{3-3}$ is:
(1) —O—,
(2) —S—,
(3) nothing (a bond),
(4) —C≡C—,
(5) —C(R$_{3-3A}$)(R$_{3-3B}$)— where $R_{3-3A}$ and $R_{3-3B}$ are the same or different and are:
(a) —H,
(b) $C_1$–$C_4$alkyl,
(6) cis and trans —C(R$_{3-3C}$)=(R$_{3-3D}$)C— where $R_{3-4}$ and $R_{3-5}$ are the same or different and are:
(a) —H,
(b) $C_1$–$C_4$alkyl,
where $R_{3-4}$ is:
(1) —O—,
(3) —N(C$_1$–C$_4$alkyl)-,
(4) —C(R$_{3-4A}$)(R$_{3-4B}$)— where $R_{3-4A}$ and $R_{3-4B}$ are the same or different and are:
(a) —H,
(b) $C_1$–$C_4$ alkyl,
with the provisos:
(1) that when $R_{3-2}$ is —O— or —N(C$_1$–C$_4$ alkyl)-, then $n_3$ is 1 only when $R_{3-3}$ is nothing (a bond), —C≡C—, —C(R$_{3-3A}$)(R$_{3-3B}$)— or —C(R$_{3-3C}$)=(R$_{3-3D}$)C— and
(2) that when $R_{3-4}$ is —O—, —N(C$_1$–C$_4$ alkyl)-, then $n_4$ is 1 only when $R_{3-3}$ is nothing (a bond), —C≡C—, —C(R$_{3-3A}$)(R$_{3-3B}$)— or —C(R$_{3-3C}$)=(R$_{3-3D}$)C—,
where $n_4$ is 1 thru 5;
where (IV) $R_4$ is:
(A) —N=,
(B) —CH=,
(C) —CF=,
(D) —C(CF$_3$)=,
(E) —C(CN)=,
(F) —CCl=;
where (V) $R_5$ is:
(A) —N=,
(B) —CH=,
(C) —CF=,
(D) —CCl=,
(E) —C(CF$_3$)=,
(F) —C(CN)=;
where (VI) $R_6$ is:
(A) —N=,
(B) —CH=,
(C) —CF=,
(D) —CCl=,
(E) —C(CF$_3$)=,
(F) —C(CN)=;
where (VII) $R_7$ is:
(A) —N=,
(B) —CH=,
where (VIII) $R_8$ is:
(A) $C_1$–$C_6$ alkyl,
(B) $C_3$–$C_5$ cycloalkyl,
(C) —CH$_2$—O—R$_{8-1}$ where $R_{8-1}$ is $C_1$–$C_3$ alkyl,
(D) —(CH$_2$)$_{n2}$—Si(CH$_3$)$_3$ where $n_2$ is 0 thru 2,
(E) —CH$_2$—CH$_2$—CF$_3$,
(F) —CH$_2$—CH$_2$—O—CH$_3$,
(G) —CH$_2$—S—R$_{8-1}$ where $R_{8-1}$ is as defined above,
(H) —CH$_2$—CH$_2$—CO—O—R$_{8-2}$ where $R_{8-2}$ is $C_1$–$C_2$ alkyl,
(I) —CH$_2$—CH$_2$—C≡N;

(J) —CH=CR$_{8-2}$R$_{8-3}$ where R$_{8-2}$ and R$_{8-3}$ are the same or different and are:
(1) —H,
(2) C$_1$–C$_2$ alkyl,
with the proviso that at least one but not more than two of R$_4$, R$_5$, R$_6$ and R$_7$ are —N=; and pharmaceutically acceptable salts thereof.

Also disclosed are the compounds of EXAMPLES 56–61, 65–68, 72–75, 79–83, 85, 89, 93, 97, 98, 102, 106, 110, 111, 116, 118, 120, 125, 127–130, 134, 135, 137, 139–142, 144–150, 155, 156, 160, 163, 164, 166–168, 172, 173, 180–182, 186, 188–190, 193, 194, 198, 203, 207–211, 218, 220, 222–234 and 236.

Also disclosed are the compounds of EXAMPLES 238–245, 249–251, 256, 259, 266, 267 and 271.

DETAILED DESCRIPTION OF TIE INVENTION

The Anti-AIDS Amines (I) includes the Anti-AIDS piperazines (II), the Anti-AIDS Aminopiperidines (III) and the Anti-AIDS Piperidines (IV), see CHART A.

The Anti-AIDS Pyridines (V) are compounds within the generic disclosures of International Publication No. WO91/09849 based on PCT patent application PCT/US90/07390 and International Publication No. WO93/01181 based on PCT application PCT/US92/05067. Both the Anti-AIDS Amines (I) and the Anti-AIDS Pyridines (V) are prepared by methods well known to those skilled in the art. The invention here are the compounds themselves not the processes to make them.

CHART A discloses the claimed Anti-AIDS Amines (I) which consists of the Anti-AIDS piperazines (II), the Anti-AIDS Aminopiperidines (III) and the Anti-AIDS Piperidines (IV). The Anti-AIDS Pyridines (V) are novel species, some of which were previously generically disclosed in International Publication No. WO91/09849 based on PCT patent application PCT/US90/07390 or International Publication No. WO93/01181 based on PCT application PCT/US92/05067.

The Anti-AIDS Amines (I) are made by means known to those skilled in the art. The invention here is the compounds themselves not the process chemistry to make them. The novel Anti-AIDS Amines (I) are produced by methods known to those skilled in the art starting with either compounds known to those skilled in the art or which can be prepared by known methods from known compounds. Since all the process chemistry is well known to those skilled in the art and all that is novel with regard to the process chemistry is the order of reactions and the particular starting materials, the terminology "well known to those skilled in the art" is applicable to each step, and is stated here that it is applicable to each step and will not be repeated each time. There are a number of different processes by which the claimed compounds can be made. Often the preferred process will depend on the particular groups or substituents present.

The Anti-AIDS Amines (I) are defined by the compounds of formulas (II), (III) and (IV). These compounds can be thought of as having four parts, (1) R$_1$ a aryl/heteroaryl moiety, (2) R$_2$ a linking group, (3) R$_3$ a cyclic amine and (4) an alkyl substituted aromatic/heteroaromatic ring.

The various (substituted) aryl/heteroaryl moieties defined by "R$_1$" are known to those skilled in the art or can be prepared by means known to those skilled in the art from known compounds. It is preferred that the aryl/heteroaryl moiety R$_1$ be 2-pyrrolyl (R$_1$-I) or 2-indolyl (R$_1$-II). When the R$_1$ group is 2-pyrrolyl (R$_1$-I) it is preferred that R$_{1-1}$ is —H, R$_{1-2}$ is —H and R$_{13}$ is —H. When the R$_1$ group is 2-indolyl (R$_1$-II) it is preferred that it be substituted in the 5-position. To prepare 5-substituted-2-indoles where the substituent is an amino or substituted amino group. it is preferred to start with a 5-nitroindole-2-carbonyl compound which has an acid at the 2-position protected. The nitro group is reduced to an amino group by known methods and the desired modification made at the 5-position and the 2-position unprotected and transformed, if needed, to a carboxylate function. It is preferred that R$_{1-5}$ and R$_{1-6}$ be methane sulfonamido (CH$_3$—SO$_2$—NH—), but only one on each molecule. When the R$_1$ group is a substituted-2-pyrrolyl (R$_1$-I) it is preferred that R$_{1-1}$, R$_{1-2}$ and R$_{1-3}$ are all —H. When the R$_1$ group is 5-substituted-2-indolyl (R$_1$-V) it is preferred that R$_{1-6}$ is methanesulfonamido or —NH—CO-piperazinyl-N-methyl. When the R$_1$ group is a substituted-7-indolyl (R$_1$-X) it is preferred that R$_{1-9}$ is —H and R$_{1-8}$ is =NH.

The linker R$_2$ is either —CO— or —CH$_2$—. The —CO— group is formed during the coupling of the R$_1$ and the R$_3$ groups. The —CH$_2$— is produced by reduction of the —CO— group by known means for example with lithium aluminum hydride. It is preferred that the R$_2$ group be —CO—.

There are five different types of R$_3$ amino groups: piperazinyl (I), piperidinyl (II), aminopiperidinyl (III), aminomethylpiperidinyl (V) and bicyclic diamino (V). Di-nitrogen substituted piperazinyl groups are very well known to those skilled in the art. See for example International Publication No. WO91/09849 based on PCT patent application PCT/US90/07390 and International Publication No. WO93/01181 based on PCT application PCT/US92/05067.

Often it is useful to form a "protected-R$_3$-[alkyl substituted aromatic/heteroaromatic ring] as part of one process.

CHART A discloses the claimed Anti-AIDS Amines (I) which consists of the Anti-AIDS piperazines (II), the Anti-AIDS Aminopiperidines (III) and the Anti-AIDS Piperidines (IV).

CHART B discloses two alternative ways of preparing the protected substituted aminopiperidines (VII) which are used in the process to prepare the Anti-AIDS aminopiperidines (III). Suitable protecting groups (X$_1$) include for example benzyl, benzyloxycarbonyl and t-butoxycarbonyl, preferred is benzyl. By one method a protected aminopiperidine (VI) is transformed to the corresponding protected aminopiperidine amide (VII) where R is an alkyl or cycloalkyl group, preferably methyl. The protected aminopiperidine amide (VII) is then reduced by known means, such as lithium aluminum hydride, to the corresponding protected substituted aminopiperidine (VIII). Alternatively, a piperidinone (IX) is reacted with an alkyl amine (X) to produce the desired protected substituted aminopiperidine (VIII). The protected substituted aminopiperidine (VIII) is used as such in the processes to produced the desired Anti-AIDS aminopiperidines (III).

CHART C discloses a process for the preparation of an R$_1$ group being a 5-nitrogen-substituted indole. The starting material, 5-nitro indoles (XI) are known and are reduced by known means such as catalytic hydrogenation with a palladium catalyst, to the corresponding 5-amino indole (XII). The 5-amino indole (XII) is then reacted with the appropriate reagent to produce the 5-(substituted)amino indole ester (XIII) which is then transformed to the corresponding 5-(substituted)amino indole acid (XIV). The 5-(substituted) amino indole acid (XIV) can then be reacted with the appropriate R$_3$-aryl/heteroaryl moiety in the presence of CDI or EDC to produce the desired Anti-AIDS amine (I). The process is virtually the same if the substituted amino group is at the $C_6$ position of the indole rather than at the $C_5$ position.

CHART D discloses a very generic process regardless of the nature of the $R_3$ group but exemplifies a particular protecting group, BOC. BOC is 1,1-dimethylethoxy carbonyl or tert-butoxycarbonyl —CO—O—C(CH$_3$)$_3$. Other suitable blocking groups include benzyl and benzyloxycarbonyl. This process combines a BOC-protected-$R_3$ (XV) with an aldehyde-substituted aryl/heteroaryl (XVI) to produce the BOC-protected-$R_3$-aryl/heteroaryl aldehyde (XVII), see EXAMPLE 2. The aldehyde functionality is then converted to an olefin by a Wittig reaction to give the BOC-protected-$R_3$-aryl/heteroaryl olefin (XVIII), see EXAMPLES 3 and 6. The protecting group is then removed by known means such as by acid and then the $R_3$-aryl/heteroaryl group is acylated to give the $R_1$—$R_2$—$R_3$-aryl/heteroaryl olefin (XIX) by known means, see EXAMPLES 4 and 7. The olefin is then reduced by known means such as by hydrogenation in the presence of palladium on carbon to give the desired Anti-AIDS amine (I), see EXAMPLES 5 and 8. Also disclosed is an alternate process once the protected-$R_3$-arylheteroaryl olefin (XVIII) is produced. In the alternative process the olefin is first reduced, then deprotected and finally acylated to give the desired Anti-AIDS amine (I).

CHART E discloses a process for producing Anti-AIDS aminopiperidines (III) which starts with a protected aminopiperidine (XX) which is coupled (see EXAMPLES 12 and 13) with an aldehyde-substituted aryl/heteroaryl (XVI) as in CHART D to form a protected aminopiperidine-aryl/heteroaryl aldehyde (XXI). The particular protecting group exemplified is benzyl (φ—CH$_2$—). Other suitable protecting groups include BOC and benzyloxycarbonyl. The aldehyde functionality is then transformed to the olefin by a Wittig reaction (see EXAMPLES 14, 16, 17, 19 and 32) to produce the corresponding protected aminopiperidine-aryl/heteroaryl olefin (XXII). The protected aminopiperidine-aryl/heteroaryl olefin (XXII) then has the protecting group removed and is acylated to form the desired Anti-AIDS aminopiperidine (III), see EXAMPLES 15, 20, 23, 30, 31 and 33 where the $R_1$ group is an indole and EXAMPLES 21, 22, 24 and 25 where the $R_1$ group is a pyrrole.

CHART F discloses a procedure similar to that of CHART E to produce Anti-AIDS aminopiperidines (III) but where the protecting group is BOC rather than benzyl. The major difference is that if the protecting group is benzyl during reduction of the olefin by hydrogenation the benzyl group is removed during reduction of the olefin. When the protecting group is BOC an additional step is required to remove the BOC group. The EXAMPLES which exemplify CHART F are 26–29.

CHART G discloses a procedure to produce the Anti-AIDS Amines (I) where the $R_8$ group contains a oxygen atom, —CH$_2$—O—$R_{8-1}$. A protected-$R_3$ (XXVII) is coupled with an ester-substituted aryl/heteroaryl (XXVIII) to produce the protected-$R_3$-aryl/heteroaryl ester (XXIX), see EXAMPLES 34 and 38. Next the protected-$R_3$-aryl/heteroaryl ester (XXIX) is transformed to the corresponding protected-$R_3$-aryl/heteroaryl alcohol (XXX) by a reduction using an agent such as lithium aluminum hydride, see EXAMPLES 35 and 39. The protected-$R_3$-aryl/heteroaryl alcohol (XXX) is then transformed to the corresponding protected-$R_3$-aryl/heteroaryl ether (XXXI), see EXAMPLES 36 and 40. Lastly, the $X_1$ group is replaced by the $R_1$ group and in the process the $R_2$ group is formed to produce the Anti-AIDS amines (I) where the $R_8$ group is —CH$_2$—O—$R_{8-1}$, see EXAMPLES 37 and 41.

CHART H discloses a process to produce Anti-AIDS amines (I) where $R_8$ is $C_1$–$C_6$ alkyl. The process begins with the coupling of a protected-$R_3$ (XXVII) with a nitrile-substituted aryl/heteroaryl (XXXII) to produce the protected-$R_3$-substituted aryl/heteroaryl nitrile (XXXIII), see EXAMPLES 42, 46 and 50. The protected-$R_3$-substituted aryl/heteroaryl nitrile (XXXIII) is then transformed to the corresponding protected-$R_3$-substituted aryl/heteroaryl ketone (XXXIV), see EXAMPLES 43, 47 and 51, followed by reduction of the ketone the corresponding alkyl group forming the protected-$R_3$-substituted aryl/heteroaryl alkyl (XXXV), see EXAMPLES 44, 48 and 52. The protected-$R_3$-substituted aryl/heteroaryl alkyl (XXXV) is then deprotected and acylated to form the desired Anti-AIDS amine (I), see EXAMPLES 45, 49 and 53.

It is preferred that $R_1$ is the pyrrole ($R_1$-I) or the indole ($R_1$-II). With the pyrrole ($R_1$-I) it is preferred that $R_{1-1}$, $R_{1-2}$ and $R_{1-3}$ are —H. With the indole ($R_1$-II) it is preferred that $R_{1-4}$ and $R_{1-5}$ are —H and $R_{1-6}$ is —H, —NH—SO$_2$—CH$_3$, —O—$R_{1-5A}$ and —F. It is preferred that $R_2$ is —CO—. It is preferred that $R_3$ is the piperazinyl moiety (I)

and the aminopiperidinyl moiety (III)

Within the piperazinyl ($R_3$-I) group it is preferred that $n_1$ is 1. Within the aminopiperidinyl ($R_3$-III) group it is preferred that $R_{3-1}$ is $C_1$–$C_3$ alkyl.

The only place in the process to produce the compounds of the present invention isomers are involved is with the olefins (XVIII, XIX, XXII and XXV). They exist as geometric isomers (E and Z). Upon reduction, both E and Z isomers produce the same saturated compound. Hence, isomers do not have any real effect on the processes to produced the compounds of the invention.

The Anti-AIDS Amines (I) are amines and as such can form acid addition salts depending on the strength of the particular basic substituent(s) when reacted with acids of sufficient strength. Because of the need for a rather strong acid, the pharmaceutically acceptable salts include salts are generally those of the inorganic acids rather than the organic acids. The pharmaceutically acceptable salts are preferred over the corresponding free amines since they produce compounds which are more water soluble and more crystalline. For all the Anti-AIDS Amines (I), the preferred pharmaceutically acceptable salts include salts of the following acids: methanesulfonic, hydrochloric, hydrobromic, sulfuric, phosphoric and nitric, more preferred is methanesulfonic. When there is a more basic amine substituent such as CH$_3$-piperazinyl-SO$_2$—NH—CO—NH—, then the following pharmaceutically acceptable salts are also useful: benzoic, citric, tartaric, fumaric, maleic, CH$_3$—(CH$_2$)$_n$—COOH where n is 0 thru 4, HOOC—(CH$_2$)n-COOH where n is as defined above.

The free amine Anti-AIDS Amines (I) of the present invention in addition to forming salts also form hydrates/solvates of the free amines and pharmaceutically acceptable salts. These hydrates and solvates are deemed equivalent to the nonhydrated or solvated forms because they are bound with and carry the same free base or salt form and therefore have the same pharmacological effect.

The Anti-AIDS Amines (I) are useful in the treatment of such diseases as AIDS and those individuals who are HIV positive but do not as of yet have AIDS.

Patients to be treated would include those individuals (1) infected with one or more than one strain of a human retrovirus as determined by the presence of either measurable viral antibody or antigen in the serum and (2) having either a symptomatic AIDS defining infection such as (a) disseminated histoplasmosis. (b) isopsoriasis, (c) bronchial and pulmonary candidiasis including pneumocystic pneumonia (d) non-Hodgkin's lymphoma or (e) Kaposi's sarcoma and being less than sixty years old; or having an absolute CD4 lymphocyte count of less than $500/m^3$ in the peripheral blood.

The Anti-AIDS Amines (I) can be given orally. Suitable dosage forms include tablets, capsules, suspensions, solutions and elixirs. An effective amount is from about 0.1 to about 500 mg/kg/day. A typical unit dose for a 70 kg human would be from about 10 mg to about 2000 mg, preferably about 100 mg to about 1000 mg taken one to six times per day.

The exact dosage and frequency of administration depends of the particular Anti-AIDS Amines (I) used, the particular condition being treated, the severity of the condition being treated, the age, weight, general physical condition of the particular patient, other medication the individual may be taking as is well known to those skilled in the art and can be more accurately determined by measuring the blood level or concentration of the Anti-AIDS piperazines (II), the Anti-AIDS Aminopiperidines (III) and/or the Anti-AIDS Piperidines (IV) in the patient's blood and/or the patient's response to the particular condition being treated.

The Anti-AIDS Amines (I) of this invention can be used in conjunction with other antiviral agents such as AZT, ddC, ddI, d4T and with non-nucleoside anti-AIDS agents such as those disclosed in International Publication No. WO91/09849, published Jul. 11, 1991 and International Publication No. WO93/01181, published Jan. 21, 1993 and with protease inhibitors.

The exact dosage and frequency of administration depends on the particular Anti-AIDS Amine (I) used, the particular condition being treated, the severity of the condition being treated, the age, weight, general physical condition of the particular patient, other medication the individual may be taking as is well known to those skilled in the art and can be more accurately determined by measuring the blood level or concentration of the Anti-AIDS Amine (I) in the patient's blood and/or the patient's response to the particular condition being treated.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)$($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—$C*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —$C(\alpha$-$R_{i-j})(\beta$-$R_{i-k})$—. For example, when the bivalent variable $R_6$, —$C(=R_6)$— is defined to consist of two monovalent variable substituents, the two monovalent variable substituents are $\alpha$-$R_{6-1}$:$\beta R_{6-2}$, . . . $\alpha$-$R_{6-9}$:$\beta$-$R_{6-10}$, etc, giving —$C(\alpha$-$R_{6-1})(\beta$-$R_{6-2})$—, . . . —$C(\alpha$-$R_{6-9})(\beta$-$R_{6-10})$—, etc.

Likewise, for the bivalent variable $R_{11}$, $-C(=R_{11})-$, two monovalent variable substituents are $\alpha\text{-}R_{11\text{-}1}$:$\beta\text{-}R_{11\text{-}2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form $-CH_2-CH_2-O-CO-$ . . . " means a lactone in which the carbonyl is bonded to $C_2$. However, when designated " . . . $R_j$ and $R_i$ are taken together to form $-CO-O-CH_2-CH_2-$ the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "4" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3-(CH_2)_n-O-CO-$ where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$) alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. Definitions

All temperatures are in degrees Centigrade.

TLC refers to thin-layer chromatography.

THF refers to tetrahydrofuran.

DMF refers to dimethylformamide.

Saline refers to an aqueous saturated sodium chloride solution.

Chromatography (column and flash chromatography) refers to purification/separation of compounds expressed as (support; eluent). It is understood that the appropriate fractions are pooled and concentrated to give the desired compound(s).

IR refers to infrared spectroscopy.

CMR refers to C-13 magnetic resonance spectroscopy, chemical shifts are reported in ppm ($\delta$) downfield from TMS.

NMR refers to nuclear (proton) magnetic resonance spectroscopy, chemical shifts are reported in ppm ($\delta$) downfield from tetramethylsilane.

—$\phi$ refers to phenyl ($C_6H_5$).

MS refers to mass spectrometry expressed as m/e or mass/charge unit. $[M+H]^+$ refers to the positive ion of a parent plus a hydrogen atom. EI refers to electron impact. CI refers to chemical ionization. FAB refers to fast atom bombardment.

HRMS refers to high resolution MS.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include mesylate, chloride, sulfate, phosphate, nitrate, citrate, $CH_3-(CH_2)_{n1}-COO^{-1}$ where $n_1$ is 0 thru 4, $^{-1}OOC-(CH_2)_{n1}-COO^{-1}$ where n is as defined above, $^{-1}OOC-CH=CH-COO^{-1}$, $\phi-COO^{-1}$, depending on the particular Anti-AIDS Amine (I).

When solvent pairs are used, the ratios of solvents used are volume/volume (v/v).

Pearlman's catalyst refers to palladium hydroxide on carbon.

Hunig's base refers to diisopropyl ethyl amine.

BOC refers to 1,1-dimethylethoxy carbonyl or tert-butoxycarbonyl $-CO-O-C(CH_3)_3$.

CDI refers to 1,1'-carbonyldiimidazole.

EDC refers to 1-(3-dimethylaminopropyl)-3-ethylcarbodiimide hydrochloride.

Anti-AIDS Amines (I) refers to and includes the Anti-AIDS piperazines (II), the Anti-AIDS Aminopiperidines (III) and the Anti-AIDS Piperidines (IV).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

Conversion of Ethyl 5-nitroindole-2-carboxylate To Ethyl 5-aminoindole-2-carboxylate A 30 gallon autoclave was charged with ethyl 5-nitroindolyl-2-carboxylate (14.6 kg, 62.3 moles), THF (61.5 kg) and 5% palladium on carbon (1.8 kg). The mixture is hydrogenated at 20°–25° and 60 psi hydrogen for 15 hr at which time the reaction is complete as measured by TLC (ethyl acetate/heptane, (50/50)). The catalyst is removed by filtration and rinsed with THF (30 kg). The resulting product, the title compound in solution is used directly in the next step.

Preparation 2

Conversion of Ethyl 5-aminoindole-2-carboxylate To Ethyl 5-methanesulfonamidoindole-2-carboxylate The solution of ethyl 5-aminoindole-2-carboxylate (PREPARATION 1, 12.7 kg, 62.3 moles) in THF is diluted with water (30 l), then treated with methanesulfonyl chloride (5.84 kg, 75.45 moles) which is added over 45 min while maintaining the temperature below 30°. Aqueous sodium bicarbonate (11.0 kg, 131 moles) in water (120 l) is added simultaneously to maintain the pH between 4.5 and 5.0. At the end of the addition GC analysis indicated complete reaction (less than 2% starting material); the remainder of the sodium bicarbonate solution is added to adjust the pH to 7.2. The organic phase is separated, the aqueous phase is diluted with saline and extracted with THF. The combined organic phases are analyzed by GC and HPLC, then used directly in the next step.

Preparation 3

Conversion of Ethyl 5-methanesulfonamidoindole-2-carboxylate

To 5-Methanesulfonamidoindole-2-carboxylic acid

A mixture of the THF solution of ethyl 5-methanesulfonamidoindole-2-carboxylate (PREPARATION 2, 15.85 kg, 62.3 moles), sodium hydroxide (50%, 15.0 kg, 186.9 moles) and water is stirred 12 hrs at 30° at which time HPLC analysis indicates complete reaction (less than 2% starting material). The THF is removed by vacuum distillation at 40°, the resulting solution is diluted with ethyl acetate and water and the pH of the aqueous phase adjusted to 7.3 with hydrochloric acid (12M, 3.1 kg). The phases are separated and the pH of the aqueous layer is adjusted to 1.3 with hydrochloric acid (12M, 18.44 kg). The precipitated solids are collected on a filter, washed with water and dried with 20° nitrogen for 16 hrs to give the title compound.

Preparation 4

1-Benzyl-4-[N-ethyl-N-(3-amino-2-pyridinyl)amino]piperidine

Following the general procedure of EXAMPLE 204, Part B), and making non-critical variations but substituting 1-benzyl-4-[N-ethyl-N-(3-nitro-2-pyridinyl)amino]piperidine (EXAMPLE 204, Part A) for 1-benzyl-4-[N-propyl-N-(3-nitro-2-pyridinyl)amino]piperidine, the title compound is obtained, NMR (CDCl$_3$) 7.84, 7.31, 7.26, 6.96, 6.85, 3.97, 3.50, 3.18, 3.07, 2.89, 2.02, 1.75 and 0.89δ.

Example 1

2-Bromo-3-formylpyridine (XVI)

Lithium diisopropylamide (1.0M in THF, 12.6 mmol) is added to a stirring solution of 2-bromopyridine (2.0 g, 12.6 mmol) in THF (10 ml) at −78° under nitrogen. The resulting mixture is stirred at −78° for two hours followed by addition of dimethylformamide (12.6 mmol) in THF (5 ml) at −78°. The mixture is allowed to warm to 20°–25°, poured into a saturated aqueous solution of ammonium chloride (100 ml), and extracted with ethyl acetate (3×50 ml). The organic phases are combined, dried over sodium sulfate and solvent removed under reduced pressure. The resulting residue is purified via flash chromatography (silica gel; hexane/ethyl acetate (4/1)) to give the title compound, mp 74°–76°; NMR (CDCl$_3$) 7.45, 8.19, 8.59, 10.35δ; MS (EI, m/e) 185 (M+).

Example 2

1-(tert-Butoxycarbonyl)-4-(3-formyl-2-pyridinyl)piperazine (XVII)

To a stirring solution of 2-bromo-3-formylpyridine (XVI, EXAMPLE 1, 2.0 g, 10.80 mmol), and diisopropylethylamine (1.39 g, 10.80 mmol) in THF is added 1-(tert-butoxycarbonyl)-piperazine (Aldrich, 2.01 g, 10.80 mmol). The mixture is heated in a sealed tube at 100° for 16 hr, cooled to 20°–25° and poured into water (100 ml). The aqueous layer is extracted with ethyl acetate (100 ml), the organic layer separated, dried over sodium sulfate and solvent evaporated to dryness. The residue is purified via flash column chromatography (silica gel; hexane/ethyl acetate (4/1)) to give the title compound, mp 88°–89°; NMR (CDCl$_3$) 1.48, 3.42, 3.60, 6.96, 8.01, 8.39 and 10.03δ; MS (EI, m/e) 291 (M+).

Example 3

1-(tert-Butoxycarbonyl)-4-[3-(1'-propenyl)-2-pyridinyl]piperazine (XVIII)

To a stirring suspension of (ethyl)triphenylphosphonium bromide (3.05 g, 8.23 mmol) in THF (150 ml) at 20°–25° is added n-butyl lithium (1.6M in hexanes, 5.14 ml, 8.23 mmol) under nitrogen. Additional n-butyl lithium added until the mixture became homogeneous (about 6 ml). The resulting mixture is stirred for 15 min followed by the addition of 1-(tert-butoxycarbonyl)-4-(3-formyl-2-pyridinyl)piperazine (EXAMPLE 2, 2.0 g, 6.86 mmol) in THF (15 ml) via nitrogen pressure. The resulting mixture is stirred for 2 hr, quenched with water (100 ml) and extracted with ethyl acetate (100 ml). The organic layer is separated, dried over sodium sulfate, and the solvent evaporated to dryness. The residue is purified by flash column chromatography (silica gel; hexane/ethyl acetate (4/1)) to give the title compound, NMR (CDCl$_3$) 1.48, 1.89, 3.19, 3.53, 5.86, 6.21 6.32, 6.45, 6.89, 7.54 and 8.16δ; MS (EI, m/e) 303 (M+).

Example 4

1-(Indolyl-2-carbonyl)-4-[3-(1'-propenyl-2-pyridinyl]piperazine (XIX)

1-(tert-Butoxycarbonyl)-4-[3-(1'-propenyl)-2-pyridinyl]piperazine (EXAMPLE 3, 1.40 g, 4.6 mmol) is dissolved in hydrochloric acid (1.4N)/acetic acid (25 ml) and stirred at 20°–25°. After 1 hr the mixture is triturated with ether and the solid collected by filtration. The solid is partitioned between ethyl acetate/saturated aqueous sodium bicarbonate (50 ml each), the phases shaken and the organics separated, the organic phase is dried over sodium sulfate, and solvent removed under reduced pressure to give a residue. This material is dried of residual solvent under high reduced pressure for 1 hr, then taken up in methylene chloride (10 ml) and THF (5 ml). Indolyl-2-carboxylic acid (0.17 g, 1.05 mmol) and EDC 0.20 g, 1.05 mmol) are added and the mixture stirred for 16 hr. The mixture is poured into water (100 ml) and extracted with methylene chloride (2×50 ml). The organic phases are combined, dried over sodium sulfate, and the solvent removed by reduced pressure. The residue is purified by flash column chromatography (silica gel; hexane/ethyl acetate (2/1)) to give the title compound, NMR (CDCl$_3$) 1.92, 3.36, 4.12, 5.89, 6.27, 6.50, 6.82, 6.93, 7.13, 7.25, 7.43, 7.53, 7.63, 8.18 and 9.69δ; MS (EI, m/e) 346 (M+).

Example 5

1-(Indolyl-2-carbonyl)-4-[3-(propyl)-2-pyridinyl]piperazine (I)

To a solution of 1-(indolyl-2-carbonyl)-4-[3-(1'-propenyl)-2-pyridinyl]piperazine (EXAMPLE 4, 0.12 g, 0.34 mmol) in methanol (25 ml) is added palladium on carbon (10%, 0.025 g) and the resulting mixture is hydrogenated at 40 psi for 3 hr. The mixture is filtered through diatomaceous earth and the solvent evaporated to dryness. The residue is purified via flash column chromatography (silica gel; hexane/ethyl acetate (4/1)) to give the title compound, mp 141°–143°; NMR (CDCl$_3$) 1.01, 1.71, 2.64, 3.24, 4.09, 6.84, 7.00, 7.14, 7.29, 7.43, 7.52, 7.65, 8.19 and 9.19δ; MS (EI, m/e) 348 (M+).

Example 6

1-(tert-Butoxycarbonyl)-4-[3-(2'-methyl-1'-propenyl)-2-pyridinyl]-piperazine (XVIII)

To a stirring suspension of (isopropyl)triphenylphosphonium iodide (1.11 g, 2.57 mmol) in dry THF (15 ml) under nitrogen at 20°–25° is added n-butyl lithium (1.6M in hexane, 1.6 ml, 2.57 mmol). The resulting mixture is stirred at 20°–25° for 30 min followed by dropwise addition of 1-(tert-butoxycarbonyl)-4-(3-formyl-2-pyridinyl)piperazine (EXAMPLE 2, 0.75 g) in THF (8 ml) via syringe. The mixture is stirred for 3 hr, quenched with ammonium chloride (10 ml) and poured into water (100 ml). The aqueous layer is extracted with ethyl acetate (3×75 ml), the organics separated, dried over sodium sulfate, and the solvent removed by reduced pressure. The residue is purified via flash column chromatography (silica gel; hexane/ethyl acetate (4/1)) to give the title compound, NMR (CDCl$_3$) 1.48, 1.82, 1.92, 3.19, 5.07, 6.86, 7.40, 8.13δ; MS (EI, m/e) 317 (M+).

Example 7

1-(Indolyl-2-carbonyl)-4-[3-(2'-methyl-1'-propenyl)-2-pyridinyl]piperazine (XIX)

To a stirring solution of 1-(tert-butoxycarbonyl)-4-[3-(2'-methyl-1'-propenyl)-2-pyridinyl]piperazine (EXAMPLE 6, 0.5 g, 1.57 mmol) in acetic acid (3 ml) is added hydrochloric acid (1.4N) in acetic acid (8 ml). After 1.5 hr the solvent is evaporated to dryness and partitioned between saturated aqueous sodium bicarbonate (50 ml) and extracted with ethyl acetate (3×75 ml). The organic phases are combined, dried over sodium sulfate and solvent evaporated to dryness to give the free base. This material is dissolved in THF/methylene chloride (1/1, 20 ml) and cooled to 0°. To this mixture is added EDC (0.62 g, 3.2 mmol) followed by indolyl-2-carboxylic acid (0.52 g, 3.2 mmol). The mixture is allowed to slowly warm to 20°–25° and stirred for 16 hr. The solvent is removed by reduced pressure and partitioned between saturated aqueous sodium bicarbonate and ethyl acetate (100 ml each). The phases are shaken, the organic layer separated, dried over sodium sulfate, and solvent evaporated to dryness. Recrystallization from ethyl acetate/hexane resulted in the title compound, mp 173°–175°; NMR (CDCl$_3$) 1.85, 1.96, 3.37, 4.05, 6.13, 6.82, 6.90, 7.13, 7.28, 7.43, 8.16 and 9.55δ; MS (EI, m/e) 360 (M+).

Example 8

1-(Indolyl-2-carbonyl)-4-[3-(2'-methylpropyl)-2-pyridinyl]piperazine (I)

To a solution of 1-(indolyl-2-carbonyl)-4-[3-(2'-methyl-1'-propenyl)-2-pyridinyl]piperazine (EXAMPLE 7, 0.21 g, 0.58 mmol) in methanol (15 ml) is added palladium on carbon (10%, 0.05 g) and the mixture hydrogenated at 40 psi for 2 hr. The solvent is filtered through diatomaceous earth and concentrated to dryness. The residue is purified via flash column chromatography (silica gel; hexane/ethyl acetate (4/1)) to give the title compound, mp 174°–175°; NMR (CDCl$_3$) 0.92, 2.03, 2.54, 3.20, 4.08, 6.84, 6.97, 7.14, 7.29, 7.45, 7.65, 8.20 and 9.25δ; MS (EI, m/e) 362 (M+).

Example 9

1-Benzyl-4-N-methylaminopiperidine (XX)

1-Benzyl-4-aminopiperidine (14.36 g, 75.46 mmol) is dissolved in ethyl formate (75 ml) and refluxed under nitrogen overnight. The reaction is concentrated by reduced pressure, the concentrate is chromatographed (silica gel, 8×20 cm column; ethyl acetate/methanol (9/1)). The formulated derivative is taken up in THF (150 ml) and lithium aluminum hydride (1M, 75 ml) is added dropwise at 0° under nitrogen. The reaction is warmed to 20°–25° and refluxed for 2 days. The reaction is cooled to 0° and quenched with water (4.5 ml), sodium hydroxide (15%, 4.5 ml) and water (13.5 ml). The precipitate is filtered off and the filtrate is concentrated by reduced pressure. The concentrate is partitioned between chloroform and sodium hydroxide (1N). The organic phase is washed with saline and dried (sodium sulfate). Removal of the solvent gives a concentrate which is used without further purification, NMR (300 MHz, CDCl$_3$) 1.31–1.43, 1.75–1.85, 1.90–1.97, 2.37, 2.37–2.45, 2.70–2.80, 3.40, 3.70 and 7.12–7.21δ.

Example 10

1-Benzyl-4-N-acetylaminopiperidine (XX)

1-Benzyl-4-aminopiperidine (20 g, 0.105 mol) is dissolved in benzene and a solution of acetic anhydride (16.1 g, 0.158 mol) in benzene is added dropwise. The reaction is refluxed under nitrogen for 2 hr and the solvent is removed by reduced pressure to give a solid which is crystallized from ether to give the title compound, mp 140°–141°.

Example 11

1-Benzyl-4-N-ethylaminopiperidine (XX)

1-Benzyl-4-N-acetylaminopiperidine (EXAMPLE 10, 21 g, 90.4 mmol) is dissolved in dry THF (250 ml) and cooled to 0°. Lithium aluminum hydride (1M, 45 ml) is added dropwise under nitrogen and the reaction is refluxed for 2 hr. The reaction is cooled to 0° and quenched with water (2.7 ml), sodium hydroxide (15%, 2.7 ml), and water (8.1 ml). The precipitate is filtered off and the filtrate is concentrated by reduced pressure. The concentrate obtained is partitioned between chloroform and water. The organic layer is washed with saline and dried (sodium sulfate). Removal of solvent by reduced pressure gives a residue which is chromatographed (silica gel, chloroform/methanol (9/1, 1% triethylamine)) to give the title compound, NMR (300 MHz, CDCl$_3$) 1.10, 1.30–1.44, 1.59, 1.82–1.87, 1.96–2.03, 2.40–2.60, 2.65, 2.82–2.86, 3.48 and 7.22–7.30δ.

Example 12

1-Benzyl-4-[N-ethyl-N-(3-(formyl)-2-pyridinyl)amino]piperidine (XXI)

2-Bromo-3-formylpyridine (EXAMPLE 1, 0.98 g, 5.3 mmol), 1-benzyl-4-N-ethylaminopiperidine (EXAMPLE 11, 1.15 g, 5.3 mmol) and diisopropylethylamine (0.92 ml, 5.3 mmol) are heated in a sealed tube at 100° for 2 days. The reaction is cooled and partitioned between water and chloroform. The organic layer is washed with saline and dried (sodium sulfate). The solvent is removed by reduced pressure and the residue is chromatographed (silica gel, 2×40 cm column; ethyl acetate/hexane (1/3 to 1/1)) to give the title compound, NMR (300 MHz, CDCl$_3$) 0.90, 1.55–1.64, 1.68–1.83, 2.69–2.75, 3.15–3.25, 3.29, 3.33, 6.68, 7.03–7.16, 7.81 and 8.20δ.

Example 13

1-Benzyl-4-[N-methyl-N-(3-(formyl)-2-pyridinyl)amino]piperidine (XXI)

Following the general procedure of EXAMPLE 12 and making non-critical variations but starting with 2-bromo-3-formylpyridine (XVI, EXAMPLE 1, 5.0 g, 26.9 mmol), 1-benzyl-4-N-methylaminopiperidine (XX, EXAMPLE 9, 5.49 g, 26.9 mmol) and diisopropylethylamine (4.7 ml, 26.9 mmol) the title compound is obtained, NMR (300 MHz, CDCl$_3$) 1.80–1.86, 1.94–2.07, 2.09–2.18, 2.99, 3.00–3.05, 3.57, 3.99–4.09, 6.81, 7.27–7.40, 7.99 and 8.34δ.

Example 14

1-Benzyl-4-[N-methyl-N-(3-(1-propenyl)-2-pyridinyl)amino]piperidine (XXII)

To a stirring suspension of (ethyl)triphenylphosphonium bromide (1.75 g, 4.72 mmol) in dry THF (150 ml) at 20°–25° under nitrogen is added n-butyl lithium (1.6M in hexane, 2.95 ml, 4.72 mmol). The resulting mixture is stirred for 10 min followed by addition of 1-benzyl-4-[N-methyl-N-(3-formyl-2-pyridinyl)amino]piperidine (XXI, EXAMPLE 13, 1.40 g, 4.72 mmol) in THF (10 ml) under nitrogen. The mixture is stirred at 20°–25° for 1 hr and quenched with saturated aqueous ammonium chloride (50 ml). Water is added (100 ml) and the aqueous is extracted with ethyl acetate (3×75 ml). The organic phases are combined, dried over sodium sulfate and the solvent evaporated to dryness. The residue is purified via flash column chromatography (silica gel; hexane/ethyl acetate (6/1→1/1)) to give the title compound, NMR (CDCl$_3$) 1.64, 1.81–1.93, 2.80, 2.91, 3.46, 5.77, 6.13, 6.26, 6.40, 6.78, 7.20–7.56 and 8.11δ; MS (EI, m/e) 321 (M+).

Example 15

1-[5-(Methanesulfonamido)indolyl-2-carbonyl]-4-[N-methyl-N-(3-propyl-2-pyridinyl)amino]piperidine (III)

To a solution of 1-benzyl-4-[N-methyl-N-(3-(1-propenyl)-2-pyridinyl)amino]piperidine (XXII, EXAMPLE 14, 0.35 g, 1.0 mmol) in methanol (100 ml) is added Pearlman's catalyst (10%) and the mixture hydrogenated at 40 psi for 16 hr. The mixture is filtered and the solvent removed under reduced pressure to give crude amine intermediate. The residue is taken up in methylene chloride/THF/DMF (10 ml/5 ml/2 ml) and the mixture cooled to 0°. 5-(Methanesulfonamido)indolyl-2-carboxylic acid (XIV, 0.128 g, 0.50 mmol) is added followed by EDC (0.096 g, 0.50 mmol). The mixture allowed to warm to 20°–25° and react for 16 hr. The mixture is then poured into water (100 ml) and extracted with ethyl acetate (100 ml). The organic phase is separated, dried over sodium sulfate and the solvent removed by reduced pressure. The residue is purified via flash column chromatography (silica gel; hexane/ethyl acetate (1/1)) to give the title compound, HRMS calcd for C$_{24}$H$_{31}$N$_5$O$_3$S=469.2147, found=469.2138.

Example 16

1-Benzyl-4-[N-methyl-N-(3-(2-methyl-1-propenyl)-2-pyridinyl)amino]piperidine (XXII)

n-Butyl lithium (1.6M, 8.1 ml, 12.93 mmol) is added to a suspension of isopropyltriphenylphosphonium iodide (5.6 g, 12.93 mmol) in dry THF. The ylide is allowed to generate for 45 min at 20°–25° under nitrogen before a solution of 1-benzyl-4-[N-methyl-N-(3-(formyl)-2-pyridinyl)amino]piperidine (XXI, EXAMPLE 13, 2.0 g, 6.5 mmol) in dry THF is added. The reaction is stirred an additional 30 min before being quenched with water and extracted with chloroform. The extracts are washed with saline and dried (sodium sulfate). Removal of the solvent gives a residue which is chromatographed (silica gel, 4×35 cm column; ethyl acetate/hexane (1/3→1/1) to give the title compound, NMR (300 MHz, CDCl$_3$) 1.55–1.65, 1.74, 1.79–1.85, 1.85, 2.75, 2.87–2.90, 3.40–3.48, 3.42, 5.97, 6.69, 7.16–7.28 and 8.04δ.

Example 17

1-Benzyl-4-[N-ethyl-N-(3-(2-methyl-1-propenyl)-2-pyridinyl)amino]piperidine (XXII)

Following the general procedure of EXAMPLE 16 and making non-critical variations but starting with n-butyl lithium (1.6M, 4.3 ml, 6.8 mmol), isopropyltriphenylphosphonium iodide (2.9 g, 6.8 mmol), and 1-benzyl-4-[N-ethyl-N-(3-(formyl)-2-pyridinyl)amino]piperidine (XXI, EXAMPLE 12, 1.1 g, 3.4 mmol), the title compound is obtained, NMR (300 MHz, CDCl$_3$) 1.08, 1.71–1.80, 1.90, 1.90–2.00, 2.01, 2.98–3.03, 3.30–3.45, 3.43, 3.57, 6.18, 6.89, 7.32–7.45, 7.46 and 8.24δ.

Example 18

Example 19

1-Benzyl-4-(N-ethyl-N-(3-(1-propenyl)-2-pyridinyl)amino)piperidine (XXII)

Following the general procedure of EXAMPLE 14 and making non-critical variations but starting with n-butyl lithium (1.6M, 1.16 ml, 1.86 mmol), ethyltriphenylphosphonium bromide (0.69 g, 1.86 mmol), and 1-benzyl-4-[N-ethyl-N-(3-(formyl)-2-pyridinyl)amino]piperidine (XXI, EXAMPLE 12, 0.40 g, 1.24 mmol), the title compound is obtained.

Example 20

1-[5-(Methanesulfonamido)indolyl-2-carbonyl]-4-[N-ethyl-N-(3-(2-methylpropyl)-2-pyridinyl)amino]piperidine (I)

1-Benzyl-4-(N-ethyl-N-(3-(2-methyl-1-propenyl)-2-pyridinyl)amino)piperidine (XXII, EXAMPLE 17, 0.67 g, 1.92 mmol) is hydrogenated at 40 psi in methanol for 24 hr using Pearlman's catalyst (0.1 g). The reaction is filtered and concentrated by reduced pressure. In a separate flask CDI (0.33 g, 2.06 mmol) and 5-(methanesulfonamido)indol-2-carboxylic acid (0.53 g, 2.06 mmol) are stirred in dry THF at 20°–25° for 1 hr. This solution is then cooled to 0° and a mixture of the above concentrate (0.27 g, 1.03 mmol) in dry THF is added and the reaction is stirred at 20°–25° overnight. The reaction is partitioned between sodium hydroxide (0.5N) and chloroform. The organic phase is washed with saline and dried (sodium sulfate). The solvent is removed by reduced pressure and the residue is chromatographed (silica gel, 2×40 cm column; ethyl acetate/hexane (1/1 to 1/0), HRMS Calcd. for $C_{26}H_{35}N_5O_3S$=497.2460, found=497.2472.

Example 21

1-[Pyrrole-2-carbonyl]-4-(N-ethyl-N-(3-(2-methylpropyl)-2-pyridinyl)amino)piperidine (I)

Following the general procedure of EXAMPLE 20 and making non-critical variations but starting with 1-benzyl-4-[N-ethyl-N-(3-(2-methyl-1-propenyl)-2-pyridinyl)amino]piperidine (XXII, EXAMPLE 17, 0.67 g, 1.92 mmol), Pearlman's catalyst (0.1 g), CDI (0.31 g, 1.92 mmol) and pyrrole-2-carboxylic acid (0.213 g, 1.92 mmol), the title compound is obtained, HRMS Calcd. for $C_{21}H_{30}N_4O$=354.2419, found=354.2413.

Example 22

1-[Pyrrole-2-carbonyl]-4-[N-ethyl-N-(3-(propyl)-2-pyridinyl)amino]piperidine (I)

Following the general procedure of EXAMPLE 20 and making non-critical variations but starting with 1-benzyl-4-[N-ethyl-N-(3-(1-propenyl)-2-pyridinyl)amino]piperidine (XXII, EXAMPLE 19, 0.40 g, 1.20 mmol), Pearlman's catalyst (0.1 g), CDI (0.39 g, 2.4 mmol), and pyrrole-2-carboxylic acid (0.27 g, 2.4 mmol), the title compound is obtained, mp 115°–116°.

Example 23

1-[5-(Methanesulfonamido)indolyl-2-carbonyl]-4-[N-ethyl-N-(3-propyl-2-pyridinyl)amino]piperidine (I)

Following the general procedure of EXAMPLE 20 and making non-critical variations but starting with 1-benzyl-4-[N-ethyl-N-(3-(1-propenyl)-2-pyridinyl)amino]piperidine (XII, EXAMPLE 19, 0.60 g, 1.8 mmol), Pearlman's catalyst (0.1 g), CDI (0.33 g, 2.04 mmol) and 5-(methanesulfonamido)indolyl-2-carboxylic acid (0.52 g, 2.04 mmol), the title compound is obtained, HRMS Calcd. for $C_{25}H_{33}N_5O_3S$=483.2304, found=483.2303.

Example 24

1-[Pyrrole-2-carbonyl]-4-[N-methyl-N-(3-(propyl)-2-pyridinyl)amino]piperidine (I)

Following the general procedure of EXAMPLE 20 and making non-critical variations but starting with 1-benzyl-4-(N-methyl-N-(3-(1-propenyl)-2-pyridinyl)amino)piperidine (XXII, EXAMPLE 14, 0.46 g, mmol), Pearlman's catalyst (0.1 g), CDI (0.46 g, 2.85 mmol) and pyrrole-2-carboxylic acid (0.32 g, 2.85 mmol), the title compound is obtained, mp 88°–90°.

Example 25

1-[Pyrrole-2-carbonyl]-4-[N-methyl-N-(3-(2-methylpropyl)-2-pyridinyl)amino]piperidine (I)

Following the general procedure of EXAMPLE 20 and making non-critical variations but starting with 1-benzyl-4-[N-methyl-N-(3-(2-methyl-1-propenyl)-2-pyridinyl)amino]piperidine (XXII, EXAMPLE 16, 0.27 g, 0.80 mmol), Pearlman's catalyst (0.1 g), CDI (0.26 g, 1.6 mmol) and pyrrole-2-carboxylic acid (0.18 g, 1.6 mmol), the title compound is obtained, HRMS Calcd. for $C_{20}H_{28}N_4O$=340.2263, found=340.2277.

Example 26

1-tert-Butoxycarbonyl-4-[N-methyl-N-(3-(formyl)-2-pyridinyl)amino]piperidine (XXIV)

Following the general procedure of EXAMPLE 12 and making non-critical variations but starting with 2-bromo-3-formylpyridine (XVI, EXAMPLE 1, 2.67 g, 14.4 mmol), 1-tert-butoxycarbonyl-4-methylaminopiperidine (XIII, 2.8 g, 13.1 mmol), and diisopropylethylamine (2.3 ml), the title compound is obtained, mp 90°–91°.

Example 27

1-tert-Butoxycarbonyl-4-[N-methyl-N-(3-(2-methyl-1-propenyl)-2-pyridinyl)amino]piperidine (XXV)

Following the general procedure of EXAMPLE 16 and making non-critical variations but starting with n-butyl lithium (1.6M, 3.9 ml, 6.26 mmol), isopropyltriphenylphosphonium iodide (2.71 g, 6.26 mmol), and 1-tert-butoxycarbonyl-4-[N-methyl-N-(3-(formyl)-2-pyridinyl)amino]piperidine (XXIV, EXAMPLE 26) (1.0 g, 3.13 mmol), the title compound is obtained, NMR (300 MHz, CDCl$_3$) 1.30, 1.50–1.59, 1.64, 1.75, 2.42–2.50, 2.61, 3.40–3.50, 3.95–4.06, 5.88, 6.62, 7.18 and 7.95δ.

Example 28

1-tert-Butoxycarbonyl-4-[N-methyl-N-(3-(2-methylpropyl)-2-pyridinyl)amino]piperidine (XXVI)

1-tert-Butoxycarbonyl-4-[N-methyl-N-(3-(2-methyl-1-propenyl)-2-pyridinyl]amino]-piperidine (XXV, EXAMPLE 27, 1.07 g, 3.1 mmol) is hydrogenated at 20 psi over night using palladium on carbon (10%, 0.1 g) as catalyst. The reaction is filtered, the solvent evaporated and the concentrate is used without further purification, NMR (300 MHz, CDCl$_3$) 0.66, 1.25, 1.34–1.42, 1.50–1.56, 1.72–1.81, 2.28, 2.46, 2.50–2.56, 3.50–3.13, 3.88, 6.70, 7.21 and 7.98.

Example 29

1-[(5-Methanesulfonamido)indolyl-2-carbonyl]-4-[N-methyl-N-(3-(2 -methylpropyl)-2-pyridinyl)amino]piperidine (I)

1-tert-Butoxycarbonyl-4-[N-methyl-N-(3-(2-methylpropyl)-2-pyridinyl)amino]piperidine (XXVI, EXAMPLE 28, 1.08 g, 3.1 mmol) is deprotected in hydrochloric acid (4N)/dioxane for 15 min. The solvent is removed by reduced pressure and the residue is taken up in methylene chloride and stripped of solvent. The concentrate is dried under high reduced pressure for 1 hr. In a separate flask a solution of 5-(methanesulfonamido)indolyl-2- carboxylic acid (XIV, 1.6 g, 6.2 mmol) and CDI (1.0 g, 6.2 mmol) are stirred for 1 hr in dry THF. This is cooled to 0° and a solution of the above concentrate and triethylamine (0.45 ml, 3.2 mmol) in dry THF is added. The reaction is stirred at 20°–25° overnight and partitioned between chloroform and sodium hydroxide (1N). The organic phase is separated, washed with saline and dried (sodium sulfate). Removal of solvent gives a residue which is chromatographed (silica gel, 3×40 cm column; ethyl acetate) to give the title compound, mp 100°–201°.

Example 30

1-[5-(Methoxy)indolyl-2-carbonyl]-4-[N-ethyl-N-(3-propyl-2-pyridinyl)amino]piperidine (I)

5-Methoxyindolyl-2-carboxylic acid (XIV, 0.28 g) and CDI (0.24 g) are dissolved in THF (3 ml) and stirred 1 hr at 20°–25°. Then the reaction is cooled to 0° and 4-[N-ethyl-N-(3-(1-propyl))-2-pyridinyl)amino]piperidine, from hydrogenation of 1-benzyl-4-[N-ethyl-N-(3-propenyl)-2-pyridinyl)amino]piperidine, see EXAMPLE 19 and 20, 0.3 g) dissolved in THF is added. The reaction is slowly warmed to 20°–25° and stirred for 2 hr. Then it is diluted with ethyl acetate, washed with sodium hydroxide (1N), saline, dried over sodium sulfate and concentrated by reduced pressure. Purification by flash column chromatography (silica gel; ethyl acetate/hexane (1/1)) gives the title compound, mp 156°–158°.

Example 31

1-[Indolyl-2-carbonyl]-4-[N-ethyl-N-(3-propyl)-2-pyridinyl)amino]piperidine (I)

Following the general procedure of EXAMPLE 30 and making non-critical variations but starting with 4-[N-ethyl-N-(3-(1-propyl))-2-pyridinyl)amino]piperidine (X, from hydrogenation of 1-benzyl-4-[N-ethyl-N-(3-propenyl)-2-pyridinyl)amino]piperidine XXII, see EXAMPLE 19 and 20, 0.3 g), indolyl-2-carboxylic acid (0.24 g), CDI (0.24 g), the title compound is obtained, mp 158°–160°.

Example 32

1-Benzyl-4-[N-ethyl-N-(3-(2'-trimethylsilylvinyl)-2-pyridinyl)amino]piperidine (XXII)

Following the general procedure of EXAMPLE 16 and making non-critical variations but starting with 1-benzyl-4-(N-ethyl-N-(3-(formyl)-2-pyridinyl)amino)piperidine (XXI, EXAMPLE 12, 2.3 g), trimethylsilylmethyltriphenylphosphonium iodide (6.77 g) and n-butyl lithium (8.89 ml, 1.6M in hexane), the title compound is obtained, NMR (300 MHz, CDCl$_3$) 8.04, 7.55, 7.20–7.07, 6.83, 6.70, 6.20, 3.47, 3.17, 2.98, 2.72, 1.82–1.61, 1.60–1.45, 0.83 and 0.00δ.

Example 33

1-[5-(Methanesulfonamido)indolyl-2-carbonyl]-4-[N-ethyl-N-(3-(2'-trimethylsilylethyl)-2-pyridinyl)amino]piperidine (I)

Following the general procedure of EXAMPLE 20 and making non-critical variations but starting with 1-benzyl-4-(N-ethyl-N-(3-(2'-trimethylsilylvinyl)-2-pyridinyl)amino)piperidine (XXII, EXAMPLE 32, 0.15 g), Pearlman's catalyst (0.1 g), CDI (0.076 g) and 5-(methanesulfonamido)indolyl-2-carboxylic acid (XIV, 0.12 g), the title compound is obtained, mp 163°–165°.

Example 34

1-Benzyl-4-(N-methyl-N-(3-methoxycarbonyl-2-pyridyl)amino)piperidine (XXIX)

A mixture of 1-benzyl-4-methylaminopiperidine (XX, EXAMPLE 9, 8.00 g) and methyl 2-chloro-3-nicotinate (XXVIII, 3.36 g) is placed in a sealed tube and maintained at 115°–120° for 2 hrs. The residue is diluted with methylene chloride (125 ml), washed with water (2×50 ml) and saline (25 ml), dried over sodium sulfate and concentrated under reduced pressure. The resulting concentrate is then chromatographed (silica gel, gradient of ethyl acetate/hexane (25/75→50/50)) to give the title compound, mp 109°–110°.

Example 35

1-Benzyl-4-(N-methyl-N-(3-hydroxymethyl-2-pyridyl)amino)piperidine (XXX)

To a flame-dried flask containing 1-benzyl-4-(N-methyl-N-(3-methoxycarbonyl-2-pyridyl)amino)piperidine (XXIX, EXAMPLE 34, 750 mg) in dry tetrahydrofuran (22 ml) at 0° under nitrogen is added lithium aluminum hydride (84 mg) in two portions. The mixture is stirred at 0° for 1.5 hrs, quenched carefully with aqueous sodium hydroxide (5%, 5 ml), diluted with water (10 ml) and filtered through a pad of diatomaceous earth. The filtrate is then extracted with methylene chloride (2×30 ml) and the combined organic phases are washed with saline (10 ml), dried over sodium sulfate and concentrated under reduced pressure to give the title compound, NMR (CDCl$_3$, 400 MHz) 8.28, 7.53, 7.31, 7.24, 6.99, 4.90, 4.71, 3.48, 3.16, 2.91, 2.74, 1.99 and 1.74δ.

Example 36

1-Benzyl-4-(N-methyl-N-(3-methoxymethyl-2-pyridyl)amino)piperidine (XXXI)

To a mixture of powdered potassium hydroxide (356 mg) in dry dimethylsulfoxide (2 ml) under nitrogen is added a solution of 1-benzyl-4-(N-methyl-N-(3-hydroxymethyl-2-pyridyl)amino)piperidine (XXX, EXAMPLE 35, 494 mg) in dry dimethylsulfoxide (1.2 ml) followed by methyl iodide (118 μl). The resulting mixture is stirred at 20°–25° for 30 min and is then diluted with water (15 ml) and extracted with methylene chloride (2×20 ml). The combined organic phases are washed with water (2×10 ml) and saline (10 ml), dried over sodium sulfate and concentrated under reduced pressure to give a concentrate which is then chromatographed (silica gel, a gradient of ethyl acetate/hexane (20/80→40/60)) to give the title compound, NMR (CDCl$_3$, 400 MHz) 8.22, 7.67, 7.31, 7.25, 6.89, 4.40, 3.50, 3.41, 3.28, 2.94, 2.77, 2.01, 1.86 and 1.70δ.

Example 37

1-(5-(Methanesulfonamido)indolyl-2-carbonyl)-4-(N-methyl-N-(3-methoxymethyl-2-pyridyl)amino)piperidine (I)

A mixture containing 1-benzyl-4-(N-methyl-N-(3-methoxymethyl-2-pyridyl)amino)piperidine (XXXI, EXAMPLE 36, 150 mg), ammonium formate (87 mg) and palladium on carbon (10%, 150 mg) in methanol (9.2 ml) under nitrogen is degassed and refluxed for 1 hr. The catalyst is removed by filtration through diatomaceous earth and the filtrate is concentrated under reduced pressure to give the debenzylated intermediate. To a flame-dried flask under nitrogen is added 5-(methanesulfonamido)indolyl-2- carboxylic acid (XIV, 116 mg), 1,1-carbonyldiimidazole (74 mg) and dry tetrahydrofuran (2.5 ml) and the mixture is stirred at 20°–25° for 1 hr. Then a solution of the intermediate (102 mg) in dry tetrahydrofuran (2.5 ml) is added and the resultant mixture is stirred at 20°–25° for 20 hrs and concentrated under reduced pressure to remove solvent. The residue is diluted with methylene chloride (20 ml), washed with water (10 ml), saturated aqueous sodium bicarbonate (10 ml) and saline (10 ml), dried over sodium sulfate, concentrated under reduced pressure and flushed through a pad of silica gel (70–230 mesh, 10 g, eluting with methanol/methylene chloride (5/95)). Pooling of fractions with an $R_f$=0.17 by TLC (methanol/chloroform, 5/95) and removal of solvent gives the crude product which is purified by radial chromatography (4000μ silica gel plate; eluting with methanol/methylene chloride (5/95)), to give the title compound, NMR (CDCl$_3$, 400 MHz) 9.40, 8.27, 7.72, 7.60, 7.41, 7.16, 6.97, 6.77, 6.57, 4.71, 4.45, 3.80, 3.45, 3.15, 2.97, 2.78, 1.97 and 1.81δ.

Example 38

1-Benzyl-4-(N-ethyl-N-(3-methoxycarbonyl-2-pyridyl)amino)piperidine (XXIX)

Following the general procedure of EXAMPLE 34, and making non-critical variations but substituting 1-benzyl-4-ethylaminopiperidine (XX, EXAMPLE 11) for 1-benzyl-4-methylaminopiperidine and maintaining the reaction mixture at 115°–120° for 24 hrs, the title compound is obtained, Anal. Calc'd: C=71.36, H=7.70, N=11.89; found: C=71.36, H=7.55, N=11.68.

Example 39

1-Benzyl-4-(N-ethyl-N-(3-hydroxymethyl-2-pyridyl)amino)piperidine (XXX)

Following the general procedure of EXAMPLE 35, and making non-critical variations but substituting 1-benzyl-4-(N-ethyl-N-(3-methoxycarbonyl-2-pyridyl)amino)piperidine (XXIX, EXAMPLE 38) for 1-benzyl-4-(N-methyl-N-(3-methoxycarbonyl-2-pyridyl)amino)piperidine, the title compound is obtained, NMR (CDCl$_3$, 300 MHz) 8.34, 7.48, 7.27, 7.03, 5.75, 4.75, 3.47, 3.26, 3.05, 2.89, 1.95, 1.75 and 0.93δ.

Example 40

1-Benzyl-4-(N-ethyl-N-(3-methoxymethyl-2-pyridyl)amino)piperidine (XXXI)

Following the general procedure of EXAMPLE 36, and making non-critical variations but substituting 1-benzyl-4-(N-ethyl-N-(3-hydroxymethyl-2-pyridyl)amino)piperidine (XXX, EXAMPLE 39) for 1-benzyl-4-(N-methyl-N-(3-hydroxymethyl-2-pyridyl)amino)piperidine, the title compound is obtained, NMR (CDCl$_3$, 400 MHz) 8.28, 7.73, 7.31, 7.27, 6.97, 4.46, 3.48, 3.41, 3.24, 3.05, 2.90, 1.95, 1.73 and 0.90δ.

Example 41

1-(5-(Methanesulfonamido)indolyl-2-carbonyl)-4-(N-ethyl-N-(3-methoxymethyl-2-pyridyl)amino)piperidine (I)

Following the general procedure of EXAMPLE 37, and making non-critical variations but substituting 1-benzyl-4-(N-ethyl-N-(3-methoxymethyl-2-pyridyl)amino)piperidine (XXXI, EXAMPLE 40) for 1-benzyl-4-(N-methyl-N-(3-methoxymethyl-2-pyridyl)amino)piperidine, the title compound is obtained, Anal. Calc'd: C=59.36, H=6.43, N=14.42; found: C=59.06, H=6.45, N=14.14.

Example 42

1-Benzyl-4-(N-methyl-N-(3-cyano-2-pyridyl)amino)piperidine (XXXIII)

Following the general procedure of EXAMPLE 34, and making non-critical variations but substituting 2-chloronicotinonitrile (XXXII) for methyl 2-chloro-3-nicotinate (XXVIII), the title compound is obtained, mp 58°–60°.

Example 43

1-Benzyl-4-(N-methyl-N-(3-acetyl-2-pyridyl)amino)piperidine (XXXIV)

To a flame-dried flask containing a mixture of methyllithium (1.5M in ether as complexed with lithium bromide, 5.2 ml) in anhydrous ether (5.2 ml) at −78° under nitrogen is added a solution of 1-benzyl-4-(N-methyl-N-(3-cyano-2-pyridyl)amino)piperidine (XXXIII, EXAMPLE 42, 1.2 g) in anhydrous ether (5.3 ml) over 5 min. The resulting mixture is allowed to warm up to 0° over approximately 2.25 hrs and is quenched with sulfuric acid (2N, 3.9 ml) and stirred at 20°–25° for 2 hrs. The biphasic mixture is then adjusted to pH 10–11 with aqueous sodium hydroxide (5%), diluted with ether (10 ml) and water (10 ml) and the phases are separated. The aqueous phase is extracted with additional ether (30 ml), and the combined organic phases are washed with saline (10 ml), dried over anhydrous magnesium sulfate, concentrated under reduced pressure, and chromatographed (silica gel, 70–230 mesh, 50 g; ethyl acetate/hexane (50/50)) to give the title compound, mp=93°–94°.

Example 44

1-Benzyl-4-(N-methyl-N-(3-ethyl-2-pyridyl)amino)piperidine (XXXV)

A mixture of 1-benzyl-4-(N-methyl-N-(3-acetyl-2-pyridyl)amino)piperidine (XXXIV, EXAMPLE 43, 260 mg), hydrazine monohydrate (0.78 ml) and powdered potassium hydroxide (0.90 g) in triethylene glycol (16 ml) is stirred at 120° for 2 hrs. The condenser is removed, the mixture is heated up to approximately 185°–190°, the condenser is replaced, and the mixture is stirred at 190° for 3 hrs. After cooling to 20°–25°, the mixture is added to water (50 ml) and extracted with methylene chloride (2×50 ml), and the organic phase is washed with water (20 ml) and saline (20 ml), dried over sodium sulfate, concentrated under reduced pressure and chromatographed (silica gel, 70–230 mesh, 25 g; eluting with a gradient of ethyl acetate/hexane (25/75→50/50)) to give the title compound, NMR (CDCl$_3$, 400 MHz) 8.16, 7.46, 7.31, 7.26, 6.88, 3.50, 3.15, 2.92, 2.73, 2.63, 2.00, 1.82, 1.73 and 1.23δ.

Example 45

1-(5-(Methanesulfonamido)indolyl-2-carbonyl)-4-(N-methyl-N-(3-ethyl-2-pyridyl)amino)piperidine (I)

Following the general procedure of EXAMPLE 37, and making non-critical variations but substituting 1-benzyl-4-(N-methyl-N-(3-ethyl-2-pyridyl)amino)piperidine (XXXV, EXAMPLE 44) for 1-benzyl-4-(N-methyl-N-(3- methoxymethyl-2-pyridyl)amino)piperidine, the title compound is obtained, NMR (CDCl$_3$, 300 MHz) 10.38, 8.20, 7.72, 7.59, 7.51, 7.39, 7.15, 6.95, 6.72, 4.67, 3.57, 3.17, 2.94, 2.71, 2.67, 1.95, 1.75 and 1.24 $\delta$.

Example 46

1-Benzyl-4-(N-ethyl-N-(3-cyano-2-pyridyl)amino) piperidine (XXXIII)

Following the general procedure of EXAMPLE 34, and making non-critical variations but substituting 1-benzyl-4-ethylaminopiperidine (XX, EXAMPLE 11) for 1-benzyl-4-methylaminopiperidine and 2-chloronicotinonitrile for methyl 2-chloro-3-nicotinate and maintaining the reaction at 115°–120° for 24 hrs, the title compound is obtained, Anal. Calc'd: C=74.95, H=7.55, N=17.48; found: C=75.15, H=7.42, N, 17.38.

Example 47

1-Benzyl-4-(N-ethyl-N-(3-acetyl-2-pyridyl)amino) piperidine (XXXIV)

Following the general procedure of EXAMPLE 43, and making non-critical variations but substituting 1-benzyl-4-(N-ethyl-N-(3-cyano-2-pyridyl)amino)piperidine (XXXIII, EXAMPLE 46) for 1-benzyl-4-(N-methyl-N-(3-cyano-2-pyridyl)amino)piperidine the title compound is obtained, NMR (CDCl$_3$, 400 MHz) 8.30, 7.66, 7.30, 7.26, 6.81, 3.48, 3.40, 2.90, 2.56, 1.98, 1.84, 1.75 and 1.04 $\delta$.

Example 48

1-Benzyl-4-(N-ethyl-N-(3-ethyl-2-pyridyl)amino) piperidine (XXXV)

Following the general procedure of EXAMPLE 44, and making non-critical variations but substituting 1-benzyl-4-(N-ethyl-N-(3-acetyl-2-pyridyl)amino)piperidine (XXXIV, EXAMPLE 47) for 1-benzyl-4-(N-methyl-N-(3-acetyl-2-pyridyl)amino)piperidine, the title compound is obtained, NMR (CDCl$_3$, 300 MHz) 8.20, 7.47, 7.31, 7.26, 6.91, 3.47, 3.22, 3.01, 2.89, 2.65, 1.94, 1.74, 1.20 and 0.88 $\delta$.

Example 49

1-(5-(Methanesulfonamido)indolyl-2-carbonyl)-4-(N-ethyl-N-(3-ethyl-2-pyridyl)amino)piperidine (I)

Following the general procedure of EXAMPLE 37, and making non-critical variations but substituting 1-benzyl-4-(N-ethyl-N-(3-ethyl-2-pyridyl)amino)piperidine (XXXV, EXAMPLE 48) for 1-benzyl-4-(N-methyl-N-(3-methoxymethyl-2-pyridyl)amino)piperidine, the title compound is obtained, NMR (CDCl$_3$, 400 MHz) 9.65, 8.27, 7.59, 7.55, 7.40, 7.16, 7.00, 6.85, 6.73, 4.65, 3.47, 3.22, 3.15, 2.97, 2.71, 1.96, 1.72, 1.24 and 0.92 $\delta$.

Example 50

1-Benzyl-4-(N-propyl-N-(3-cyano-2-pyridyl)amino) piperidine (XXXIII)

Following the general procedure of EXAMPLE 34, and making non-critical variations but substituting 1-benzyl-4-propylaminopiperidine (EXAMPLE 112) for 1-benzyl-4-methylaminopiperidine (XX, EXAMPLE 9) and 2-chloronicotinonitrile for methyl 2-chloro-3-nicotinate and maintaining the reaction at 115°–120° for 16 hrs, the title compound is obtained, NMR (CDCl$_3$, 400 MHz) 8.28, 7.71, 7.34, 7.26, 6.61, 4.42, 3.54, 3.50, 2.99, 2.15, 1.89, 1.81, 1.60 and 0.92 $\delta$.

Example 51

1-Benzyl-4-(N-propyl-N-(3-acetyl-2-pyridyl)amino) piperidine (XXXIV)

Following the general procedure of EXAMPLE 43, and making non-critical variations but substituting 1-benzyl-4-(N-propyl-N-(3-cyano-2-pyridyl)amino)piperidine (XXXIII, EXAMPLE 50) for 1-benzyl-4-(N-methyl-N-(3-cyano-2-pyridyl)amino)piperidine, the title compound is obtained, NMR (CDCl$_3$, 400 MHz) 8.28, 7.65, 7.31, 7.27, 6.80, 3.49, 3.40, 3.30, 2.92, 2.56, 1.98, 1.88, 1.75, 1.46 and 0.85 $\delta$.

Example 52

1-Benzyl-4-(N-propyl-N-(3-ethyl-2-pyridyl)amino) piperidine (XXXV)

Following the general procedure of EXAMPLE 44, and making non-critical variations but substituting 1-benzyl-4-(N-propyl-N-(3-acetyl-2-pyridyl)amino)piperidine (XXXIV, EXAMPLE 51) for 1-benzyl-4-(N-methyl-N-(3-acetyl-2-pyridyl)amino)piperidine, the title compound is obtained, NMR (CDCl$_3$, 400 MHz) 8.19, 7.48, 7.31, 7.27, 6.91, 3.49, 3.16, 2.93, 2.65, 1.95, 1.82, 1.59, 1.29, 1.22 and 0.80 $\delta$.

Example 53

1-(5-(Methanesulfonamido)indolyl-2-carbonyl)-4-(N-propyl-N-(3-ethyl-2-pyridyl)amino)piperidine (I)

Following the general procedure of EXAMPLE 37, and making non-critical variations by substituting 1-benzyl-4-(N-propyl-N-(3-ethyl-2-pyridyl)amino)piperidine (XXXV, EXAMPLE 52) for 1-benzyl-4-(N-methyl-N-(3-methoxymethyl-2-pyridyl)amino)piperidine, the title compound is obtained, NMR (CDCl$_3$, 400 MHz) 9.54, 8.25, 7.59, 7.56, 7.41, 7.16, 7.00, 6.83, 6.74, 4.69, 3.39, 3.10, 2.97, 2.71, 1.96, 1.75, 1.31, 1.25 and 0.82 $\delta$.

Example 54

1-(1,1-Dimethylethoxycarbonyl)-4-[N-methyl-N-(3-(1-methylethylamino)-2-pyridinyl)amino]piperidine To a mixture of 1-(1,1-dimethylethoxycarbonyl)-4-[N-methyl-N-(3-nitro-2-pyridinyl)amino]piperidine (International Publication No. WO 91/09849, PREPARATION 125, 5.17 g) in methanol (250 ml) under nitrogen is added palladium black (1.0 g), and the mixture is stirred under a hydrogen atmosphere (balloon) for 2 hrs, palladium black (1.0 g) being added after 1 hr. The mixture is then filtered and concentrated under reduced pressure to give 1-(1,1-dimethylethoxycarbonyl)-4-[N-methyl-N-(3-amino-2-pyridinyl)amino]piperidine. The concentrate is dissolved in absolute ethanol (50 ml) and treated with acetone (17 ml) and sodium cyanoborohydride (950 mg). The pH is adjusted to 5 with glacial acetic acid as measured on moistened pH test paper. The mixture is stirred at 20°–25° for 24 hrs during which additional sodium cyanoborohydride (300 mg) is added, the pH being adjusted after the addition. The mixture is then adjusted to pH 3.5 with 10% aqueous hydrochloric acid, neutralized with aqueous sodium hydroxide (5%) and concentrated to remove ethanol. The residue is diluted with methylene chloride (200 ml) and water (75 ml), the layers are separated, and the organic phase is washed with saturated aqueous potassium carbonate (75 ml) and saline (75 ml), dried over sodium sulfate, and concentrated to give the crude product which is chromatographed (silica gel, 70–230 mesh, 400 g; eluting with a gradient of methanol/chloroform (0.5/95.5–2/98)) to give the title compound, C,H,N: Anal. Calcd for $C_{19}H_{32}N_4O_2$: C=65.49, H=9.26, N=16.08-found: C=65.34, H=9.34, N=15.98.

Example 55

1-(5-Nitroindolyl-2-carbonyl)-4-[N-methyl-N-(3-(1-methylethylamino)-2-pyridinyl)amino]piperidine
(V)

A mixture of 1-(1,1-dimethylethoxycarbonyl)-4-[N-methyl-N-(3-(1-methylethylamino)-2-pyridinyl)amino] piperidine (EXAMPLE 54, 4.30 g) in dry methylene chloride (100 ml) under nitrogen is cooled in an ice bath and treated with trifluoroacetic acid (12.3 ml). The mixture is stirred at 20°–25° for 24 hrs and then carefully added to a mixture of sodium hydroxide (6.4 g) in ice water (75 ml). The layers are separated and the aqueous phase is extracted with methylene chloride (3×100 ml). The combined organic phases are washed with saline (100 ml), dried over sodium sulfate, and concentrated under reduced pressure to give the deprotected intermediate, $R_f$=0.5 by TLC ((4M ammonia in methanol)/chloroform, 10/90). A mixture of 5-nitroindolyl-2-carboxylic acid (2.39 g) and EDC (2.33 g) in dry tetrahydrofuran (100 ml) under nitrogen is stirred at 20°–25° for 15 min and is then treated with a mixture of the deprotected intermediate (2.88 g) in dry tetrahydrofuran (20 ml). The resulting mixture is stirred for 1.5 days, during which an additional EDC.HCl (220 mg) is added in one portion, and the supernatant is concentrated to remove tetrahydrofuran, diluted with methylene chloride (75 ml) and water (25 ml), and the layers are separated. The aqueous phase is extracted with methylene chloride (2×20 ml) and the combined organic phases are washed with saturated sodium bicarbonate (30 ml) and saline (30 ml), dried over sodium sulfate, and concentrated under reduced pressure to give the crude product which is then chromatographed (silica gel, 70–230 mesh, 400 g; eluting with methanol/chloroform (0.5/95.5–5/95)) to give the title compound, mp=204°–206°.

Example 56

1-(5-Aminoindolyl-2-carbonyl)-4-[N-methyl-N-(3-(1-methylethylamino)-2-pyridinyl)amino]piperidine
(V)

To a mixture of 1-(5-nitroindolyl-2-carbonyl)-4-[N-methyl-N-(3-(1-methylethylamino)-2-pyridinyl)amino] piperidine (EXAMPLE 55, 1.20 g) in methanol/tetrahydrofuran (20/80, 125 ml) under nitrogen is added palladium-on-carbon (10%, 200 mg), and the mixture is stirred under a hydrogen atmosphere (balloon) for 20 hrs during which additional palladium-on-carbon (10%, 50 mg) is added in one portion. The mixture is then filtered, concentrated, and chromatographed (silica gel, 70–230 mesh, 85 g; eluting with a gradient of methanol/chloroform (2/98–5/95)) to give the title compound, NMR ($CDCl_3$) 9.84, 7.71, 7.20, 6.94, 6.85, 6.71, 6.56, 4.65, 4.50, 3.75, 3.55, 3.43, 3.10, 2.63, 1.91 1.64 and 1.21δ.

Example 57

1-[5-(N,N-Dimethylformamido)indolyl-2-carbonyl]-4-[N-methyl-N-(3-(1-methylethyl-amino)-2-pyridinyl)amino]piperidine (V)

A mixture containing 1-(5-aminoindolyl-2-carbonyl)-4-[N-methyl-N-(3-(1-methylethylamino)-2-pyridinyl)amino] piperidine (EXAMPLE 56, 1.00 g) and N,N-dimethylformamide dimethyl acetal (0.49 ml) in dimethylformamide/toluene (2/98, 113 ml) is heated to reflux for 1 hr, cooled to 20°–25°, and washed with water (3×25 ml) and saline (30 ml). The combined organic phases are dried over anhydrous magnesium sulfate and concentrated to give the crude product which is chromatographed (silica gel, 70–230, 80 g; eluting with a gradient of methanol/chloroform (2.5/97.5–20/80)) to give the title compound, NMR ($CDCl_3$) 10.05, 7.71, 7.56, 7.30, 7.15, 6.95, 6.83, 6.66, 4.66, 4.50, 3.54, 3.44, 3.10, 2.99, 2.63, 1.92, 1.65 and 1.22δ.

Example 58

1-[5-(Methanesulfonamido)indolyl-2-carbonyl]-4-[N-methyl-N-(3-(1-methylethylamino)-2-pyridinyl) amino]piperidine (V)

To a mixture of 1-(5-aminoindolyl-2-carbonyl)-4-[N-methyl-N-(3-(1-methylethylamino)-2-pyridinyl)amino] piperidine (EXAMPLE 56, 93 mg) in dry methylene chloride (5 ml) at 0° under nitrogen is added triethylamine (31.9 μl) and methanesulfonyl chloride (17.7 μl). The mixture is stirred at 20°–25° for 3 days during which additional triethylamine (96 μl) and methanesulfonyl chloride (35.4 μl) are added in two portions and then diluted with methylene chloride (25 ml), washed with water (10 ml) and saline (10 ml), dried over sodium sulfate, and concentrated to give a crude mixture which is chromatographed (two 2000μ preparative silica gel plates, eluting with methanol/chloroform (5/95)). Isolation of the band with $R_f$=0.20–0.30 gives the title compound, mp=217°–220° (decomp).

Example 59

1-[5-(Dimethylaminosulfonylamino)indolyl-2-carbonyl]-4-[N-methyl-N-(3-(1-methylethylamino)-2-pyridinyl)amino]piperidine (V)

To a mixture of 1-(5-aminoindolyl-2-carbonyl)-4-[N-methyl-N-(3-(1-methylethylamino)-2-pyridinyl)amino] piperidine (EXAMPLE 56, 91 mg) in pyridine (0.5 ml) under nitrogen is added N,N-dimethylsulfamoyl chloride (26 μl). The mixture is stirred at 20°–25° for 16 hrs and then diluted with methylene chloride (35 ml) and hydrochloric acid (1M, 20 ml). The layers are separated and the organic phase is washed with hydrochloric acid (1M, 20 ml) and saline (20 ml), dried over sodium sulfate, concentrated and chromatographed on two 2000μ preparative silica gel plates, eluting with methanol/chloroform (5/95). The band with an $R_f$=0.35–0.42 is isolated to give the title compound, NMR ($CDCl_3$) 10.34, 7.72, 7.64, 7.56, 7.37, 7.16, 6.95, 6.84, 6.70, 4.65, 4.50, 3.56, 3.46, 3.40–3.00, 3.80, 2.63, 1.93, 1.64 and 1.22δ.

Example 60

1-[5-(Methylaminocarbonylamino)indolyl-2-carbonyl]-4-[N-methyl-N-(3-(1-methylethylamino)-2-pyridinyl)amino]piperidine (V)

To a mixture of 1-(5-aminoindolyl-2-carbonyl)-4-[N-methyl-N-(3-(1-methylethylamino)-2-pyridinyl)amino] piperidine (EXAMPLE 56, 93 mg) in dry methylene chloride (1 ml) at 0° under nitrogen is added methyl isocyanate (14 μl), and the mixture is stirred at 0° for 3 hrs and at 20°–25° for 16 hrs. The mixture is then concentrated, diluted with chloroform (20 ml), washed with water (10 ml) and saline (10 ml), dried over sodium sulfate, and concentrated to give the crude product which is chromatographed on two 2000μ preparative silica gel plates, eluting with methanol/chloroform (5/95). Isolation of the band with $R_f$=0.14–0.24 gives the title compound, NMR (MeOH-$d_4$) 7.60, 7.32, 7.10, 6.98, 6.69, 4.46, 3.57, 3.37, 3.08, 2.75, 2.60, 1.82, 1.59 and 1.19δ.

Example 61

1-[5-(4-Methyl-1-piperazinylsulfonylamino)indolyl-2-carbonyl]-4-[N-methyl-N-(3-(1-methylethylamino)-2-pyridinyl)amino]-piperidine (V)

To a mixture of 1-methylpiperazine (1.11 ml) in dry methylene chloride (20 ml) at 0° under argon is added sulfuryl chloride (1.6 ml) dropwise. The mixture is warmed to 20°–25°, stirred for 1.5 hrs, and concentrated to give 4-methyl-1-piperazinyl sulfamoyl chloride intermediate. To a mixture of 1-(5-aminoindolyl-2-carbonyl)-4-[N-methyl-N-(3-(1-methylethylamino)-2-pyridinyl)amino]piperidine (EXAMPLE 56, 162 mg) in pyridine (1.5 ml) under nitrogen is added the sulfamoyl chloride hydrochloride intermediate (187 mg), and the resulting mixture is stirred at 20°–25° for 20 hrs, diluted with water (25 ml), and extracted with methylene chloride (4×25 ml). The organic phase is then washed with saturated sodium bicarbonate (30 ml) and saline (50 ml), dried over sodium sulfate, and concentrated under reduced pressure to give a solid which is then chromatographed on four 2000μ preparative silica gel plates, eluting with methanol/chloroform (5/95) twice. Isolation of the band with $R_f$=0.19–0.23 gives the title compound, NMR (CDCl$_3$) 9.94, 7.71, 7.54, 7.30, 7.13, 6.95, 6.84, 6.69, 4.64, 4.50, 3.56, 3.45, 3.30–2.90, 2.63, 2.36, 2.23, 1.95, 1.64 and 1.22δ.

Example 62

1-[1,1-Dimethylethoxycarbonyl]-4-[N-methyl-N-(3-(1,1-dimethylprop-2-enylamino)-2-pyridinyl)amino]piperidine To a mixture of 1-(1,1-dimethylethoxycarbonyl)-4-[N-methyl-N-(3-nitro-2-pyridinyl)amino]piperidine (International Publication No. WO 91/09849, PREPARATION 125, 5.00 g) in methanol (85 ml) is added palladium-on-carbon (10%, 800 mg). The mixture is put under a hydrogen atmosphere at 40 psi for 5.5 hrs, filtered through diatomaceous earth, and concentrated under reduced pressure to give an amine intermediate ($R_f$=0.23 by TLC, ethyl acetate/hexane, 50/50). This intermediate is then dissolved in dry dimethylformamide (20 ml) under nitrogen at 0° and copper powder (750 mg) and cuprous chloride (750 mg) are added. To this is added a mixture of 3-chloro-3-methyl-1-butyne (1.51 g) in dry dimethylformamide (4 ml) in 5 portions over 15 min. The resulting mixture is stirred at 20°–25° for 2 hrs, concentrated to remove dimethylformamide, and diluted with methylene chloride (75 ml) and water (25 ml). The phases are separated and the organic phase is washed with saline (25 ml), dried over sodium sulfate, and concentrated under reduced pressure to give the crude product which is chromatographed (silica gel, 70–230 mesh, 600 g; eluting with a gradient of ethyl acetate/hexane (10/90–40/60)) to give the title compound, NMR (CDCl$_3$) 7.79, 7.51, 6.95, 4.92, 4.05, 3.19, 2.75, 2.61, 2.38, 1.75, 1.62, 1.49 and 1.45δ.

Example 63

1-[1,1-Dimethylethoxycarbonyl]-4-[N-methyl-N-(3-(1,1-dimethylpropyl amino)- 2-pyridinyl)amino]piperidine To a mixture of 1-[1,1-dimethylethoxycarbonyl]-4-[N-methyl-N-(3-(1,1-dimethylprop-2-enylamino)-2-pyridinyl) amino]piperidine (EXAMPLE 62, 2.41 g) in absolute ethanol (40 ml) under nitrogen is added wet Raney Nickel (620 mg). The mixture is put under a hydrogen atmosphere at 40 psi for 21 hrs, filtered through diatomaceous earth, and concentrated to give an oil which is chromatographed (silica gel, 70–230 mesh, 250 g; eluting with a gradient of ethyl acetate/hexane (10/90–35/65)), to give the title compound, NMR (CDCl$_3$) 7.67, 7.04, 6.87, 4.87, 4.04, 3.20, 2.76, 2.61, 1.71, 1.50, 1.45, 1.31 and 0.86δ.

Example 64

4-[N-Methyl-N-(3-(1,1-dimethylpropylamino)-2-pyridinyl)amino]piperidine

To a mixture of 1-[1,1-dimethylethoxycarbonyl]-4-[N-methyl-N-(3-(1,1-dimethylpropylamino)-2-pyridinyl)amino]piperidine (EXAMPLE 63, 2.39 g) in dry methylene chloride (30 ml) under nitrogen at 0° is added trifluoroacetic acid (6.37 ml) over 1 min. The resulting mixture is warmed to 20°–25°, stirred for 1.5 hrs, and then added to a mixture of sodium hydroxide (3.31 g) in water (40 ml) at 0°. The layers are separated, the aqueous phase is extracted with methylene chloride (4×40 ml), and the combined organic phases are washed with saline (40 ml), dried over sodium sulfate, and concentrated under reduced pressure to give the title compound, NMR (CDCl$_3$) 7.66, 7.02, 6.84, 4.86, 3.39, 3.13, 2.63, 1.81–1.52, 1.31 and 0.87δ.

Example 65

1-[Indolyl-2-carbonyl]-4-[N-methyl-N-(3-(1,1-dimethylpropylamino)-2-pyridinyl)amino]piperidine (V)

In a flame-dried flask under nitrogen, indolyl-2-carboxylic acid (204 mg) and 1,1'-carbonyldiimidazole (226 mg) are dissolved in dry tetrahydrofuran (3 ml) and stirred at 20°–25° for 1 hr. A mixture of 4-[N-methyl-N-(3-(1,1-dimethylpropylamino)-2-pyridinyl)amino]piperidine (EXAMPLE 64, 350 mg) in dry tetrahydrofuran (2 ml) is then added, and the mixture is stirred for 18 hrs and concentrated. The residue is taken up in methylene chloride (25 ml), washed with saturated sodium bicarbonate (10 ml), water (10 ml) and saline (10 ml), dried over sodium sulfate, and concentrated under reduced pressure to give the crude product which is chromatographed (silica gel, 230–400 mesh, 56 g; eluting with a gradient of ethyl acetate/hexane (30/70–40/60)) to give the title compound, NMR (CDCl$_3$) 9.82. 7.70, 7.63, 7.43, 7.26, 7.10, 6.91, 6.76, 4.91, 4.67, 3.45, 3.16, 2.64, 1.94, 1.67, 1.32 and 0.87δ.

Example 66

1-[5-Nitroindolyl-2-carbonyl]-4-[N-methyl-N-(3-(1,1-dimethylpropylamino)- 2-pyridinyl)amino]piperidine (V)

Following the general procedure of EXAMPLE 65, and making non-critical variations but substituting 5-nitroindolyl-2-carboxylic acid for indolyl-2-carboxylic acid, the title compound is obtained, mp=205.5°–207.5°.

Example 67

1-[5-Aminoindolyl-2-carbonyl]-4-[N-methyl-N-(3-(1,1-dimethylpropylamino)-2-pyridinyl)amino]piperidine (V)

To a mixture of 1-[5-nitroindolyl-2-carbonyl]-4-[N-methyl-N-(3-(1,1-dimethylpropylamino)-2-pyridinyl)

amino]piperidine (EXAMPLE 66, 1.50 g) in dimethylformamide/methanol (25/75) under nitrogen is added palladium-on-carbon (10%, 750 mg). The mixture is put under a hydrogen atmosphere (balloon) for 3 hrs and nitrogen for 64 hrs, filtered through diatomaceous earth, and concentrated under reduced pressure to give a residue which is then chromatographed (silica gel, 230–400 mesh, 100 g; eluting with a gradient of methanol/chloroform (1/99–3/97)) to give the title compound, NMR (CDCl$_3$) 9.95, 7.69, 7.20, 7.05, 6.88, 6.71, 6.55, 4.91, 4.64, 3.86, 3.40, 3.11, 2.62, 1.91, 1.63, 1.31 and 0.86δ.

Example 68

1-[5-(Methanesulfonamido)indolyl-2-carbonyl]-4-[N-methyl-N-(3-(1,1-dimethylpropylamino)-2-pyridinyl)amino]piperidine (V)

A mixture of 1-[5-aminoindolyl-2-carbonyl]-4-[N-methyl-N-(3-(1,1-dimethylpropylamino)-2-pyridinyl)amino]piperidine (EXAMPLE 67, 508 mg), pyridine (189 μl), methanesulfonyl chloride (91 μl), and methylene chloride (5 ml) is prepared and stirred at 20°–25° for 20 hrs. The mixture is diluted with methylene chloride (25 ml) and water (10 ml), the layers are separated, and the organic layer is washed with saline (10 ml), dried over sodium sulfate, and concentrated under reduced pressure to give a residue which is then chromatographed (silica gel, 230–400 mesh, 70 g; eluting with methanol/chloroform (3/97)) to give the title compound, NMR (CDCl$_3$) 10.06, 7.70, 7.58, 7.39, 7.16, 7.08, 6.91, 6.71, 4.90, 4.63, 3.45, 3.20, 2.95, 2.64, 1.94, 1.68, 1.32 and 0.87δ.

Example 69

2-Bromo-3-ethoxypyridine

A mixture of 2-bromopyridin-3-ol (3.00 g), ethyl iodide (3.44 ml), anhydrous potassium carbonate (4.28 g) and dry dimethylformamide (34 ml) is stirred under nitrogen at 80°–85° for 2.5 hrs, concentrated to remove solvent, diluted with ethyl acetate (75 ml) and water (40 ml), and the layers are separated. The aqueous phase is extracted with ethyl acetate (75 ml) and the combined organic phase is washed with saline (30 ml), dried over sodium sulfate, and concentrated under reduced pressure to give the title compound, NMR (CDCl$_3$) 7.97, 7.20, 7.12, 4.11 and 1.50δ.

Example 70

1-Benzyl-4-[N-methyl-N-(3-ethoxy-2-pyridinyl)amino]piperidine

A mixture of 1-benzyl-4-(methylamino)piperidine (EXAMPLE 9, 2.92 g) and 2-bromo-3-ethoxypyridine (EXAMPLE 69, 1.44 g) is stirred at 160°–165° in a sealed tube for 2 days, diluted with methylene chloride (50 ml), washed with water (10 ml) and saline (10 ml), dried over sodium sulfate, and concentrated under reduced pressure. The residue is chromatographed on silica gel (230–400 mesh, 300 g; eluting with a gradient of ethyl acetate/hexane (10/90–50/50)) to give the title compound, C,H,N: Anal. Calcd for $C_{20}H_{27}N_3O_1$: C=73.81, H=8.36, N=12.91-found: C=73.59, H=8.37, N=12.83.

Example 71

4-[N-Methyl-N-(3-ethoxy-2-pyridinyl)amino]piperidine

A mixture of 1-benzyl-4-[N-methyl-N-(3-ethoxy-2-pyridinyl)amino]piperidine (EXAMPLE 70, 1.40 g), palladium-on-carbon (10%, 1.4 g) and ammonium formate (813 mg) in methanol (25 ml) is degassed, stirred at 65° for 45 min, cooled to 20°–25°, and filtered to remove catalyst. The filtrate is concentrated under reduced pressure to give the title compound, NMR (CDCl$_3$) 7.83, 6.97, 6.71, 4.02, 3.88, 3.15, 2.88, 2.63, 1.75 and 1.46δ.

Example 72

1-[Indolyl-2-carbonyl]-4-[N-methyl-N-(3-ethoxy-2-pyridinyl)amino]piperidine (V)

Following the general procedure of EXAMPLE 65, and making non-critical variations but substituting 4-[N-methyl-N-(3-ethoxy-2-pyridinyl)amino]piperidine (EXAMPLE 71) for 4-[N-methyl-N-(3-(1,1-dimethylpropylamino)-2-pyridinyl)amino]piperidine, the title compound is obtained, Anal. Calcd for $C_{22}H_{26}N_4O_2$: C=69.82, H=6.92, N=14.80, found: C=69.46, H=6.92, N=14.66.

Example 73

1-[5-Nitroindolyl-2-carbonyl]-4-[N-methyl-N-(3-ethoxy-2-pyridinyl)amino]piperidine (V)

Following the general procedure of EXAMPLE 65, and making non-critical variations but substituting 5-nitroindolyl-2-carboxylic acid for indolyl-2-carboxylic acid and 4-[N-methyl-N-(3-ethoxy-2-pyridinyl)amino]piperidine (EXAMPLE 71) for 4-[N-methyl-N-(3-(1,1-dimethylpropylamino)-2-pyridinyl)amino]piperidine, the title compound is obtained, NMR (CDCl$_3$) 10.84, 8.63, 8.15, 7.86, 7.49, 7.04, 6.97, 6.78, 4.86, 4.20, 4.06, 3.4–2.8, 2.90, 1.96 and 1.49δ.

Example 74

1-[5-Aminoindolyl-2-carbonyl]-4-[N-methyl-N-(3-ethoxy-2-pyridinyl)amino]piperidine (V)

Following the general procedure of EXAMPLE 67, and making non-critical variations but substituting 1-[5-nitroindolyl-2-carbonyl]-4-[N-methyl-N-(3-ethoxy-2-pyridinyl)amino]piperidine (EXAMPLE 73) for 1-[5-nitroindolyl-2-carbonyl]-4-[N-methyl-N-(3-(1,1-dimethylpropylamino)-2-pyridinyl)amino]piperidine, the title compound is obtained, NMR (CDCl$_3$) 7.81, 7.25, 7.04, 6.95, 6.79, 6.62, 4.79. 4.07, 3.00, 2.87, 2.63, 1.91 and 1.48δ.

Example 75

1-[5-(Methanesulfonamido)indolyl-2-carbonyl]-4-[N-methyl-N-(3-ethoxy-2-pyridinyl)amino]piperidine (V)

Following the general procedure of EXAMPLE 68, and making non-critical variations but substituting 1-[5-aminoindolyl-2-carbonyl]-4-[N-methyl-N-(3-ethoxy-2-pyridinyl)amino]piperidine (EXAMPLE 74) for 1-[5-aminoindolyl-2-carbonyl]-4-[N-methyl-N-(3-(1,1-dimethylpropylamino)-2-pyridinyl)amino]piperidine, the title compound is obtained, NMR (CDCl$_3$) 9.81, 7.85, 7.61, 7.42, 7.16, 7.02, 6.98, 6.75, 4.83, 4.16, 4.05, 3.20–2.85, 2.96, 2.88, 1.95 and 1.48δ.

Example 76

2-Bromo-3-(1-methylethoxy)pyridine

Following the general procedure of EXAMPLE 69, and making non-critical variations but substituting isopropyl iodide for ethyl iodide, the title compound is obtained, NMR (CDCl$_3$) 7.98, 7.20, 7.17, 4.55, 1.42 and 1.40δ.

Example 77

1-Benzyl-4-[N-methyl-N-(3-(1-methylethoxy)-2-pyridinyl)amino]piperidine

Following the general procedure for EXAMPLE 70, and making non-critical variations but substituting 2-bromo-3-(1-methylethoxy)pyridine (EXAMPLE 76) for 2-bromo-3-ethoxypyridine, the title compound is obtained, Anal. Calcd for C$_{21}$H$_{29}$N$_3$O$_1$: C=74.30, H=8.61, N=12.38, found: C=74.00, H=8.71, N=12.04.

Example 78

4-[N-Methyl-N-(3-(1-methylethoxy)-2-pyridinyl) amino]piperidine

Following the general procedure of EXAMPLE 71, and making non-critical variations but substituting 1-benzyl-4-[N-methyl-N-(3-(1-methylethoxy)-2-pyridinyl)amino]piperidine (EXAMPLE 77) for 1-benzyl-4-[N-methyl-N-(3-ethoxy-2-pyridinyl)amino]piperidine, the title compound is obtained, NMR (CDCl$_3$) 7.82, 6.98, 6.71, 4.54, 3.92, 3.15, 2.87, 2.62, 1.74 and 1.35δ.

Example 79

1-[Indolyl-2-carbonyl]-4-[N-methyl-N-(3-(1-methylethoxy)-2-pyridinyl)amino]piperidine (V)

Following the general procedure of EXAMPLE 65, and making non-critical variations but substituting 4-[N-methyl-N-(3-(1-methylethoxy)-2-pyridinyl)amino]piperidine (EXAMPLE 78) for 4-[N-methyl-N-(3-(1,1-dimethylpropylamino)-2-pyridinyl)amino]piperidine, the title compound is obtained, C,H,N: Anal. Calcd for C$_{23}$H$_{28}$N$_4$O$_2$: C=70.38, H=7.19, N=14.27-found: C=70.06, H=7.08, N=14.30.

Example 80

1-[5-Nitroindolyl-2-carbonyl]-4-[N-methyl-N-(3-(1-methylethoxy)-2-pyridinyl)amino]piperidine (V)

Following the general procedure of EXAMPLE 65, and making non-critical variations but substituting 5-nitroindolyl-2-carboxylic acid for indolyl-2-carboxylic acid and 4-[N-methyl-N-(3-(1-methylethoxy)-2-pyridinyl) amino]piperidine (EXAMPLE 78) for 4-[N-methyl-N-(3-(1,1-dimethylpropylamino)-2-pyridinyl)amino]piperidine, the title compound is obtained, mp=184°–185°.

Example 81

1-[5-Aminoindolyl-2-carbonyl]-4-[N-methyl-N-(3-(1-methylethoxy)-2-pyridinyl)amino]piperidine (V)

Following the general procedure of EXAMPLE 67, and making non-critical variations but substituting 1-[5-nitroindolyl-2-carbonyl]-4-[N-methyl-N-(3-(1-methylethoxy)-2-pyridinyl)amino]piperidine (EXAMPLE 80) for 1-[5-nitroindolyl-2-carbonyl]-4-[N-methyl-N-(3-(1,1-dimethylpropylamino)-2-pyridinyl)amino]piperidine, the title compound is obtained, NMR (CDCl$_3$) 9.55, 7.83, 7.24, 7.03, 6.91, 6.75, 6.62, 4.81, 4.55, 4.14, 2.95, 2.86, 2.39, 1.90, 1.37δ.

Example 82

1-[5-(Methanesulfonamido)indolyl-2-carbonyl]-4-[N-methyl-N-(3-(1-methylethoxy)-2-pyridinyl) amino]piperidine (V)

Following the general procedure of EXAMPLE 68, and making non-critical variations but substituting 1-[5-aminoindolyl-2-carbonyl]-4-[N-methyl-N-(3-(1-methylethoxy)-2-pyridinyl)amino]piperidine (EXAMPLE 81) for 1-[5-aminoindolyl-2-carbonyl]-4-[N-methyl-N-(3-(1,1-dimethylpropylamino)-2-pyridinyl)amino]piperidine, the title compound is obtained, NMR (CDCl$_3$) 9.98, 7.84, 7.60, 7.41, 7.20, 7.16, 7.03, 6.75, 4.83, 4.56, 4.18, 3.10, 2.96, 2.86, 1.90 and 1.37δ.

Example 83

1-[Pyrrolyl-2-carbonyl]-4-[N-methyl-N-(3-(1-methylethoxy)-2-pyridinyl)amino]piperidine (V)

Following the general procedure of EXAMPLE 65, and making non-critical variations but substituting pyrrolyl-2-carboxylic acid for indolyl-2-carboxylic acid and 4-[N-Methyl-N-(3-(1-methylethoxy)-2-pyridinyl)amino] piperidine (EXAMPLE 78) for 4-[N-methyl-N-(3-(1,1-dimethylpropylamino)-2-pyridinyl)amino]piperidine, the title compound is obtained, NMR (CDCl$_3$) 9.98, 7.84, 7.02, 6.91, 6.74, 6.54, 6.23, 4.76, 4.55, 4.13, 2.97, 2.84, 1.87 and 1.36δ.

Example 84

1-Benzyl-4-[N-ethyl-N-(3-(1-methylethoxy)-2-pyridinyl)amino]piperidine

Following the general procedure of EXAMPLE 70, and making non-critical variations but substituting 1-benzyl-4-(ethylamino)piperidine (EXAMPLE 11) for 1-benzyl-4-(methylamino)piperidine and 2-bromo-3-(1-methylethoxy) pyridine (EXAMPLE 76) for 2-bromo-3-ethoxypyridine, the title compound is obtained, NMR (CDCl$_3$) 7.84, 7.32–7.22, 6.99, 6.68, 4.52, 3.82, 3.49, 3.40, 2.94, 2.00, 1.85, 1.73, 1.31 and 1.02δ.

Example 85

1-[Pyrrolyl-2-carbonyl]-4-[N-ethyl-N-(3-(1-methylethoxy)-2-pyridinyl)amino]piperidine (V)

A mixture of 1-benzyl-4-[N-ethyl-N-(3-(1-methylethoxy)-2-pyridinyl)amino]piperidine (EXAMPLE 84, 28 mg), palladium-on-carbon (10%, 30 mg) and ammonium formate (15 mg) in methanol (1.6 ml) is degassed, stirred at 65° for 45 min, cooled to 20°–25°, and filtered to remove catalyst. The filtrate is concentrated under reduced pressure to give the deprotected intermediate. In a flame-dried flask under nitrogen, pyrrole-2-carboxylic acid (10 mg) and 1,1'-carbonyldiimidazole (14 mg) are dissolved in dry tetrahydrofuran (0.4 ml) and stirred at 20°–25° for 1 hr. A mixture of the piperidine intermediate (21 mg) in dry tetrahydrofuran (1 ml) is then added, and the mixture is stirred for 18 hrs and concentrated. The residue is taken up in methylene chloride (10 ml), washed with saturated sodium bicarbonate (5 ml), water (5 ml) and saline (5 ml), dried over sodium sulfate, and concentrated under reduced pressure to give the crude product which is chromatographed on a 2000μ preparative silica gel plate eluting with methanol/methylene chloride (2/98 and 4/96). The product band with an R$_f$=0.33–0.39 is then isolated to give the title compound, NMR (CDCl$_3$) 9.60, 7.86, 7.04, 6.92, 6.73, 6.55, 6.25, 4.71, 4.55, 4.13, 3.37, 2.99, 1.93, 1.80, 1.34 and 1.03δ.

Example 86

1-(1,1-Dimethylethoxycarbonyl)-4-(butylamino) piperidine

A mixture of 1-(1,1-dimethylethoxycarbonyl)-4-piperidone (IX, 1.50 g) in methanol (15 ml) under nitrogen is cooled in an ice bath, treated with butylamine (X, 0.93 ml) and sodium cyanoborohydride (235 mg), adjusted to pH 5 with glacial acetic acid as determined on moistened pH test paper, and stirred at 20°–25° for 24 hrs during which additional sodium cyanoborohydride (115 mg) is added. The mixture is then adjusted to pH 3 using hydrochloric acid (3M) and concentrated under reduced pressure, the residue is diluted with water (20 ml) and extracted with ether (2×20 ml), and the organic phase is discarded. The aqueous phase is adjusted to pH 12 with potassium hydroxide, saturated with sodium chloride, and extracted with methylene chloride (3×25 ml). The combined organic phase is dried over sodium sulfate and concentrated under reduced pressure to give the title compound, Anal. Calcd for $C_{14}H_{28}N_2O_2$: C=65.59, H=11.01, N=10.93, found: C=65.44, H=11.05, N=10.81.

Example 87

1-(1,1-Dimethylethoxycarbonyl)-4-[N-butyl-N-(3-nitro-2-pyridinyl)amino]piperidine A mixture of 1-(1,1-dimethylethoxycarbonyl)-4-(butylamino)piperidine (VIII, EXAMPLE 86, 1.30 g), 2-chloro-3-nitropyridine (804 mg) and diisopropylethylamine (1.77 ml) in N-methyl-2-pyrrolidinone (15 ml) is stirred at 85° for 24 hrs, diluted with water (75 ml) and methylene chloride (150 ml), and the layers are separated. The aqueous phase is extracted with methylene chloride (2×25 ml) and the combined organic phase is washed with saline (25 ml), dried over sodium sulfate, and concentrated under reduced pressure at approximately 75°. The residue is chromatographed on silica gel (230–400 mesh, 100 g; eluting with ethyl acetate/hexane (5/95)) to give the title compound, NMR (CDCl$_3$) 8.33, 8.05, 6.73, 4.20, 3.82, 3.30, 2.73, 1.84–1.71, 1.47, 1.40–1.20 and 0.86δ.

Example 88

1-[Indolyl-2-carbonyl]-4-[N-butyl-N-(3-nitro-2-pyridinyl)amino]piperidine

A mixture of 1-(1,1-dimethylethoxycarbonyl)-4-[N-butyl-N-(3-nitro-2-pyridyl)amino]piperidine (EXAMPLE 87, 0.84 g) in dry methylene chloride (10 ml) under nitrogen is cooled in an ice bath and treated with trifluoroacetic acid (2.2 ml). The mixture is stirred at 20°–25° for 4 hrs and then carefully added to a mixture of sodium hydroxide (1.15 g) in ice water (12 ml). The layers are separated and the aqueous phase is extracted with methylene chloride (3×20 ml). The combined organic layer is washed with saline (10 ml), dried over sodium sulfate, and concentrated under reduced pressure to give the deprotected intermediate. A mixture of indolyl-2-carboxylic acid (350 mg) and 1,1'-carbonyldiimidazole (352 mg) in dry tetrahydrofuran (9 ml) under nitrogen is stirred at 20°–25° for 2 hrs and is then treated with a mixture of the deprotected intermediate (550 mg) in dry tetrahydrofuran (4 ml). The resulting mixture is stirred overnight at 20°–25°, concentrated, diluted with methylene chloride (40 ml), washed with water (10 ml), saturated sodium bicarbonate (10 ml) and saline (10 ml), dried over sodium sulfate, and concentrated to give the crude product which is then chromatographed (silica gel, 70–230 mesh, 400 g; eluting with a gradient of ethyl acetate/hexane (25/75–50/50)). Pooling of fractions giving an R$_f$=0.35 by TLC (ethyl acetate/hexane, 50/50) and removal of solvent under reduced pressure gives the title compound, mp 169°–171°.

Example 89

1-[Indolyl-2-carbonyl-4-[N-butyl-N-(3-(1-(methylethylamino)-2-pyridinyl)amino]piperidine (V)

Following the general procedure of EXAMPLE 54, and making non-critical variations but substituting 1-[indolyl-2-carbonyl]-4-[N-butyl-N-(3-nitro-2-pyridinyl)amino]piperidine (EXAMPLE 88) for 1-(1,1-dimethylethoxycarbonyl)-4-[4-N-methyl-N-(3-nitro-2-pyridinyl)amino]piperidine, the title compound is obtained, NMR (CDCl$_3$) 9.51, 7.74, 7.63, 7.42, 7.26, 7.12, 6.95, 6.84, 6.76, 4.68, 3.56, 3.27, 3.09, 1.93, 1.67, 1.24, 1.21 and 0.84δ.

Example 90

1-(1,1-Dimethylethoxycarbonyl)-4-(2-methylpropylamino)piperidine

Following the general procedure of EXAMPLE 86, and making non-critical variations but using 2-methylpropylamine, the title compound is obtained, NMR (CDCl$_3$) 4.03, 2.79, 2.57, 2.43, 1.83, 1.71, 1.45, 1.23 and 0.91δ.

Example 91

1-(1,1-Dimethylethoxycarbonyl)-4-[N-(2-methylpropyl)-N-(3-nitro-2-pyridinyl)amino]piperidine Following the general procedure of EXAMPLE 87, and making non-critical variations but substituting 1-(1,1-dimethylethoxycarbonyl)-4-(2-methylpropylamino)piperidine (EXAMPLE 90) for 1-(1,1-dimethylethoxycarbonyl)-4-(butylamino)piperidine, the title compound is obtained, NMR (CDCl$_3$) 8.35, 8.09, 6.77, 4.20, 3.58, 3.10, 2.70, 1.85–1.65, 1.47 and 0.83δ.

Example 92

1-[Indolyl-2-carbonyl]-4-[N-(2-methylpropyl)-N-(3-nitro-2-pyridinyl)amino]piperidine Following the general procedure of EXAMPLE 88, and making non-critical variations but substituting 1-(1,1-dimethylethoxycarbonyl)-4-[N-(2-methylpropyl)-N-(3-nitro-2-pyridinyl)amino]piperidine (EXAMPLE 91) for 1-(1,1-dimethylethoxycarbonyl)-4-[N-butyl-N-(3-nitro-2-pyridinyl)amino]piperidine, the title compound is obtained, mp 189°–190°.

Example 93

1-[Indolyl-2-carbonyl]-4-[N-(2-methylpropyl)-N-(3-(1-methylethylamino)-2-pyridinyl)amino]piperidine (V)

Following the general procedure of EXAMPLE 54, and making non-critical variations but substituting 1-[indolyl-2-carbonyl]-4-[N-(2-methylpropyl)-N-(3-nitro-2-pyridinyl)amino]piperidine (EXAMPLE 92) for 1-(1,1-dimethylethoxycarbonyl)-4-[4-N-methyl-N-(3-nitro-2-pyridinyl)amino]piperidine and using a dimethylformamide/ethanol (50/50) solvent mixture in the reductive alkylation step, the title compound is obtained, mp=206°–208°.

Example 94

1-(1,1-Dimethylethoxycarbonyl)-4-(cyclopropylamino)piperidine

Following the general procedure of EXAMPLE 86, and making non-critical variations but substituting cyclopropylamine for butylamine, the title compound is obtained, C,H,N: Anal. Calcd for $C_{13}H_{24}N_2O_2$: C=64.97, H=10.07, N=11.66-found: C=65.02, H=10.46, N=11.68.

Example 95

1-(1,1-Dimethylethoxycarbonyl)-4-[N-cyclopropyl-N-(3-nitro-2-pyridinyl)amino]piperidine Following the general procedure of EXAMPLE 87, and making non-critical variations but substituting 1-(1,1-dimethylethoxycarbonyl)-4-(cyclopropylamino)piperidine (EXAMPLE 94) for 1-(1,1-dimethylethoxycarbonyl)-4-(butylamino)piperidine, the title compound is obtained, NMR (CDCl$_3$) 8.28, 8.05, 6.72, 4.50, 4.23, 2.83, 2.57, 2.06, 1.49, 0.70 and 0.45δ.

Example 96

1-(1,1-Dimethylethoxycarbonyl)-4-[N-cyclopropyl-N-(3-(1-methylethylamino)-2-pyridinyl)amino]piperidine Following the general procedure of EXAMPLE 54, and making non-critical variations but substituting 1-(1,1-dimethylethoxycarbonyl)-4-[N-cyclopropyl-N-(3-nitro-2-pyridinyl)amino]piperidine (EXAMPLE 95) for 1-(1,1-dimethylethoxycarbonyl)-4-[4-N-methyl-N-(3-nitro-2-pyridinyl)amino]piperidine, the title compound is obtained, C,H,N: Anal. Calcd for C$_{21}$H$_{34}$N$_4$O$_2$: C=67.35. H=9.15, N=14.96-found: C=66.95, H=9.31, N=14.57.

Example 97

1-[Indolyl-2-carbonyl]-4-[N-cyclopropyl-N-(3-(1-methylethylamino)-2-pyridinyl)amino]piperidine
(V)

Following the general procedure of EXAMPLE 88, and making non-critical variations but substituting 1-(1,1-dimethylethoxycarbonyl)-4-[N-cyclopropyl-N-(3-(1-methylethylamino)-2-pyridinyl)amino]piperidine (EXAMPLE 96) for 1-(1,1-dimethylethoxycarbonyl)-4-[N-butyl-N-(3-nitro-2-pyridinyl)amino]piperidine, the title compound is obtained, NMR (CDCl$_3$) 9.38, 7.77, 7.63, 7.26, 7.12, 6.98, 6.83, 6.76, 4.70, 4.50, 3.60–3.40, 3.05, 2.61, 2.30, 1.70, 1.17, 0.54 and 0.37δ.

Example 98

1-[5-(Methanesulfonamido)indolyl-2-carbonyl]-4-[N-cyclopropyl-N-(3-(1-methylethylamino)-2-pyridinyl)amino]piperidine (V)

Following the general procedure of EXAMPLE 88, and making non-critical variations but substituting 1-(1,1-dimethylethoxycarbonyl)-4-[N-cyclopropyl-N-(3-(1-methylethylamino)-2-pyridinyl)amino]piperidine (EXAMPLE 96) for 1-(1,1-dimethylethoxycarbonyl)-4-[N-butyl-N-(3-nitro-2-pyridyl)amino]piperidine and 5-(methanesulfonamido)indolyl-2-carboxylic acid for indolyl-2-carboxylic acid, the title compound is obtained, mp 138°–140° (decomp).

Example 99

1-Benzyl-4-(1-methylethylamino)piperidine

Following the general procedure of EXAMPLE 86, and making non-critical variations but substituting 1-benzyl-4-piperidone for 1-(1,1-dimethylethoxycarbonyl)-4-piperidone and isopropylamine for butylamine, the title compound is obtained, NMR (CDCl$_3$) 7.32–7.22, 3.49, 2.97, 2.85, 2.53, 2.00, 1.85, 1.39–1.15 and 1.03δ.

Example 100

1-Benzyl-4-[N-(1-methylethyl)-N-(3-nitro-2-pyridinyl)amino]piperidine

Following the general procedure of EXAMPLE 70, and making non-critical variations but substituting 1-benzyl-4-(1-methylethylamino)piperidine (EXAMPLE 99) for 1-benzyl-4-(methylamino)piperidine and 2-chloro-3-nitropyridine for 2-bromo-3-ethoxypyridine and using a reaction time of 2 hrs, the title compound is obtained, NMR (CDCl$_3$) 8.24, 7.90, 7.31–7.23, 6.62, 3.61, 3.49, 2.97, 2.27, 1.96, 1.77 and 1.39δ.

Example 101

1-Benzyl-4-[N-(1-methylethyl)-N-(3-(1-methylethylamino)-2-pyridinyl)amino]piperidine A mixture of 1-benzyl-4-[N-(1-methylethyl)-N-(3-nitro-2-pyridinyl)amino]piperidine (EXAMPLE 100, 205 mg) in aqueous titanium (III) chloride (2.36 ml, 19 wt % in 20% aqueous hydrochloric acid) is stirred under reduced pressure for 18 hrs and then added to concentrated aqueous ammonium hydroxide (15 ml), and the resulting mixture is extracted with methylene chloride (3×30 ml). The combined organic phase is washed with saline (10 ml), dried over sodium sulfate, and concentrated under reduced pressure. The concentrate in absolute ethanol (4 ml) under nitrogen is treated with acetone (0.50 ml) and sodium cyanoborohydride (14 mg) and the pH is adjusted to 5 with glacial acetic acid as measured on moistened pH test paper. The resulting mixture is stirred at 20°–25° for 48 hrs, during which additional acetone (0.50 ml) and sodium cyanoborohydride (14 mg) is added, and is then adjusted to pH 3 with hydrochloric acid (3M), neutralized with aqueous sodium hydroxide (5%), and concentrated under reduced pressure. The residue is chromatographed (silica gel, 70–230 mesh, 16 g; eluting with a gradient of ethyl acetate/hexane (10/90–25/75)) to give the title compound, NMR (CDCl$_3$) 7.72, 7.30–7.18, 6.91, 6.74, 5.06, 3.60–3.47, 3.44, 3.22, 2.83, 1.95, 1.75, 1.46, 1.16 and 1.01δ.

Example 102

1-[Indolyl-2-carbonyl]-4-[N-(1-methylethyl)-N-(3-(1-methylethylamino)-2-pyridinyl)amino]piperidine
(V)

Following the general procedure of EXAMPLE 85, and making non-critical variations but substituting 1-benzyl-4-[N-(1-methylethyl)-N-(3-(1-methylethylamino)-2-pyridinyl)amino]piperidine (EXAMPLE 101) for 1-benzyl-4-[N-ethyl-N-(3-(1-methylethoxy)-2-pyridinyl)amino]piperidine and indolyl-2-carboxylic acid for pyrrole-2-carboxylic acid, the title compound is obtained, mp 172°–174°.

Example 103

1-Benzyl-4-(cyclopentylamino)piperidine

Following the general procedure of EXAMPLE 86, and making non-critical variations but substituting 1-benzyl-4-piperidone for 1-(1,1-dimethylethoxycarbonyl)-4-piperidone and cyclopentylamine for butylamine, the title compound is obtained, NMR (CDCl$_3$) 7.31–7.20, 3.49, 3.20, 2.85, 2.49, 2.00, 1.85, 1.67 and 1.24δ.

Example 104

1-Benzyl-4-[N-cyclopentyl-N-(3-nitro-2-pyridinyl)amino]piperidine

Following the general procedure of EXAMPLE 70, and making non-critical variations but substituting 1-benzyl-4-

(1-cyclopentylamino)piperidine (EXAMPLE 103) for 1-benzyl-4-(methylamino)piperidine and 2-chloro-3-nitropyridine for 2-bromo-3-ethoxypyridine and using a reaction time of 2 hrs, the title compound is obtained, NMR (CDCl$_3$) 8.26, 7.91, 7.33–7.21, 6.67, 3.78, 3.47, 2.97–2.86, 2.11, 1.98–1.75 and 1.50$\delta$.

Example 105

1-Benzyl-4-[N-cyclopentyl-N-(3-(1-methylethylamino)-2-pyridinyl)amino]piperidine Following the general procedure of EXAMPLE 101, and making non-critical variations but substituting 1-benzyl-4-[N-cyclopentyl-N-(3-nitro-2-pyridinyl)amino]piperidine (EXAMPLE 104) for 1-benzyl-4-[N-(1-methylethyl)-N-(3-nitro-2-pyridinyl)amino]piperidine, the title compound is obtained, NMR (CDCl$_3$) 7.71, 7.24, 6.91, 6.74, 5.03, 3.74, 3.50, 3.45, 3.08, 2.86, 2.05–1.20 and 1.17$\delta$.

Example 106

1-[Indolyl-2-carbonyl]-4-[N-cyclopentyl-N-(3-(1-methylethylamino)-2-pyridinyl)amino]piperidine
(V)

Following the general procedure of EXAMPLE 85, and making non-critical variations but substituting 1-benzyl-4-[N-cyclopentyl-N-(3-(1-methylethylamino)-2-pyridinyl)amino]piperidine (EXAMPLE 105) for 1-benzyl-4-[N-ethyl-N-(3-(1-methylethoxy)-2-pyridinyl)amino]piperidine and indolyl-2-carboxylic acid for pyrrole-2-carboxylic acid, the title compound is obtained, mp 177°–180° (decomp).

Example 107

1-Benzyl-4-(2-(methoxy)ethylamino)piperidine

Following the general procedure of EXAMPLE 86, and making non-critical variations but substituting 1-benzyl-4-piperidone for 1-(1,1-dimethylethoxycarbonyl)-4-piperidone and 2-(methoxy)ethylamine for butylamine, the title compound is obtained, NMR (CDCl$_3$) 7.32–7.21, 3.50, 3.35, 2.85, 2.79, 2.45, 2.01, 1.84, 1.63 and 1.41$\delta$.

Example 108

1-Benzyl-4-[N-(2-methoxyethyl)-N-(3-nitro-2-pyridinyl)amino]piperidine

Following the general procedure of EXAMPLE 70, and making non-critical variations but substituting 1-benzyl-4-(2-(methoxy)ethylamino)piperidine (EXAMPLE 107) for 1-benzyl-4-(methylamino)piperidine and 2-chloro-3-nitropyridine for 2-bromo-3-ethoxypyridine and using a reaction time of 2 hrs, the title compound is obtained, C,H,N: Anal. Calcd for $C_{20}H_{26}N_4O_3$: C=64.85, H=7.07, N=15.12-found: C=64.66, H=7.08, N=14.88.

Example 109

1-Benzyl-4-[N-(2-methoxyethyl)-N-(3-(1-methylethylamino)-2-pyridinyl)amino]piperidine Following the general procedure of EXAMPLE 101, and making non-critical variations but substituting 1-benzyl-4-[N-(2-methoxyethyl)-N-(3-nitro-2-pyridinyl)amino]piperidine (EXAMPLE 108) for 1-benzyl-4-[N-(1-methylethyl)-N-(3-nitro-2-pyridinyl)amino]piperidine, the title compound is obtained, NMR (CDCl$_3$) 7.68, 7.29, 6.91, 6.79, 4.81, 3.49, 3.29, 3.24, 3.21, 2.90, 1.95, 1.74 and 1.19$\delta$.

Example 110

1-[Indolyl-2-carbonyl]-4-[N-(2-methoxyethyl)-N-(3-(1-methylethylamino)-2-pyridinyl)amino]piperidine
(V)

Following the general procedure of EXAMPLE 85, and making non-critical variations but substituting 1-benzyl-4-[N-(2-methoxyethyl)-N-(3-(1-methylethylamino)-2-pyridinyl)amino]piperidine (EXAMPLE 109) for 1-benzyl-4-[N-ethyl-N-(3-(1-methylethoxy)-2-pyridinyl)amino]piperidine and indolyl-2-carboxylic acid for pyrrole-2-carboxylic acid, the title compound is obtained, mp=164°–165°.

Example 111

1-[Pyrrole-2-carbonyl]-4-[N-(2-methoxyethyl)-N-(3-(1-methylethylamino)-2-pyridinyl)amino]piperidine
(V)

Following the general procedure of EXAMPLE 85, and making non-critical variations but substituting 1-benzyl-4-[N-(2-methoxyethyl)-N-(3-(1-methylethylamino)-2-pyridinyl)amino]piperidine (EXAMPLE 109) for 1-benzyl-4-[N-ethyl-N-(3-(1-methylethoxy)-2-pyridinyl)amino]piperidine, the title compound is obtained, NMR (CDCl$_3$) 10.04, 7.71, 6.95, 6.87, 6.82, 6.49, 6.20, 4.88, 4.58, 3.54, 3.32–3.21, 2.97, 1.91, 1.60 and 1.20$\delta$.

Example 112

1-Benzyl-4-(propylamino)piperidine

Following the general procedure of EXAMPLE 86, and making non-critical variations but substituting 1-benzyl-4-piperidone for 1-(1,1-dimethylethoxycarbonyl)-4-piperidone and propylamine for butylamine, the title compound is obtained, NMR (CDCl$_3$) 7.31, 7.24, 3.50, 2.85, 2.59, 2.46, 2.02, 1.85, 1.50, 1.39 and 0.92$\delta$.

Example 113

1-Benzyl-4-[N-propyl-N-(3-nitro-2-pyridinyl)amino]piperidine

Following the general procedure of EXAMPLE 70, and making non-critical variations but substituting 1-benzyl-4-(propylamino)piperidine (EXAMPLE 112) for 1-benzyl-4-(methylamino)piperidine and 2-chloro-3-nitropyridine for 2-bromo-3-ethoxypyridine and using a reaction time of 10 min, the title compound is obtained, C,H,N: Anal. Calcd for $C_{20}H_{26}N_4O_2$: C=67.77, H=7.39, N=15.81-found: C=67.44, H=7.42, N=15.60.

Example 114

1-Benzyl-4-[N-propyl-N-(3-amino-2-pyridinyl)amino]piperidine

A mixture of 1-benzyl-4-[N-propyl-N-(3-nitro-2-pyridinyl)amino]piperidine (EXAMPLE 113, 2.61 g) in aqueous titanium (III) chloride (30 ml, 19 wt % in 20% aqueous hydrochloric acid) is stirred under reduced pressure for 18 hrs and then added to concentrated aqueous ammonium hydroxide (250 ml), and the resulting mixture is extracted with methylene chloride (4×100 ml). The combined organic phase is washed with saline (50 ml), dried over sodium sulfate, and concentrated under reduced pressure to give the crude product which is then chromatographed (silica gel, 230–400 mesh, 150 g; eluting with a gradient of methanol/methylene chloride (2.5/97.5–5/95)) to give the title compound, mp=73°–74°.

Example 115

1-Benzyl-4-[N-propyl-N-(3-ethylamino-2-pyridinyl) amino]piperidine

A mixture of 1-benzyl-4-[N-propyl-N-(3-amino-2-pyridinyl)amino]piperidine (EXAMPLE 114, 0.35 g) in absolute ethanol (4.3 ml) under nitrogen is treated with acetaldehyde (120 μl) and sodium cyanoborohydride (84 mg) and the pH is adjusted to 5 with glacial acetic acid as measured on moistened pH test paper. The resulting mixture is stirred at 20°–25° for 48 hrs, during which additional acetaldehyde (180 μl) and sodium cyanoborohydride (70 mg) is added, and is then adjusted to pH 3 with hydrochloric acid (3M), neutralized with sodium hydroxide (5%), and concentrated under reduced pressure. The residue is chromatographed (silica gel, 70–230 mesh, 35 g; eluting with a gradient of methanol/methylene chloride (1/99–2/98)) to give the title compound, NMR (CDCl$_3$) 7.72, 7.31, 7.27, 6.91, 6.79, 4.66, 3.51, 3.10, 2.92, 2.05, 1.74, 1.27 and 0.79δ.

Example 116

1-[5-(Methanesulfonamido)indolyl-2-carbonyl]-4-[N-propyl-N-(3-ethylamino-2-pyridinyl)amino] piperidine (V)

Following the general procedure of EXAMPLE 85, and making non-critical variations but substituting 1-benzyl-4-[N-propyl-N-(3-ethylamino-2-pyridinyl)amino]piperidine (EXAMPLE 115) for 1-benzyl-4-[N-ethyl-N-(3-(1-methylethoxy)-2-pyridinyl)amino]piperidine and 5-(methanesulfonamido)indolyl-2-carboxylic acid for pyrrole-2-carboxylic acid, the title compound is obtained, mp 133°–135° (decomp).

Example 117

1-Benzyl-4-[N-propyl-N-(3-(1-methylethylamino-2-pyridinyl)amino]piperidine

Following the general procedure of EXAMPLE 115, and making non-critical variations but substituting acetone for acetaldehyde, the title compound is obtained, C,H,N: Anal. Calcd for $C_{23}H_{34}N_4$: C=75.37, H=9.35, N=15.28-found: C=75.02, H=9.24, N=15.00.

Example 118

1-[5-(Methanesulfonamido)indolyl-2-carbonyl]-4-[N-propyl-N-(3-(1-methylethylamino)-2-pyridinyl) amino]piperidine (V)

Following the general procedure of EXAMPLE 85, and making non-critical variations but substituting 1-benzyl-4-[N-propyl-N-(3-(1-methylethylamino)-2-pyridinyl)amino] piperidine (EXAMPLE 117) for 1-benzyl-4-[N-ethyl-N-(3-(1-methylethoxy)-2-pyridinyl)amino]piperidine and 5-(methanesulfonamido)indolyl-2-carboxylic acid for pyrrole-2-carboxylic acid, the title compound is obtained, mp 177°–179° (decomp).

Example 119

1-Benzyl-4-[N-propyl-N-(3-(1,1-dimethylethylamino)-2-pyridinyl)amino]-piperidine A mixture of 1-benzyl-4-[N-propyl-N-(3-amino-2-pyridinyl)amino]piperidine (EXAMPLE 114, 0.50 g), 2-methoxypropene (0.74 ml) and pyridinium 4-toluenesulfonate (19 mg) is stirred at 100° in a sealed tube for 4 hrs, cooled to 20°–25°, diluted with saturated aqueous sodium carbonate (10 ml), and extracted with ether (3×10 ml). The combined organic phase is dried over anhydrous potassium carbonate and concentrated under reduced pressure to give the imine intermediate in quantitative yield. A mixture of this intermediate in dry toluene in a flame-dried flask under nitrogen at −78° is then treated with methyllithium lithium bromide (1.5M in ether, 5.1 ml) dropwise, and the resulting mixture is warmed to 0° over 2 hrs, stirred at 0° for 1 hr, quenched carefully with half-saturated aqueous sodium carbonate (10 ml), diluted with ether, and stirred at 0° for an additional hour. The mixture is then diluted with water (10 ml), the layers are separated, the aqueous phase is extracted with ether (20 ml), and the combined organic phases are washed with saline (10 ml), dried over sodium sulfate, and concentrated under reduced pressure. The crude product is chromatographed (silica gel, 230–400 mesh, 40 g; eluting with a gradient of methanol/methylene chloride (1/99–3/97)) to give the title compound, NMR (CDCl$_3$) 7.69, 7.31, 7.25, 7.05, 6.85, 5.13, 3.49, 3.05, 2.89, 1.97, 1.73, 1.36, 1.25 and 0.81δ.

Example 120

1-[5-(Methanesulfonamido)indolyl-2-carbonyl]-4-[N-propyl-N-(3-(1,1-dimethylethylamino)-2-pyridinyl)amino]piperidine (V)

Following the general procedure of EXAMPLE 85, and making non-critical variations but substituting 1-benzyl-4-[N-propyl-N-(3-(1,1-dimethylethylamino)-2-pyridinyl) amino]-piperidine (EXAMPLE 119) for 1-benzyl-4-[N-ethyl-N-(3-(1-methylethoxy)-2-pyridinyl)amino]-piperidine and 5-(methanesulfonamido)indolyl-2-carboxylic acid for pyrrole-2-carboxylic acid, the title compound is obtained, mp 195°–197° (decomp).

Example 121

1-Benzyl-4-[N-methyl-N-(3-nitro-2-pyridinyl) amino]piperidine

A mixture of 1-benzyl-4-methylaminopiperidine (EXAMPLE 9, 10.8 g), 2-chloro-3-nitropyridine (6.7 g) and anhydrous potassium carbonate (14.6 g) in dry acetonitrile (211 ml) is stirred under nitrogen at 20°–25° for 5 days. The mixture is then concentrated under reduced pressure, diluted with methylene chloride (200 ml) and water (50 ml), and the phases are separated. The organic phase is washed with saline (50 ml), dried over sodium sulfate and concentrated under reduced pressure to give the crude product which is then chromatographed (silica gel, 70–230 mesh, 100 g; eluting with ethyl acetate/hexane (50/50) to give the title compound, mp=92°–95°.

Example 122

1-Benzyl-4-[N-methyl-N-(3-amino-2-pyridinyl) amino]piperidine

Following the general procedure of EXAMPLE 114, and making non-critical variations but substituting 1-benzyl-4-[N-methyl-N-(3-nitro-2-pyridinyl)amino]piperidine (EXAMPLE 121) for 1-benzyl-4-[N-propyl-N-(3-nitro-2-pyridinyl)amino]piperidine, the title compound is obtained, NMR (CDCl$_3$) 7.80, 7.25, 6.93, 6.82, 3.85, 3.48, 3.14, 2.88, 2.68, 2.00 and 1.74δ.

Example 123

1-Benzyl-4-[N-methyl-N-(3-(1-ethoxycyclopropylamino)-2-pyridinyl)amino]piperidine A mixture of 1-benzyl-4-[N-methyl-N-(3-amino-2-pyridinyl)amino]piperidine (EXAMPLE 122, 825 mg), 1-bromo-1-ethoxycyclopropane (919 mg) and triethylamine (0.78 ml) in dry tetrahydrofuran (1.4 ml) under nitrogen is refluxed for 48 hrs, cooled to 20°–25°, diluted with methylene chloride (30 ml), washed with saline (10 ml), dried over sodium sulfate and concentrated under reduced pressure to give the crude product. The residue is chromatographed (silica gel, 70–230 mesh, 140 g; eluting with a gradient of methanol/methylene chloride (1/99–5/95)) to give the title compound, NMR ($CDCl_3$) 7.80, 7.41, 7.25, 6.93, 5.62, 3.51, 3.48, 3.03, 2.87, 2.60, 1.98, 1.71, 1.64, 1.13 and 0.85$\delta$.

Example 124

1-Benzyl-4-[N-methyl-N-(3-(cyclopropylamino)-2-pyridinyl)amino]piperidine

A mixture of 1-benzyl-4-[N-methyl-N-(3-(1-ethoxycyclopropylamino)-2-pyridinyl)amino]piperidine (EXAMPLE 123, 178 mg) in dry tetrahydrofuran (4.7 ml) under nitrogen is treated with lithium aluminum hydride (18 mg), and the resulting mixture is stirred at 20°–25° for 1 hr, quenched with saturated aqueous ammonium chloride (5 ml), diluted with water (30 ml) and methylene chloride (20 ml), and filtered through diatomaceous earth. The layers of the filtrate are separated, the aqueous phase is extracted with methylene chloride (2×10 ml), and the combined organic phase is washed with saline (10 ml), dried over sodium sulfate and concentrated under reduced pressure. The crude product is then chromatographed (silica gel 230–400 mesh, 40 g; eluting with a gradient of methanol/methylene chloride (2.5/97.5–5/95)) to give the title compound, NMR ($CDCl_3$) 7.75, 7.31. 7.24, 7.21, 6.92, 4.92, 3.50, 3.04, 2.89, 2.62, 2.35, 1.99, 1.70, 0.75 and 0.51$\delta$.

Example 125

1-[5-(Methanesulfonamido)indolyl-2-carbonyl]-4-[N-methyl-N-(3-(cyclopropylamino)-2-pyridinyl)amino]piperidine (V)

Following the general procedure of EXAMPLE 85, and making non-critical variations but substituting 1-benzyl-4-[N-methyl-N-(3-(cyclopropylamino)-2-pyridinyl)amino]piperidine (EXAMPLE 124) for 1-benzyl-4-[N-ethyl-N-(3-(1-methylethoxy)-2-pyridinyl)amino]piperidine and 5-(methanesulfonamido)indolyl-2-carboxylic acid for pyrrole-2-carboxylic acid, the title compound is obtained, mp 175° (decomp).

Example 126

1-Benzyl-4-[N-methyl-N-(3-(1-methylcyclopropylamino)-2-pyridinyl)amino]piperidine To a mixture of methyllithium-lithium bromide (1.5M in ether, 2.28 ml) in dry toluene (6.3 ml) at −78° under nitrogen in a flame-dried flask is added a mixture of 1-benzyl-4-[N-methyl-N-(3-(1-ethoxycyclopropylamino)-2-pyridinyl)amino]piperidine (EXAMPLE 123, 325 mg) in dry toluene (8.5 ml) at −78°. The mixture is stirred at −78° C. for 1 hr, quenched carefully with saturated aqueous ammonium chloride (10 ml) and water (10 ml) and warmed to 20°–25°. The mixture is extracted with ethyl acetate (25 ml) and the organic phase is washed with water (10 ml) and saline (10 ml), dried over magnesium sulfate and concentrated to give the crude product which is chromatographed (silica gel, 230–400 mesh, 35 g; eluting with a gradient of methanol/chloroform (1/99–4/96)) to give the title compound, NMR ($CDCl_3$) 7.72, 7.31, 7.25, 7.17, 6.91, 5.02, 3.50, 3.02, 2.88, 2.59, 2.01, 1.71, 1.32, 0.75 and 0.65$\delta$.

Example 127

1-[5-(Methanesulfonamido)indolyl-2-carbonyl]-4-[N-methyl-N-(3-(1-methylcyclopropylamino)-2-pyridinyl)amino]piperidine (V)

Following the general procedure of EXAMPLE 85, and making non-critical variations but substituting 1-benzyl-4-[N-methyl-N-(3-(1-methylcyclopropylamino)-2-pyridinyl)amino]piperidine (EXAMPLE 126) for 1-benzyl-4-[N-ethyl-N-(3-(1-methylethoxy)-2-pyridinyl)amino]piperidine and 5-(methanesulfonamido)indolyl-2-carboxylic acid for pyrrole-2-carboxylic acid, the title compound is obtained, mp 201°–204° (decomp).

Example 131 cis- and trans-1-Benzyl-3-methyl-4-[N-methyl-N-(3-nitro-2-pyridinyl)amino]piperidine A mixture of methylamine hydrochloride (1.40 g) in methanol (30 ml) at 0° under nitrogen is treated with potassium hydroxide pellets (331 mg) followed by the racemic 1-benzyl-3-methyl-4-piperidone (3.00 g) and is stirred at 0° for 20 min. Then sodium cyanoborohydride (371 mg) is added, and the reaction mixture is warmed to 20°–25° and stirred at 20°–25° for 18 hrs. The mixture is then adjusted to pH 2.5 with 3M aqueous hydrochloric acid, concentrated under reduced pressure, diluted with water (40 ml), adjusted to pH 12 with potassium hydroxide pellets, saturated with sodium chloride, and extracted with methylene chloride (3×40 ml). The combined organic phase is dried over sodium sulfate and concentrated under reduced pressure to give the 1-benzyl-3-methyl-4-(methylamino)piperidine intermediate as a diastereomeric mixture.

Then, following the general procedure of EXAMPLE 121, and making non-critical variations but substituting the 1-benzyl-3-methyl-4-(methylamino)piperidine intermediate for 1-(1-benzyl)-4-(methylamino)piperidine, the title compounds are obtained, NMR ($CDCl_3$) (cis isomer) 8.26, 8.07, 7.35–7.22, 6.62, 4.73, 3.48, 3.01, 2.75, 2.67, 2.41, 2.33–2.11, 1.67 and 1.15$\delta$ and (trans isomer) 8.26, 8.09, 7.34–7.23, 6.62, 4.19, 3.53, 2.96, 2.66, 2.18, 2.02, 1.96–1.77 and 0.84$\delta$.

Example 132 cis-1-Benzyl-3-methyl-4-[N-methyl-N-(3-(1-methylethylamino)-2-pyridinyl)amino]piperidine Following the general procedure of EXAMPLE 101, and making non-critical variations but substituting cis-1-benzyl-3-methyl-4-[N-methyl-N-(3-nitro-2-pyridinyl)amino]piperidine (EXAMPLE 131) for 1-benzyl-4-[N-(1-methylethyl)-N-(3-nitro-2-pyridinyl)amino]piperidine, the title compound is obtained, NMR ($CDCl_3$) 7.69, 7.33–7.20, 6.92, 6.80, 4.89, 3.55, 3.42, 3.20, 2.77, 2.67, 2.48, 2.12–1.94, 1.55, 1.42, 1.21 and 1.04$\delta$.

Example 133 trans-1-Benzyl-3-methyl-4-[N-methyl-N-(3-(1-methylethylamino)-2-pyridinyl)amino]piperidine Following the general procedure of EXAMPLE 101, and making non-critical variations but substituting trans-1-benzyl-3-methyl-4-[N-methyl-N-(3-nitro-2-pyridinyl) amino]piperidine (EXAMPLE 131) for 1-benzyl-4-[N-(1-methylethyl)-N-(3-nitro-2-pyridinyl)amino]piperidine, the title compound is obtained, NMR (CDCl$_3$) 7.68, 7.34–7.22, 6.85, 6.77, 4.22, 3.59–3.40, 2.84, 2.72, 2.71, 2.10–1.85, 1.69, 1.49, 1.24, 1.19 and 1.00$\delta$.

Example 134 cis-1-[5-(Methanesulfonamido)indolyl-2-carbonyl]-3-methyl-4-[N-methyl-N-(3-(1-methylethylamino)-2-pyridyl)amino]piperidine (V)

Following the general procedure of EXAMPLE 85, and making non-critical variations but substituting cis-1-benzyl-3-methyl-4-[N-methyl-N-(3-(1-methylethylamino)-2-pyridinyl)amino]piperidine (EXAMPLE 132) for 1-benzyl-4-[N-ethyl-N-(3-(1-methylethoxy)-2-pyridinyl)amino]piperidine and 5-(methanesulfonamido)indolyl-2-carboxylic acid for pyrrole-2-carboxylic acid, the title compound is obtained, NMR (CDCl$_3$) 9.95, 7.72, 7.58, 7.39, 7.35, 7.14, 6.97, 6.84, 6.72, 4.75–4.50, 3.56, 3.30–2.80, 2.95, 2.52, 2.28, 1.66, 1.58, 1.20 and 0.92$\delta$.

Example 135 trans-1-[5-(Methanesulfonamido)indolyl-2-carbonyl]-3-methyl-4-[N-methyl-N-(3-(1-methylethylamino)-2-pyridyl)amino]piperidine (V)

Following the general procedure of EXAMPLE 85, and making non-critical variations but substituting trans-1-benzyl-3-methyl-4-[N-methyl-N-(3-(1-methylethylamino)-2-pyridinyl)amino]piperidine (EXAMPLE 133) for 1-benzyl-4-[N-ethyl-N-(3-(1-methylethoxy)-2-pyridinyl) amino]piperidine and 5-(methanesulfonamido)indolyl-2-carboxylic acid for pyrrole-2-carboxylic acid, the title compound is obtained, NMR (CDCl$_3$) 9.95, 7.71, 7.60, 7.40, 7.22, 7.16, 6.91, 6.85, 6.72, 4.68, 4.28, 3.58, 3.08, 2.96, 2.70, 3.10–2.50 (low, broad), 2.05, 1.90, 1.79. 1.28, 1.22 and 1.15$\delta$.

Example 136

1-Benzyl-4-[N-methyl-N-(3-methoxycarbonyl-2-pyridyl)amino]piperidine

A mixture of 1-benzyl-4-(methylamino)piperidine (EXAMPLE 9, 8.00 g) and methyl 2-chloro-3-nicotinate (3.36 g) is placed in a sealed tube and maintained at 115°–120° for 2 hrs. The residue is diluted with methylene chloride (125 ml), washed with water (2×50 ml) and saline (25 ml), dried over sodium sulfate and concentrated under reduced pressure. The resulting semi-solid is then chromatographed (silica gel, 230–400 mesh, 350 g; eluting with a gradient of ethyl acetate/hexane (25/75–50/50)) to give the title compound, mp 109°–110°.

Example 137

1-[5-(Methanesulfonylamino)indolyl-2-carbonyl]-4-[N-methyl-N-(3-methoxycarbonyl-2-pyridyl)amino] piperidine (V)

A mixture of 1-benzyl-4-[N-methyl-N-(3-methoxycarbonyl-2-pyridyl)amino]piperidine (EXAMPLE 136, 250 mg) and palladium hydroxide-on-carbon (20%, 45% moisture, 100 mg) in methanol (14 ml) is shaken on a Parr hydrogenation apparatus under a hydrogen atmosphere at 40 psi for 2 hrs and at 28 psi for 16 hrs. The catalyst is then removed by filtration through diatomaceous earth and the filtrate is concentrated under reduced pressure and flushed through a short pad of silica gel (70–230 mesh, 5 g), eluting with a gradient of methanol/methylene chloride (5/95–20/80). Pooling of fractions with an R$_f$=0.06 by TLC (methanol/chloroform, 20/80) and removal of solvent under reduced pressure gives 4-[N-methyl-N-(3-methoxycarbonyl-2-pyridyl)amino]piperidine. To a flame-dried flask under nitrogen is added 5-(methanesulfonylamino)indolyl-2-carboxylic acid (135 mg), 1,1-carbonyldiimidazole (754 mg) and dry tetrahydrofuran (2.5 ml) and the mixture is stirred at 20°–25° for 1 hr. Then a mixture of the debenzylated intermediate 4-[N-methyl-N-(3-methoxycarbonyl-2-pyridyl)amino]piperidine (110 mg), in dry tetrahydrofuran (3 ml) is added and the resultant mixture is stirred at 20°–25° for 20 hrs and concentrated under reduced pressure to remove solvent. The residue is diluted with methylene chloride (20 ml), washed with water (5 ml), saturated aqueous sodium bicarbonate (5 ml) and saline (5 ml), dried over sodium sulfate, concentrated under reduced pressure and chromatographed (silica gel, 230–400 mesh, 25 g; eluting with a gradient of methanol/methylene chloride (1/99–3/97)). Pooling of fractions with an R$_f$=0.28 by TLC (methanol/chloroform, 5/95) and removal of solvent under reduced pressure gives the title compound, mp 223°–224°.

Example 138

1-Benzyl-4-[N-ethyl-N-(3-(1-methylethylamino)-2-pyridinyl)amino]piperidine

Following the general procedure of EXAMPLE 115 and making non-critical variations but substituting 1-benzyl-4-[N-ethyl-N-(3-amino-2-pyridinyl)amino]piperidine (PREPARATION 4) for 1-benzyl-4-[N-propyl-N-(3-amino-2-pyridinyl)amino]piperidine and acetone for acetaldehyde, the title compound is obtained, NMR (CDCl$_3$) 7.71, 7.30, 7.25, 6.80, 4.72, 3.55, 3.50, 3.11, 3.00, 2.88, 2.00, 1.74, 1.66, 1.20 and 0.86$\delta$.

Example 139

1-[5-Nitroindolyl-2-carbonyl]-4-[N-ethyl-N-(3-(1-methylethylamino)-2-pyridinyl)amino]piperidine (V)

Following the general procedure of EXAMPLE 137 and making non-critical variations but substituting 1-benzyl-4-[N-ethyl-N-(3-(1-methylethylamino)-2-pyridinyl)amino] piperidine (EXAMPLE 138) for 1-benzyl-4-[N-methyl-N-(3-methoxycarbonyl-2-pyridyl)amino]piperidine and 5-nitroindolyl-2-carboxylic acid for 5-(methanesulfonamido)indolyl-2-carboxylic acid and triturating the crude product with methanol, the title compound is obtained, mp=198°–200°.

Example 140

1-[5-Aminoindolyl-2-carbonyl]-4-[N-ethyl-N-(3-(1-methylethylamino)-2-pyridinyl)amino]piperidine (V)

Following the general procedure of EXAMPLE 67 and making non-critical variations but substituting 1-[5-nitroindolyl-2-carbonyl]-4-[N-ethyl-N-(3-(1- methylethylamino)-2-pyridinyl)amino]piperidine (EXAMPLE 139) for 1-[5-nitroindolyl-2-carbonyl]-4-[N-methyl-N-(3-(1,1-dimethylpropylamino)-2-pyridinyl)amino]piperidine and triturating the crude product with diethyl ether to give a powder after filtration, the title compound is obtained, mp 159°–162° C. (decomp).

Example 141

1-[5-(4-Methyl-1-piperazinylcarbonylamino)indolyl-2-carbonyl]-4-[N-ethyl-N-(3-(1-methylethylamino)-2-pyridinyl)amino]piperidine (V)

A mixture of 1-[5-aminoindolyl-2-carbonyl]-4-[N-ethyl-N-(3-(1-methylethylamino)-2-pyridinyl)amino]piperidine (EXAMPLE 140, 350 mg), 4-methyl-1-piperazinylcarbamoyl chloride hydrochloride (EXAMPLE 219, 199 mg) and pyridine (0.14 mL) in dry methylene chloride (8.3 mL) is stirred at RT under nitrogen in a flame-dried flask for 2.75 days. The mixture is then diluted with saturated aqueous sodium bicarbonate (5 ml), the layers are separated, and the organic phase is washed with water (5 ml) and saline (5 ml), dried over anhydrous sodium sulfate, and concentrated under reduced pressure to give the crude product which is then chromatographed (silica gel, 230–400 mesh, 40 g; eluting with a gradient of methanol/methylene chloride (5/95–10/90)) to give the title compound, NMR (CDCl$_3$) 9.25, 7.75, 7.66, 7.29, 7.13, 6.95, 6.84, 6.66, 6.44, 4.71, 4.62, 3.54, 3.35, 3.13, 3.20–2.90, 2.46, 2.33, 1.92, 1.61, 1.21 and 0.89δ.

Example 142

1-[5-(4-Methyl-1-piperazinylsulfonylamino)indolyl-2-carbonyl]-4-[N-ethyl-N-(3-(1-methylethylamino)-2-pyridinyl)amino]piperidine (V)

Following the general procedure of EXAMPLE 141, and making non-critical variations but substituting 4-methyl-1-piperazinylsulfamoyl chloride hydrochloride (prepared as in EXAMPLE 61) for 4-methyl-1-piperazinylcarbamoyl chloride hydrochloride, the title compound is obtained, NMR (CDCl$_3$) 9.50, 7.75, 7.54, 7.33, 7.14, 6.96, 6.85, 6.70, 4.70, 4.63, 3.55, 3.37, 3.28, 3.13, 3.10, 2.40, 2.26, 1.96. 1.62, 1.22 and 0.90δ.

Example 143

1-Benzyl-4-[N-ethyl-N-(3-(1,1-dimethylethylamino)-2-pyridinyl)amino]piperidine

Following the general procedure of EXAMPLE 119 and making non-critical variations but substituting 1-benzyl-4-[N-ethyl-N-(3-amino-2-pyridinyl)amino]piperidine (PREPARATION 4) for 1-benzyl-4-[N-propyl-N-(3-amino-2-pyridinyl)amino]piperidine, the title compound is obtained, NMR (CDCl$_3$) 7.71, 7.30, 7.25, 7.05, 6.86, 5.17, 3.48, 3.10, 2.92, 2.87, 1.97, 1.73, 1.65, 1.36 and 0.86δ.

Example 144

1-[5-Nitroindolyl-2-carbonyl]-4-[N-ethyl-N-(3-(1,1-dimethylethylamino)-2-pyridinyl)amino]piperidine (V)

Following the general procedure of EXAMPLE 137 and making non-critical variations but substituting 1-benzyl-4-[N-ethyl-N-(3-(1,1-dimethylethylamino)-2-pyridinyl)amino]piperidine (EXAMPLE 143) for 1-benzyl-4-[N-methyl-N-(3-methoxycarbonyl-2-pyridyl)amino]piperidine and 5-nitroindolyl-2-carboxylic acid for 5-(methanesulfonamido)indolyl-2-carboxylic acid and triturating the crude product with ether, the title compound is obtained, mp 182°–184°.

Example 145

1-[5-Aminoindolyl-2-carbonyl]-4-[N-ethyl-N-(3-(1,1-dimethylethylamino)-2-pyridinyl)amino]piperidine (V)

Following the general procedure of EXAMPLE 67 and making non-critical variations but substituting 1-[5-nitroindolyl-2-carbonyl]-4-[N-ethyl-N-(3-(1,1-dimethylethylamino)-2-pyridinyl)amino]piperidine (EXAMPLE 144) for 1-[5-nitroindolyl-2-carbonyl]-4-[N-methyl-N-(3-(1,1-dimethylpropylamino)-2-pyridinyl)amino]piperidine and triturating the crude product with ether to give a powder after filtration, the title compound is obtained, mp 104° (decomp).

Example 146

1-[5-(4-Methyl-1-piperazinylcarbonylamino)indolyl-2-carbonyl]- 4-[N-ethyl-N-(3-(1,1-dimethylethylamino)-2-pyridinyl)amino]piperidine (V)

Following the general procedure of EXAMPLE 141 and making non-critical variations but substituting 1-[5-aminoindolyl-2-carbonyl]-4-[N-ethyl-N-(3-(1,1-dimethylethylamino)-2-pyridinyl)amino]piperidine (EXAMPLE 145) for 1-[5-aminoindolyl-2-carbonyl]-4-[N-ethyl-N-(3-(1-methylethylamino)-2-pyridinyl)amino]piperidine, the title compound is obtained, NMR (CDCl$_3$) 9.20, 7.74, 7.67, 7.30, 7.14, 7.10, 6.91, 6.66, 6.42, 5.18, 4.62, 3.55, 3.30, 3.11, 3.20–2.95, 2.47, 2.34, 1.92, 1.62, 1.37 and 0.90δ.

Example 147

1-[5-(4-Methyl-1-piperazinylsulfonylamino)indolyl-2-carbonyl]-4-[N-ethyl-N-(3-(1,1-dimethylethylamino)-2-pyridinyl)amino]piperidine (V)

Following the general procedure of EXAMPLE 141 and making non-critical variations but substituting 1-[5-aminoindolyl-2-carbonyl]-4-[N-ethyl-N-(3-(1,1-dimethylethylamino)-2-pyridinyl)amino]piperidine (EXAMPLE 145) for 1-[5-aminoindolyl-2-carbonyl]-4-[N-ethyl-N-(3-(1-methylethylamino)-2-pyridinyl)amino]piperidine and 4-methyl-1-piperazinylsulfamoyl chloride hydrochloride (prepared as in EXAMPLE 61) for 4-methyl-1-piperazinylcarbamoyl chloride hydrochloride, the title compound is obtained, NMR (CDCl$_3$) 9.60, 7.74, 7.54, 7.32, 7.14, 7.10, 6.92, 6.85, 6.70, 5.18, 4.62, 3.32, 3.27, 3.12, 3.20–3.00, 2.38, 2.25, 1.95, 1.61, 1.37 and 0.90δ.

Example 148

1-(Indolyl-2-carbonyl)-4-[N-methyl-N-(3-tert-butylamino-2-pyridinyl)amino]piperidine (V)

Part A

1-Benzyl-4-[N-methyl-N-(3-tert-butylamino-2-pyridinyl)amino]piperidine

Following the general procedure of EXAMPLE 119 and making non-critical variations, but starting with 1-benzyl- 4-[N-methyl-N-(3-amino-2-pyridinyl)amino]piperidine (EXAMPLE 122), the compound of Part A is obtained.

Part B

4-[N-methyl-N-(3-tert-butylamino-2-pyridinyl) amino]piperidine

Following the general procedure of EXAMPLE 206 and making non-critical variations, but starting with 1-benzyl-4-[N-methyl-N-(3-tert-butylamino-2-pyridinyl)amino] piperidine (Part A), the compound of Part B is obtained.

Part C 1-(Indolyl-2-carbonyl)-4-[N-methyl-N-(3-tert-butylamino-2-pyridinyl)amino]piperidine Indolyl-2-carboxylic acid (187 mg, 1.16 mmol) and 4-[N-methyl-N-(3-tert-butylamino-2-pyridinyl)amino]piperidine (Part B, 304 mg, 1.16 mmol) are dissolved in THF (3 ml) at 20°–25°. Then EDC (223 mg, 1.16 mmol) is added and the reaction is stirred 3 days (for convenience). The reaction is poured into saturated aqueous sodium bicarbonate solution, extracted with chloroform and dried over sodium sulfate. It is then filtered through a small silica gel plug, washing with ethyl acetate. The filtrate is evaporated to give the title compound, mp=88°–90°; NMR (300 MHz, $CD_3OD$) 7.50, 7.33, 7.13, 6.92, 6.69, 4.40, 3.21, 2.53, 1.77, 1.51 and 1.30δ; MS (m/e, rel %) 405 (95), 348 (18), 230 (27), 219 (18), 188 (21), 177 (41), 162 (32), 144 (100); IR (mineral oil mull) 3260, 3197, 1600, 1575, 1527, 1488, 1411, 1392, 1366, 1340, 1268 and 1238 $cm^{-1}$.

Example 149

1-(5-Methanesulfonamidoindolyl-2-carbonyl)-4-[N-methyl-N-(3-tert-butylamino-2-pyridinyl)amino] piperidine (V)

5-Methanesulfonamidoindolyl-2-carboxylic acid (1.11 g, 4.36 mmol) is dissolved in THF (10 ml). CDI (761 mg, 4.69 mmol) is added and the reaction stirred one hr at 20°–25°. The mixture is then cooled to 0° and 4-[N-methyl-N-(3-tert-butylamino-2-pyridinyl)amino]piperidine (EXAMPLE 148, Part B, 1.14 g 4.36 mmol) is added in THF (15 ml). The reaction is allowed to warm to 20°–25° and stirred for 6.5 hrs. It is then poured into sodium hydroxide (1N) and extracted with a chloroform/methanol mixture. The extract is dried over sodium sulfate, filtered and evaporated to give a residue. The residue is chromatography (silica gel column; ethyl acetate) to give the title compound, mp=192°–193°; NMR (300 MHz, $CD_3OD$) 7.48, 7.41, 7.29, 7.12, 7.02, 6.87, 6.66, 4.33, 3.2–2.9, 2.76, 2.50, 1.74, 1.47 and 1.26δ.

Example 150

1-(5-Fluoroindolyl-2-carbonyl)-4-[N-methyl-N-(3-tert-butylamino-2-pyridinyl)amino]piperidine (V)

5-Fluoroindolyl-2-carboxylic acid (683 mg, 3.81 mmol) is dissolved in THF (5 ml). CDI (618 mg, 3.81 mmol) is added and reaction mixture stirred two hr at 20°–25°. The reaction is cooled to 0°, and 4-[N-methyl-N-(3-tert-butylamino-2-pyridinyl)amino]-piperidine (EXAMPLE 148, Part B, 500 mg, 1.90 mmol) dissolved in THF (3 ml) is added. The reaction is warmed to 20°–25° and stirred overnight. It is then poured into saturated aqueous sodium bicarbonate and extracted with chloroform. The extract is dried over sodium sulfate, filtered and concentrated. The concentrate is chromatographed (silica gel; methanol/ toluene (10/90)), followed by crystallization from toluene/hexane to give the title compound, mp 188°–189°; NMR ($CD_3OD$) 7.53, 7.31, 7.19, 6.93, 6.70, 4.41, 3.30–3.00, 2.56, 1.80, 1.56 and 1.32δ; MS (m/e, rel %) 423 (54), 408 (8), 366 (9), 230 (14), 177 (29), 162 (100), 148 (22) and 134 (34); IR (mineral oil mull) 3245, 1599, 1576, 1532, 1488, 1366, 1268, 1241, 1222, 1217 and 1153 $cm^{-1}$.

Example 151

1-Benzyl-4-[N-methyl-N-(3-nitro-6-fluoro-2-pyridinyl)amino]piperidine

1-Benzyl-4-methylaminopiperidine (EXAMPLE 9, 6.44 g, 31.23 mmol), 2,6-difluoro-3-nitropyridine[1,2] (5.00 g, 31.23 mmol), and potassium carbonate (5.18 g, 37.48 mmol) in acetonitrile (100 ml) are refluxed for 18 hrs. An additional 1.2 g of 1-benzyl-4-methylaminopiperidine (EXAMPLE 9) is added and refluxing continued one hr. The mixture is cooled, poured into water and extracted with chloroform. The extract is dried over sodium sulfate filtered and concentrated. The concentrate is chromatography (silica gel, 300 g; ethyl acetate/hexane (25/75)) to give the title compound, NMR (300 MHz, $CD_3OD$) 8,47, 7.43–7.51, 6.49, 4.42–4.51, 3.72, 3.19, 2.86, 2.30–2.37, 2.04–2.12 and 1.95δ.

Example 152

1-Benzyl-4-[N-methyl-N-(3-(1-methyl-1-cyanoethyl)amino-6-fluoro-2-pyridinyl)amino] piperidine 1-Benzyl-4-[N-methyl-N-(3-nitro-6-fluoro-2-pyridinyl) amino]piperidine (EXAMPLE 151, 5.81 g, 16.87 mmol) and platinum oxide (2.5 g) in ethanol (150 ml) is hydrogenated at 10 p.s.i. of hydrogen for one hr. Filtration and removal of the solvent gives 1-benzyl-4-[N-methyl-N-(3-amino-6-fluoro-2-pyridinyl)amino]piperidine. Without further purification, this material is dissolved in 85 ml acetonitrile and cooled to 0°. Acetone (3.76 ml, 51.2 mmol) and fused zinc chloride (465 mg, 3.4 mmol) are added and the mixture refluxed for 8 hrs. It is then poured into water and extracted with chloroform. The extract is dried over sodium sulfate, filtered and concentrated. Chromatography of the concentrate (silica gel, 300 g; ethyl acetate/hexane (50/50)) gives the title compound, NMR (300 MHz, $CD_3OD$) 7.64, 7.36–7.41, 6.73, 3.60, 3.35, 3.00, 2.74, 2.10–2.20, 1.81 and 1.77δ.

Example 153

1-Benzyl-4-[N-methyl-N-(3-tert-butylamino-6-fluoro-2-pyridinyl)amino]piperidine

Methyllithium (53 ml, 74.2 mmol, 1.4M in ether) is added to toluene (15 ml) in a dry flask under a nitrogen atmosphere at –78°. 1-Benzyl-4-[N-methyl-N-(3-(1-methyl-1-cyanoethyl)amino-6-fluoro-2-pyridinyl)amino]piperidine (EXAMPLE 152, 2.83 g, 7.42 mmol) in toluene (15 ml) is cooled to –78° and cannulated into the methyllithium mixture. The mixture is allowed to warm gradually to 20°–25°, then quenched cautiously with water. The mixture is extracted with chloroform and the extract dried over sodium sulfate, filtered and concentrated. The concentrate is chromatography (silica gel, 100 g; ethyl acetate/hexane (20/80)) to give the title compound; NMR (300 MHz, $CD_3OD$) 7.55, 7.48, 6.78, 3.68, 3.25, 3.10, 2.74, 2.20–2.30, 1.75–1.90 and 1.52δ.

Example 154

4-[N-methyl-N-(3-tert-butylamino-6-fluoro-2-pyridinyl)amino]piperidine

1-Benzyl-4-[N-methyl-N-(3-tert-butylamino-6-fluoro-2-pyridinyl)amino]piperidine (EXAMPLE 153, 900 mg, 2.43 mmol) and palladium hydroxide on carbon (350 mg) in 50 ml ethanol is hydrogenated at 40 p.s.i. hydrogen for 24 hrs. Filtration and removal of the solvent gives the title compound, which is used without further purification, NMR (300 MHz, $CD_3OD$) 7.38, 6.61, 3.16–3.27, 2.71–2.79, 2.56, 1.84, 1.61–1.66 and 1.33$\delta$.

Example 155

1-(Indolyl-2-carbonyl)-4-[N-methyl-N-(3-tert-butylamino-6-fluoro-2-pyridinyl)amino]piperidine (V)

Indolyl-2-carboxylic acid (345 mg, 2.14 mmol) is dissolved in THF (4 ml). CDI (348 mg, 2.14 mmol) is added and the reaction stirred at 20°–25° for 1.5 hrs. It is then cooled to 0° and 4-[N-methyl-N-(3-tert-butylamino-6-fluoro-2-pyridinyl)amino]-piperidine (EXAMPLE 154, 350 mg, 1.25 mmol) dissolved in THF (2.5 ml) is added. The reaction is allowed to warm to 20°–25° and stirred overnight. The mixture is poured into sodium hydroxide (1N) and extracted with chloroform. The extract is dried over sodium sulfate, filtered and the solvent evaporated to give a concentrate. The concentrate is chromatographed (silica gel; methanol/chloroform (1/99)), followed by crystallization from methyl t-butyl ether and hexane to give the title compound, NMR (300 MHz, $CD_3OD$) 7.46, 7.28, 7.25, 7.06, 6.93, 6.66, 6.48, 4.38, 3.0–3.3, 2.47, 1.72, 1.53 and 1.21$\delta$; MS (m/e, rel %) 423 (36), 366 (3), 197 (14), 180 (17), 166 (9) and 144 (100); IR (mineral oil mull) 3248, 1594, 1534, 1488, 1414, 1367, 1270, 1241, 1215 $cm^{-1}$.

Example 156

1-[5-Methanesulfonamidoindolyl-2-carbonyl)-4-[N-methyl-N-(3-tert-butylamino-6-fluoro-2-pyridinyl)amino]piperidine (V)

5-Methanesulfonamidoindolyl-2-carboxylic acid (635 mg, 2.50 mmol) is dissolved in THF (4 ml). CDI (405 mg, 2.50 mmol) is added and the reaction stirred 1.75 hrs at 20°–25°. The reaction is cooled to 0°, and 4-[N-methyl-N-(3-tert-butylamino-6-fluoro-2-pyridinyl)amino]piperidine (EXAMPLE 154, 350 mg, 1.25 mmol) in THF (2.5 ml) is added. The reaction is warmed to 20°–25° and stirred overnight. It is then poured into sodium hydroxide (1N) and extracted with chloroform. The extract is dried over sodium sulfate, filtered and the solvent concentrated to give a residue which is chromatographed (silica gel; methanol/chloroform (5/95)), followed by crystallization from acetone/methyl-t-butyl to give the tide compound; NMR (300 MHz, $CD_3OD$) 7.57, 7.43, 7.19, 6.82, 6.65, 4.55, 3.2–3.4, 2.92, 2.65, 1.90, 1.70 and 1.39$\delta$; MS (m/e rel %) 516 (73), 501 (4), 459 (5), 237 (86), 223 (18), 197 (41), 180 (52) and 158 (61); IR (mineral oil mull) 3301, 1600, 1531, 1492, 1461, 1447, 1427, 1370, 1331, 1267, 1249 and 1152 $cm^{-1}$.

Example 157

4-Isopropylamino-3,5-dichloropyridazine

3,4,5-Trichloropyridazine (9.2 g 0.05 mol) is dissolved in toluene (24 ml). Isopropylamine (16.5 g, 0.28 mol) is added and the mixture refluxed three hrs. The solution is cooled, diluted with chloroform and sodium hydroxide (1N). The organic phase is separated, washed with water and saline, then dried over sodium sulfate, filtered and concentrated. The concentrate is chromatographed (silica gel, 300 g; ethyl acetate/hexane (30/70)) to give the title compound, NMR (300 MHz, $CDCl_3$) 8.50, 4.74, 4.47 and 1.20$\delta$.

Example 158

1-Benzyl-4-[N-methyl-N-(4-isopropylamino-5-chloro-3-pyridazinyl)amino]piperazine

1-Benzyl-4-methylaminopiperazine (EXAMPLE 9, 2.30 g, 11.4 mmol) and 4-isopropylamino-3,5-dichloropyridazine (EXAMPLE 157, 1.0 g, 4.8 mmol) are heated in a sealed tube under a nitrogen atmosphere to 155° for 3 hr. The mixture is then chromatographed (silica gel, 150 g; 50–100% ethyl acetate/hexane) to give the title compound, NMR (300 MHz, $CD_3OD$) 8.43, 7.30, 4.5, 3.51, 2.90, 2.72, 2.05, 1.75 and 1.21$\delta$.

Example 159

4-[N-Methyl-N-(4-isopropylamino-3-pyridazinyl)amino]piperidine

1-Benzyl-4-[N-methyl-N-(4-isopropylamino-5-chloro-3-pyridazinyl)amino]piperazine (EXAMPLE 158, 800 mg, 2.14 mmol) and palladium hydroxide on carbon (400 mg) in ethanol is hydrogenated at 276 kPa (40 psi) hydrogen for 36 hr. Filtration and removal of the solvent gives the title compound; NMR (300 MHz, $CD_3OD$) 8.54, 6.84, 3.89, 3.67, 3.54, 3.15, 2.86, 2.26, 2.05 and 1.42$\delta$.

Example 160

1-(5-Methanesulfonamidoindolyl-2-carbonyl)-4-[N-methyl-N-(3-isopropylamino-2-pyridazinyl)amino]piperidine (V)

Following the general procedure of EXAMPLE 148 and making non-critical variations, but using 5-methanesulfonamidoindolyl-2-carboxylic acid, (354 mg, 1.39 mmol) and 4-[N-methyl-N-(3-isopropylamino-2-pyridazinyl)amino]piperidine (EXAMPLE 159, 330 mg, 1.33 mmol), the crude product is obtained. Chromatography (silica gel; methanol/chloroform (5/95)), followed by crystallization from ethyl acetate/hexane gives the title compound, mp=193°–194°; NMR (300 MHz, $CD_3OD$) 8.17, 7.34, 7.21, 6.95, 6.59, 6.47, 4.35, 3.53, 3.32, 2.68, 2.53, 1.75, 1.55 and 1.07$\delta$; IR (mineral oil mull) 3253, 1600, 1579, 1560, 1532, 1495, 1448, 1412, 1326 and 1269 $cm^{-1}$; MS (m/z, rel %) 485 (100), 470 (27), 442 (21), 406 (26), 237 (30), 167 (77).

Example 161

1-tert-Butyloxycarbonyl-4-[N-methyl-N-(3-cyclopropylmethylamino-2-pyridinyl)amino]piperidine

1-tert-Butyloxycarbonyl-4-[N-methyl-N-(3-amino-2-pyridinyl)amino]piperidine (1.64 g, 5.37 mmol) is dissolved in methanol (0.2M) and cooled to 0°. Cyclopropylcarboxaldehyde (0.40 ml, 5.37 mmol) is added. After stirring 5 min, sodium cyanoborohydride (337 mg, 5.37 mmol) is added. The reaction is refluxed one hour, then stirred overnight at 20°–25°. Acetic acid (53.7 mmol) is added and the reaction refluxed 3 hr. After cooling to 20°–25°, cyclopropylcarboxaldehyde (820 mg, 2.68 mmol) and sodium cyanoborohydride (168 mg 2.68 mmol) are added and the reaction stirred 16 hr at 20°–25°. The mixture is diluted with water, adjusted to pH 9 with sodium hydroxide (1N) and extracted with chloroform. The extract is filtered and concentrated. The concentrate is chromatographed (silica gel; ethyl acetate/hexane (20/80) to give the title compound; NMR (300 MHz, CD$_3$OD) 7.39, 6.79, 3.79, 3.07, 2.80, 2.63, 2.44, 1.52, 1.33, 1.27, 0.93, 0.35 and 0.05δ.

Example 162

4-[N-methyl-N-(3-cyclopropylmethylamino-2-pyridinyl) amino]piperidine 1-tert-Butyloxycarbonyl-4-[N-methyl-N-(cyclopropylmethylamino-2-pyridinyl)amino]piperidine (EXAMPLE 161, 1.46 g, 4.05 mmol) is dissolved in 10 ml dioxane. Hydrochloric acid (30 ml of 4.0M in dioxane) is added. The solvent is removed by evaporation and the residue is suspended in water. The water is adjusted to pH=12 with sodium hydroxide (1N) and extracted with chloroform/methanol. The organic phase is dried over sodium sulfate and the solvent evaporated to give the title compound, NMR (300 MHz, CD$_3$OD) 7.37, 6.77, 3.3–3.5, 2.85, 2.79, 2.45, 2.36, 1.53, 1.40, 0.92, 0.33 and 0.56δ.

Example 163

1-(5-Methanesulfonamidoindolyl-2-carbonyl)-4-N-methyl-N-(3-cyclopropylmethylamino-2-pyridinyl) amino]piperidine (V)

Following the general procedure of EXAMPLE 149, and making non-critical variations but using 5-methanesulfonamidoindolyl-2-carboxylic acid (498 mg, 1.95 mmol) and 4-[N-methyl-N-(3-cyclopropylmethylamino-2-pyridinyl)amino]piperidine (EXAMPLE 162, 510 mg, 1.95 mmol), 776 mg of the crude product is obtained. Crystallization from ethyl acetate/hexane gives the title compound, mp=187°189°; NMR (300 MHz, CD$_3$OD) 7.59, 7.53, 7.41, 7.14, 7.00, 6.78, 4.45, 3.45, 3.00, 2.88, 2.66, 1.85, 1.70, 1.10, 0.55 and 0.25δ; IR (mineral oil mull) 3249, 1573, 1544, 1480, 1450, 1427, 1333, 1324, 1268 and 1222 cm$^{-1}$; MS (m/z, rel %) 496 (84), 259 (17), 237 (47), 228 (36), 217 (27), 204 (21) and 176 (100).

Example 164

1-(Pyrrolyl-2-carbonyl-4-[N-methyl-N-(cyclopropylmethylamino-2-pyridinyl)amino] piperidine (V)

Following the general procedure of EXAMPLE 149 and making non-critical variations, but using pyrrole-2-carboxylic acid (297 mg, 2.67 mmol) and 4-[N-methyl-N-(3-cyclopropylmethylamino-2-pyridinyl)amino]piperidine, (EXAMPLE 162, 673 mg, 2.58 mmol), the title compound is obtained, NMR (300 MHz, CD$_3$OD) 7.59, 7.00, 6.90, 6.54, 6.16, 4.45, 3.45, 3.10, 3.00, 2.65, 1.85, 1.65, 1.10, 0.55 and 0.25δ; IR (liquid): 3245, 1585, 1479, 1471, 1451, 1405, 1367, 1290, 1267 and 1252 cm$^{-1}$; MS (m/z, rel %) 353 (86), 259 (12), 228 (31), 217 (17), 202 (17), 176 (70), 134 (49) and 94 (100).

Example 165

4-[N-methyl-N-(3-isopropylamino-2-pyridinyl) amino]piperidine

Following the general procedure used for EXAMPLE 162 and using 1-tert-butyloxycarbonyl-4-[N-methyl-N-(3-isopropylamino-2-pyridinyl)amino]piperidine (EXAMPLE 54, 2.41 g, 6.91 mmol), the title compound is obtained, NMR (300 MHz, CD$_3$OD) 7.55, 6.97, 3.60, 3.1, 3.0, 2.61, 2.52, 1.70, 1.50 and 1.20δ.

Example 166

1-(Pyrrolyl-2-carbonyl)-4-[N-methyl-N-(3-isopropylamino-2-pyridinyl)amino]piperidine (V)

Following the general procedure of EXAMPLE 149 and making non-critical variations, but using pyrrole-2-carboxylic acid (666 mg, 6.0 mmol) and 4-[N-methyl-N-(3-isopropylamino-2-pyridinyl)amino]piperidine (EXAMPLE 165, 745 mg, 3.0 mmol), the crude product is obtained. Chromatography (silica gel column, 50 g; ethyl acetate/hexane (50/50)) gives the title compound, NMR (300 MHz, CD$_3$OD) 7.71, 7.13, 7.02, 6.67, 6.30, 4.58, 3.73, 3.51, 3.22, 2.75, 1.97, 1.71 and 1.34δ.

Example 167

1-(Pyrrolyl-2-carbonyl)-4-[N-methyl-N-(3-tert-butylamino-2-pyridinyl)amino]piperidine (V)

Following the general procedure of EXAMPLE 149 and making non-critical variations, but using pyrrole-2-carboxylic acid (279 mg, 2.52 mmol) and 4-[N-methyl-N-(3-tert-butylamino-2-pyridinyl)amino]piperidine (EXAMPLE 148B, 330 mg, 2.52 mmol), gives the tide compound, NMR (300 MHz, CD$_3$OD) 7.45, 7.11, 6.84, 6.76, 6.40, 6.03, 4.30, 3.20, 2.97, 2.47, 1.68, 1.44 and 1.24δ; MS (m/z, rel %) 355 (100), 340 (10), 298 (20), 230 (33), 219 (16), 177 (52) and 94 (99).

Example 168

1-(Pyrrolyl-2-carbonyl)-4-[N-methyl-N-(4-isopropylamino-3-pyridazinyl)amino]piperidine (V)

Following the general procedure of EXAMPLE 149 and making non-critical variations, but using pyrrole-2-carboxylic acid (508 mg 4.57 mmol) and 4-[N-methyl-N-(4-isopropylamino-3-pyridazinyl)amino]piperidine (EXAMPLE 159, 568 mg, 2.28 mmol), 2.22 g of the crude product is obtained. Chromatography (silica gel column, 150 g; methanol/chloroform (5/95)), followed by chromatography (silica gel; methanol/ethyl acetate (10/90)) gives the title compound, mp=68°–70°; NMR (300 MHz, CD$_3$OD) 8.45, 6.98, 6.74, 6.64, 6.25, 4.60, 3.81, 3.57, 3.10–3.30, 2.80, 2.01, 1.70 and 1.34δ.

Example 169

1-Benzyl-4-[N-methyl-N-(2-nitro-4-fluorophenyl) amino]piperidine 2,5-Difluoronitrobenzene (2.69 ml, 24.84 mmol), 1-benzyl-4-methylaminopiperidine (EXAMPLE 9, 5.00 g, 24.84 mmol), and potassium carbonate (4.12 g, 29.81 mmol) are refluxed in acetonitrile for 21 hr. The mixture is then poured into water and extracted with chloroform. The extract is dried over sodium sulfate, filtered and concentrated. The concentrate is chromatographed (silica gel; ethyl acetate/hexane) to give the title compound, NMR (300 MHz, CD$_3$OD) 7.45, 7.37, 7.29, 3.46, 2.99, 2.87, 2.64, 1.98 and 1.67δ.

Example 170

1-Benzyl-4-[N-methyl-N-(2-isopropylamino-4-fluorophenyl) amino]piperidine

1 Benzyl-4-[N-methyl-N-(2-nitro-4-fluorophenyl)amino] piperidine (EXAMPLE 169, 3.0, 8.73 mmol) and platinum oxide (1.5 g) in 100 ml ethanol is hydrogenated under 69 kPa (10 psi) hydrogen for one hr. Filtration and evaporation of the solvent gives a product which is dissolved in methanol (0.2M) and cooled to 0°. Acetone (0.71 ml, 9.60 mmol) and acetic acid (5.0 ml, 87.3 mmol) is added. After 10 minutes of stirring, sodium cyanoborohydride (628 mg, 9.25 mmol) is added and the mixture warmed to 20°–25°. Twice more the mixture is cooled to 0° and acetone (9.60 mmol) and sodium cyanoborohydride (9.25 mmol) are added, warming to 20°–25° each time. The mixture is diluted with sodium hydroxide (1N) and extracted with chloroform. The extract is dried over sodium sulfate, filtered, and evaporated to give the tide compound, NMR (300 MHz, $CD_3OD$) 7.29, 7.0, 6.30, 6.22, 3.55, 3.47, 2.95, 2.70, 2.50, 2.0, 1.50 and 1.18$\delta$.

Example 171

4-[N-methyl-N-(2-isopropylamino-4-fluorophenyl) amino]piperidine

1-Benzyl-4-[N-methyl-N-(2-isopropylamino-4-fluorophenyl)amino]piperidine (EXAMPLE 170, 2.90 g, 8.16 mmol) and platinum hydroxide on carbon (1.0 g) in 50 ml ethanol is hydrogenated at 276 kPa (40 psi) hydrogen for 25 hrs. Filtration and evaporation of the solvent gives the tide compound, NMR (300 MHz, $CD_3OD$) 7.02, 6.32, 6.24, 3.60, 3.15, 2.90, 2.75, 2.54, 1.8–2.0, 1.50 and 1.18$\delta$.

Example 172

1-(5-Methanesulfonamidoindolyl-2-carbonyl)-4-[N-methyl-N-(2-isopropylamino-4-fluorophenyl)amino] piperidine (V)

Following the general procedure of EXAMPLE 149 and making non-critical variations, but using 5-methanesulfonamidoindolyl-2-carboxylic acid (1.69 g, 6.64 mmol) and 4-[N-methyl-N-(2-isopropylamino-4-fluorophenyl)amino]piperidine (EXAMPLE 171, 881 mg, 3.32 mmol), the crude product is obtained. Flash column chromatography (silica gel; first with ethyl acetate/in hexane (10/90)) followed by crystallization from acetone/methyl tert-butyl ether gives the tide compound, mp=233°–234°.

Example 173

1-(Pyrrolyl-2-carbonyl)-4-[N-methyl-N-(2-isopropylamino-4-fluorophenyl)amino]piperidine (V)

Following the general procedure of EXAMPLE 149 and making non-critical variations, but using pyrrole-2-carboxylic acid (1.30 g, 11.68 mmol) and 4-[N-methyl-N-(2-isopropylamino-4-fluorophenyl)amino]piperidine (EXAMPLE 171, 1.55 g, 5.84 mmol), the crude product is obtained. Flash column chromatography (silica gel column, 150 g; ethyl acetate/hexane (40/60)) followed by crystallization from acetone/methyl tert-butyl ether gives the title compound, mp=154°–155°.

Example 174

N-Ethyl-1-benzyl-4-piperidinyl carboxamide

Ethylamine hydrochloride (6.59 g, 80.8 mmol) is dissolved in 40 ml dry toluene and cooled to 0°. Trimethylaluminum (2M in toluene, 40.4 ml, 80.8 mmol) is slowly added and after 30 min at 0° the mixture is warmed to 20°–25°. After one hr gas evolution has ceased. Then ethyl 1-benzylpiperidine-4-carboxylate (10.0 g, 40.4 mmol) is added in 20 ml of toluene and the mixture is heated to 85° for 2 hr. The reaction is quenched cautiously with 5% hydrochloric acid, then adjusted to pH 8 with sodium hydroxide and extracted with chloroform. The extract is dried over sodium sulfate, filtered and evaporated to give the title compound; NMR (300 MHz, $CDCl_3$) 7.32, 3.58, 3.27, 3.00, 2.0–2.2, 1.7–2.0 and 1.11$\delta$.

Example 175

1-Benzyl-4-[N-ethylamino]methylpiperidine

N-Ethyl-1-benzyl-4-piperidinyl carboxamide (EXAMPLE 174, 8.03 g, 32.60 mmol) is dissolved in THF and cooled to 0°. Lithium aluminum hydride (1M in THF) is added dropwise. The solution is refluxed 4.5 hr, then quenched at 0° by adding 1.24 ml water, 1.24 ml 15% aqueous sodium hydride, and 3.71 ml water. Filtration through a pad of diatomaceous earth and sodium sulfate and then evaporation of the solvent gives the title compound; NMR (300 MHz, $CDCl_3$) 7.14, 3.32, 2.73, 2.50, 2.35, 1.79, 1.55, 1.34, 1.12 and 0.97$\delta$.

Example 176

1-Benzyl-4-[N-ethyl-N-(3-nitro-2-pyridinyl)amino] methylpiperidine

1-Benzyl-4-[N-ethylamino]methylpiperidine (EXAMPLE 175, 7.59, 32.64 mmol), 2-chloro-3-nitropyridine (5.17 g, 32.64 mmol) and potassium carbonate (5.41 g, 39.17 mmol) in acetonitrile (0.25M) are refluxed 48 hr. The mixture is diluted with water and extracted with ethyl acetate and then dichloromethane. The combined extracts are dried over sodium sulfate, concentrated and chromatographed (silica gel column, 300 g; eluting with 15–80% ethyl acetate/hexane), to give the title compound, NMR (300 MHz, $CD_3OD$) 8.43, 8.20, 7.42, 6.90, 3.61, 3.52, 3.49, 3.00, 2.10, 1.80, 1.37 and 1.25$\delta$.

Example 177

1-Benzyl-4-[N-ethyl-N-(3-amino-2-pyridinyl)amino] methyl piperidine

1-Benzyl-4-[N-ethyl-N-(3-nitro-2-pyridinyl)amino] methylpiperidine (EXAMPLE 176, 9.8 g, 27.6 mmol) and 10% palladium on carbon (3 g) in ethanol (250 ml) are hydrogenated at 40 p.s.i. hydrogen for one hr. Filtration and evaporation of the solvent gives the title compound, NMR (300 MHz, $CD_3OD$) 7.60, 7.28, 7.05, 6.86, 3.46, 3.01, 2.84, 1.90, 1.70, 1.40, 1.19 and 1.0$\delta$.

Example 178

1-Benzyl-4-[N-ethyl-N-(3-isopropylamino-2-pyridinyl)amino]methylpiperidine

Following the general procedure of EXAMPLE 201 and making non-critical variations, but using 1-benzyll-4-[N-ethyl-N-(3-amino-2-pyridinyl)amino]methylpiperidine (EXAMPLE 177, 8.78 g, 27.06 mmol), and chromatographing the crude product (silica gel; ethyl acetate/hexane (50/50)) gives the title compound, NMR (300 MHz, $CD_3OD$) 7.52, 7.21, 6.93, 3.56, 3.42, 2.90, 2.81, 1.86, 1.64, 1.33, 1.22, 1.+w and 0.95$\delta$.

Example 179

4-[N-ethyl-N-(3-isopropylamino-2-pyridinyl)amino] methylpiperidine

1-Benzyl-4-[N-ethyl-N-(3-isopropyl-2-pyridinyl)amino] methylpiperidine (EXAMPLE 178, 1.82 g, 4.97 mmol) and platinum hydroxide on carbon (675 mg) in 30 ml ethanol is hydrogenated at 40 p.s.i. hydrogen for 48 hrs. Filtration and evaporation of the solvent gives the title compound, NMR (300 MHz, CD$_3$OD) 7.56, 6.97, 3.60, 2.94, 2.44, 1.69, 1.48, 1.20, 1.10 and 0.99δ.

Example 180

1-(Pyrrolyl-2-carbonyl)-4-[N-ethyl-N-(3-isopropylamino-2-pyridinyl)amino]methylpiperidine (V)

Following the general procedure of EXAMPLE 149 and making non-critical variations, but using pyrrole-2-carboxylic acid (1.56 g, 10.40 mmol) and 4-[N-ethyl-N-(3-isopropylamino-2-pyridinyl)amino]methylpiperidine (EXAMPLE 179, 1.44 g, 10.40 mmol), the crude product is obtained. Flash column chromatography (silica gel; ethyl acetate/hexane (50/50)) gives the title compound, NMR (300 MHz, CD$_3$OD) 7.76, 7.17, 7.07, 6.68, 6.34, 4.65, 3.80, 3.17, 3.10, 2.0, 1.90, 1.40 and 1.19δ.

Example 181

1-(5-Fluoroindolyl-2-carbonyl)-4-[N-ethyl-N-(3-isopropylamino-2-pyridinyl)amino]methylpiperidine (V)

Following the general procedure of EXAMPLE 149 and making non-critical variations, but using 5-fluoroindolyl-2-carboxylic acid (648 mg, 3.62 mmol) and 4-[N-ethyl-N-(2-isopropylamino-2-pyridinyl)amino]methylpiperidine (EXAMPLE 179, 500 mg, 1.81 mmol), the crude product is obtained. Crystallization from toluene/hexane gives the title compound, mp=186°–187°.

Example 182

1-(5-Methanesulfonamidoindolyl-2-carbonyl)-4-[N-ethyl-N-(3-isopropylamino-2-pyridinyl)amino]methylpiperidine (V)

Following the general procedure of EXAMPLE 149 and making non-critical variations, but using 5-methane sulfonamidoindolyl-2-carboxylic acid (1.84 g, 7.24 mmol) and 4-[N-ethyl-N-(3-isopropylamino-2-pyridinyl)amino]methylpiperidine (EXAMPLE 179, 1.0 g, 3.62 mmol), a crude residue is obtained. Flash column chromatography (silica gel; methanol/toluene (5/95)), followed by crystallization from methanol/toluene gives the title compound, mp=227°–228°.

Example 183

1-Benzyl-4-[N-methyl-N-(3-nitro-6-chloro-2-pyridinyl)amino]piperidine

1-Benzyl-4-methylaminopiperidine (EXAMPLE 9, 5.34 g, 25.9 mmol), 2,6-dichloro-3-nitropyridine (5.0 g, 25.9 mmol), and potassium carbonate (4.3 g, 31.1 mmol) in 100 ml acetonitrile are stirred at 20°–25° for 20 hr. The mixture is poured in water and extracted with chloroform. The extract is dried over sodium sulfate, filtered and evaporated to give the crude product. Chromatography (silica gel, 300 g; with 15–25% ethyl acetate in hexane) gives the title compound, NMR (300 MHz, CDCl$_3$) 7.92, 7.19, 6.47, 4.23, 3.40, 2.86, 4.23, 3.40, 2.86, 2.57, 2.02 and 1.69–1.71δ.

Example 184

1-Benzyl-4-[N-methyl-N-(3-isopropylamino-6-chloro-2-pyridinyl)amino]piperidine

1-Benzyl-4-[N-methyl-N-(3-nitro-6-chloro-2-pyridinyl) amino]piperidine (EXAMPLE 183, 2.5 g, 6.92 mmol) and platinum oxide (1.0 g) in 100 ml ethanol is hydrogenated under 10 p.s.i. hydrogen for 50 minutes. Filtration and evaporation of the solvent gives a concentrate.

Following the general procedure of EXAMPLE 170, and making non-critical variations, but using this concentrate, acetic acid (3.97 ml, 69.2 mmol), acetone (2.8 ml, 38.1 mmol), and sodium cyanoborohydride (2.49 g, 36.7 mmol), gives the title compound, NMR (300 MHz, CD$_3$OD) 7.43, 7.07, 3.71, 3.63, 3.24, 3.02, 2.72, 2.17, 1.85 and 1.33, δ.

Example 185

4-[N-methyl-N-(3-isopropylamino-6-chloro-2-pyridinyl)amino]piperidine

1-Benzyl-4-[N-methyl-N-(3-isopropylamino-6-chloro-2-pyridinyl)amino]piperidine (EXAMPLE 184, 1.60 g, 4.84 mmol) is dissolved in dichloromethane (0.2M) and cooled to 0°. 1-Chloroethyl-chloroformate (0.57 ml, 5.32 mmol) is added dropwise. The mixture is allowed to warm to 20°–25°, then refluxed one half hour. The solvent is removed to one third volume, 15 ml methanol is added and the mixture is refluxed 2 hr. Extraction with chloroform, drying the extract over sodium sulfate and removal of the solvent gives the crude product. Flash column chromatography (silica gel, 100 g; methanol/chloroform (10/90)) gives the title compound, NMR (300 MHz, CD$_3$OD) 6.88, 3.49, 3.23, 2.87, 2.50, 1.95, 1.70 and 1.12δ.

Example 186

1-(5-Methanesulfonamidoindolyl-2-carbonyl)-4-[N-methyl-N-(3-isopropylamino-6-chloro-2-pyridinyl) amino]piperidine (V)

Following the general procedure of EXAMPLE 149 and making non-critical variations, but using 5-methanesulfonamidoindolyl-2-carboxylic acid (580 mg, 2.28 mmol) and 4-[N-methyl-N-(3-isopropylamino-6-chloro-2-pyridinyl)amino]piperidine (EXAMPLE 185, 430 mg, 1.52 mmol), the product is obtained. Crystallization from chloroform/methyl tert-butyl ether gives the title compound, mp=101°–102°.

Example 187

1-Benzyl-4-[N-ethyl-N-(3-ethylamino-2-pyridinyl)amino]methylpiperidine

1-Benzyl-4-[N-ethyl-N-(3-amino-2-pyridinyl)amino]methylpiperidine (EXAMPLE 177, 2.35 g, 7.27 mmol) is dissolved in 18 ml methanol and cooled to 0°. Acetaldehyde (0.45 ml, 8.0 mmol) and sodium cyanoborohydride (685 mg, 10.9 mmol) is added. The mixture is stirred at 0° for one hr, then warmed to 20°–25°. Acetaldehyde and sodium cyanoborohydride are added in the same amounts as above two more times, cooling to 0° before and warming to 20°–25° after each addition. The mixture is poured into 1N sodium hydroxide, extracted with chloroform, dried over sodium sulfate, filtered and concentrated. Flash column chromatography (silica gel, 100 g; methanol/chloroform (5/95)), gives the title compound, NMR (300 MHz, CD$_3$OD) 7.58, 7.31, 6.98, 3.49, 3.18, 3.00, 2.87. 1.93, 1.70, 1.40, 1.15 and 1.01δ.

Example 188

1-(5-Methanesulfonamidoindolyl-2-carbonyl)-4-N-ethyl-N-(3-ethylamino-2-pyridinyl)amino]piperidine (V)

1-Benzyl-4-[N-ethyl-N-(3-ethylamino-2-pyridinyl)amino]methylpiperidine (EXAMPLE 187, 2.38 g, 6.75 mmol) and palladium hydroxide on carbon (1.5 g) in 100 ml ethanol is hydrogenated under 40 p.s.i. hydrogen for 42 hr. Filtration and evaporation of the solvent gives 4-[N-ethyl-N-(3-ethylamino-2-pyridinyl)aminomethyl]piperidine.

Following the general procedure of EXAMPLE 149 and making non-critical variations, but using 5-methanesulfonamidoindolyl-2-carboxylic acid (1.16 g, 4.57 mmol) and 4-[N-ethyl-N-(3-ethylamino-2-pyridinyl) aminomethyl]piperidine (800 mg, 3.05 mmol), a solid residue is obtained. Chromatography (silica gel; ethyl acetate/hexane (50/50)), followed by crystallization from methanol gives the title compound, mp=227°–228°.

Example 189

1-(Pyrrole-2-carbonyl)-4-[N-ethyl-N-(3-ethylamino-2-pyridinyl) amino]methylpiperidine (V)

1-Benzyl-4-[N-ethyl-N-(3-ethylamino-2-pyridinyl) aminomethyl]piperidine (EXAMPLE 187, 2.38, 6.75 mmol) and palladium hydroxide on carbon (1.5 g) in 100 ml ethanol is hydrogenated under 40 p.s.i. hydrogen for 42 hr. Filtration and evaporation of the solvent gives 4-[N-ethyl-N-(3-ethylamino-2-pyridinyl)aminomethyl]piperidine.

Following the general procedure of EXAMPLE 149 and making non-critical variations, but using pyrrole-2-carboxylic acid (823 mg, 7.40 mmol) and 4-[N-ethyl-N-(3-ethylamino-2-pyridinyl)aminomethyl]piperidine (970 mg, 3.70 mmol), a crude product is obtained. Chromatography [with 40–100% ethyl acetate/hexane], followed by crystallization from ether/hexane gives the title compound, mp=109°–110°.

Example 190

1-(5-Methanesulfonamidoindolyl-2-methyl)-4-[N-methyl-N-(3-tert-butylamino-2-pyridinyl)amino] piperidine (V)

1-(5-Methanesulfonamidoindolyl-2-carbonyl)-4-[N-methyl-N-(3-tert-butylamino-2-pyridinyl)amino]piperidine (EXAMPLE 149, 1.0 g 2.0 mmol) is dissolved in tetrahydrofuran (0.3M) and cooled to 0°. Lithium aluminum hydride (1M in THF) is added dropwise and the solution allowed to warm to 20°–25°. The reaction is refluxed for three hr, then cooled to 0° and quenched by adding 0.075 ml water, 0.075 ml 15% aqueous sodium hydroxide and 0.225 ml water. The mixture is filtered through a diatomaceous earth pad, washing with chloroform and methanol. After drying the filtrate over sodium sulfate it is concentrated. Chromatography (silica gel; methanol/chloroform (5/95)), followed by crystallization from methanol/ether gives the title compound, mp=242°–243°.

Example 191

1-Benzyl-4-[N-ethyl-N-(3-propylamino-2-pyridinyl) amino]piperidine

1-Benzyl-4-[N-ethyl-N-(3-amino-2-pyridinyl)amino] piperidine (EXAMPLE 204B, 6.37 g, 20.56 mmol) and propionaldehyde (1.63 ml, 22.6 mmol) are dissolved in 50 ml methanol and cooled to 0°. Sodium cyanoborohydride (1.42 g, 22.6 mmol) is added and the mixture is warmed to 20°–25°. Twice more propionaldehyde (22.6 mmol) and sodium cyanoborohydride (22.6 mmol) are added, cooling the mixture to 0° before and warming to 20°–25° after each addition. The mixture is stirred 16 hr, then poured into 1N sodium hydroxide and extracted with dichloromethane. The extract is dried over sodium sulfate, filtered and concentrated. Chromatography (silica gel, 300 g; ethyl acetate/hexane (25/75)), gives the title compound, NMR (400 MHz, CDCl$_3$) 7.72, 7.30, 6.91, 6.78, 4.79, 3.49, 3.14, 3.04, 2.87, 1.98, 1.73, 1.63, 1.01 and 0.86δ.

Example 192

4-[N-ethyl-N-(3-propylamino-2-pyridinyl)amino] piperidine

1-Benzyl-4-[N-ethyl-N-(3-propylamino-2-pyridinyl) amino]piperidine (EXAMPLE 191, 4.34 g, 12.3 mmol) and palladium hydroxide on carbon (2.0 g) in 50 ml ethanol is hydrogenated at 40 p.s.i. hydrogen for 40 hr. Filtration and removal of the solvent gives the title compound, NMR (400 MHz, CDCl$_3$) 7.72, 6.95, 6.83, 3.72, 3.42, 3.09, 2.87, 2.00, 1.66, 1.24, 1.00 and 0.87δ.

Example 193

1-(Pyrrolyl-2-carbonyl)-4-[N-ethyl-N-(3-propylamino-2-pyridinyl)amino]piperidine (V)

Following the general procedure of EXAMPLE 192 and making non-critical variations, but using pyrrole-2-carboxylic acid (325 mg, 2.93 mmol) and 4-[N-ethyl-N-(3-propylamino-2-pyridinyl)amino]piperazine (EXAMPLE 192, 512 mg; 1.95 mmol), 886 mg crude product is obtained. Chromatography (silica gel; with 40–100% ethyl acetate in hexane) gives the title compound, NMR (300 MHz, CD$_3$OD) 7.74, 7.13, 7.03, 6.65, 6.29, 4.58, 3.24, 1.98, 1.76, 1.68, 1.12 and 0.99δ.

Example 194

1-(5-Methanesulfonamidoindolyl-2-carbonyl)-4-[N-ethyl-N-(3-propylamino-2-pyridinyl)amino] piperidine (V)

Following the general procedure of EXAMPLE 149 and making non-critical variations, but using 5-methanesulfonamidoindolyl-2-carboxylic acid (735 mg, 2.89 mmol) and 4-[N-ethyl-N-(3-propylamino-2-pyridinyl) amino]piperazine (EXAMPLE 192, 506 mg, 1.93 mmol), 1.2 g the crude product is obtained. Chromatography (silica gel, 100 g; methanol/chloroform (8/92)), followed by crystallization from methanol gives the title compound, mp=208°–209°.

Example 195

1-Benzyl-4-[N-ethyl-N-(6-fluoro-3-(nitro)-2-pyridinyl)amino]piperidine 2,6-Difluoro-3-nitropyridine (*Recl. Trav. Chim.*, 95, 127–156 (1976) and *Tetrahedron Lett.*, 28, 111–114 (1987), 2.4 g, 15.0 mmol) and 1-benzyl-4-ethylaminopiperidine (EXAMPLE 11, 3.3 g, 15 mmol) are dissolved in 37.5 mmol of acetonitrile at 0°. Then solid potassium carbonate (2.49 g, 18 mmol) is added and the reaction is slowly warmed to 20°–25°. After the reaction is complete by TLC (ethyl acetate/hexane, (25/75)), it is poured into water and extracted with ethyl acetate. The organic phase is washed with saline, dried over sodium sulfate and concentrated under reduced pressure. Purification via flash column chromatography (5% ethyl acetate/hexane to 10% ethyl acetate/hexane) gives the title compound, mp=99°–100°; NMR (300 MHz, CDCl$_3$) 8.00, 7.13–7.04, 6.02, 3.43, 3.31, 3.28, 2.77, 1.85, 1.71, 1.63 and 0.86δ; CMR (75 MHz, CDCl$_3$) 163.5, 160.2, 151.2, 140.9, 130.4, 128.9, 128.0, 126.9, 96.9, 62.6, 59.6, 52.9, 38.7, 29.3 and 14.0δ.

Example 196

1-Benzyl-4-[N-ethyl-N-(6-fluoro-3-(isopropylamino) -2-pyridinyl)amino]piperidine 1-Benzyl-4-[N-ethyl-N-(6-fluoro-3-(nitro)-2-pyridinyl) amino]piperidine (EXAMPLE 195, 3.0 g, 8.37 mmol) is dissolved in ethanol (500 ml) and 0.75 g of platinum oxide is added. The reaction is placed on a Parr hydrogenator at 10 psi for 1 hr and then filtered through diatomaceous earth and concentrated under reduced pressure. The crude 1-benzyl-4-[N-ethyl-N-(6-fluoro-3-(amino)-2-pyridinyl)amino] piperidine (3.0 g, 9.13 mmol) is immediately dissolved in methanol (18 ml) and acetone (0.74 ml, 10.04 mmol) and acetic acid (13.1 ml, 228.3 mmol) are added. The reaction is stirred for 10 min, then cooled to 0° and sodium cyanoborohydride (0.61 g, 9.7 mmol) is added. The reaction is slowly warmed to 20°–25° and stirred for 18 hr. Then solid sodium bicarbonate is added with caution and the reaction is extracted with chloroform, washed with saline, dried over sodium sulfate and concentrated under reduced pressure. Purification via flash column chromatography (5% ethyl acetate/hexane to 10% ethyl acetate/hexane) gives the title compound, NMR (300 MHz, CDCl$_3$) 7.26–7.15, 6.88, 6.49, 4.28, 3.40, 3.44, 3.04, 2.93, 2.82, 1.93, 1.72–1.52, 1.13 and 0.81δ; CMR (CDCl$_3$, 75 MHz) 155.9, 152.5, 146.1, 138.0, 129.1, 128.1, 126.9, 121.8, 104.3, 62.9, 57.5, 52.7, 44.4, 41.2, 29.7 and 22.8δ.

Example 197

4-[N-Ethyl-N-(6-fluoro-3-(isopropylamino)-2-pyridinyl)amino]piperidine

1-Benzyl-4-[N-ethyl-N-(6-fluoro-3-(isopropylamino)-2-pyridinyl)amino]piperidine (EXAMPLE 196, 2.1 g, 5.76 mmol) is dissolved in ethanol (100 ml) and 0.96 g of palladium hydroxide is added. The reaction is placed on a Parr hydrogenator at 40 psi for 12 hr. Then the reaction is filtered through diatomaceous earth, concentrated under reduced pressure, and used without further purification, NMR (300 MHz, CDCl$_3$) 6.93, 6.55, 4.32, 3.51, 3.11, 3.10–2.95, 2.59, 1.77, 1.55, 1.18 and 0.86δ.

Example 198

1-(Pyrrolyl-2-carbonyl)-4-[N-ethyl-N-(6-fluoro-3-(isopropylamino)-2-pyridinyl)amino]piperidine (V)

Pyrrole-2-carboxylic acid (0.59 g, 5.34 mmol) is dissolved in 6.7 ml of THF and 1,1'-carbonyldiimidazole (0.87 g, 5.34 mmol) is added at 20°–25°. The reaction is stirred for 1 hr, then cooled to 0° and 4-[N-ethyl-N-(6-fluoro-3-(isopropylamino)-2-pyridinyl)amino]piperidine (EXAMPLE 197, 0.75 g, 2.67 mmol) dissolved in THF is added. The reaction is slowly warmed to 20°–25° and stirred for 20 hr. Then it is poured into sodium hydroxide (1N) and extracted with ethyl acetate. The organic phase is washed with water and saline, dried over anhydrous sodium sulfate and concentrated under reduced pressure. Purification by flash column chromatography (silica gel; ethyl acetate/hexane (25/75)), gives the title compound, NMR (300 MHz, CDCl$_3$) 7.24, 6.98, 6.74, 6.62, 6.26, 4.57, 3.67, 3.39, 3.21, 3.12, 1.95, 1.67, 1.27 and 0.96δ.

Example 199

1-Benzyl-4-[N-ethyl-N-(5-fluoro-2-nitro-1-phenyl) amino]piperidine

1-Benzyl-4-ethylaminopiperidine (EXAMPLE 11, 8.25 g, 37.8 mmol), 2,4-difluoronitrobenzene (4.1 ml, 37.8 mmol) and potassium carbonate (6.27 g, 45.4 mmol) are placed in acetonitrile (95 ml) and refluxed for 18 hrs. The reaction is diluted with water, extracted with ethyl acetate, washed with saline and dried over sodium sulfate and concentrated under reduced pressure. Purification by flash column chromatography (silica gel; ethyl acetate/hexane (25/75)), gives the title compound, NMR (300 MHz, CDCl$_3$) 7.53, 7.06, 6.63, 6.46, 3.27, 2.98, 2.79, 2.70, 1.75, 1.56 and 0.81δ.

Example 200

1-Benzyl-4-[N-ethyl-N-(5-fluoro-2-amino-1-phenyl) amino]piperidine

1-Benzyl-4-[N-ethyl-N-(5-fluoro-2-nitro-1-phenyl) amino]piperidine (EXAMPLE 199, 4.0 g) is dissolved in ethanol (350 ml) and 1.0 g of platinum oxide is added. The reaction is placed on a Parr hydrogenator at 10 psi for 1 hr, then it is filtered through diatomaceous earth and concentrated under reduced pressure to give the title compound, NMR (300 MHz, CDCl$_3$) 7.15, 6.67, 6.57, 3.38, 2.88, 2.77, 2.65, 1.86 and 0.78δ.

Example 201

1-Benzyl-4-[N-ethyl-N-(5-fluoro-2-(isopropylamino) -1-phenyl)amino]piperidine

1-Benzyl-4-[N-ethyl-N-(5-fluoro-2-amino-1-phenyl) amino]piperidine (EXAMPLE 200, 3.94 g, 12.0 mmol) is dissolved in methanol (9 ml) and acetic acid (25.8 ml, 450 mmol) and acetone (1.45 ml, 19.8 mmol) are added. The reaction is cooled to 0° and then sodium cyanoborohydride (1.20 g, 19.8 mmol) is added. The reaction is slowly warmed to 20°–25° and stirred for 18 hr. Then it is diluted with chloroform and extracted with saturated aqueous sodium bicarbonate, saline, dried over sodium sulfate and concentrated under reduced pressure. Purification by flash column chromatography (silica gel, methanol/chloroform (2.5/97.5) ), gives the title compound, NMR (300 MHz, CDCl$_3$) 7.20, 6.68, 6.45, 4.55, 3.50, 3.44, 2.89, 2.83, 2.64, 1.90, 1.72, 1.58, 1.10 and 0.80δ.

Example 202

4-[N-ethyl-N-(5-fluoro-2-(isopropylamino)-1-phenyl)amino]piperidine

1-Benzyl-4-[N-ethyl-N-(5-fluoro-2-(isopropylamino)-1-phenyl)amino]piperidine (EXAMPLE 201, 3.6 g, 9.74 mmol) is dissolved in ethanol (100 ml) and 0.9 g of palladium hydroxide is added. The reaction is placed on a Parr hydrogenator for 18 hrs, filtered through diatomaceous earth and concentrated under reduced pressure to give the title compound, NMR (300 MHz, CDCl$_3$) 6.80, 6.59, 4.50, 3.60, 3.48, 3.01, 3.02, 2.88, 2.03, 1.24 and 0.93δ.

Example 203

1-(Pyrrolyl-2-carbonyl)-4-[N-ethyl-N-(5-fluoro-2-(isopropylamino)-1-phenyl)amino]piperidine (V)

Following the general procedure of EXAMPLE 198, but utilizing 4-[N-ethyl-N-(5-fluoro-2-(isopropylamino)-1-phenyl)amino]piperidine (EXAMPLE 202, 0.5 g, 1.8 mmol), pyrrole-2-carboxylic acid (0.4 g, 3.6 mmol) and CDI (0.58 g, 3.6 mmol) and purifying by crystallization from ethyl acetate/hexane gives the title compound, mp=103°–105°; NMR (300 MHz, CD$_3$OD) 6.72, 6.59, 6.46, 6.35, 5.99, 4.30, 3.41, 3.41, 2.87, 1.72, 1.32, 0.99 and 0.70δ.

Example 204

1-Benzyl-4-[N-ethyl-N-(3-amino-2-pyridinyl)amino]piperidine

Part A

1-Benzyl-4-[N-ethyl-N-(3-nitro-2-pyridinyl)amino]piperidine

1-Benzyl-4-N-ethylaminopiperidine (EXAMPLE 11, 12.91 g, 59.1 mmol) and 2-chloro-3-nitropyridine (9.37 g, 59.1 mmol) are dissolved in acetonitrile (118 ml) and 8.17 g (59.1 mmol) of solid potassium carbonate is added. The reaction is heated to reflux and stirred for 18 hr, cooled to 20°–25°, diluted with chloroform, washed with water, saline, dried over sodium sulfate and concentrated under reduced pressure. Purification by flash column chromatography (silica gel; ethyl acetate/hexane (10/90)), gives the title compound.

Part B

1-Benzyl-4-[N-ethyl-N-(3-amino-2-pyridinyl)amino]piperidine

1-Benzyl-4-[N-ethyl-N-(3-nitro-2-pyridinyl)amino]piperidine (EXAMPLE 204, Part A, 1.0 g, 3.05 mmol) is dissolved in ethanol (170 ml) and 0.25 g of platinum oxide is added. The reaction is placed on a Parr hydrogenator at 10 psi for 1 hr and then it is filtered through diatomaceous earth and concentrated under reduced pressure to give the title compound, NMR (300 MHz, $CD_3OD$) 7.52, 7.17, 6.97, 6.79, 3.37, 3.02, 2.94, 2.75, 1.90, 1.60, 1.52 and 0.74δ.

Example 205

1-Benzyl-4-[N-ethyl-N-(3-(ethylamino)-2-pyridinyl)amino]piperidine

1-Benzyl-4-[N-ethyl-N-(3-(amino)-2-pyridinyl)amino]piperidine (EXAMPLE 204 Part B, 1.0 g, 3.22 mmol) is dissolved in methanol (8 ml) and cooled to 0°. The acetaldehyde (0.20 ml, 3.54 mmol) and sodium cyanoborohydride (0.31 g, 3.54 mmol) are added and the reaction is slowly warmed to 20°–25° and stirred for 18 hr. Then a further sodium cyanoborohydride (2 eq.) and 1.6 eq. of acetaldehyde are added and the reaction is stirred a further 20 hr. Then it is diluted with ethyl acetate and poured into water, washed with saline, dried over anhydrous sodium sulfate and concentrated under reduced pressure. Purification by flash column chromatography (silica gel; methanol/methylene chloride (2.5/97.5)), gives the title compound, NMR (300 MHz, $CDCl_3$) 7.65, 7.40–7.17, 6.83, 6.71, 4.63, 3.42, 3.10–3.00, 2.93, 2.81, 1.92, 1.72–1.51, 1.17 and 0.79δ.

Example 206

4-[N-ethyl-N-(3-(ethylamino)-2-pyridinyl)amino]piperidine

1-Benzyl-4-[N-ethyl-N-(3-(ethylamino)-2-pyridinyl)amino]piperidine (EXAMPLE 205, 0.41 g, 1.2 mmol) is dissolved in 20 ml of ethanol and 0.20 g of palladium hydroxide is added. The reaction is placed on a Parr hydrogenator under 40 psi for 24 hrs. Then it is filtered through diatomaceous earth and concentrated under reduced pressure to give the title compound, NMR (300 MHz, $CDCl_3$) 7.60, 6.80, 6.67, 4.53, 3.76, 3.76, 3.15–2.95, 2.56, 1.76, 1.54, 1.12 and 0.73δ.

Example 207

1-(2-Pyrrolyl-2-carbonyl)-4-[N-ethyl-N-(3-(ethylamino)-2-pyridinyl)amino]piperidine (V)

Following the general procedure of EXAMPLE 198, but starting with 4-[N-ethyl-N-(3-(ethylamino)-2-pyridinyl)amino]piperidine (EXAMPLE 206, 0.24 g, 0.97 mmol) and pyrrole-2-carboxylic acid (0.22 g, 1.93 mmol) and purifying by flash column chromatography (silica gel; methanol/chloroform (2.5/97.5)), gives the crude product. Recrystallization from ethyl acetate/hexane gives the title compound, mp=104°–105°; NMR (300 MHz, $CD_3OD$) 7.61, 7.02, 6.97, 6.88, 6.52, 6.16, 4.45, 3.35, 3.15, 3.04, 1.87, 1.55, 1.25 and 0.86δ.

Example 208

1-(2-Pyrrolyl-2-carbonyl)-4-[N-ethyl-N-(3-(1-methylpropyl)amino)-2-pyridinyl)amino]piperidine (V)

Part A

1-Benzyl-4-[N-ethyl-N-(3-(1-methylpropyl)amino)-2-pyridinyl)amino]piperidine

1-Benzyl-4-[N-ethyl-N-(3-amino-2-pyridinyl)amino]piperidine (EXAMPLE 204 Part B, 1.5 g, 4.83 mmol) and 2-butanone (0.476 ml, 5.3 mmol) are dissolved in methanol (26 ml) and cooled to 0°. Then acetic acid (6.9 ml, 120.8 mmol) is added and the reaction is stirred for 15 min. Then sodium cyanoborohydride (0.32 g, 5.11 mmol) is added and the reaction is warmed to 20°–25° and stirred for 18 hrs. Since the reaction is incomplete by TLC, sodium cyanoborohydride and 2-butanone are added several more times. Then the reaction is poured into cold sodium hydroxide (1N) and extracted with chloroform. The organic phase is washed with saline, dried over sodium sulfate and concentrated under reduced pressure. Purification by flash column chromatography (silica gel; ethyl acetate/hexane (25/75)), gives the title compound.

Part B

4-[N-ethyl-N-(3-(1-methylpropyl)amino)-2-pyridinyl)amino]piperidine

Following the general procedure of EXAMPLE 206 and making non-critical variations, but utilizing 1-benzyl-4-[N-ethyl-N-(3-(1-methylpropyl)amino)-2-pyridinyl)amino]piperidine (EXAMPLE 208, Part A, 0.89 g, 2.44 mmol), the title compound is obtained.

Part C 1-(2-Pyrrolyl-2-carbonyl)-4-[N-ethyl-N-(3-(1-methylpropyl)amino)-2-pyridinyl)amino]piperidine Following the general procedure of EXAMPLE 198, but utilizing 4-[N-ethyl-(3-(1-methylpropylamino)-2-pyridinyl)amino]piperidine (EXAMPLE 208, Part B, 0.55 g, 2.0 mmol), pyrrole-2-carboxylic acid (0.45 g, 4.0 mmol) and CDI (0.65 g, 4.0 mmol) and purifying by chromatography (silica gel; 25–50% ethyl acetate/hexane) gives the title compound, HRMS theory=369.2528, found=369.2535.

Example 209

1-(4-Acetyl-2-pyrrolyl-2-carbonyl)-4-[N-methyl-N-(3-(isopropylamino)-2-pyridinyl)amino]piperidine (V)

Part A

4-[N-methyl-N-(3-(isopropylamino)-2-pyridinyl)amino]piperidine

Following the general procedure of EXAMPLE 206, but utilizing 1-benzyl-4-[N-methyl-N-(3-(1-isopropylamino)-2-pyridinyl)amino]piperidine (EXAMPLE 138), gives the title compound.

Part B

1-(4-Acetyl-2-pyrrolyl-2-carbonyl)-4-[N-ethyl-N-(3-(isopropylamino)-2-pyridinyl)amino]piperidine 4-[N-methyl-N-(3-(isopropylamino)-2-pyridinyl)amino] piperidine (EXAMPLE 209, Part A, 2.31 g, 9.3 mmol) and trichloromethyl 4-acetylpyrrolyl-2-carboxylate (*Tetrahedron Lett.*, 2505 (1976), 2.36 g, 9.3 mmol) are dissolved in warm acetonitrile and stirred for 2 hrs at 20°–25°. The reaction is poured into water, extracted with chloroform, washed with saline, dried over sodium sulfate and concentrated under reduced pressure. Purification by flash column chromatography (silica gel; 50% ethyl acetate/hexane to 100% ethyl acetate/hexane) gives the title compound, mp 156°–158°.

Example 210

1-(4-Bromo-2-pyrrolyl-2-carbonyl)-4-[N-methyl-N-(3-(isopropylamino)-2-pyridinyl)amino]piperidine (V)

Following the general procedure for the synthesis of EXAMPLE 209, Part B, but utilizing 4-[N-methyl-N-(3-(isopropylamino)-2-pyridinyl)amino]piperidine (EXAMPLE 55, 0.72 g, 0.29 mmol), trichloromethyl 4-bromopyrrolyl-2-carboxylate (*Tetrahedron Letters*, 2505 (1979), 0.8 g, 0.29 mmol) and purifying by chromatography (silica gel; ethyl acetate/hexane (50/50)), gives the title compound, HRMS theory=327.2059, found=327.2045.

Example 211

1-(4-Bromo-2-pyrrolyl-2-carbonyl)-4-[N-ethyl-N-(3-(isopropylamino)-2-pyridinyl)amino]piperidine (V)

Following the general procedure for the synthesis of EXAMPLE 209, but utilizing 4-[N-ethyl-N-(3-(isopropylamino)-2-pyridinyl)amino]piperidine (EXAMPLE 209, Part A, 0.88 g, 3.4 mmol), trichloromethyl 4-bromopyrrolyl-2-carboxylate (*Tetrahedron Letters*, 2505 (1979), 0.93 g, 3.4 mmol) and purifying by chromatography (silica gel; 25–50% ethyl acetate/hexane) and crystallization from ethyl acetate/hexane gives the title compound, mp=141°–143°.

Example 212

1-Benzyl-4-[N-ethyl-N-(3-(1-methylethylamino)-2-pyridinyl)amino]piperidine

Following the general procedure of EXAMPLE 201, and making non-critical variations, but using 1-benzyl-4-[N-ethyl-N-(3-amino-2-pyridinyl)amino]piperidine (EXAMPLE 204, Part B), gives the title compound.

Example 213

1-Benzyl-4-[N-ethyl-N-(6-fluoro-3-nitro-2-pyridyl)amino]piperidine 2,6-Difluoro-3-nitropyridine (5.00 g) is dissolved in acetonitrile (10 ml) and 1-benzyl-4-ethylaminopiperidine (EXAMPLE 11, 6.81 g) dissolved in 10 ml of acetonitrile is added via cannula. Then an additional 58 ml of acetonitrile is added and the reaction is cooled to 0°. Then 5.1 g of potassium carbonate is added and the reaction is stirred 10 min and allowed to warm to 20°–25°. After 6 hrs, the reaction is poured into water, extracted with ethyl acetate, washed with saline and dried over sodium sulfate. Flash column chromatography (silica gel; 5% ethyl acetate/hexane to 10% ethyl acetate/hexane) gives the title compound, NMR (300 MHz, CDCl$_3$) 8.22, 7.37–7.23, 6.25, 3.66, 3.55, 3.50, 3.01, 2.10, 1.95, 1.83 and 1.09δ.

Example 214

1-Benzyl-4-[N-ethyl-N-(3-amino-6-fluoro-2-pyridyl)amino]piperidine

Following the general procedure of EXAMPLE 204, Part B and making non-critical variations, but using 1-benzyl-4-[N-ethyl-N-(6-fluoro-3-nitro-2-pyridyl)amino]piperidine (EXAMPLE 213, 6.53 g), gives the title compound, NMR (300 MHz, CD$_3$OD) 7.42, 7.30, 6.65, 3.61, 3.26, 3.21, 3.01, 2.14, 1.90–1.73 and 1.00δ.

Example 215

1-Benzyl-4-[N-ethyl-N-((3-(1,1-dimethylethylamino)-6-fluoro)-2-pyridyl)amino]piperidine

Part A

1-Benzyl-4-[N-ethyl-N-((3-(1-cyano-1-methylethyl)amino)-6-fluoro)-2-pyridyl)amino]piperidine Following the general procedure of EXAMPLE 152 and making non-critical variations, but using 1-benzyl-4-[N-ethyl-N-(3-amino-6-fluoro-2-pyridyl)amino]piperidine (EXAMPLE 214, 1.4 g) in place of 1-benzyl-4-[N-methyl-N-(3-amino-6-fluoro-2-pyridinyl)amino]piperidine, gives the title compound, NMR (300 MHz, CDCl$_3$) 7.39, 7.25–7.12, 6.58, 4.88, 3.43, 3.02, 2.89, 2.82, 1.91, 1.67–1.51, 1.63 and 0.78δ.

Part B

1-Benzyl-4-[N-ethyl-N-((3-(1,1-dimethylethylamino)-6-fluoro)-2-pyridyl)amino]piperidine Following the general procedure of EXAMPLE 153 and making non-critical variations, but using 1-benzyl-4-N-ethyl-N-((3-(1-cyano-1-methylethylamino)-6-fluoro)-2-pyridyl)amino]piperidine (EXAMPLE 215, Part A, 1.28 g) gives the title compound, NMR (300 MHz, CDCl$_3$) 7.23, 7.13, 6.44, 4.68, 3.42, 3.01, 2.88, 2.82, 1.90, 1.64, 1.25 and 0.78δ.

Example 216

4-[N-ethyl-N-((3-(1,1-dimethylethylamino)-6-fluoro)-2-pyridyl)amino]piperidine Following the general procedure of EXAMPLE 119, but using 4-[N-ethyl-N-(3-amino-6-fluoro-2-pyridyl)amino] piperidine (EXAMPLE 214, 27.3 g, 83.2 mmol), gives the title compound.

Example 217

4-[N-Ethyl-N-((3-(1,1-dimethylethylamino)-6-fluoro)-2-pyridyl)amino]piperidine Following the general procedure of EXAMPLE 206 and making non-critical variations, but using 1-benzyl-4-[N-ethyl-N-((3-(1,1-dimethylethylamino)-6-fluoro)-2-pyridyl)amino]piperidine (EXAMPLE 215, Part B or 216

(preferred), 0.97 g), gives the title compound, NMR (300 MHz, CDCl$_3$) 7.15, 6.46, 4.68, 3.06, 3.00, 2.94, 2.53, 1.72, 1.52, 1.26 and 0.80δ.

Example 218

1-(5-Methanesulfonamidoindolyl-2-carbonyl)-4-[N-ethyl-N-((3-(1,1-dimethylethylamino)-6-fluoro)-2-pyridyl)amino]piperidine (V)

Following the general procedure of EXAMPLE 149 and making noncritical variations, but using 4-[N-ethyl-N-((3-(1,1-dimethylethylamino)-6-fluoro)-2-pyridyl)amino]piperidine (EXAMPLE 217, 0.34 g) and 5-methanesulfonamidoindolyl-2-carboxylic acid (0.35 g) gives the title compound, mp=221°–223°.

Example 219

4-Methyl-1-piperazinylcarbamoyl chloride, hydrochloride

Phosgene in toluene (20.73 ml, 1.93M) is dissolved in 40 ml of methylene chloride at 0°. Then N-methylpiperazine (2.0 g, 20.0 mmol) is added dropwise. The reaction is stirred 30 min, then allowed to warm to 20°–25° for 3 hrs. The mixture is concentrated under reduced pressure, rediluted with methylene chloride and concentrated (twice) to give the title compound, NMR (300 MHz, CDCl$_3$) 4.52–4.38, 4.14, 3.87, 3.60, 2.98, 2.88 and 1.68δ.

Example 220

1-(5-(4-methyl-1-piperazinyl)carbonylamino) indolyl-2-carbonyl)-4-[N-ethyl-N-((3-(1,1-dimethylethylamino)-6-fluoro)-2-pyridyl)amino] piperidine (V)

Part A 1-(5-nitroindolyl-2-carbonyl)-4-[N-ethyl-N-((3-(1,1-dimethylethylamino)-6-fluoro)-2-pyridyl)amino] piperidine Following the general procedure of EXAMPLE 149 and making non-critical variations, but using 5-nitroindolyl-2-carboxylic acid (5.0 g, 24.48 mmol) and 4-[N-ethyl-N-((3-(1,1-dimethylethylamino)-6-fluoro)-2-pyridyl)amino] piperidine (EXAMPLE 217, 6.0 g, 20.4 mmol), gives the title compound, mp=211°–212°.

Part B 1-(5-amino)indolyl-2-carbonyl-4-[N-ethyl-N-((3-(1, 1-dimethylethylamino)-6-fluoro)-2-pyridyl)amino] piperidine 1-(5-nitro)indolyl-2-carbonyl)-4-[N-ethyl-N-((3-(1,1-dimethylethylamino)-6-fluoro)-2-pyridyl)amino]piperidine (EXAMPLE 220, Part A, 6.06 g, 12.6 mmol) is dissolved in 100 ml of ethanol and 100 ml of THF and 1.52 g of 10% palladium on carbon is added. The reaction is hydrogenated on a Parr hydrogenator at 310 kPa (45 psi) for 18 hrs, filtered through diatomaceous earth, and concentrated under reduced pressure. Purification by flash column chromatography (silica gel; ethyl acetate/hexane (50/50)), gives the title compound.

Part C 1-(5-(4-methyl-1-piperazinyl)carbonylamino) indolyl-2-carbonyl)-4-[N-ethyl-N-((3-(1,1-dimethylethylamino)-6-fluoro)-2-pyridyl)amino] piperidine 1-[(5-amino)indolyl-2-carbonyl]-4-[N-ethyl-N-((3-1,1-dimethylethylamino)-6-fluoro)- 2-pyridyl)amino]piperidine (EXAMPLE 220, Part B, 0.3 g) is dissolved in 2.2 ml of methylene chloride and cooled 0°. Then pyridine (0.11 ml) and 4-methyl-1-piperazinylcarbamoyl chloride, hydrochloride (EXAMPLE 219, 0.19 g) is added. The reaction is slowly warmed to 20°–25° and stirred for 20 hrs. Then the reaction is concentrated under reduced pressure, dissolved in methylene chloride and extracted with water, saline, dried over sodium sulfate and concentrated under reduced pressure. Flash column chromatography (silica gel; 5% methanol/chloroform to 10% methanol/chloroform) and recrystallization from ethyl acetate/hexane gives the title compound, mp=203°–204°.

Example 221

4-Methyl-1-piperazinylsulfamoyl chloride, hydrochloride

Sulfuryl chloride (3.2 ml) is dissolved in 40 ml of methylene chloride and cooled to 0°. Then N-methylpiperazine (2.0 g, 20.0 mmol) is added dropwise. The reaction is stirred 30 min at 0° and then warmed slowly to 20°–25°. The liquid is decanted and the resulting slurry is concentrated under reduced pressure, reconstituted with methylene chloride and concentrated under reduced pressure (twice) to give the title compound.

Example 222

1-[(5-(4-Methyl-1-piperazinyl)sulfonylamino) indolyl-2-carbonyl]-4-[N-ethyl-N-((3-(1,1-dimethylethylamino)-6-fluoro)-2-pyridyl)amino] piperidine (V)

1-[(5-amino)indolyl-2-carbonyl]-4-[N-ethyl-N-((3-(1,1-dimethylethylamino)-6-fluoro)-2-pyridyl)amino]piperidine (EXAMPLE 220, Part B, 0.30 g) is dissolved in 2.2 ml of methylene chloride and cooled to 0°. Then pyridine (0.11 ml) is added and 0.19 g of 4-methyl-1-piperazine sulfamoyl chloride is added. The reaction is slowly warmed to 20°–25° and stirred for 4 days. Then a further 0.094 g of methyl-1-piperazinylsulfamoyl chloride and 0.056 ml of pyridine are added and the reaction is stirred a further 6 hrs. Then it is poured into water and extracted with methylene chloride, washed with saline, dried over sodium sulfate and concentrated under reduced pressure. Purification by flash column chromatography (silica gel; methanol/chloroform (5/95)), give crude product which is further purified by another column (silica gel; methanol/ethyl acetate (5/95)), to give crude product. Crystallization from ethyl acetate/hexane gives the title compound, mp 181°–183°.

Example 223

1-[(5-(1-methylimidazolyl-4-sulfamoylamino) indolyl-2-carbonyl]-4-[N-ethyl-N-((3-(1,1-dimethylethylamino)-6-fluoro)-2-pyridyl)amino] piperidine (V)

1-[(5-amino)indolyl-2-carbonyl]-4-[N-ethyl-N-((3-(1,1-dimethylethylamino)-6-fluoro)- 2-pyridyl)amino]piperidine (EXAMPLE 220, Part B, 0.30 g) is dissolved in 2.2 ml of methylene chloride and cooled to 0°. Then pyridine (0.11 ml, 1.4 mmol) and 1-methylimidazole sulfonyl chloride (0.13 g, 0.73 mmol) is added. The reaction is slowly warmed to 20°–25° and stirred until complete by TLC. Then the reaction is poured into water and extracted with methylene chloride. The organic phase is washed with saline, dried over sodium sulfate and concentrated under reduced pressure.

Example 224

1-[5-isopropylsulfonamidoindolyl-2-carbonyl]-4-[N-ethyl-N-(3-ethylamino)-2-pyridyl)amino]piperidine (V)

Following the general procedure of EXAMPLE 223 and making non-critical variations, but using isopropylsulfonyl chloride (0.09 ml) and 4-[N-ethyl-N-(3-ethylamino)-2-pyridyl)amino]piperidine (EXAMPLE 206, 0.34 g) gives the title compound, mp=206°–207°.

Example 225

1-[5-ethylsulfonamidoindolyl-2-carbonyl]-4-[N-ethyl-N-(3-ethylamino)-2-pyridyl)amino]piperidine (V)

Following the general procedure of EXAMPLE 223 and making non-critical variations, but using ethanesulfonyl chloride (0.07 ml) and 4-[N-ethyl-N-(3-ethylamino)-2-pyridyl)amino]piperidine (EXAMPLE 206, 0.34 g) gives the title compound, mp=211°–213°.

Example 226

1-[5-methylsulfonamidoindolyl-2-carbonyl]-4-[N-ethyl-N-(3-ethylamino)-2-pyridyl)amino]piperidine (V)

Following the general procedure of EXAMPLE 149 and making non-critical variations, but using 5-methylsulfonamidoindolyl-2-carboxylic acid (0.4 g) and 4-[N-ethyl-N-(3-ethylamino)-2-pyridyl)amino]piperidine (EXAMPLE 206, 0.33 g) gives the title compound, mp=204°–205°.

Example 227

1-[(5,6-methylenedioxyindolyl-2-carbonyl]-4-[N-ethyl-N-(3-ethylamino)-2-pyridyl)amino]piperidine (V)

Following the general procedure of EXAMPLE 149 and making non-critical variations, but using 5,6-methylenedioxyindolyl-2-carboxylic acid (International Patent Publication No. WO91/09849 PREPARATION 79, 0.3 g) and 4-[N-ethyl-N-(3-ethylamino)-2-pyridyl)amino] piperidine (EXAMPLE 206, 0.3 g) gives the title compound, HRMS theory=436.2348, found=436.2356.

Example 228

1-[5-methoxyindolyl-2-carbonyl]-4-[N-ethyl-N-(3-ethylamino)-2-pyridyl)amino]piperidine (V)

Following the general procedure of EXAMPLE 149 and making non-critical variations, but using 5-methoxyindolyl-2-carboxylic acid (0.28 g) and 4-[N-ethyl-N-(3-ethylamino)-2-pyridyl)amino]piperidine (EXAMPLE 206, 0.30 g) gives the title compound, NMR (300 MHz, $CD_3OD$) 7.54, 7.20, 6.97–6.90, 6.76, 6.61, 4.40, 3.70, 3.25, 3.06, 1.80, 1.51, 1.14 and 0.78$\delta$.

Example 229

1-[6-methoxyindolyl-2-carbonyl]-4-[N-ethyl-N-(3-ethylamino)-2-pyridyl)amino]piperidine (V)

Following the general procedure of EXAMPLE 149 and making non-critical variations, but using 6-methoxyindolyl-2-carboxylic acid (International Patent Publication No. WO91/09849, PREPARATION 63, 0.28 g) and 4-[N-ethyl-N-(3-ethylamino)-2-pyridyl)amino]piperidine (EXAMPLE 206, 0.30 g) gives the title compound, mp=162°–164°.

Example 230

1-[5,6-methylenedioxyindolyl-2-carbonyl]-4-[N-ethyl-N-((3-(1,1-dimethylethylamino)-5-fluoro)-2-pyridyl)amino]piperidine (V)

Following the general procedure of EXAMPLE 149 and making non-critical variations, but using 5,6-methylenedioxyindolyl-2-carboxylic acid (International Patent Publication No. WO91/09849, PREPARATION 79, 0.335 g) and 1-[N-ethyl-N-((3-(1,1-dimethylethylamino)-5-fluoro)-2-pyridyl)amino]piperidine (EXAMPLE 217, 0.4 g), gives the title compound, mp=202°–204°.

Example 231

1-[5,6-methylenedioxyindolyl-2-carbonyl]-4-[N-ethyl-N-3-(1-methylethylamino)-2-pyridyl)amino] piperidine (V)

Following the general procedure of EXAMPLE 149 and making non-critical variations, but using 5,6-methylenedioxyindolyl-2-carboxylic acid (International Patent Publication No. WO91/09849, PREPARATION 79, 0.28 g) and 4-[N-ethyl-N-3-(1-methylethylamino)-2-pyridyl)amino]piperidine (EXAMPLE 165, 0.30 g) gives the title compound, mp=145°–147°.

Example 232

1-[5-methylsulfonamidoindolyl-2-carbonyl]-4-[N-ethyl-N-3-(1-methylethylamino)-2-pyridyl)amino] piperidine (V)

Following the general procedure of EXAMPLE 149 and making non-critical variations, but using 5-methylsulfonamidoindolyl-2-carboxylic acid (0.35 g) and 4-[N- ethyl-N-3-(1-methylethylamino)-2-pyridyl)amino] piperidine (EXAMPLE 165, 0.30 g) gives the title compound, mp=215°–216°.

Example 233

1-[benzofuroyl-2-carbonyl]-4-[N-ethyl-N-3-(1-methylethylamino)-2-pyridyl)amino]piperidine (V)

Following the general procedure of EXAMPLE 149 and making non-critical variations, but using 2-benzofuran carboxylic acid (0.22 g) and 1-[N-ethyl-N-3-(1-methylethylamino)-2-pyridyl)amino]piperidine (EXAMPLE 165, 0.30 g) gives the title compound, NMR (300 MHz, $CD_3OD$) 7.68, 7.62, 7.53, 7.41, 7.31–7.24, 7.06–6.96, 4.44, 3.60, 3.30, 3.14, 2.96, 1.91, 1.60, 1.20 and 0.86$\delta$; CMR (75 MHz, $CD_3OD$) 161.5, 156.1, 149.7, 149.6, 142.8, 135.1, 128.3, 127.9, 124.9, 123.5, 122.8, 118.8, 112.7, 112.6, 58.9, 44.8, 43.4, 31.4, 23.0, 14.4 and 13.0$\delta$.

Example 234

1-(5-Fluoroindolyl-2-carbonyl)-4-[N-ethyl-N-(5-fluoro-2-(1-methylethylamino)-1-phenylamino) piperidine (V)

Following the general procedure of EXAMPLE 149 and making non-critical variations, but using 5-fluoroindolyl-2- carboxylic acid (0.51 g) and 4-[N-ethyl-N-(5-fluoro-2-1-methylethylamino)-1-phenylamino)piperidine (EXAMPLE 202, 0.40 g) gives the title compound, mp=144°–145°; NMR (300 MHz, CD₃OD) 7.30, 7.18, 6.90, 6.82, 6.71, 6.67, 6.55, 4.41, 3.51, 3.08–2.88, 1.76, 1.48, 1.10 and 0.81δ.

Example 235

4-[N-Ethyl-N-(3-(1,1-dimethylethylamino)-2-pyridinyl)amino]piperidine

Following the general procedure of EXAMPLE 206 and making non-critical variations but substituting 1-benzyl-4-[N-ethyl-N-3-(1,1-dimethylethylamino)-2-pyridinyl)amino]piperidine (EXAMPLE 143) for 1-benzyl-4-[N-ethyl-N-(3-(isopropylamino)-2-pyridinyl)amino]piperidine, the title compound is obtained.

Example 236

1-(5-Methanesulfonamidoindolyl-2-carbonyl)-4-[N-ethyl-N-(3-(1,1-dimethylethylamino)-2-pyridinyl)amino]piperidine (V)

Following the general procedure of EXAMPLE 149 and making non-critical variations but substituting 4-[N-ethyl-N-3-(1,1-dimethylethylamino)-2-pyridinyl)amino]piperidine (EXAMPLE 235) for 4-[N-methyl-N-(3-(1,1-dimethylethylamino)-2-pyridinyl)amino]piperidine, the title compound is obtained, mp=193°–194°.

Example 237

1-(5-Methanesulfonamidoindolyl-2-carbonyl)-4-[N-ethyl-N-(3-(1,1-dimethylethylamino-2-pyridinyl)amino]piperidine monomethanesulfonate (V)

1-(5-Methanesulfonamidoindolyl-2-carbonyl)-4-[N-ethyl-N-(3-(1,1-dimethylethylamino)-2-pyridinyl)amino]piperidine (V, EXAMPLE 236, 0.86 g) is dissolved in the minimum amount of methanol and 1 ml of a 1.67M solution of methanesulfonic acid in methanol is added. The mixture is concentrated to dryness, dissolved in a minimum amount of ethanol (about 4 ml)and ethyl acetate is added until the mixture turns cloudy. The salt crystallizes slowly upon scratching. The mixture is filtered, the solids dried under reduced pressure with heat to give the title compound, mp=197°–198°.

Example 238

1-(5-Fluoroindolyl-2-carbonyl)-4-[N-methyl-N-(3-isopropylamino-2-pyridinyl)amino]piperidine (V)

Following the general procedure of EXAMPLE 149 and making non-critical variations but starting with 5-fluoroindole-2-carboxylic acid (0.577 g) and 4-[N-methyl-N-(3-isopropylamino-2-pyridinyl)amino]piperidine (EXAMPLE 165, 0.4 g), the title compound is obtained, mp=168°–170° (ether/hexane).

Example 239

1-(5-benzyloxyindolyl-2-carbonyl)-4-[N-ethyl-N-(3-ethylamino-2-pyridinyl)amino]piperidine (V)

Following the general procedure of EXAMPLE 149 and making non-critical variations but starting with 5-benzyloxyindole-2-carboxylic acid (1.42 g) and 4-[N-ethyl-N-(3-ethylamino-2-pyridinyl)amino]piperidine (EXAMPLE 206, 1.1 g), the title compound is obtained, mp=141°–143° (ethyl acetate/hexane).

Example 240

1-(5-hydroxyindolyl-2-carbonyl)-4-[N-ethyl-N-(3-ethylamino-2-pyridinyl)amino]piperidine (V)

1-(5-benzyloxyindolyl-2-carbonyl)-4-[N-ethyl-N-(3-ethylamino-2-pyridinyl)amino]piperidine (EXAMPLE 239, 0.72 g) is dissolved in 70 ml of ethanol and 50 ml of THF. Then 0.25 g of palladium hydroxide is added and the reaction is placed on a Parr hydrogenator at 40 psi for 15 hr. Then it is filtered through celite and concentrated under reduced pressure to give the title compound, mp=145°–146° (methanol/hexane).

Example 241

1-(5-methanesulfonyloxyindolyl-2-carbonyl)-4-[N-ethyl-N-(3-ethylamino-2-pyridinyl)amino]piperidine (V)

1-(5-hydroxyindolyl-2-carbonyl)-4-[N-ethyl-N-(3-ethylamino-2-pyridinyl)amino]piperidine (EXAMPLE 240, 0.3 g) is dissolved in 2.45 ml of methylene chloride and cooled to 0°. Then triethylamine (0.089 ml) is added, followed by methanesulfonyl chloride (0.068 ml) and the reaction is slowly warmed to 20°–25°. After stirring for 15 hr additional methanesulfonyl chloride (0.6 eq) and triethylamine (0.6 eq) are added. After stirring 4 more hr, the reaction is diluted with chloroform, washed with sodium bicarbonate, saline, dried over sodium sulfate and concentrated under reduced pressure. Purification by flash column chromatography (50% ethyl acetate/hexane to 75% ethyl acetate/hexane) and crystallization (ethyl acetate/hexane) gives the title compound, mp=165°–167°.

Example 242

1-(5-benzyloxyindolyl-2-carbonyl)-4-[N-ethyl-N-(3-(1,1-dimethylethyl)amino-5-fluoro-2-pyridinyl)amino]piperidine (V)

Following the general procedure of EXAMPLE 149 and making non-critical variations but starting with 5-benzyloxyindole-2-carboxylic acid (4.36 g) and 4-[N-ethyl-N-(3-(1,1-dimethylethyl)amino-5-fluoro-2-pyridinyl)amino]piperidine (EXAMPLE 217, 4.00 g), the title compound is obtained, mp=146°–148° (ethyl acetate/hexane).

Example 243

1-(5-hydroxyindolyl-2-carbonyl)-4-[N-ethyl-N-(3-(1,1-dimethylethyl)amino-5-fluoro-2-pyridinyl)amino]piperidine (V)

Following the general procedure of EXAMPLE 240 and making non-critical variations but starting with 1-(5-benzyloxyindolyl-2-carbonyl)-4-[N-ethyl-N-(3-(1,1-dimethylethyl)amino-5-fluoro-2-pyridinyl)amino]piperidine (EXAMPLE 242, 5.89 g), the title compound is obtained, NMR (300 MHz, CDCl₃) 9.7, 7.42, 7.32, 7.10, 6.98, 6.74, 6.65, 4.75, 3.89, 3.40, 3.25–3.00, 2.03, 1.75, 1.49 and 1.04δ.

Example 244

1-(5-methanesulfonyloxyindolyl-2-carbonyl)-4-[N-ethyl-N-(3-(1,1-dimethylethyl)amino-5-fluoro-2-pyridinyl)amino]piperidine (V)

Following the general procedure of EXAMPLE 240 and making non-critical variations but starting with 1-(5- hydroxyindolyl-2-carbonyl)-4-[N-ethyl-N-(3-(1,1-dimethylethyl)amino-5-fluoro-2-pyridinyl)amino]piperidine (EXAMPLE 243, 0.3 g), the title compound is obtained, mp=159°–161° (ethyl acetate/hexane).

Example 245

1-[5-((4-methyl-1-piperazinyl)carbonyloxy)indolyl-2-carbonyl]-4-[N-ethyl-N-(3-(1,1-dimethylethyl)amino-5-fluoro-2-pyridinyl)amino]piperidine (V)

Following the general procedure of EXAMPLE 220, Part C, and making non-critical variations but starting with 1-(5-hydroxyindolyl-2-carbonyl)-4-[N-ethyl-N-(3-(1,1-dimethylethyl)amino-5-fluoro-2-pyridinyl)amino]piperidine (EXAMPLE 243, 0.35 g), stirring 3 days and then adding catalytic 4-dimethylaminopyridine and a further 1 eq of pyridine and 0.5 eq of 4-methyl-1-piperazinylcarbamoyl chloride, hydrochloride (EXAMPLE 219), the title compound is obtained, mp=174°–175° (ethyl acetate).

Example 246

Methyl 4-benzyloxy-α-azidocinnamate (intermediate)

4-Benzyloxybenzaldehyde (10.0 g) and methyl azidoacetate (21.7 g) are dissolved in 157 ml of methanol and cooled to −10° (ice-acetone bath). Then sodium methoxide (43.1 ml, 25% in methanol) is added dropwise such that the reaction temperature does not rise above −5°. After 2 hr, the cooling bath is removed and the reaction is warmed to 20°–25°. When no starting material remains by TLC, the reaction is diluted with ether and washed with saturated aqueous ammonium chloride. The organic layer is washed with water, saline, dried over anhydrous sodium sulfate and concentrated under reduced pressure. Purification by flash column chromatography (hexane to 5% ethyl acetate/hexane) gives the title compound.

Example 247

Methyl 6-benzyloxyindole-2-carboxylate (Intermediate)

Methyl 4-benzyloxy-α-azidocinnamate (EXAMPLE 246, 5.8 g) is dissolved in 376 ml of toluene and the reaction is heated to reflux for 1 hr. Then the reaction is cooled, concentrated under reduced pressure and the solids are recrystallized from ethyl acetate/hexane to provide the title compound.

Example 248

6-Benzyloxyindole-2-carboxylic acid (Intermediate)

Methyl 6-benzyloxyindole-2-carboxylate (EXAMPLE 247, 3.77 g) is dissolved in 33.5 ml of dioxane and 3.35 ml of water is added. Then solid potassium hydroxide (0.9 g) is added and the reaction is heated to 50° for 6 hr. Then a further 0.9 g of potassium hydroxide is added and the reaction is stirred at 20°–25° for 72 hr and heated at 50° a further 4 hr. Then it is cooled to 20°–25° and acidified to pH 4–5 with 2N hydrochloric acid. The reaction is extracted with methanol/chloroform (10/90, 3 times) and the extracts are dried over anhydrous magnesium sulfate, filtered and concentrated in vacuo to provide the title compound.

Example 249

1-(6-benzyloxyindolyl-2-carbonyl)-4-[N-ethyl-N-(3-ethylamino-2-pyridinyl)amino]piperidine (V)

Following the general procedure of EXAMPLE 149 and making non-critical variations but starting with 6-benzyloxyindole-2-carboxylic acid (EXAMPLE 248, 1.16 g) and 4-[N-ethyl-N-(3-ethylamino-2-pyridinyl)amino]piperidine (EXAMPLE 206, 0.9 g), the title compound is obtained, mp=102°–104° (ethyl acetate/hexane).

Example 250

1-(6-hydroxyindolyl-2-carbonyl)-4-[N-ethyl-N-(3-ethylamino-2-pyridinyl)amino]piperidine (V)

Following the general procedure of EXAMPLE 240 and making non-critical variations but starting with 1-(6-benzyloxyindolyl-2-carbonyl)-4-[N-ethyl-N-(3-ethylamino-2-pyridinyl)amino]piperidine (EXAMPLE 249, 0.80 g), the title compound is obtained, mp=108°–110° (ethyl acetate).

Example 251

1-(6-methanesulfonyloxyindolyl-2-carbonyl)-4-[N-ethyl-N-(3-ethylamino-2-pyridinyl)amino]piperidine (V)

Following the general procedure of EXAMPLE 241 and making non-critical variations but starting with 1-(6-hydroxyindolyl-2-carbonyl)-4-[N-ethyl-N-(3-ethylamino-2-pyridinyl)amino]piperidine (EXAMPLE 250, 0.32 g), the title compound is obtained, mp=121°–123° (ethyl acetate/hexane).

Example 252

1-Benzyl-4-[N-ethyl-N-(6-chloro-5-nitro-4-pyrimidinyl)amino]piperidine (intermediate)

4,6-Dichloro-5-nitropyrimidine (8.88 g) is dissolved in 400 ml of methylene chloride and cooled to −78°. Then triethylamine (6.7 ml) and 1-benzyl-4-N-ethylaminopiperidine (EXAMPLE 205, 10.00 g) is added and the reaction is stirred 1 hr at −78° and slowly warmed to 20°–25°. The reaction is poured into saturated aqueous sodium bicarbonate, extracted with methylene chloride, washed with saline, dried and concentrated under reduced pressure. Purification by flash column chromatography (10% ethyl acetate/hexane to 50% ethyl acetate/hexane) gives the title compound.

Example 253

1-Benzyl-4-[N-ethyl-N-(5-amino-4-pyrimidinyl)amino]piperidine (intermediate)

1-Benzyl-4-[N-ethyl-N-(6-chloro-5-nitro-4-pyrimidinyl)amino]piperidine (EXAMPLE 252, 3.00 g) is dissolved in 150 ml of ethanol and 0.75 g of palladium hydroxide is added. The reaction is placed on a Parr hydrogenator at 10 psi for 1 h, then filtered through diatemous earth and concentrated under reduced pressure. Purification by flash column chromatography (5% methanol/chloroform) gives the title compound.

Example 254

1-Benzyl-4-[N-ethyl-N-(5-(1,1-dimethylethylamino-4-pyrimidinyl)amino]piperidine (intermediate)

Following the general procedure of EXAMPLE 119 and making non-critical variations but starting with 1-Benzyl-4-[N-ethyl-N-(5-(amino-4-pyrimidinyl)amino]piperidine (EXAMPLE 253, 1.13 g), the title compound is obtained.

Example 255

4-[N-ethyl-N-(5-(1,1-dimethylethylamino-4-pyrimidinyl)amino]piperidine (intermediate)

1-Benzyl-4-[N-ethyl-N-(5-(1,1-dimethylethylamino-4-pyrimidinyl)amino]piperidine (EXAMPLE 254, 0.59 g) is dissolved in 25 ml of ethanol and 0.15 g of palladium hydroxide is added. Then the reaction is placed on a Parr hydrogenator under 40 psi of hydrogen for 15 hr. Filtration through celite and concentration under reduced pressure gives the title compound which is used without further purification.

Example 256

1-(5-Methanesulfonamidoindolyl-2-carbonyl)-4-[N-ethyl-N-(5-(1,1-dimethylethylamino-4-pyrimidinyl)amino]piperidine (V)

Following the general procedure of EXAMPLE 149 and making non-critical variations but starting with 5-methanesulfonamidoindole-2-carboxylic acid (PREPARATION 3, 0.45 g) and 4-[N-ethyl-N-(5-(1,1-dimethylethylamino-4-pyrimidinyl)amino]piperidine (EXAMPLE 255, 0.41 g), the title compound is obtained, mp 212°–214° (methanol/chloroform).

Example 257

1-Benzyl-4-[N-isopropyl-N-(3-ethylamino-2-pyridinyl)amino]piperidine (intermediate)

1-benzyl-4-[N-isopropyl-N-(3-amino-2-pyridinyl)amino]piperidine (EXAMPLE 101, after titanium chloride reduction of nitro group; 1.92 g) is dissolved in 15 ml of methanol and cooled to 0°. Then 0.5 ml of acetaldehyde and 0.56 g of sodium cyanoborohydride are added. The reaction is allowed to warm slowly to 20°–25° and stirred for 15 hr. Then it is poured into sodium hydroxide (1N) and extracted with chloroform. The extracts are dried over sodium sulfate, and concentrated under reduced pressure. Purification by flash column chromatography (20% ethyl acetate/hexane) gives the title compound.

Example 258

4-[N-isopropyl-N-(3-ethylamino-2-pyridinyl)amino]piperidine (intermediate)

Following the general procedure of EXAMPLE 255 and making non-critical variations, but starting with 1-benzyl-4-[N-isopropyl-N-(3-ethylamino-2-pyridinyl)amino]piperidine (EXAMPLE 257, 0.9 g), the title compound is obtained.

Example 259

1-(5-methanesulfonamidoindolyl-2-carbonyl)-4-[N-isopropyl-N-(3-ethylamino-2-pyridinyl)amino]piperidine (V)

Following the general procedure of EXAMPLE 149 and making non-critical variations, but starting with 4-[N-isopropyl-N-(3-ethylamino-2-pyridinyl)amino]piperidine (EXAMPLE 258, 0.665 g) and 5-methanesulfonamidoindole-2-carboxylic acid (PREPARATION 3, 0.77 g), the title compound is obtained, C,H,N analysis calculated for $C_{25}H_{34}N_6O_3S$: C=60.22, H=6.87, N=16.85, S=6.43; found C=59.96, H=6.87, N=16.67, S=6.27.

Example 260

1-Benzyl-4-[N-ethylcarboxamido]piperidine (Intermediate)

Ethylamine hydrochloride (6.59 g) is dissolved in 40 ml of dry toluene at 0° C. Then trimethyl aluminum (40.4 ml, 2M in toluene) is added dropwise. After 30 min, the reaction is warmed to 20°–25° and stirred 1 hr. Then ethyl 1-benzyl-4-piperidinecarboxylate (10.0 g) dissolved in 20 ml of toluene is added and the reaction is heated to 85° for 2 hr. The reaction is cooled to 20°–25° and quenched cautiously with 5% aqueous HCl and extracted with chloroform. Then the aqueous layers are adjusted to pH 7 with sodium hydroxide and extracted with chloroform (3 times). The organic extracts are dried over sodium sulfate and concentrated under reduced pressure to afford the title compound.

Example 261

1-Benzyl-4-[(N-ethylamino)methyl]piperidine (intermediate)

1-Benzyl-4-[N-ethylcarboxamido]piperidine (EXAMPLE 260, 6.67 g) is dissolved in 90 ml of THF and cooled to 0°. Then lithium aluminum hydride (1M in THF, 27.1 ml) is added and the reaction is slowly warmed to 20°–25° and then refluxed for 2.5 hr. Then it is cooled in an ice bath and quenched by the dropwise addition of 1.03 ml water, 1.03 ml of 15% sodium hydroxide, and 3.09 ml of water. The reaction is filtered through celite and concentrated under reduced pressure to afford the title compound.

Example 262

1-Benzyl-4-[(N-ethyl-N-(3-nitro-2-pyridinyl)amino)methyl]piperidine (intermediate)

1-Benzyl-4-[(N-ethylamino)methyl]piperidine (EXAMPLE 261, 5.68 g) and 2-chloro-3-nitropyridine (3.87 g) are dissolved in 96 ml of acetonitrile and 4.05 g of solid potassium bicarbonate is added. The reaction is refluxed for 20 hr, cooled to 20°–25°, poured into water and extracted with ethyl acetate. The organic extracts are dried (sodium sulfate), and concentrated under reduced pressure. Purification by flash column chromatography (15% ethyl acetate/hexane to 80% ethyl acetate/hexane) gives the title compound, HRMS calcd. for $C_{20}H_{26}N_4O_2$=354.2056, found=354.2045.

Example 263

1-Benzyl-4-[(N-ethyl-N-(3-amino-2-pyridinyl)amino)methyl]piperidine (intermediate)

1-Benzyl-4-[(N-ethyl-N-(3-nitro-2-pyridinyl)amino)methyl]piperidine (EXAMPLE 262, 4.70 g) is dissolved in 40 ml of THF and 1.7 g of platinum oxide is added and the reaction is placed on a Parr hydrogenator at 10 psi for 1 hr. Then a further 800 mg of platinum oxide is added and the reaction hydrogenated another hour. Then it is filtered through celite and concentrated under reduced pressure to provide the title compound.

Example 264

1-Benzyl-4-[(N-ethyl-N-(3-(1,1-dimethylethylamino)-2-pyridinyl)amino)methyl]piperidine (intermediate)

Following the general procedure of EXAMPLE 119 and making non-critical variations but starting with 1-Benzyl-4-[(N-ethyl-N-(3-amino-2-pyridinyl)amino)methyl]piperidine (EXAMPLE 263, 4.2 g), the title compound is obtained.

Example 265

4-[(N-ethyl-N-(3-(1,1-dimethylethylamino)-2-pyridinyl)amino)methyl]piperidine (intermediate)

Following the general procedure of EXAMPLE 255 and making non-critical variations but starting with 1-benzyl-4-

[(N-ethyl-N-(3-(1,1-dimethylethylamino)-2-pyridinyl) amino)methyl]piperidine (EXAMPLE 264, 1.67 g), the title compound is obtained.

Example 266

1-(Pyrrolyl-2-carbonyl)-4-[(N-ethyl-N-(3-(1,1-dimethylethylamino)-2-pyridinyl)amino)methyl] piperidine (V)

Following the general procedure of EXAMPLE 149 and making non-critical variations but starting with 4-[(N-ethyl-N-(3-(1,1-dimethylethylamino)-2-pyridinyl)amino)methyl] piperidine (EXAMPLE 265, 0.68 g) and pyrrole-2-carboxylic acid (0.26 g), the title compound is obtained, C,H,N analysis calcd. for $C_{22}H_{23}N_5O \cdot H_2O$: C=65.81, H=8.79, N=17.44; found: C=65.75, H=8.37, N=16.96.

Example 267

1-(5-Methanesulfonamidoindolyl-2-carbonyl)-4-[(N-ethyl-N-(3-(1,1-dimethylethylamino)-2-pyridinyl) amino)methyl]piperidine (V)

Following the general procedure of EXAMPLE 149 and making non-critical variations but starting with 4-[(N-ethyl-N-(3-(1,1-dimethylethylamino)-2-pyridinyl)amino)methyl] piperidine (EXAMPLE 265, 0.68 g) and 5-methanesulfonamidoindole-2-carboxylic acid (0.52 g, PREPARATION 3), the title compound is obtained, mp=175°–176° (ethyl acetate/hexane).

Example 268

1-Benzyl-4-[N-ethyl-N-(3-amino-6-chloro-2-pyridinyl)amino]piperidine (intermediate)

Following the procedure of EXAMPLE 183 and then following the first part of the procedure of EXAMPLE 184 (platinum oxide reduction to the amine), the title compound is obtained.

Example 269

1-Benzyl-4-[N-ethyl-N-(3-(1,1-dimethylethylamino)-6-chloro-2-pyridinyl)amino]piperidine (intermediate)

Following the general procedure of EXAMPLE 119 and making non-critical variations but starting with 1-benzyl-4-[N-ethyl-N-(3-amino-6-chloro-2-pyridinyl)amino] piperidine (EXAMPLE 268, 11.64 g), the title compound is obtained.

Example 270

4-[N-ethyl-N-(3-(1,1-dimethylethylamino)-6-chloro-2-pyridinyl)amino]piperidine (intermediate)

1-Benzyl-4-[N-ethyl-N-(3-(1,1-dimethylethylamino)-6-chloro-2-pyridinyl)amino]piperidine (EXAMPLE 269, 1.5 g) is dissolved in 8 ml of methylene chloride and cooled to 0°. Then 1-chloroethyl chloroformate (0.54 ml) is added dropwise. The reaction is warmed to 20°–25° and refluxed for 30 min. Then the reaction is concentrated under reduced pressure and 15 ml of methanol is added and the reaction is heated to reflux for 2 hr. Then it is poured into saturated aqueous sodium bicarbonate and extracted with chloroform. The organic extracts are dried over potassium carbonate and concentrated under reduced pressure. Purification by flash column chromatography (90:9.5:0.5; chloroform/methanol/ concentrated ammonium hydroxide) gives the title compound.

Example 271

1-(5-Methanesulfonamidoindolyl-2-carbonyl)-4-[N-ethyl-N-(3-(1,1-dimethylethylamino)-6-chloro-2-pyridinyl)amino]piperidine (V)

Following the general procedure of EXAMPLE 149 and making non-critical variations but starting with 4-[N-ethyl-N-(3-(1,1-dimethylethylamino)-6-chloro-2-pyridinyl) amino]piperidine (0.43 g, EXAMPLE 270), the title compound is obtained, mp=206°–207° (methanol).

Example 272

1-Benzyl-4-[N-ethyl-N-(ortho-(4,4-dimethyl-2-oxazolinyl)phenyl)amino]piperidine (intermediate)

1-benzyl-4-N-ethylaminopiperidine (EXAMPLE 11, 4.19 g) is dissolved in 40 ml of THF and cooled to −78°. Then n-butyl lithium (12.0 ml, 1.6M in hexane) is added dropwise. The reaction is stirred 10 min, and 4,4-dimethyl-2-(ortho-methoxyphenyl)-2-oxazoline (4.08 g) in 10 ml of THF is added dropwise. The reaction is slowly warmed to 20°–25° and stirred for 15 hr. Then it is poured into water and extracted with chloroform, dried over sodium sulfate, and concentrated under reduced pressure. Purification by flash column chromatography (4% methanol/chloroform) gives the title compound.

Example 273

1-Benzyl-4-[(N-ethyl-N-(2-ethoxycarbonyl)phenyl) amino]piperidine (intermediate)

1-Benzyl-4-[N-ethyl-N-(ortho-(4,4-dimethyl-2-oxazolinyl)phenyl)amino]piperidine (EXAMPLE 272, 4.99 g) is dissolved in 60 ml of ethanol and 3.2 ml of concentrated sulfuric acid and 1.2 ml of fuming sulfuric acid are added. The reaction is heated to reflux for 4 days. The volatiles are removed under reduced pressure, and the remaining material is basified with 10% ammonium hydroxide. Extraction with ether (2×), drying over sodium sulfate and concentration under reduced pressure provided the crude material which is purified by flash column chromatography (15% ethyl acetate/hexane) to give the title compound.

Example 274

1-Benzyl-4-[(N-ethyl-N-(2-hydroxymethyl)phenyl) amino]piperidine (intermediate)

1-Benzyl-4-[(N-ethyl-N-(2-ethoxycarbonyl)phenyl) amino]piperidine (EXAMPLE 273, 1.72 g) is dissolved in 15.6 ml of THF and cooled to 0°. Then 4.69 ml of lithium aluminum hydride (1M in THF) is added dropwise. The reaction is warmed to 20°–25° and stirred for 2 hr. Then the reaction is cooled to 0° and quenched by the careful addition of 0.178 ml of water, 0.178 ml of 15% sodium hydroxide, and 0.535 ml of water. The reaction is filtered through celite and concentrated under reduced pressure to give the title alcohol which is used without further purification.

Example 275

1-Benzyl-4-[(N-ethyl-N-(2-formyl)phenyl)amino] piperidine (intermediate)

1-Benzyl-4-[(N-ethyl-N-(2-hydroxymethyl)phenyl) amino]piperidine (EXAMPLE 274, 1.4 g) is dissolved in 10.8 ml of methylene chloride and 0.74 ml of DMSO is added. The reaction is cooled to −78° and 0.448 ml of oxalyl chloride is added dropwise. After 15 min of stirring, 3.0 ml of triethylamine is added at once and the reaction is allowed to warm to 20°–25°. Then it is diluted with chloroform, extracted with water, dried over sodium sulfate and concentrated under reduced pressure to provide the title aldehyde which is used without further purification.

Example 276

1-Benzyl-4-[(N-ethyl-N-(2-(1-propenyl))phenyl)amino]piperidine (intermediate)

Following the general procedure of EXAMPLE 19 and making non-critical variations but starting with 1-benzyl-4-[(N-ethyl-N-(2-formyl)phenyl)amino]piperidine (EXAMPLE 275, 0.93 g) instead of 1-benzyl-4-[(N-ethyl-N-(3-formyl-2-pyridinyl)amino]piperidine, the title compound is obtained.

Example 277

4-[(N-ethyl-N-(2-(1-propyl))phenyl)amino]piperidine (intermediate)

1-Benzyl-4-[(N-ethyl-N-(2-(1-propenyl))phenyl)amino]piperidine (EXAMPLE 276, 0.62 g) is dissolved in 5 ml of ethanol and 0.4 g of palladium hydroxide are added. The reaction is placed on a Parr hydrogenator at 40 psi for 48 hr. Then it is filtered through celite and concentrated under reduced pressure to give the title compound.

Example 278

1-(5-methanesulfonamidoindolyl-2-carbonyl)-4-[(N-ethyl-N-(2-(1-propyl))phenyl)amino]piperidine (I)

Following the general procedure of EXAMPLE 149 and making non-critical variations but starting with 5-methanesulfonamidoindole-2-carboxylic acid (PREPARATION 3, 0.69 g) and 4-[(N-ethyl-N-(2-(1-propyl))phenyl)amino]piperidine (EXAMPLE 277, 0.44 g), the title compound is obtained, mp=182°–183° (methanol).

FORMULAS OF THE EXAMPLES (E-#)

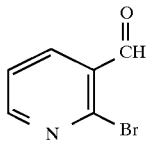

E-1

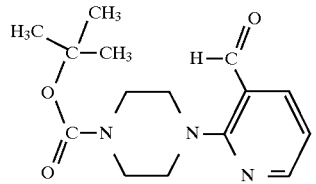

E-2

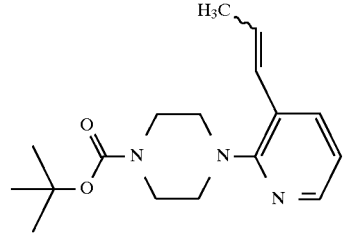

E-3

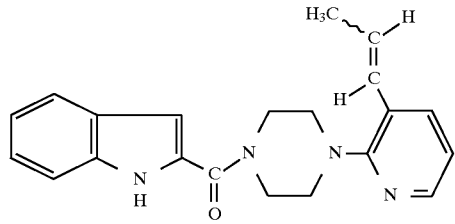

E-4

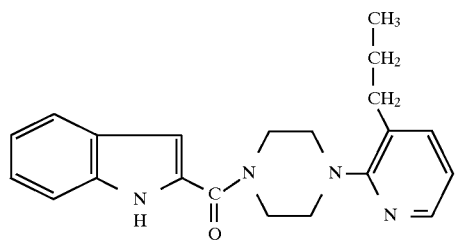

E-5

-continued
FORMULAS OF THE EXAMPLES (E-#)
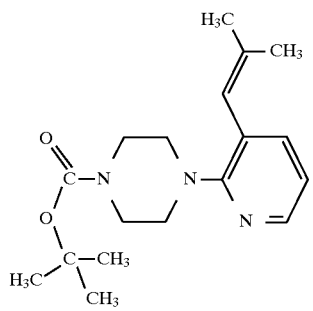
E-6
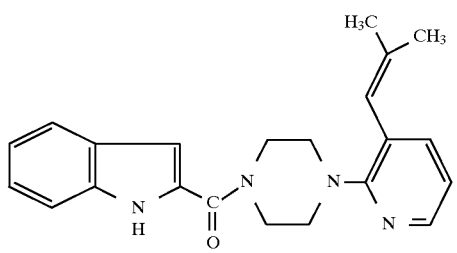
E-7
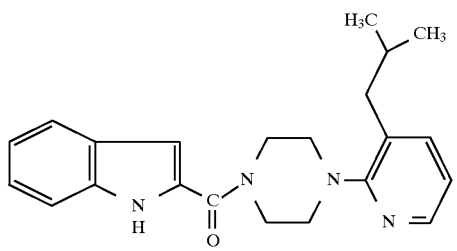
E-8
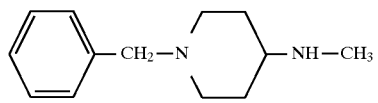
E-9
---     E-10
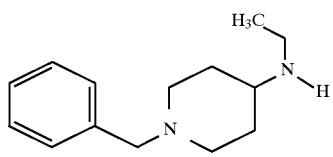
E-11
---     E-12
---     E-13
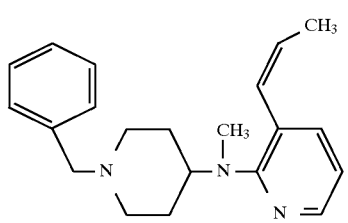
E-14

-continued
FORMULAS OF THE EXAMPLES (E-#)
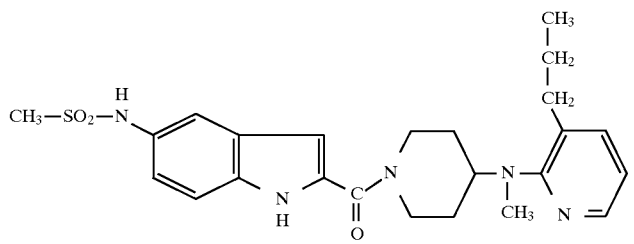 E-15
 E-16
 E-17
 E-18
 E-19
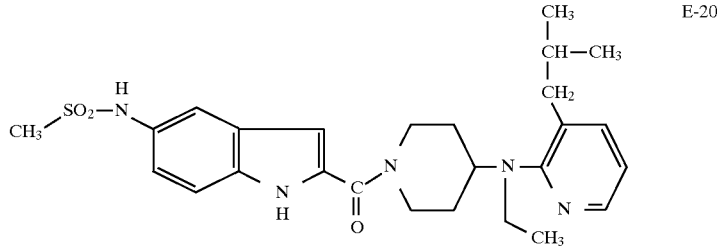 E-20
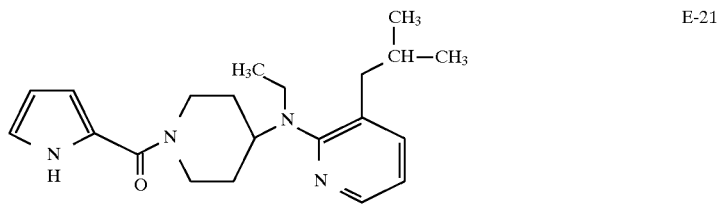 E-21
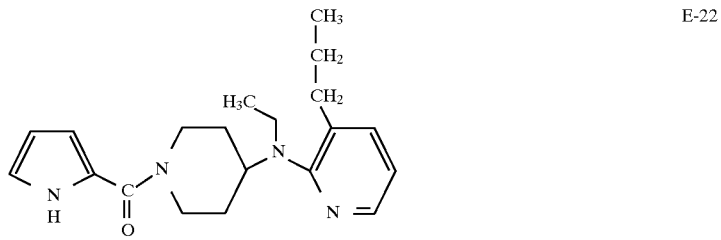 E-22
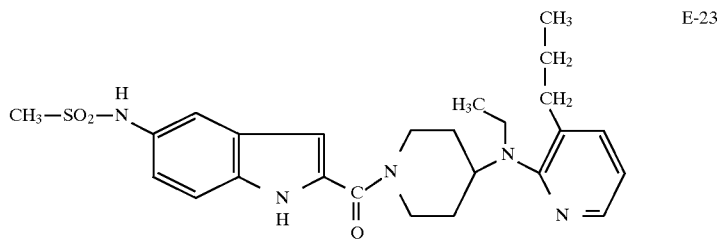 E-23
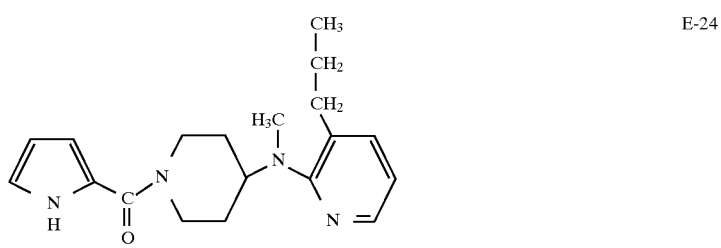 E-24

-continued
FORMULAS OF THE EXAMPLES (E-#)
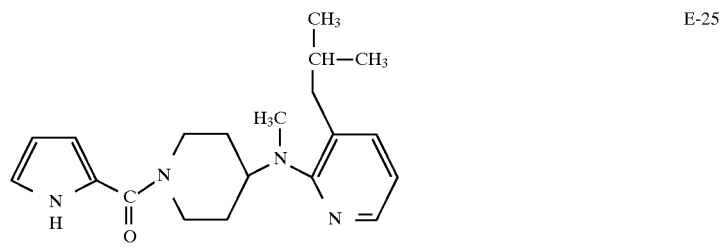
E-25
--- E-26
--- E-27
--- E-28
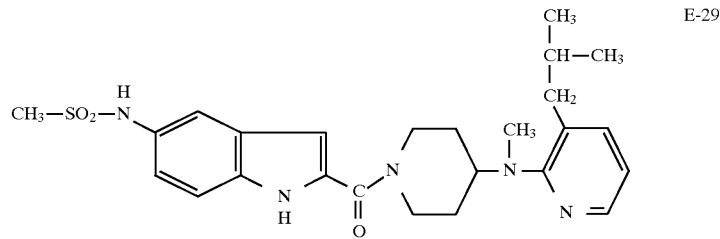
E-29
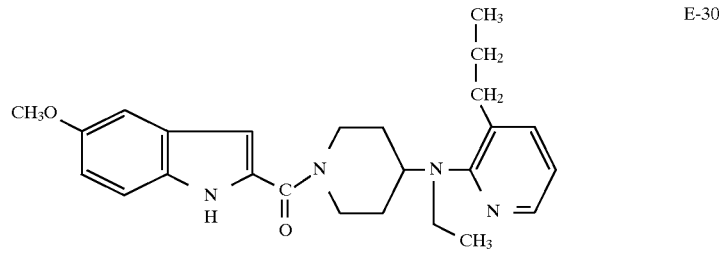
E-30
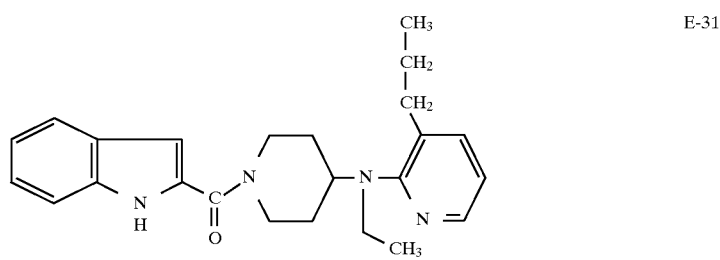
E-31
--- E-32
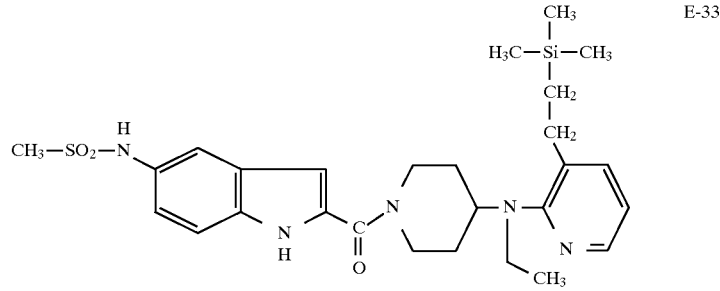
E-33

-continued
FORMULAS OF THE EXAMPLES (E-#)
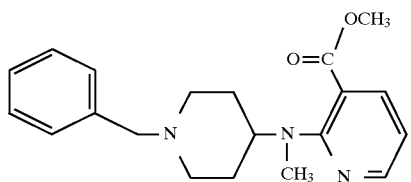
E-34
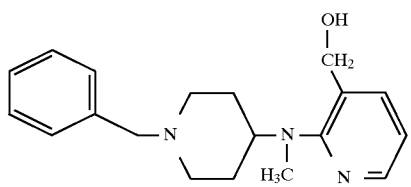
E-35
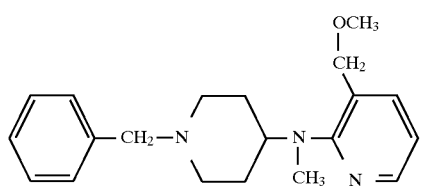
E-36
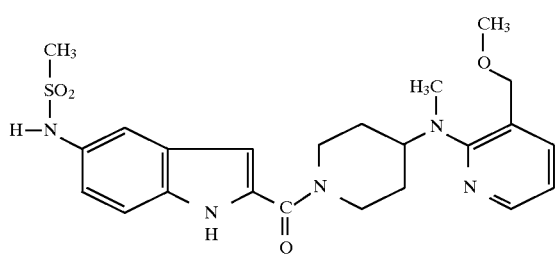
E-37
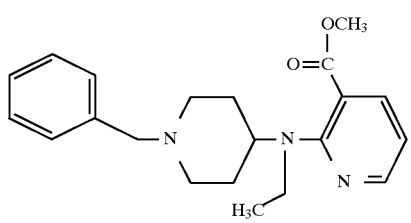
E-38
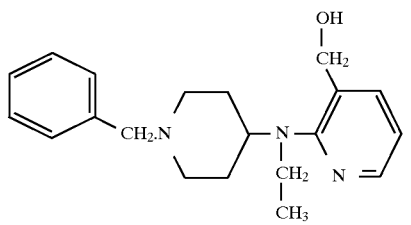
E-39
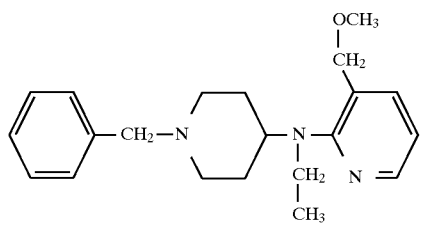
E-40

-continued
FORMULAS OF THE EXAMPLES (E-#)
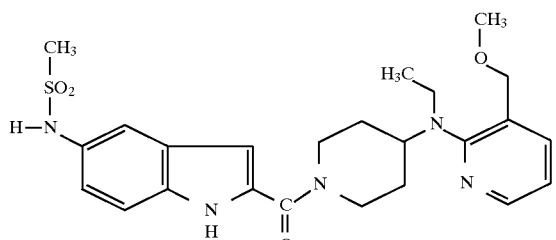 E-41
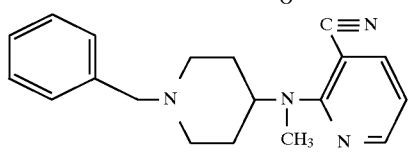 E-42
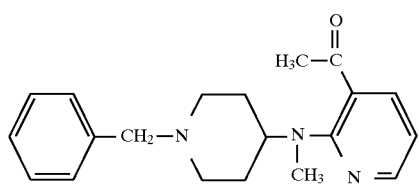 E-43
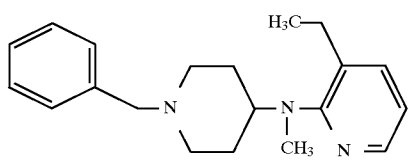 E-44
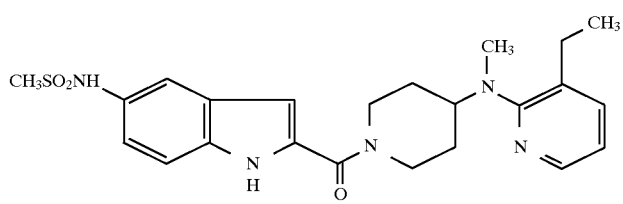 E-45
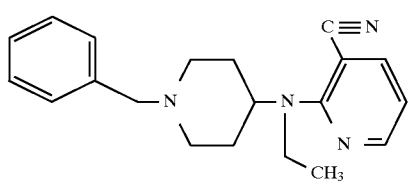 E-46
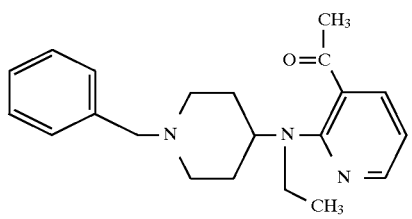 E-47
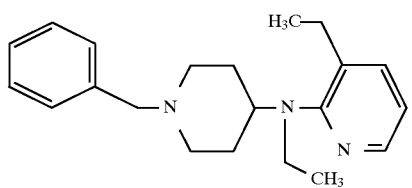 E-48

-continued
FORMULAS OF THE EXAMPLES (E-#)
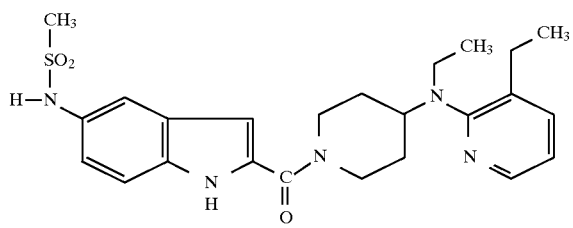
E-49
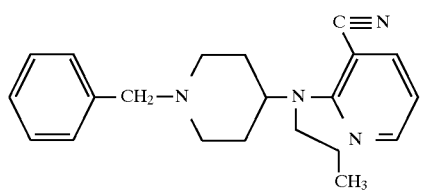
E-50
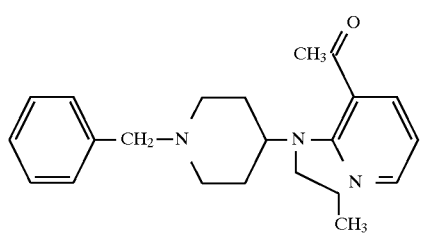
E-51
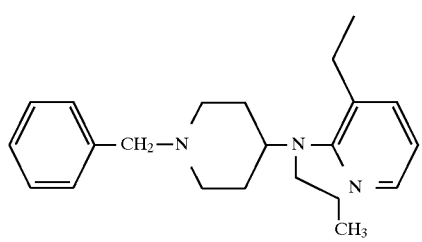
E-52
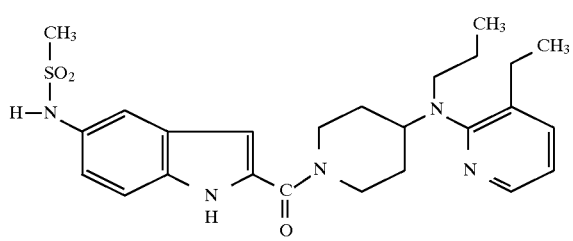
E-53
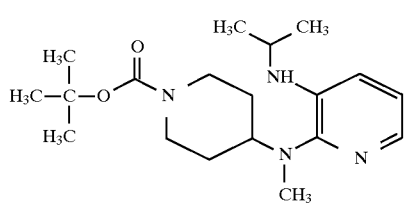
E-54
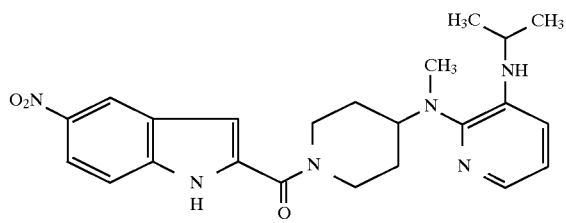
E-55

-continued
FORMULAS OF THE EXAMPLES (E-#)
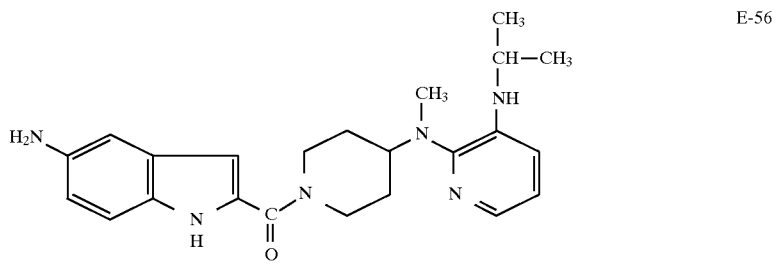
E-56
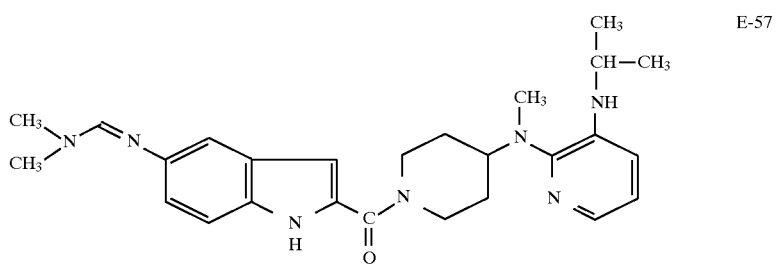
E-57
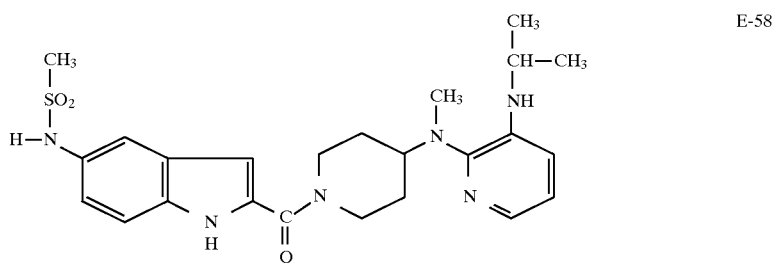
E-58
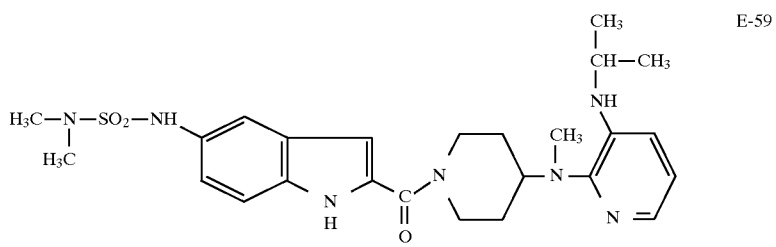
E-59
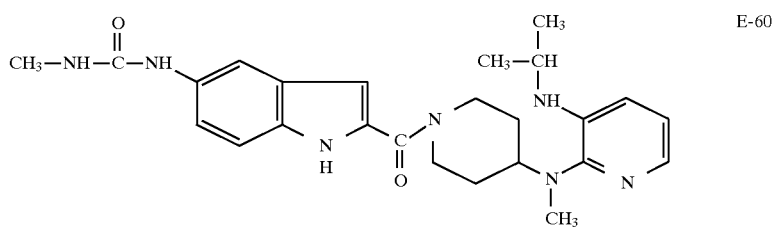
E-60
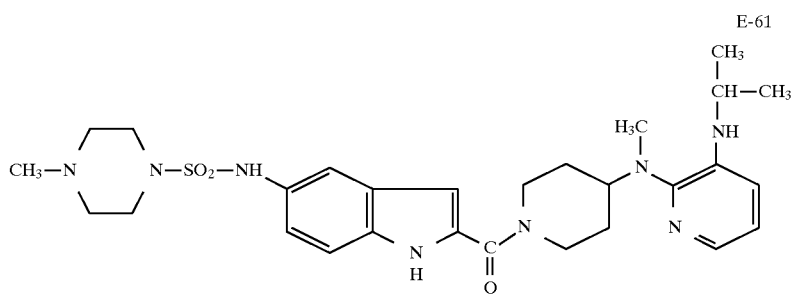
E-61

-continued
FORMULAS OF THE EXAMPLES (E-#)
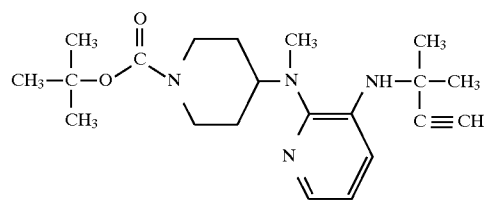
E-62
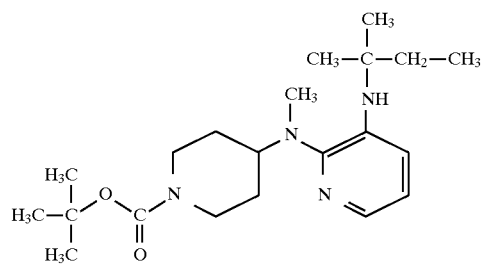
E-63
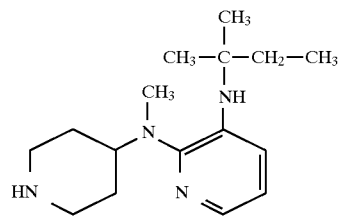
E-64
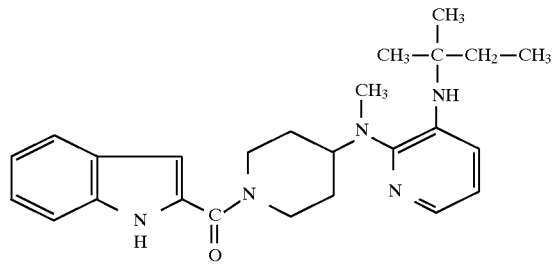
E-65
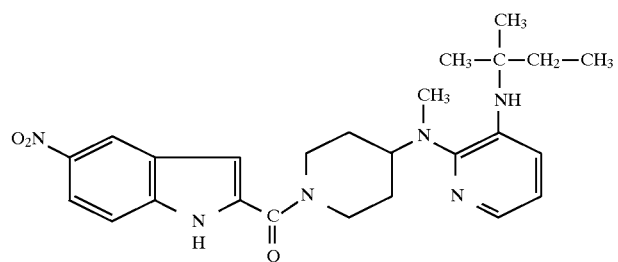
E-66
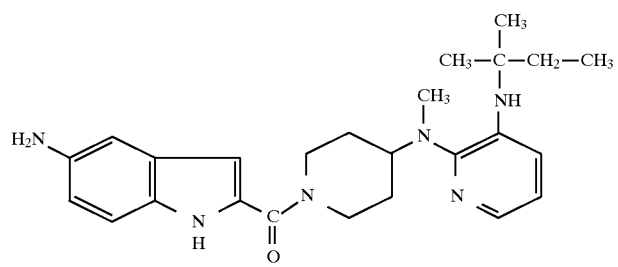
E-67

-continued
FORMULAS OF THE EXAMPLES (E-#)
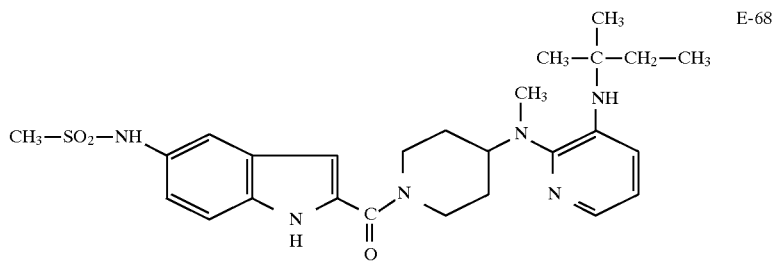
E-68
--- E-69
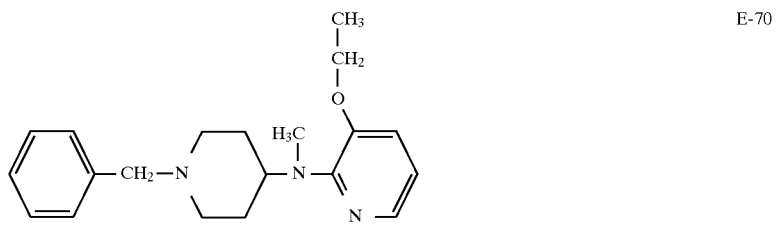
E-70
E-71
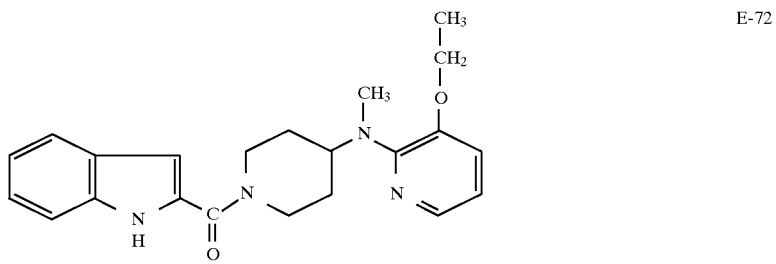
E-72
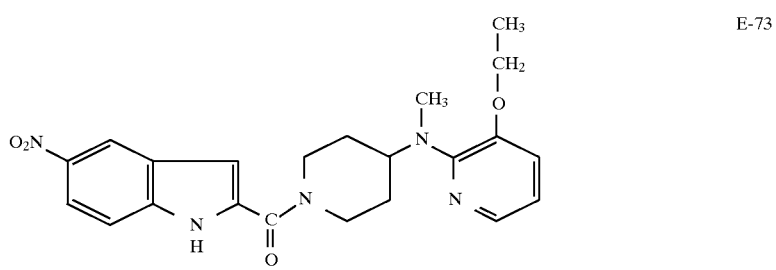
E-73
--- E-74
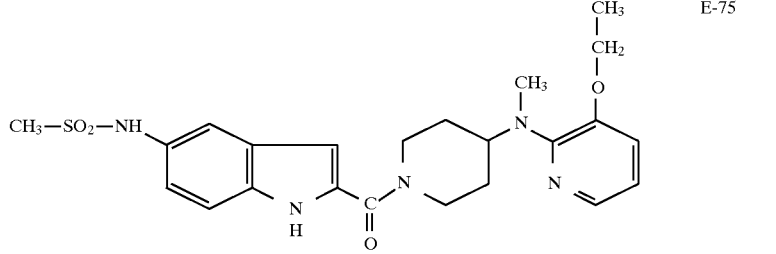
E-75
--- E-76

-continued
FORMULAS OF THE EXAMPLES (E-#)
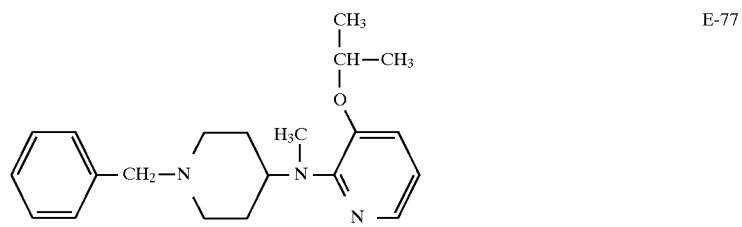
E-77
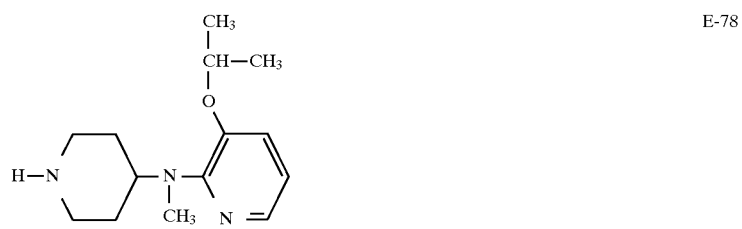
E-78
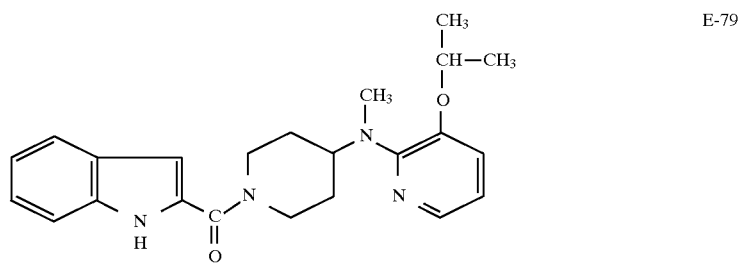
E-79
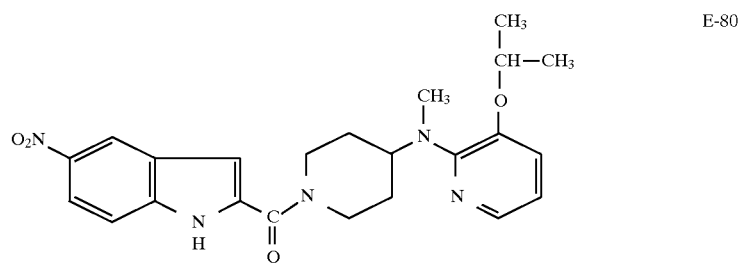
E-80
--- E-81
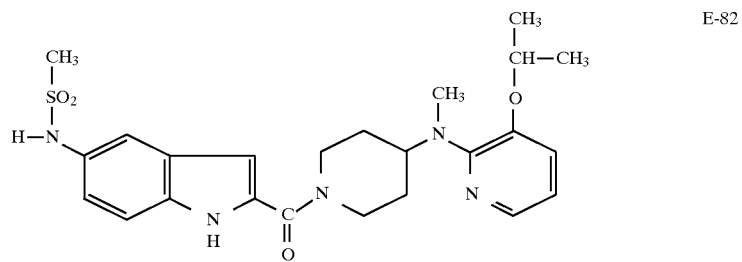
E-82
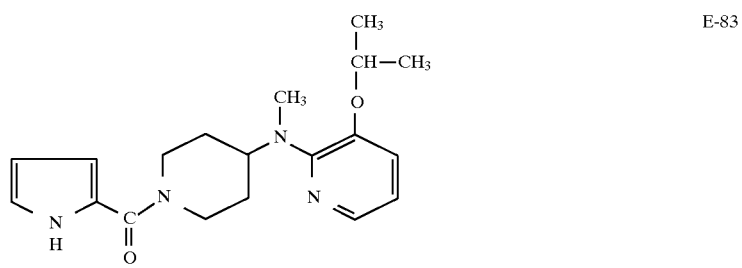
E-83

-continued
FORMULAS OF THE EXAMPLES (E-#)
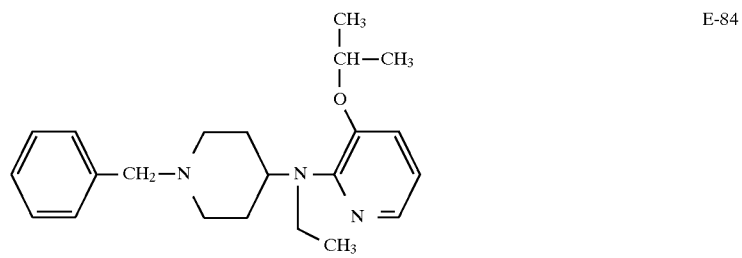
E-84
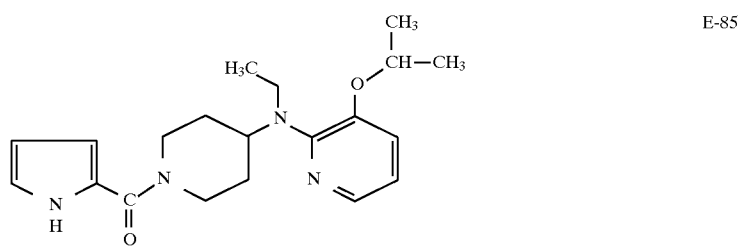
E-85
--- E-86
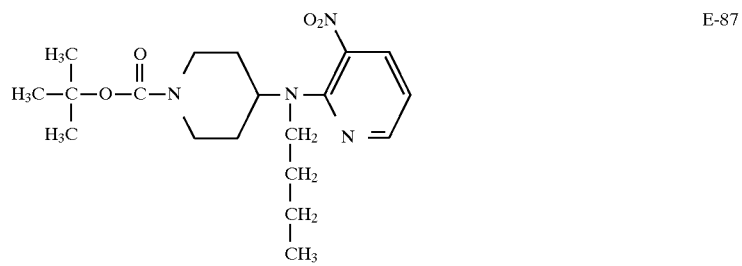
E-87
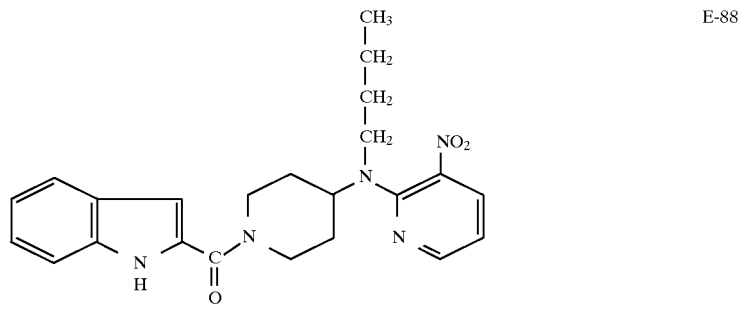
E-88
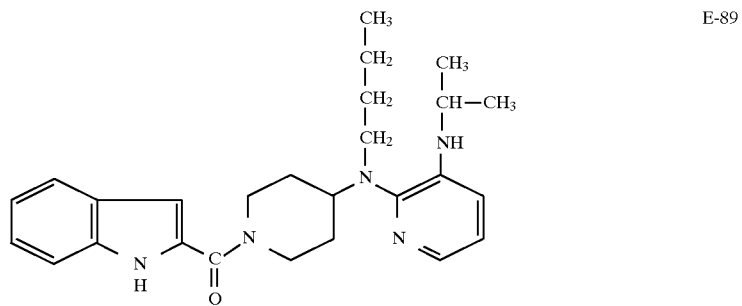
E-89
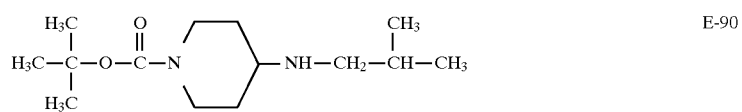
E-90

-continued
FORMULAS OF THE EXAMPLES (E-#)
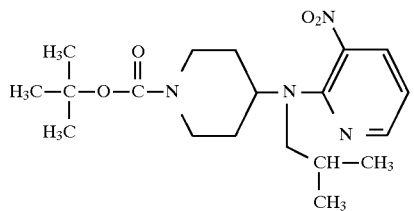
E-91
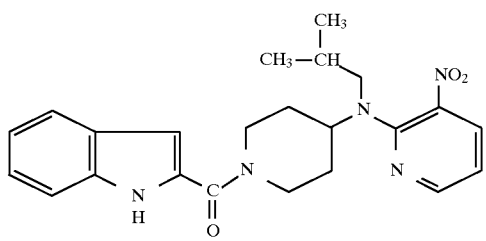
E-92
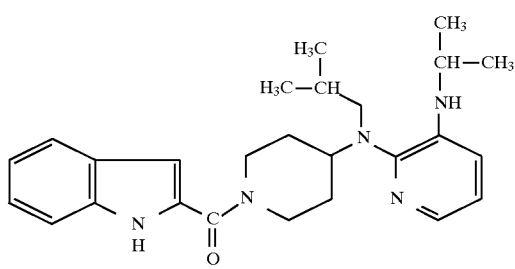
E-93
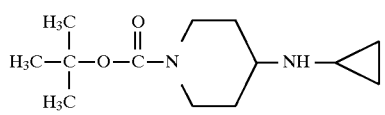
E-94
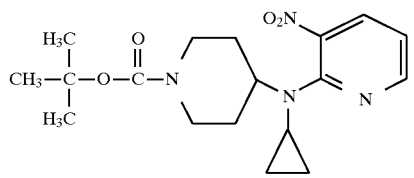
E-95
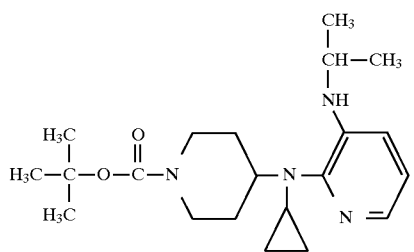
E-96
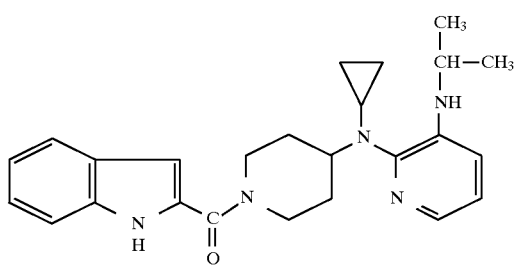
E-97

-continued
FORMULAS OF THE EXAMPLES (E-#)
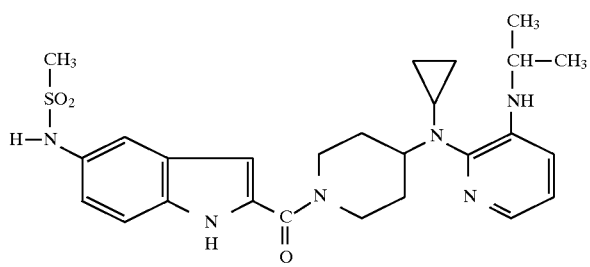
E-98
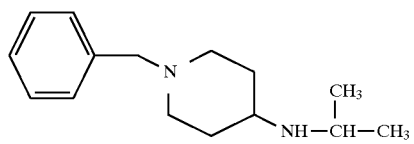
E-99
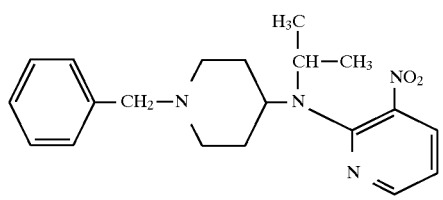
E-100
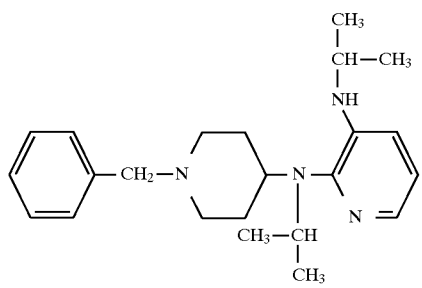
E-101
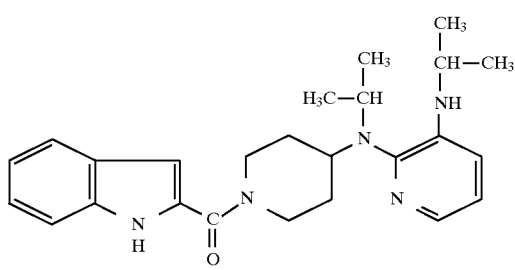
E-102
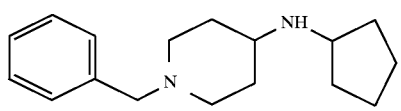
E-103
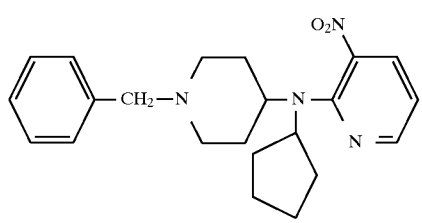
E-104

121
-continued
FORMULAS OF THE EXAMPLES (E-#)
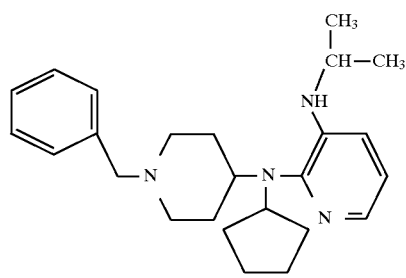
E-105
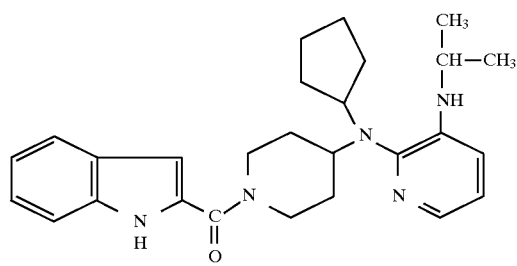
E-106
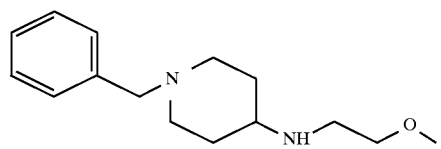
E-107
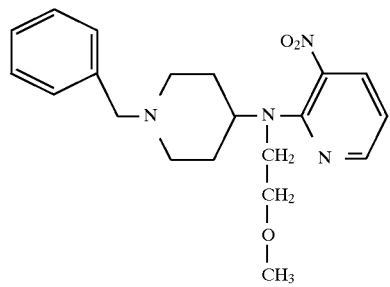
E-108
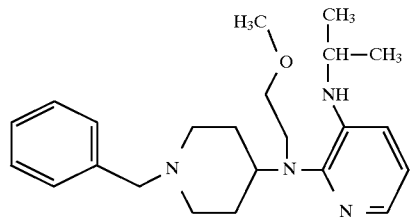
E-109
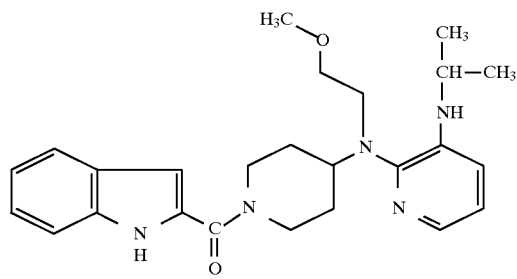
E-110

-continued
FORMULAS OF THE EXAMPLES (E-#)
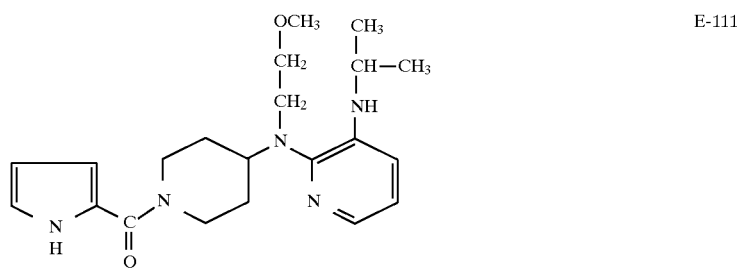
E-111
--- E-112
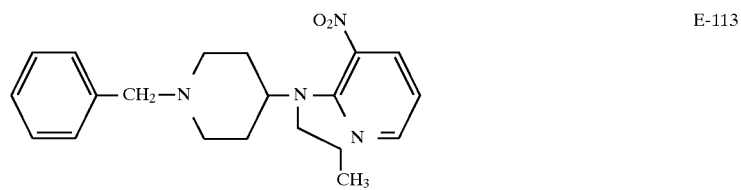
E-113
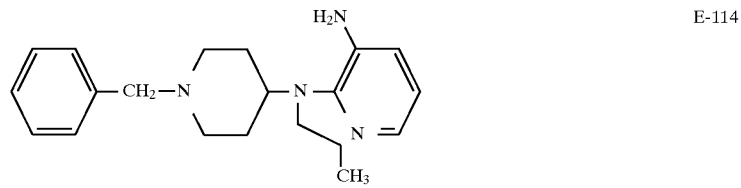
E-114
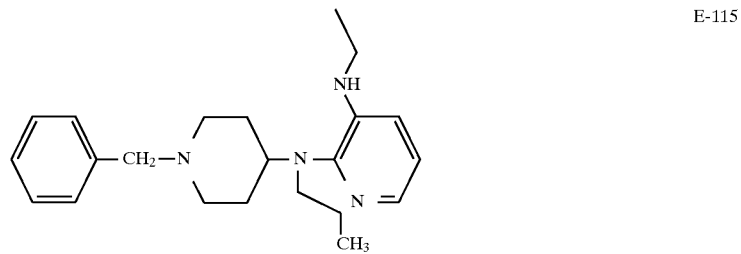
E-115
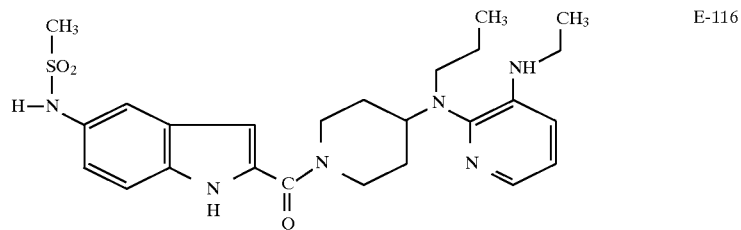
E-116
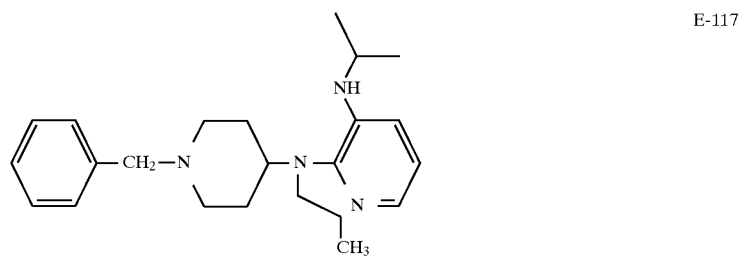
E-117

-continued
FORMULAS OF THE EXAMPLES (E-#)
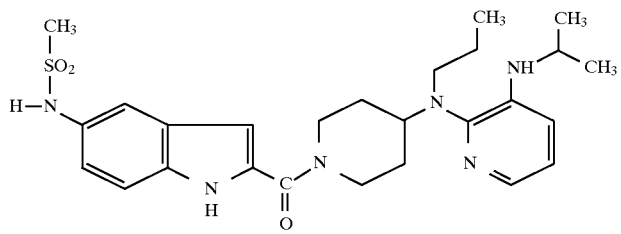 E-118
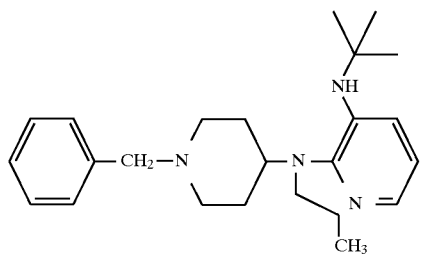 E-119
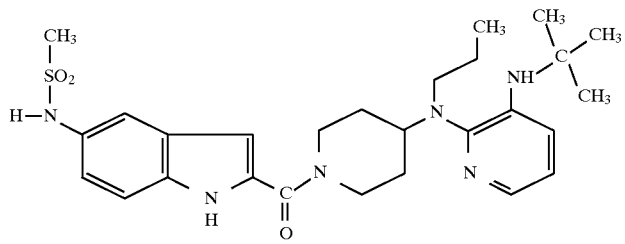 E-120
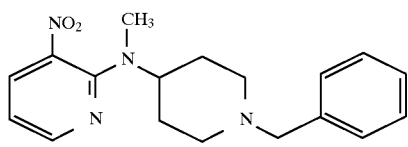 E-121
--- E-122
--- E-123
E-124
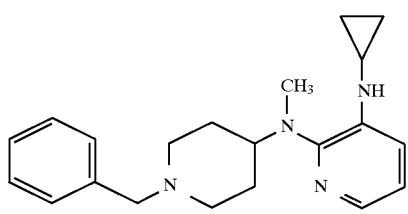
E-125
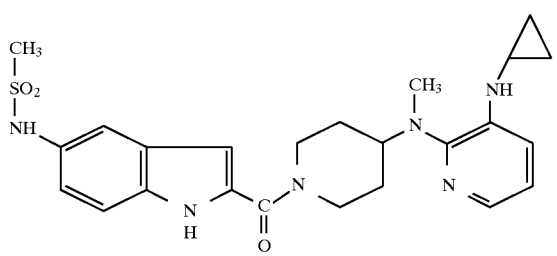
--- E-126

-continued
FORMULAS OF THE EXAMPLES (E-#)
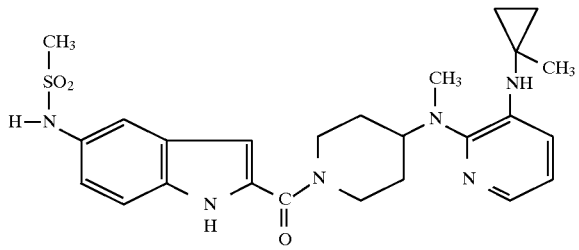
E-127
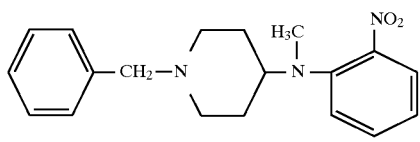
E-128
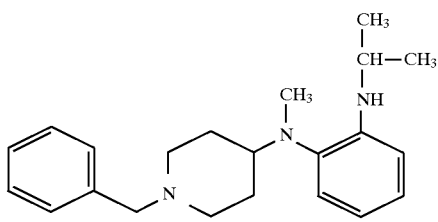
E-129
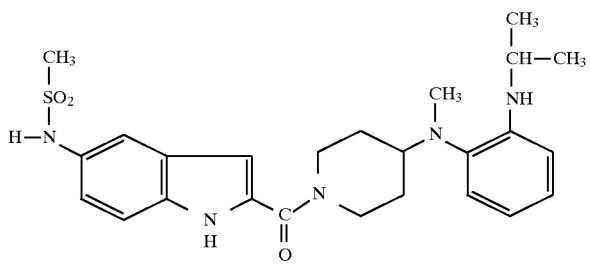
E-130
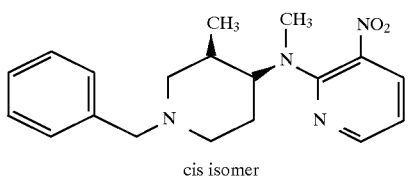
E-131
cis isomer
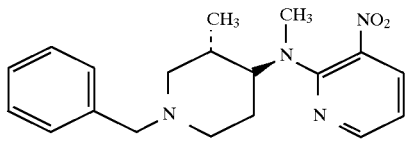
E-131
trans isomer
racemic mixture
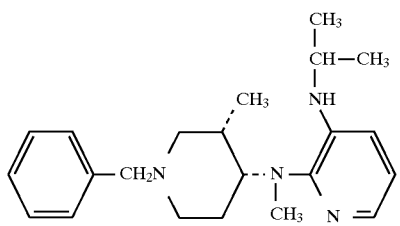
E-132
cis isomer
racemic mixture

-continued
FORMULAS OF THE EXAMPLES (E-#)
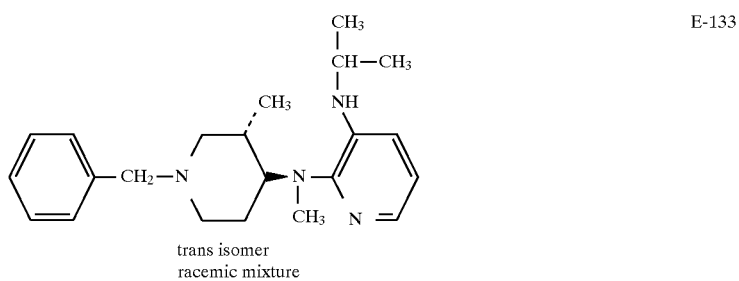
E-133
trans isomer
racemic mixture
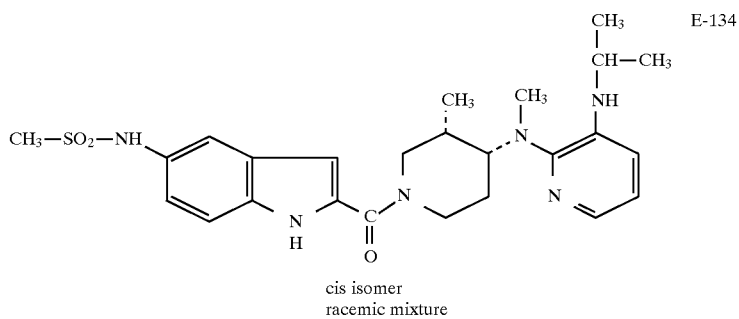
E-134
cis isomer
racemic mixture
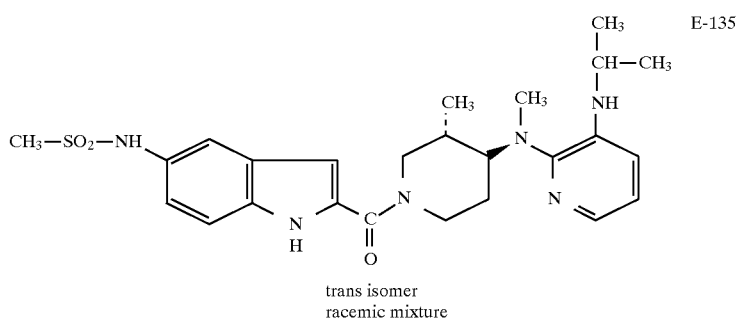
E-135
trans isomer
racemic mixture
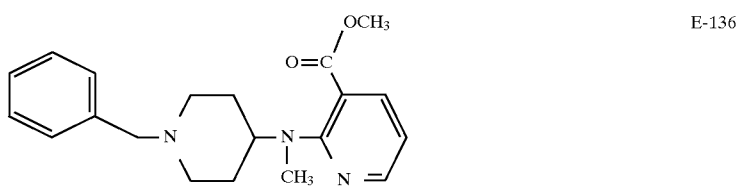
E-136
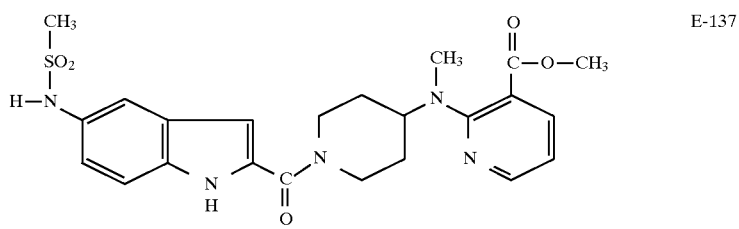
E-137
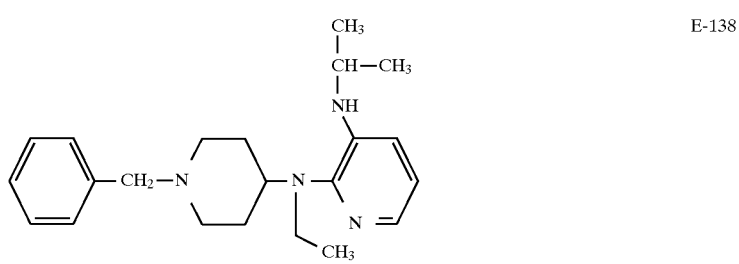
E-138

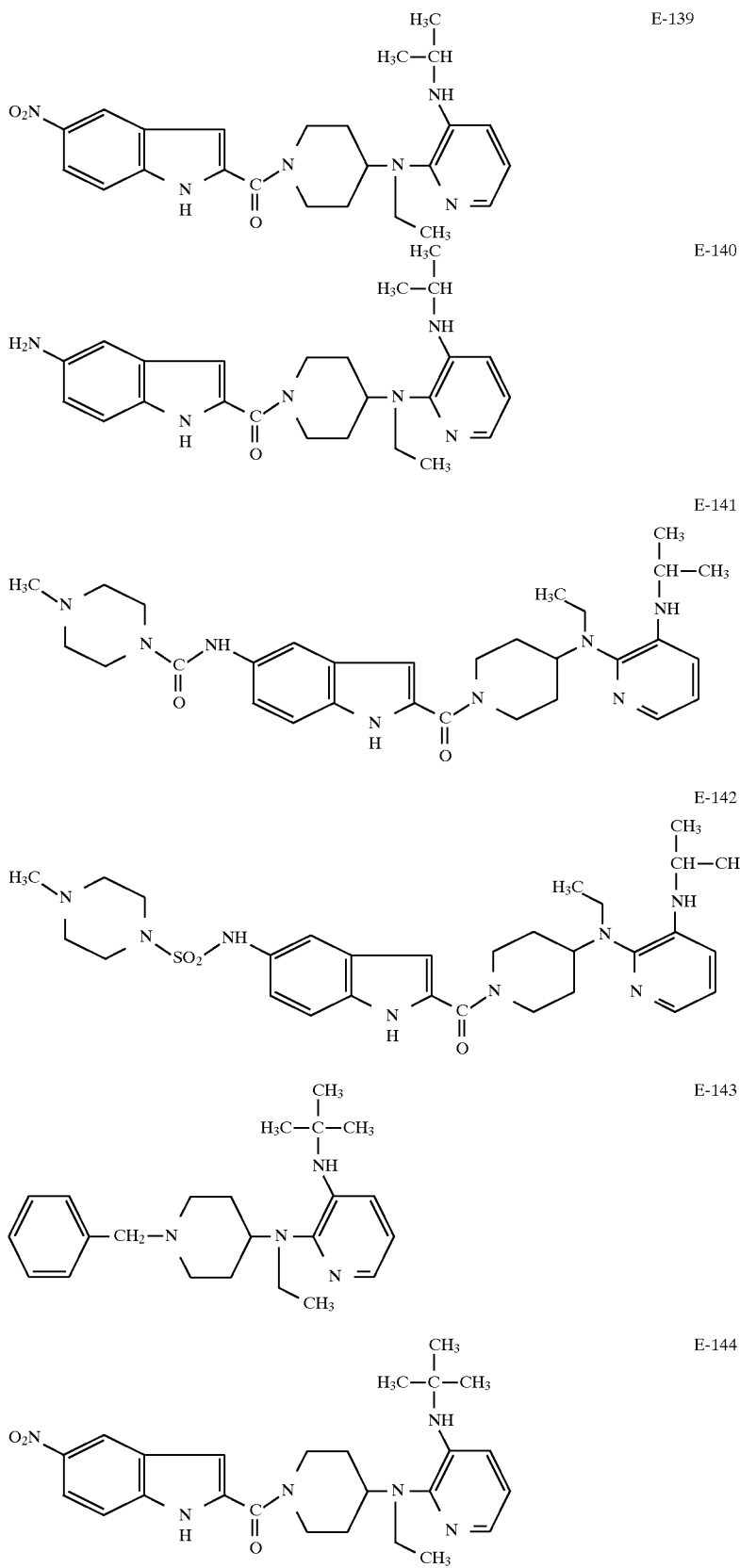

-continued
FORMULAS OF THE EXAMPLES (E-#)
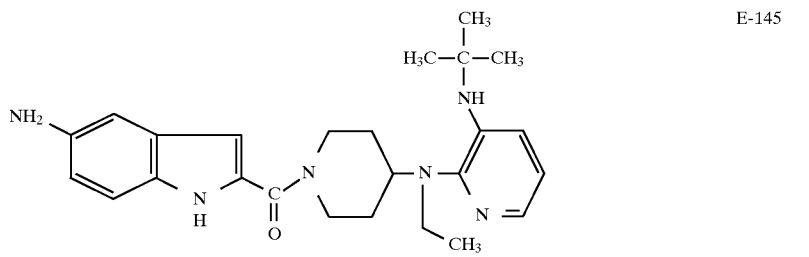
E-145
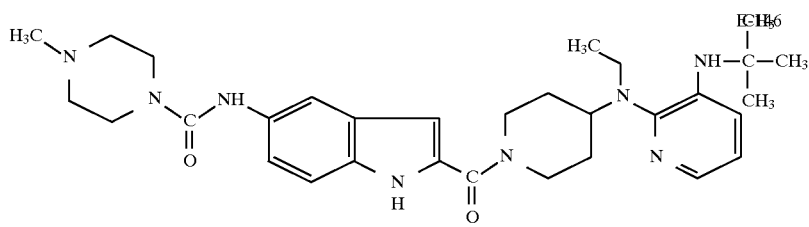
E-146
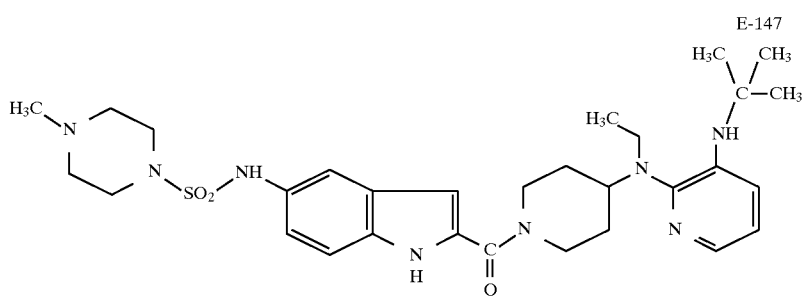
E-147
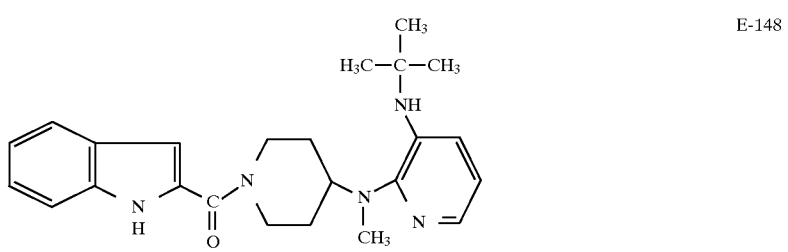
E-148
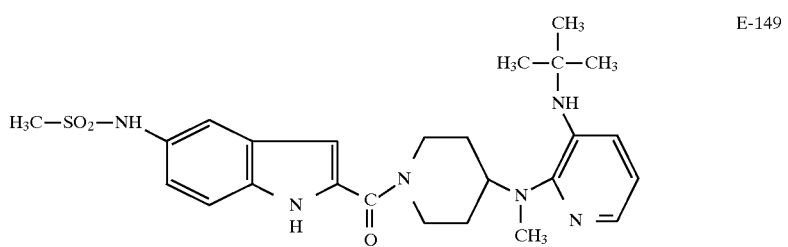
E-149
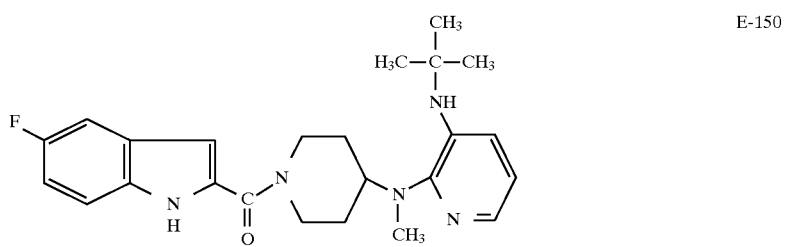
E-150
--- E-151
--- E-152
--- E-153

-continued
FORMULAS OF THE EXAMPLES (E-#)
--- E-154
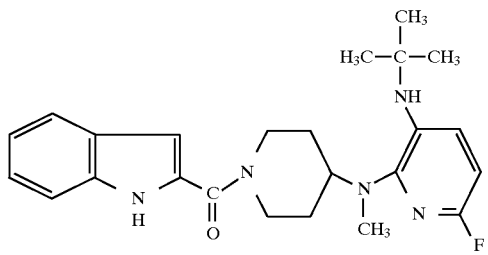 E-155
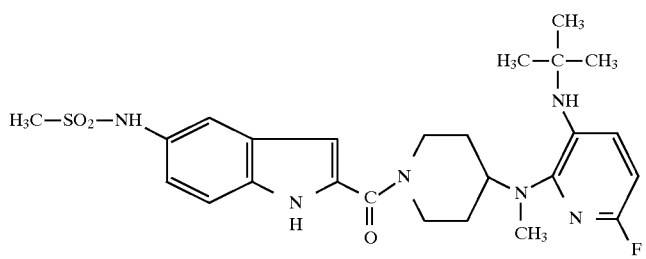 E-156
--- E-157
--- E-158
--- E-159
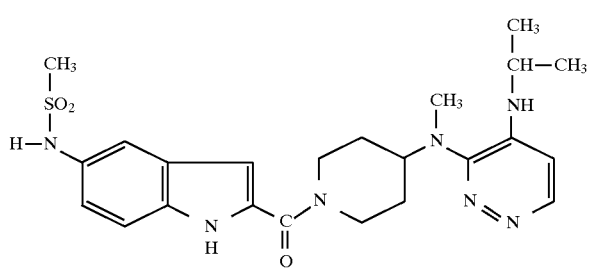 E-160
--- E-161
--- E-162
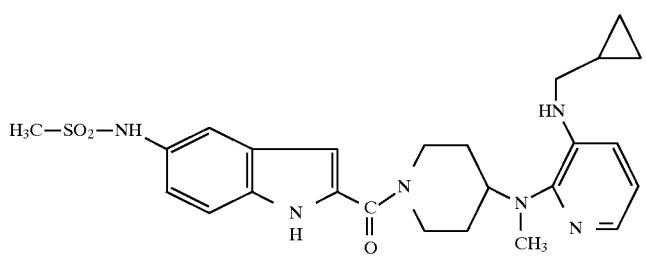 E-163
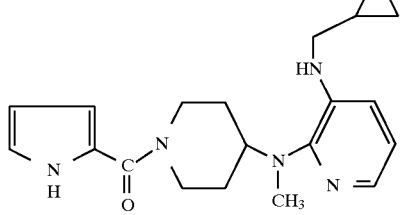 E-164
--- E-165

-continued
FORMULAS OF THE EXAMPLES (E-#)
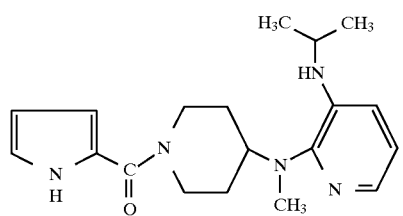 E-166
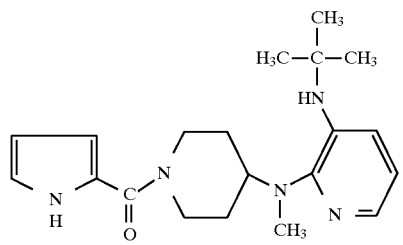 E-167
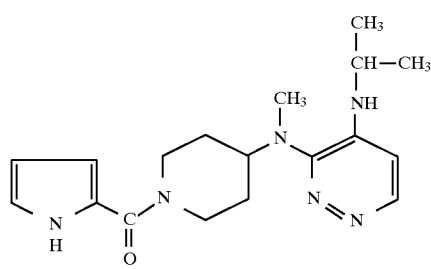 E-168
--- E-169
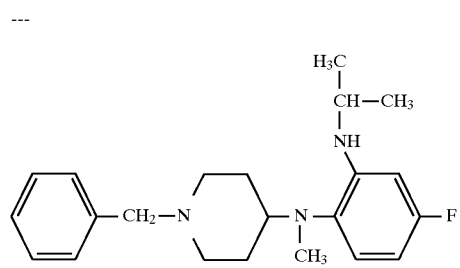 E-170
--- E-171
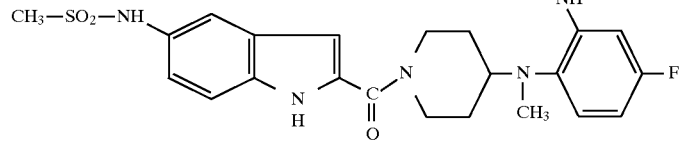 E-172
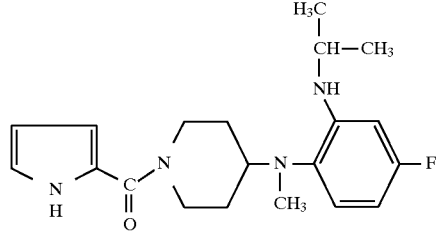 E-173
--- E-174
--- E-175

-continued
FORMULAS OF THE EXAMPLES (E-#)
--- E-176
--- E-177
--- E-178
--- E-179
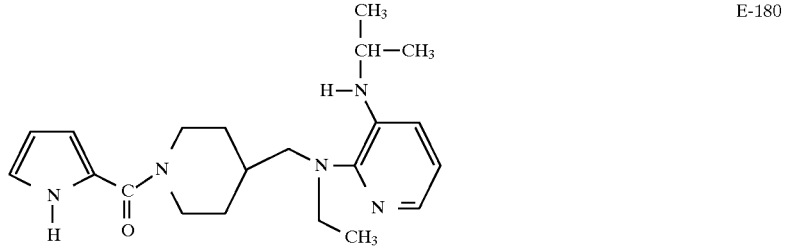 E-180
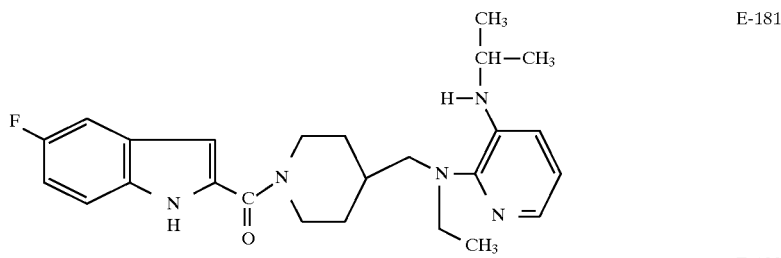 E-181
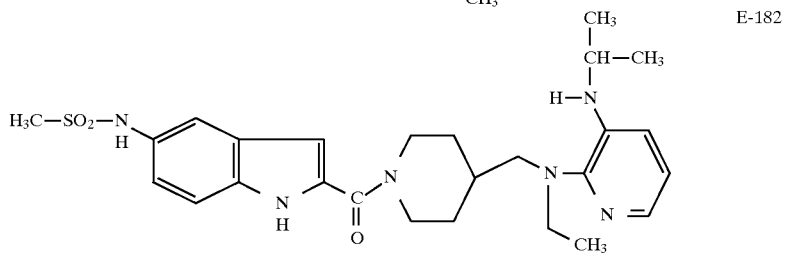 E-182
--- E-183
--- E-184
--- E-185
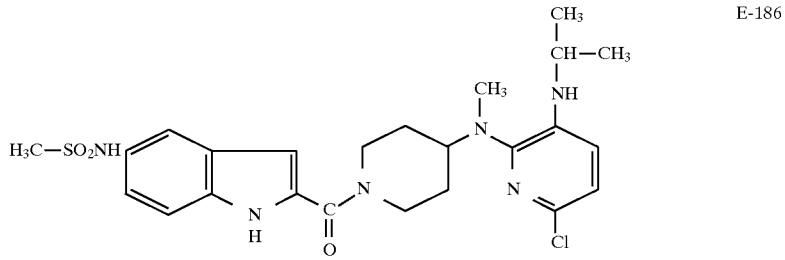 E-186
--- E-187
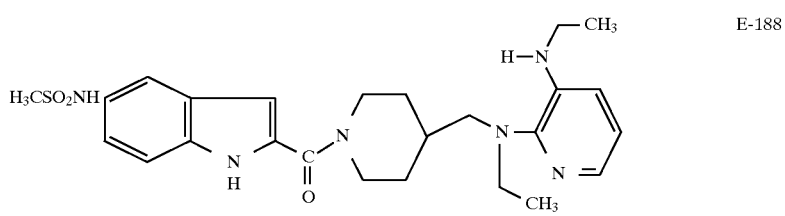 E-188

-continued
FORMULAS OF THE EXAMPLES (E-#)
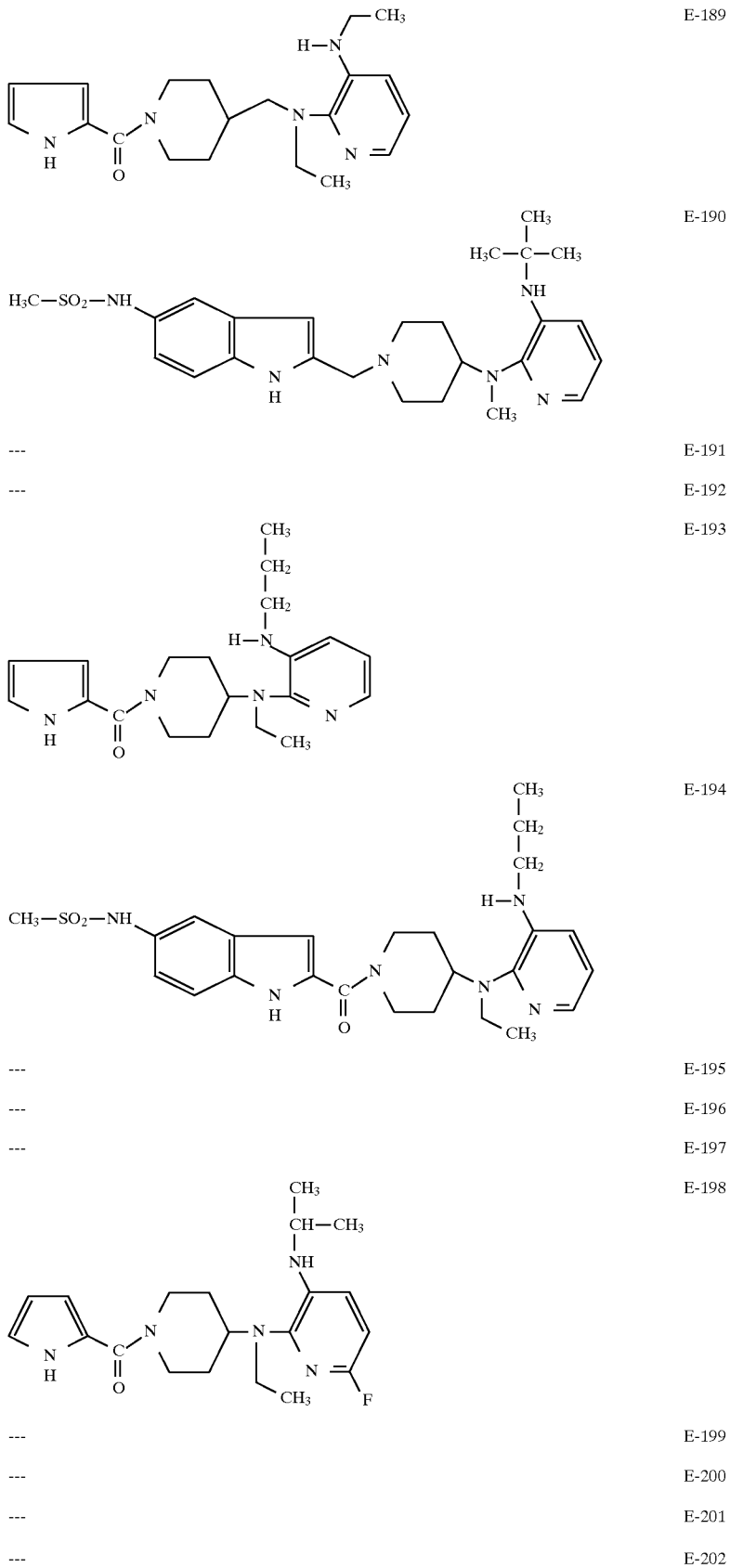
E-189
E-190
E-191
E-192
E-193
E-194
E-195
E-196
E-197
E-198
E-199
E-200
E-201
E-202

-continued
FORMULAS OF THE EXAMPLES (E-#)
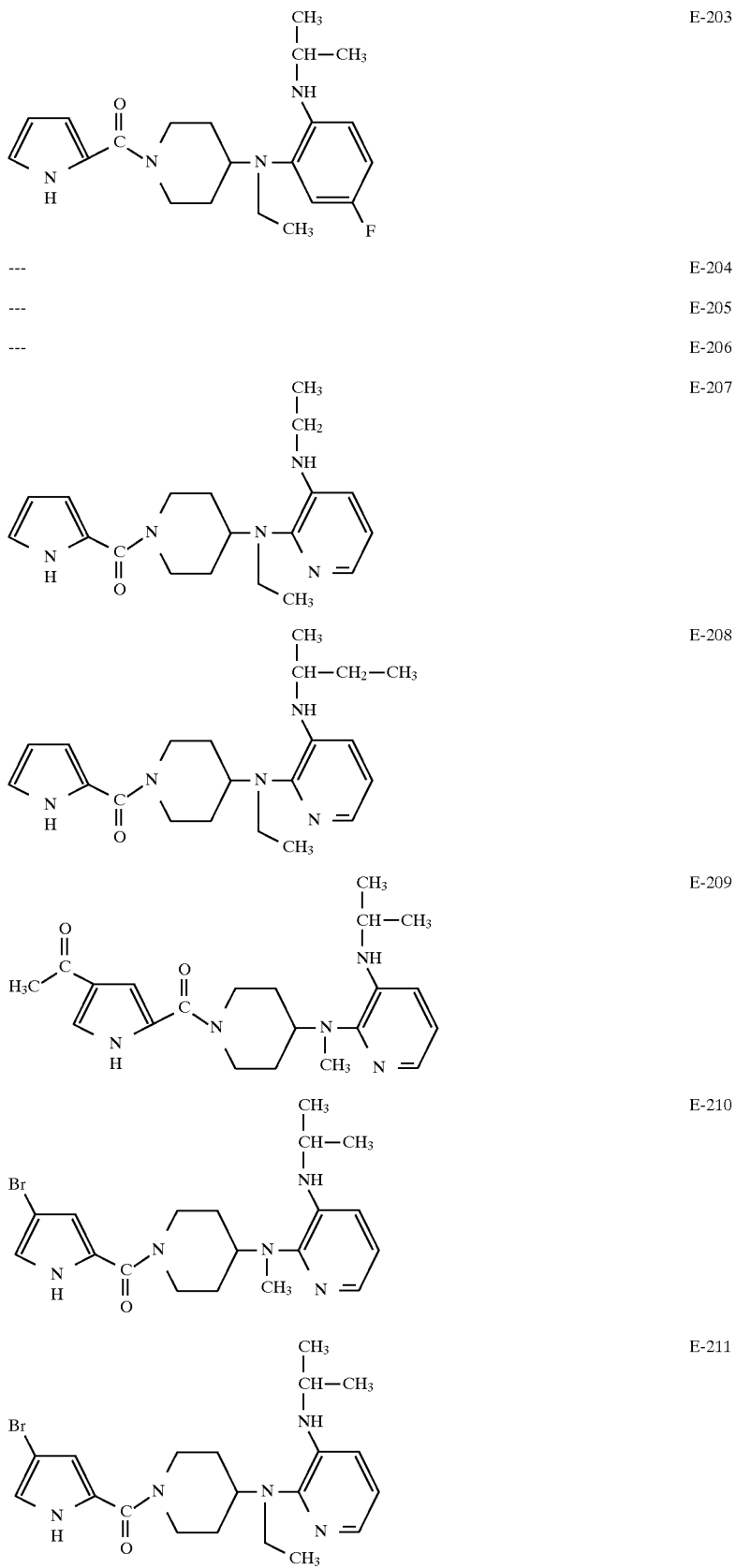
E-203
--- E-204
--- E-205
--- E-206
E-207
E-208
E-209
E-210
E-211

-continued
FORMULAS OF THE EXAMPLES (E-#)
--- E-212
--- E-213
--- E-214
--- E-215
--- E-216
--- E-217
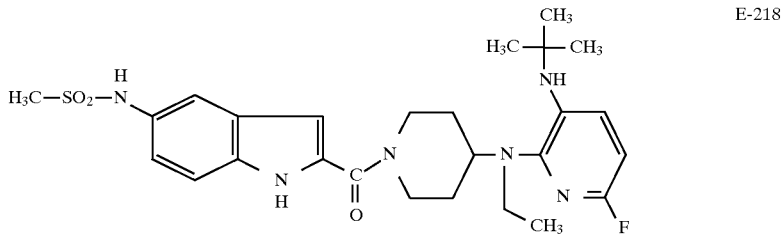
E-218
--- E-219
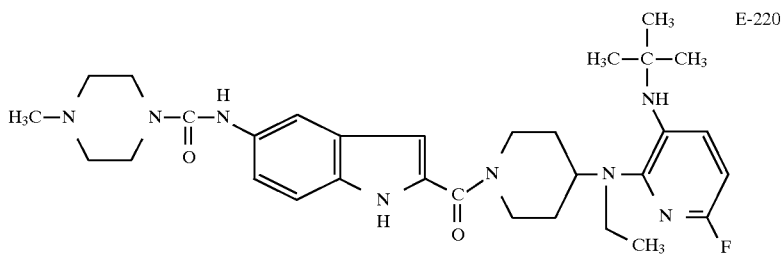
E-220
--- E-221
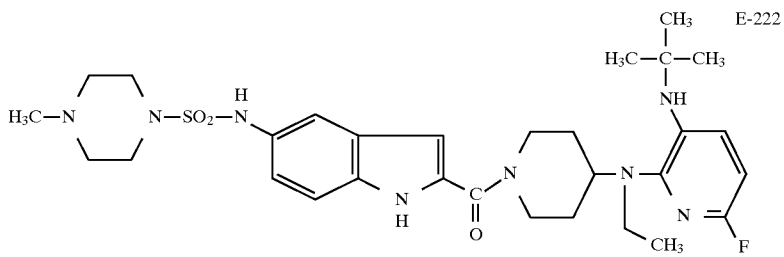
E-222
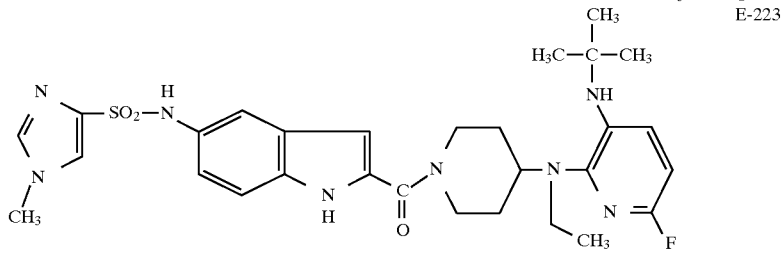
E-223
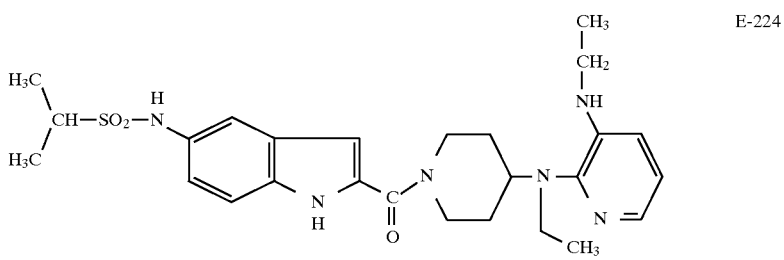
E-224

-continued
FORMULAS OF THE EXAMPLES (E-#)
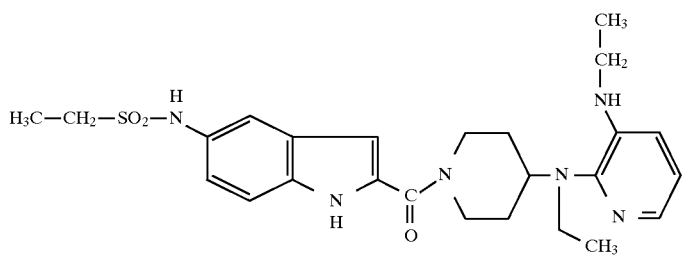
E-225
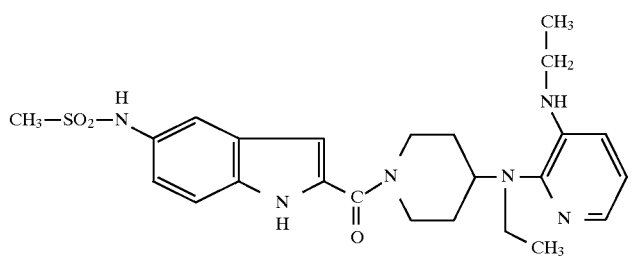
E-226
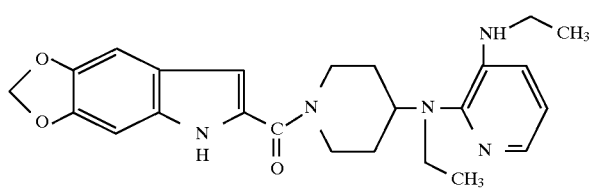
E-227
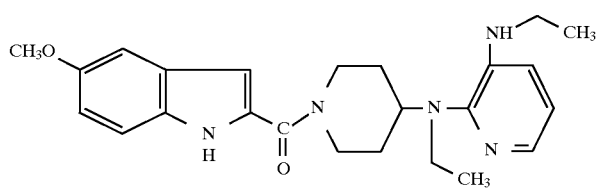
E-228
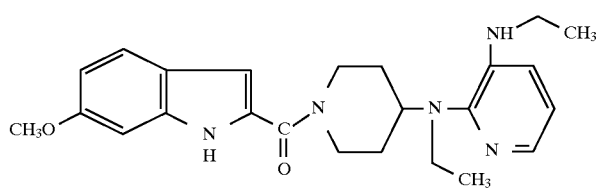
E-229
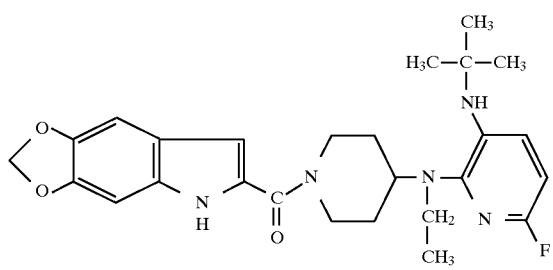
E-230
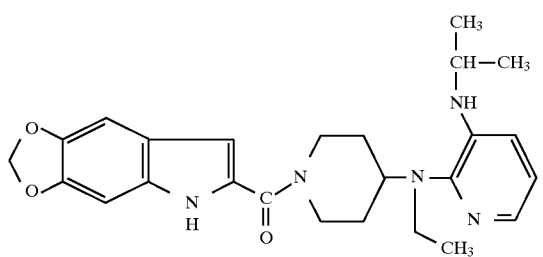
E-231

-continued
FORMULAS OF THE EXAMPLES (E-#)
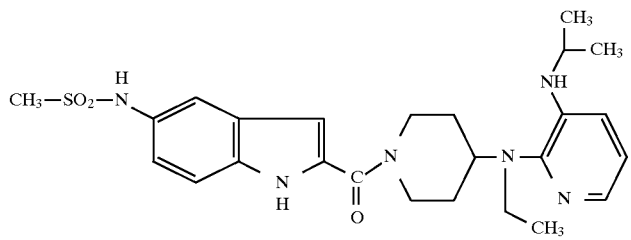
E-232
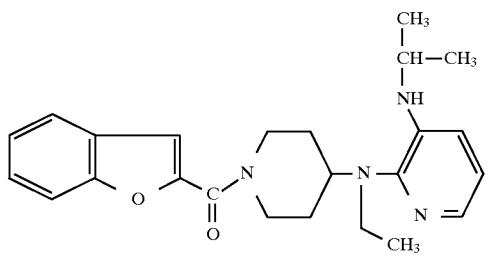
E-233
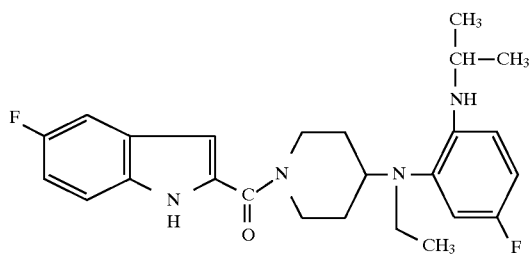
E-234
--- E-235
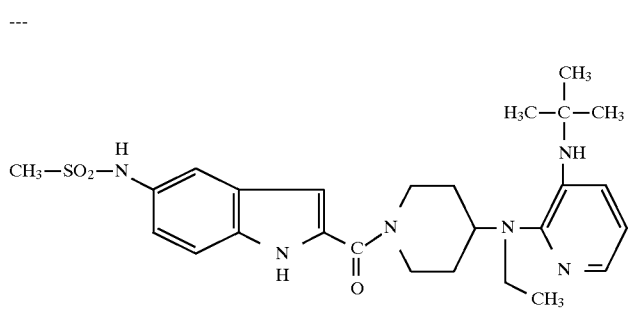
E-236
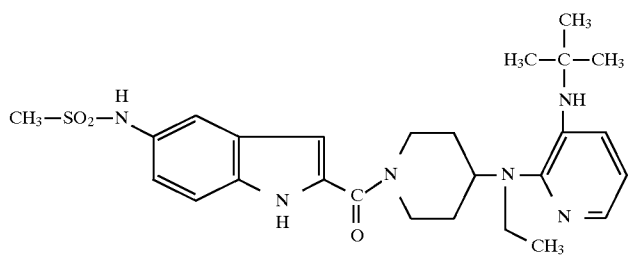
E-237
CH₃.SO₂—OH
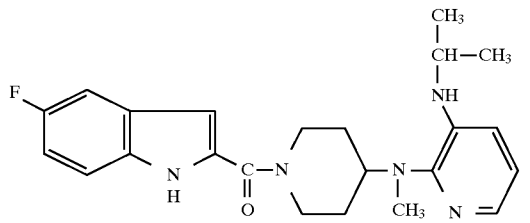
E-238

-continued
FORMULAS OF THE EXAMPLES (E-#)
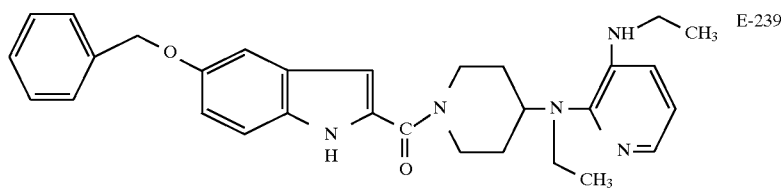
E-239
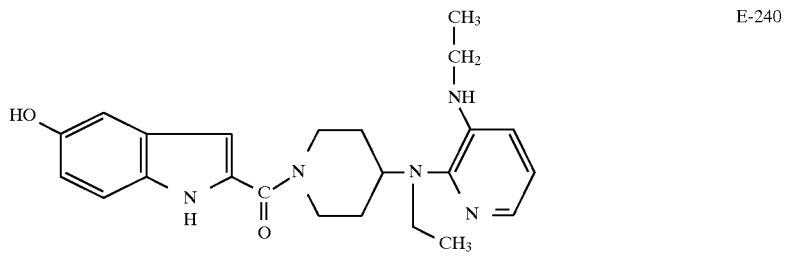
E-240
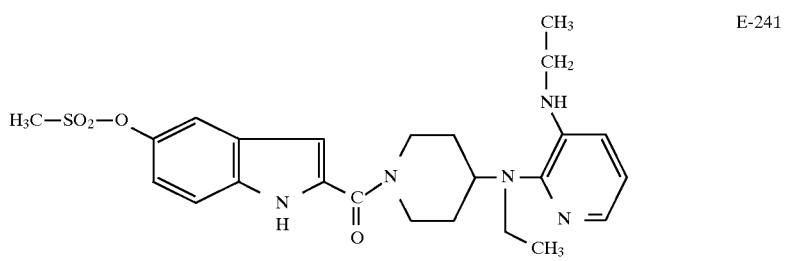
E-241
--- E-242
--- E-243
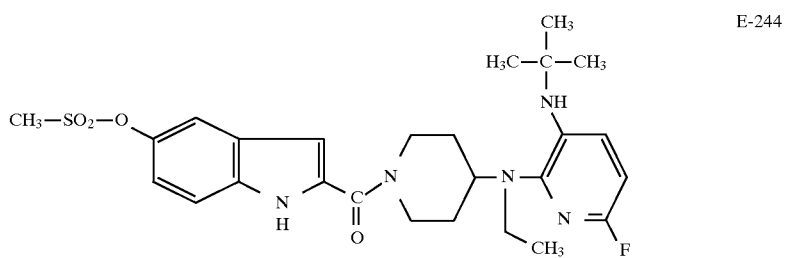
E-244
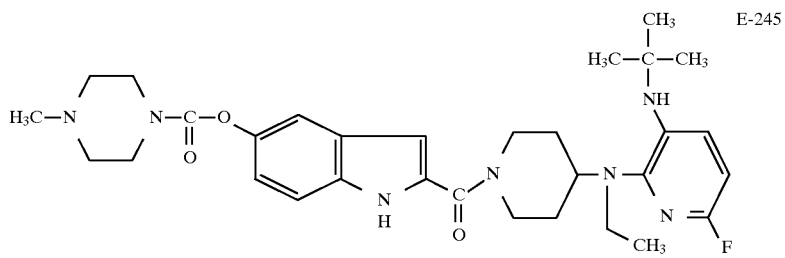
E-245
--- E-246
--- E-247
--- E-248

-continued
FORMULAS OF THE EXAMPLES (E-#)
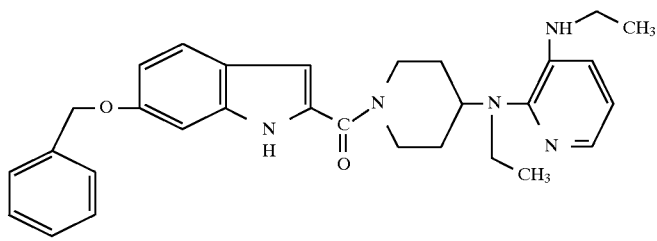 E-249
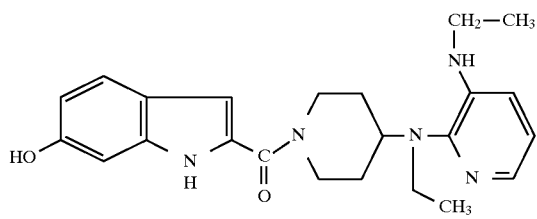 E-250
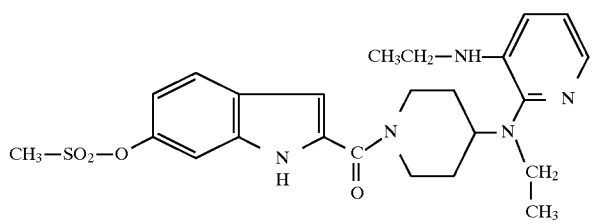 E-251
--- E-252
--- E-253
--- E-254
--- E-255
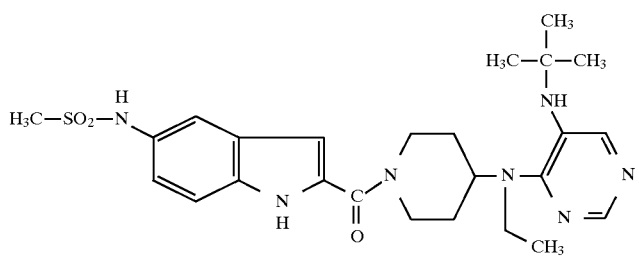 E-256
--- E-257
--- E-258
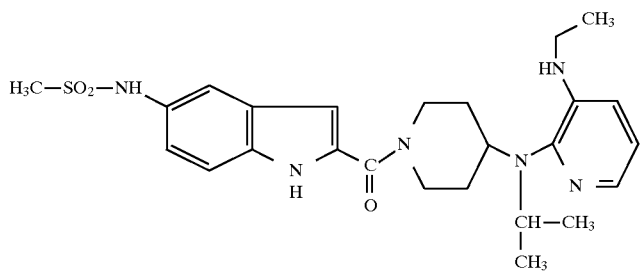 E-259
--- E-260
--- E-261
--- E-262
--- E-263

-continued
FORMULAS OF THE EXAMPLES (E-#)
--- E-264
--- E-265
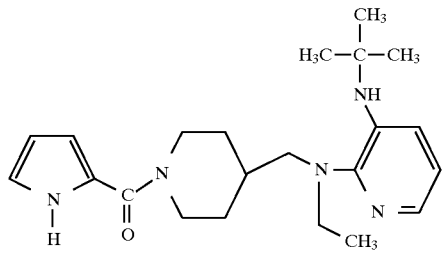 E-266
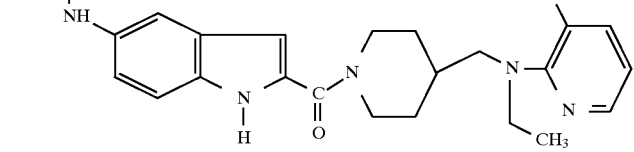 E-267
--- E-268
--- E-269
--- E-270
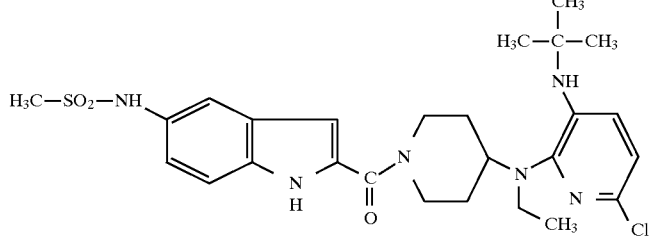 E-271
--- E-272
--- E-273
--- E-274
--- E-275
--- E-276
--- E-277
E-278
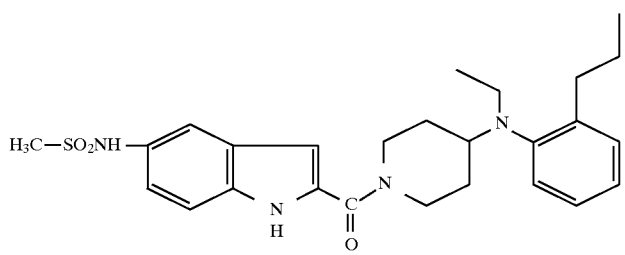

FORMULAS
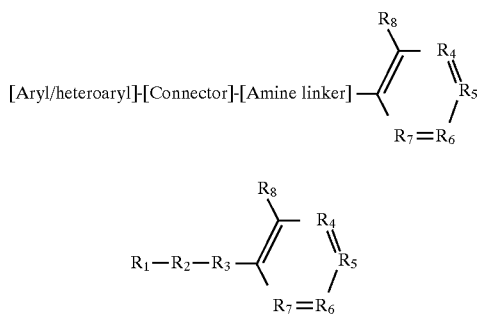
CHART A
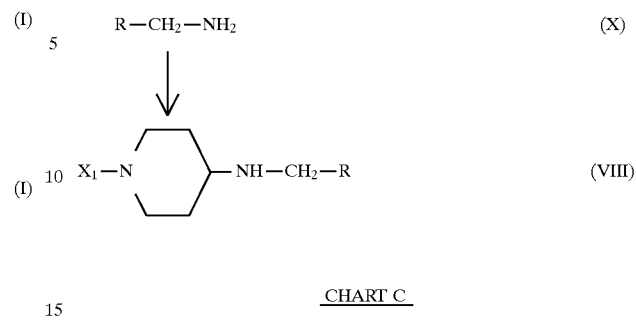
CHART B
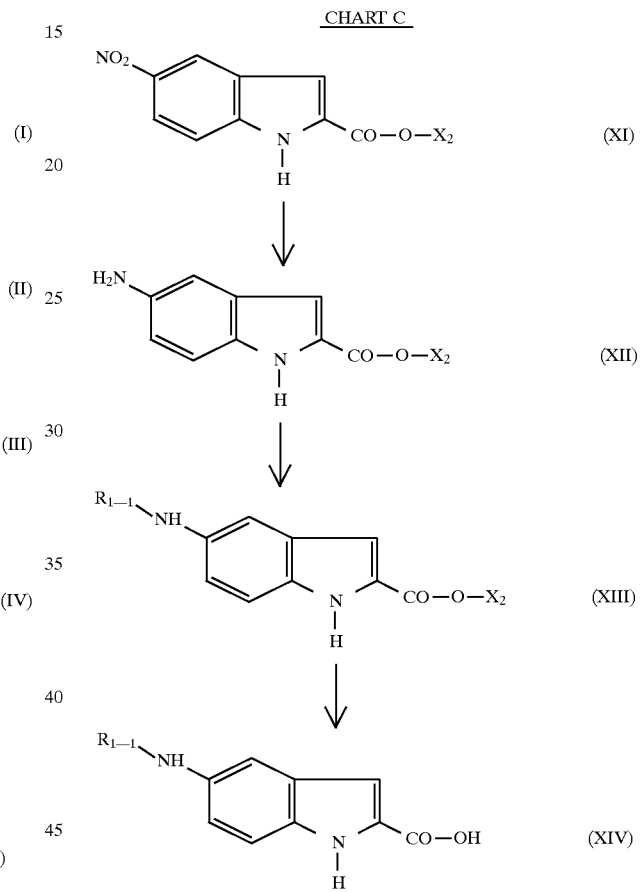
CHART C
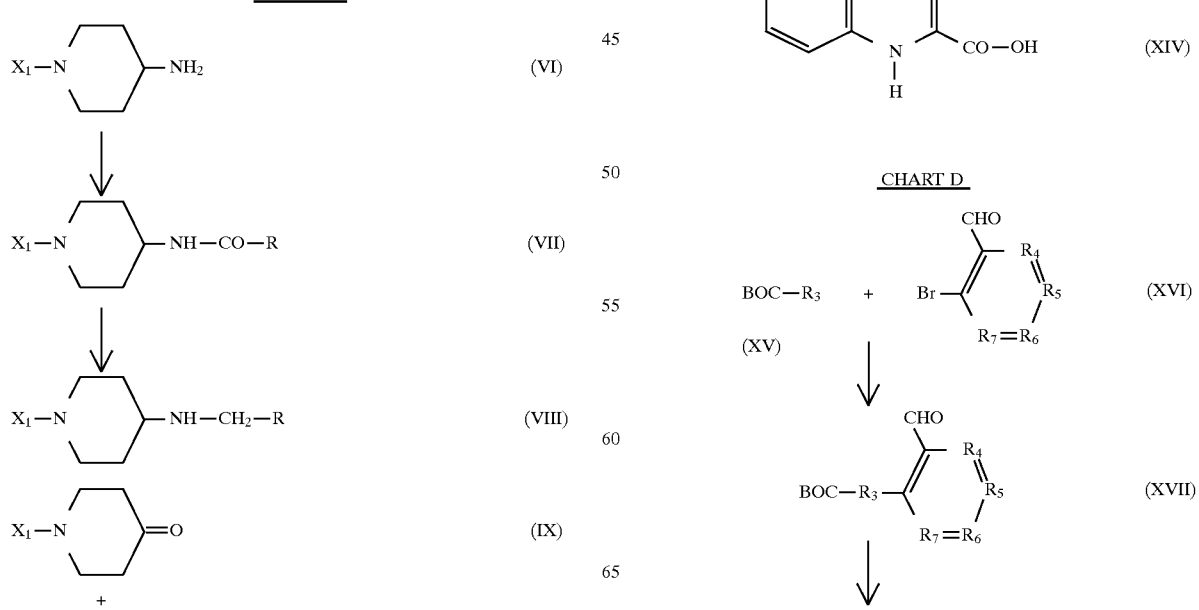
CHART D

CHART D
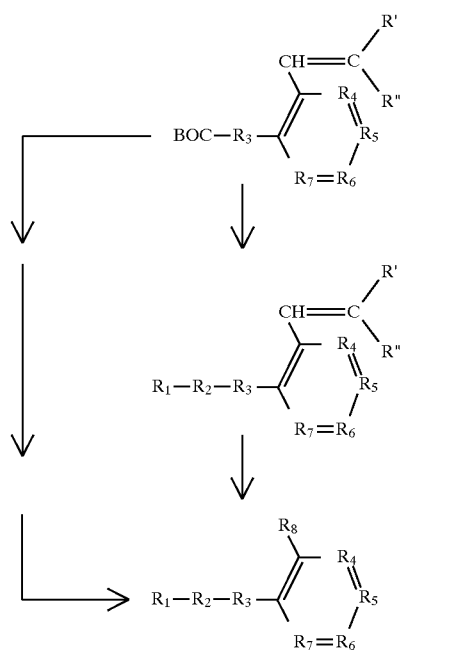
CHART E
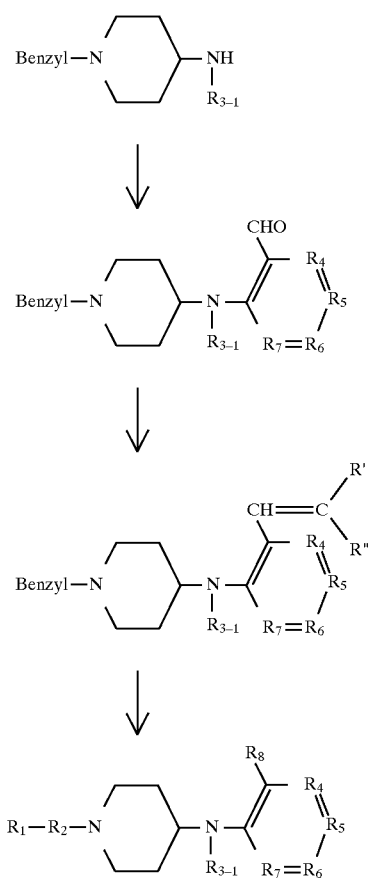
CHART F
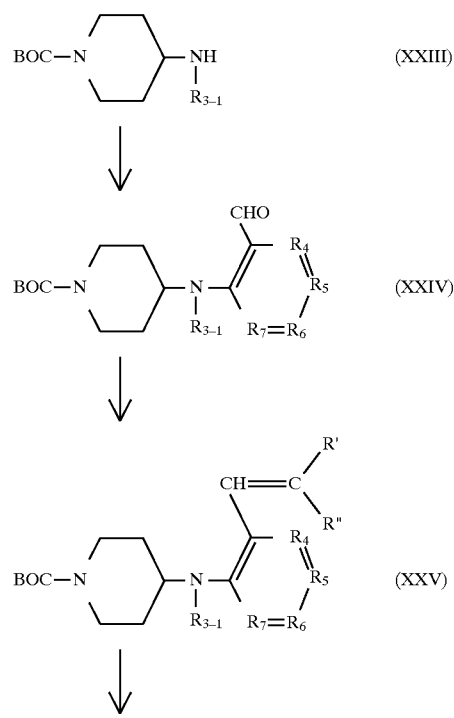
CHART G
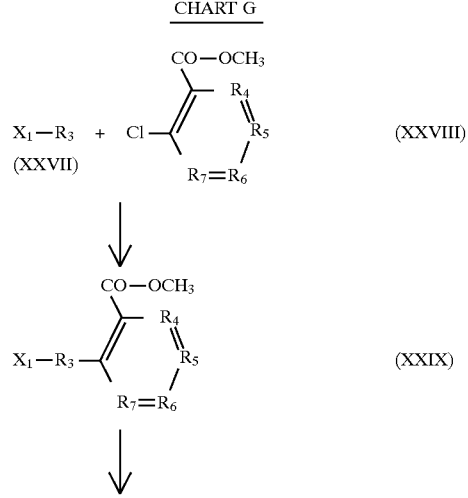

161

-continued
CHART G

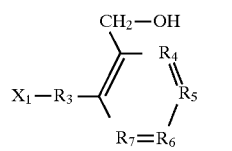
(XXX)

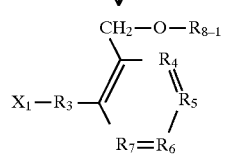
(XXXI)

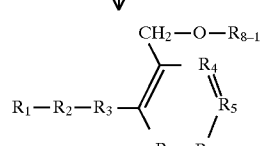
(IA)

CHART H

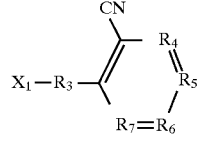
(XXXII)

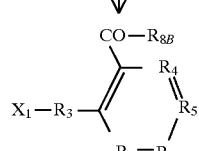
(XXXIII)

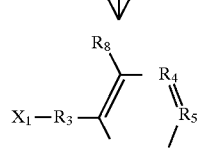
(XXXIV)

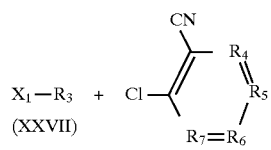
(XXXV)

162

-continued
CHART H

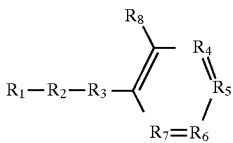  (I)

We claim:
1. Anti-AIDS compounds of the formula:

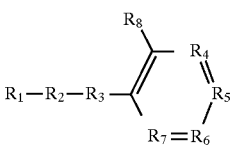  (I)

where (I) $R_1$ is:

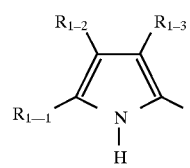  ($R_1$-I)

where $R_{1-1}$ is:
(1) —H,
(2) —F,
(3) —Cl,
(4) —Br,
(5) $C_1$–$C_5$ alkyl,
(6) —CO—$CH_3$,
(7) —CO—OH,
(8) —CO—$OR_{1-1A}$ where $R_{1-1A}$ is $C_1$–$C_3$ alkyl,
(9) —CO—$NH_2$, where $R_{1-2}$ is:
(1) —H,
(2) —F,
(3) —Cl,
(4) —Br,
(5) $C_1$–$C_5$ alkyl,
(6) —CO—$CH_3$,
(7) —CO—OH,
(8) —CO—$OR_{1-2A}$ where $R_{1-2A}$ is $C_1$–$C_3$ alkyl,
(9) —CO—$NH_2$, where $R_{1-3}$ is:
(1) —H,
(2) —F,
(3) —Cl,
(4) —Br,
(5) $C_1$–$C_5$ alkyl,
(6) —CO—$CH_3$,
(7) —CO—OH,
(8) —CO—$OR_{1-3A}$ where $R_{1-3A}$ is $C_1$–$C_3$ alkyl,
(9) —CO—$NH_2$, (B)

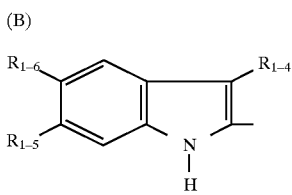

(R₁-II)

where $R_{1-4}$ is:
(1) —H,
(2) —CH$_3$,
where $R_{1-5}$ is:
(1) —H,
(2) —F,
(3) —Cl,
(4) —Br,
(5) —CN,
(6) —CHO,
(7) —(CH$_2$)$_{n1}$—OH where $n_1$ is 1 thru 5,
(8) —(CH$_2$)$_{n1}$—N(R$_{1-5A}$)(R$_{1-5B}$) where $n_1$ is as defined above and where $R_{1-5A}$ and $R_{1-5B}$ are the same or different and are:
 (a) —H,
 (b) C$_1$–C$_4$ alkyl or where $R_{1-5A}$ and $R_{1-5B}$ are taken together with the attached nitrogen atom to form a heterocyclic ring selected from the group consisting of
 (c) 1-pyrrolidinyl,
 (d) 1-piperidinyl,
 (e) 1-piperazinyl,
 (f) N-morpholinyl,
(9) —CO—O—R$_{1-5C}$ where $R_{1-5C}$ is:
 (a) C$_1$–C$_6$ alkyl,
 (b) C$_3$–C$_7$ cycloalkyl,
 (c) —φ,
(10) —CO—N(R$_{1-5D}$)(R$_{1-5E}$) where $R_{1-5D}$ and $R_{1-5E}$ are the same or different and are:
 (a) C$_1$–C$_6$ alkyl,
 (b) C$_3$–C$_7$ cycloalkyl,
 (c) —φ, and where $R_{1-5A}$ and $R_{1-5B}$ are taken together with the attached nitrogen atom to form a heterocyclic ring selected from the group consisting of
 (d) 1-pyrrolidinyl,
 (e) 1-piperidinyl,
 (f) 1-piperazinyl,
 (g) N-morpholinyl,
(11) —(CH$_2$)$_{n3}$—N(R$_{1-5M}$)(R$_{1-5N}$) where $n_3$, $R_{1-5M}$, $R_{1-5N}$ and $R_{1-5O}$ are as defined below,
(12) —NO$_2$,
(13) —NH$_2$,
(14) —N$_3$,
(15) —NH—CH$_2$—φ,
(16) —NR$_{1-5D}$R$_{1-5E}$ where $R_{1-5D}$ and $R_{1-5E}$ are the same or different and are:
 (a) —H,
 (b) C$_1$–C$_5$ alkyl or where $R_{1-5D}$ and $R_{1-5E}$ are taken together with the attached nitrogen atom to form a heterocyclic ring selected from the group consisting of
 (c) 1-pyrrolidinyl,
 (d) 1-piperidinyl,
 (e) 1-piperazinyl,
 (f) N-morpholinyl,
(17) —NR$_{1-5F}$(CH$_2$)$_{n2}$—N(R$_{1-5G}$)(R$_{1-5H}$) where $n_6$ is 2 thru 5, where $R_{1-5F}$ is:
 (a) —H,
 (b) C$_1$–C$_4$ alkyl, where $R_{1-5G}$ and $R_{1-5H}$ are the same or different and are:
 (a) —H,
 (b) C$_1$–C$_4$ alkyl and where $R_{1-5G}$ and $R_{1-5H}$ are taken together with the attached nitrogen atom to form a heterocyclic ring selected from the group consisting of:
 (c) 1-pyrrolidinyl,
 (d) 1-piperidinyl,
 (e) 1-piperazinyl,
 (f) N-morpholinyl,
(18) —N=C(R$_{1-5I}$)—N(R$_{1-5J}$)(R$_{1-5K}$) where $R_{1-5I}$ is:
 (a) $R_{1-5I}$ is
   (i) —H,
   (ii) C$_1$–C$_4$ alkyl, where
   $R_{1-5J}$ and $R_{1-5K}$ are the same or different and are
   (i) C$_1$–C$_6$ alkyl,
   (ii) C$_3$–C$_7$ cycloalkyl,
   (iii) —φ,
 (b) $R_{1-5J}$ and $R_{1-5K}$ are taken together with the attached nitrogen atom to form a heterocyclic ring selected from the group consisting of
   (i) 1-pyrrolidinyl,
   (ii) 1-piperidinyl,
   (iii) 1-piperazinyl,
   (iv) N-morpholinyl,
 (c) $R_{1-5I}$ and $R_{1-5J}$ are taken together with the attached nitrogen atom to form a heterocyclic ring selected from the group consisting of
   (i) 1-pyrrolidinyl,
   (ii) 1-piperidinyl,
(19) —NH—CO—CF$_3$,
(20) —N(R$_{1-5F}$)—CO—R$_{1-5L}$ where $R_{1-5L}$ is:
 (a) —H,
 (b) C$_1$–C$_4$ alkyl,
 (c) —φ and where $R_{1-5F}$ is defined above,
(21) —NH—CO—(CH$_2$)$_{n3}$—NR$_{1-5M}$R$_{1-5N}$ where $n_3$ is 1 thru 3, where $R_{1-5M}$ and $R_{1-5N}$ are the same or different and are:
 (a) —H,
 (b) C$_1$–C$_6$ alkyl,
 (c) —φ,
 (d) 2-pyridinyl,
 (e) 3-pyridinyl,
 (f) 4-pyridinyl and where $R_{1-5M}$ and $R_{1-5N}$ are taken together with the attached nitrogen atom, and other heteroatom if necessary, to form a ring selected from the group consisting of:
 (g) 1-pyrrolidinyl,
 (h) 1-piperidinyl,
 (i) 1-piperazinyl optionally substituted in the
   (i) 4-position with C$_1$–C$_5$ alkyl,
   (ii) 3- and/or 5-position with C$_1$–C$_3$ alkyl and N-oxides thereof,
 (j) N-morpholinyl,
(22) —N(R$_{1-5O}$)—CO—N(R$_{1-5O}$)—(CH$_2$)$_{n3}$—N(R$_{1-5M}$)(R$_{1-5N}$) where the $R_{1-5O}$'s are the same or different and are:
 (a) —H,
 (b) C$_1$–C$_3$ alkyl and where $n_3$, $R_{1-5M}$ and $R_{1-5N}$ are as defined above,
(23) —N(R$_{1-5O}$)—CO—N(R$_{1-5O}$)—(CH$_2$)$_{n4}$—R$_{1-5P}$ where $n_4$ is 0 thru 3, where $R_{1-5P}$ is:

(a) 2-pyridinyl,
(b) 3-pyridinyl,
(c) 4-pyridinyl and where $R_{1-5O}$ is as defined above,
(24) —N($R_{1-5O}$)—CO—N($R_{1-5M}$)($R_{1-5N}$) where $R_{1-5M}$, $R_{1-5N}$ and $R_{1-5O}$ are as defined above,
(25) —NH—CO-[4-(1-$R_{1-5M}$)piperidinyl] where $R_{1-5M}$ is as defined above,
(26) —N($R_{1-5O}$)—CO—O—$R_{1-5Q}$ where $R_{1-5Q}$ is:
  (a) $C_1$–$C_4$ alkyl,
(27) —NH—$SO_2$—$R_{1-5C}$ where $R_{1-5C}$ is as defined above,
(28) —NH—$SO_2$-[1-methyl-4-imidazolyl],
(29) —N($R_{1-5R}$)—$SO_2$—$R_{1-5S}$ where $R_{1-5R}$ is $C_1$–$C_3$ alkyl, where $R_{1-5S}$ is $C_1$–$C_4$ alkyl and where $R_{1-5R}$ and $R_{1-5S}$ are taken together with the attached nitrogen atom to form a heterocyclic ring of 5 or 6 atoms,
(30) —N($R_{1-5O}$)—$SO_2$—$(CH_2)_{n4}$—$R_{1-5P}$ where $n_4$, $R_{1-5O}$ and $R_{1-5P}$ are as defined above,
(31) —N($R_{1-5O}$)—$SO_2$—$(CH_2)_{n3}$—N($R_{1-5M}$)($R_{1-5N}$) where $n_3$, $R_{1-5M}$, $R_{1-5N}$ and $R_{1-5O}$ are as defined above,
(32) —NH—$SO_2$—$CF_3$,
(33) —N($R_{1-5O}$)—$SO_2$—N($R_{1-5M}$)($R_{1-5N}$) where $R_{1-5M}$, $R_{1-5N}$ and $R_{1-5O}$ are as defined above,
(34) —OH,
(35) —O—$R_{1-5T}$ where $R_{1-5T}$ is $C_1$–$C_4$ alkyl,
(36) —O—$CH_2$—φ,
(37) —O—$CF_3$,
(38) —O—$CH_2$—$COOR_{1-5U}$ where $R_{1-5U}$ is:
  (a) —H,
  (b) $C_1$–$C_4$ alkyl,
  (c) —φ,
  (d) —$CH_2$—φ,
  (e) —O—$(CH_2CH_2$—O—$)_{n5}$—$R_{1-5V}$ where $n_5$ is 1 thru 4 and where $R_{1-5V}$ is:
    (i) —H,
    (ii) $C_1$–$C_4$ alkyl,
(39) —O—CO—$(CH_2)_{n3}$—$NR_{1-5M}R_{1-5N}$ where $n_3$, $R_{1-5M}$ and $R_{1-5N}$ are as defined above,
(40) —O—$SO_2$—$CH_3$,
(41) —O—$SO_2$—$CH_2$—$CH_3$,
(42) —O—$SO_2$—$CH(CH_3)_2$,
(43) —O—$SO_2$—$(CH_2)_{n3}$—N($R_{1-5M}$)($R_{1-5N}$) where n3, $R_{1-5M}$ and $R_{1-5N}$ are as defined above,
(44) —O—$SO_2$—$(CH_2)_{n4}$—$R_{1-5P}$ where $n_4$ and $R_{1-5P}$ are as defined above,
(45) —O—$SO_2$—$CF_3$,
(46) —$NR_{1-5I}$-prodrug where $R_{1-5I}$ is as defined above and prodrug is:
  (a) —CO—$CH_2$—CO—NH—$CH_2$—$SO_2$—$O^-$ cation$^+$,
  (b) —CO—$(CH_2)_{n10}$—$R_{1-5W}$ where $n_{10}$ is 1 thru 7 and $R_{1-5W}$ is:
    (i) —$COO^-$ cation$^+$,
    (ii) —$NR_{1-5X}R_{1-5Y}$ where $R_{1-5X}$ and $R_{1-5Y}$ are the same or different and are:
      (A) —H,
      (B) $C_1$–$C_3$ alkyl,
    (iii) —$N^+R_{1-5X}R_{1-5Y}R_{1-5Z}$ halide$^-$ where $R_{1-5Z}$ is:
      (A) —H,
      (B) $C_1$–$C_3$ alkyl, where halide is:
      (C) —Cl,
      (D) —Br, and where $R_{1-5X}$ and $R_{1-5Y}$ are as defined above,
  (c) —CO—CH(amino acid)-$NH_2$ where amino acid is:
    (i) —H,
    (ii) —$CH_3$,
    (iii) —$CH(CH_3)_2$,
    (iv) —$CH_2$—$CH(CH_3)_2$,
    (v) —$CH_2$—OH,
    (vi) —CH(OH)($CH_3$),
    (vii) —$CH_2$—φ,
    (viii) —$CH_2$-[p-hydroxyphenyl],
    (ix) —$CH_2$-[3-indolyl],
    (x) —$CH_2$—S—S—$CH_2$—CH($NH_2$)—COOH,
    (xi) —$CH_2$—SH,
    (xii) —$CH_2CH_2$—S—$CH_3$,
    (xiii) —$CH_2$—COOH,
    (xiv) —$CH_2$—CO—$NH_2$,
    (xv) —$CH_2$—$CH_2$—COOH,
    (xvi) —$CH_2$—$CH_2$—CO—$NH_2$,
    (xvii) —$CH_2$-[2-histidyl],
    (xviii) —$(CH_2)_3$—NH—C(NH)—$NH_2$,
    (xix) —$(CH_2)_4$—$NH_2$,
    (xx) —$CH_2$—$CH_2$—CH(OH)—$CH_2$—$NH_2$,
    (xxi) —$(CH_2)_3$—$NH_2$,
    (xxii) —$(CH_2)_3$—NH—CO—$NH_2$,
    (xxiii) —$CH_2CH_2$—OH,
  (d) —CO—CH=CH—CO—$O^-$ cation$^+$,
  (e) —CO—N*—CH=CH—N=CH* where the atoms marked with an asterisk (*) are bonded to each other resulting in the formation of a ring,
  (f) —CO—C*=C[$(CH_2)_{n11}$—$NH_2$]—CH=CH—CH=CH* where $n_{11}$ is 1 or 2 and where the atoms marked with an asterisk (*) are bonded to each other resulting in the formation of a ring,
  (g) —CO—C*=CH—CH=C(—$NR_{1-5X}$)—CH=CH* where $R_{1-5X}$ is as defined above and where the atoms marked with an asterisk (*) are bonded to each other resulting in the formation of a ring,
  (h) —CO—$(CH_2)_{n10}$—CO—O—[$C_6H_{12}O_6$ sugars] where $n_{10}$ is as defined above,
  (i) —CO—O—CH($CH_2$—O—CO—$R_{1-5AA}$)$_2$ where the $R_{1-5AA}$'s are the same or different and are:
  (j) $C_1$–$C_{18}$ alkyl,
  (k) —CO—$(CH_2)_6$—CO—N($CH_3$)—$CH_2$—$CH_2$—$SO_3^-$ cation$^+$,
  (l) —$CH_2$—O—CO—$(CH_2)_{n10}$—$NR_{1-5X}R_{1-5Y}$ where $n_{10}$, $R_{1-5X}$ and $R_{1-5Y}$ are as defined above,
  (m) —CO—NH—$C_6H_4$—$R_{1-5BB}$ where $R_{1-5BB}$ is:
    (i) —H,
    (ii) $C_1$–$C_3$ alkyl,
    (iii) —$NO_2$,
  (n) —$NR_{1-5X}R_{1-5Y}$ where $R_{1-5X}$ and $R_{1-5Y}$ are as defined above,
where $R_{1-6}$ is:
  (1) —H,
  (2) —F,
  (3) —Cl,
  (4) —Br,
  (5) —CN,
  (6) —CHO,
  (7) —$(CH_2)_{n1}$—OH where $n_1$ is 1 thru 5,
  (8) —$(CH_2)_{n1}$—N($R_{1-6A}$)($R_{1-6B}$) where $n_1$ is as defined above and where $R_{1-6A}$ and $R_{1-6B}$ are the same or different and are:
    (a) —H,
    (b) $C_1$–$C_4$ alkyl or where $R_{1-6A}$ and $R_{1-6B}$ are taken together with the attached nitrogen atom to form a heterocyclic ring selected from the group consisting of (c) 1-pyrrolidinyl,
(d) 1-piperidinyl,
(e) 1-piperazinyl,
(f) N-morpholinyl,
(9) —CO—O—$R_{1-6C}$ where $R_{1-6C}$ is:
  (a) $C_1$–$C_6$ alkyl,
  (b) $C_3$–$C_7$ cycloalkyl,
  (c) —φ,
(10) —CO—N($R_{1-6D}$)($R_{1-6E}$) where $R_{1-6D}$ and $R_{16E}$ are the same or different and are:
  (a) $C_1$–$C_6$ alkyl,
  (b) $C_3$–$C_7$ cycloalkyl,
  (c) —φ, and where $R_{1-6A}$ and $R_{1-6B}$ are taken together with the attached nitrogen atom to form a heterocyclic ring selected from the group consisting of
  (d) 1-pyrrolidinyl,
  (e) 1-piperidinyl,
  (f) 1-piperazinyl,
  (g) N-morpholinyl,
(11) —(CH$_2$)$_{n3}$—N($R_{1-6M}$)($R_{1-6N}$) where $n_3$, $R_{1-6M}$, $R_{1-6N}$ and $R_{1-6O}$ are as defined below,
(12) —NO$_2$,
(13) —NH$_2$,
(14) —N$_3$,
(15) —NH—CH$_2$—φ,
(16) —N$R_{1-6D}R_{1-6E}$ where $R_{1-6D}$ and $R_{1-6E}$ are the same or different and are:
  (a) —H,
  (b) $C_1$–$C_5$ alkyl or where $R_{1-6D}$ and $R_{1-6E}$ are taken together with the attached nitrogen atom to form a heterocyclic ring selected from the group consisting of
  (c) 1-pyrrolidinyl,
  (d) 1-piperidinyl,
  (e) 1-piperazinyl,
  (f) N-morpholinyl,
(17) —N$R_{1-6F}$(CH$_2$)$_{n2}$—N($R_{1-6G}$)($R_{1-6H}$) where $n_6$ is 2 thru 5, where $R_{1-6F}$ is:
  (a) —H,
  (b) $C_1$–$C_4$ alkyl, where $R_{1-6G}$ and $R_{1-6H}$ are the same or different and are:
    (a) —H,
    (b) $C_1$–$C_4$ alkyl and where $R_{1-6G}$ and $R_{1-6H}$ are taken together with the attached nitrogen atom to form a heterocyclic ring selected from the group consisting of:
    (c) 1-pyrrolidinyl,
    (d) 1-piperidinyl,
    (e) 1-piperazinyl,
    (f) N-morpholinyl,
(18) —N=C($R_{1-6I}$)—N($R_{1-6J}$)($R_{1-6K}$) where $R_{1-6I}$ is:
  (a) $R_{1-6I}$ is
    (i) —H,
    (ii) $C_1$–$C_4$ alkyl, where $R_{1-6J}$ and $R_{1-6K}$ are the same or different and are
      (i) $C_1$–$C_6$ alkyl,
      (ii) $C_3$–$C_7$ cycloalkyl,
      (iii) —φ,
  (b) $R_{1-6J}$ and $R_{1-6K}$ are taken together with the attached nitrogen atom to form a heterocyclic ring selected from the group consisting of
    (i) 1-pyrrolidinyl,
    (ii) 1-piperidinyl,
    (iii) 1-piperazinyl,
    (iv) N-morpholinyl,
  (c) $R_{1-6I}$ and $R_{1-6J}$ are taken together with the attached nitrogen atom to form a heterocyclic ring selected from the group consisting of
    (i) 1-pyrrolidinyl,
    (ii) 1-piperidinyl,
(19) —NH—CO—CF$_3$,
(20) —N($R_{1-6F}$)—CO—$R_{1-6L}$ where $R_{1-6L}$ is:
  (a) —H,
  (b) $C_1$–$C_4$ alkyl,
  (c) —φ and where $R_{1-6F}$ is defined above,
(21) —NH—CO—(CH$_2$)$_{n3}$—N$R_{1-6M}R_{1-6N}$ where $n_3$ is 1 thru 3, where $R_{1-6M}$ and $R_{1-6N}$ are the same or different and are:
  (a) —H,
  (b) $C_1$–$C_6$ alkyl,
  (c) —φ,
  (d) 2-pyridinyl,
  (e) 3-pyridinyl,
  (f) 4-pyridinyl and where $R_{1-6M}$ and $R_{1-6N}$ are taken together with the attached nitrogen atom, and other heteroatom if necessary, to form a ring selected from the group consisting of:
  (g) 1-pyrrolidinyl,
  (h) 1-piperidinyl,
  (i) 1-piperazinyl optionally substituted in the
    (i) 4-position with $C_1$–$C_5$ alkyl,
    (ii) 3- and/or 5-position with $C_1$–$C_3$ alkyl and N-oxides thereof,
  (j) N-morpholinyl,
(22) —N($R_{1-6O}$)—CO—N($R_{1-6O}$)—(CH$_2$)$_{n3}$—N($R_{1-6M}$)($R_{1-6N}$) where the $R_{1-6O}$'s are the same or different and are:
  (a) —H,
  (b) $C_1$–$C_3$ alkyl and where $n_3$, $R_{1-6M}$ and $R_{1-6N}$ are as defined above,
(23) —N($R_{1-6O}$)—CO—N($R_{1-6O}$)—(CH$_2$)$_{n4}$—$R_{1-6P}$ where $n_4$ is 0 thru 3, where $R_{1-6P}$ is:
  (a) 2-pyridinyl,
  (b) 3-pyridinyl,
  (c) 4-pyridinyl and where $R_{1-6O}$ is as defined above,
(24) —N($R_{1-6O}$)—CO—N($R_{1-6M}$)($R_{1-6N}$) where $R_{1-6M}$, $R_{1-6N}$ and $R_{1-6O}$ are as defined above,
(25) —NH—CO-[4-(1-$R_{1-6M}$)piperidinyl] where $R_{1-6M}$ is as defined above,
(26) —N($R_{1-6O}$)—CO—O—$R_{1-6Q}$ where $R_{1-6Q}$ is:
  (a) $C_1$–$C_4$ alkyl,
(27) —NH—SO$_2$—$R_{1-6C}$ where $R_{1-6C}$ is as defined above,
(28) —NH—SO$_2$-[1-methyl-4-imidazolyl],
(29) —N($R_{1-6R}$)—SO$_2$—$R_{1-6S}$ where $R_{1-6R}$ is $C_1$–$C_3$ alkyl, where $R_{1-6S}$ is $C_1$–$C_4$ alkyl and where $R_{1-6R}$ and $R_{1-6S}$ are taken together with the attached nitrogen atom to form a heterocyclic ring of 5 or 6 atoms,
(30) —N($R_{1-6O}$)—SO$_2$—(CH$_2$)$_{n4}$—$R_{1-6P}$ where $n_4$, $R_{1-6O}$ and $R_{1-6P}$ are as defined above,
(31) —N($R_{1-6O}$)—SO$_2$—(CH$_2$)$_{n3}$—N($R_{1-6M}$)($R_{1-6N}$) where $n_3$, $R_{1-6M}$, $R_{1-6N}$ and $R_{1-6O}$ are as defined above,
(32) —NH—SO$_2$—CF$_3$,
(33) —N($R_{1-6O}$)—SO$_2$—N($R_{1-6M}$)($R_{1-6N}$) where $R_{1-6M}$, $R_{1-6N}$ and $R_{1-6O}$ are as defined above,
(34) —OH,
(35) —O—$R_{1-6T}$ where $R_{1-6T}$ is $C_1$–$C_4$ alkyl,
(36) —O—CH$_2$—φ,
(37) —O—CF$_3$,

(38) —O—CH$_2$—COOR$_{1-6U}$ where R$_{1-6U}$ is:
  (a) —H,
  (b) C$_1$–C$_4$ alkyl,
  (c) —φ,
  (d) —CH$_2$—φ,
  (e) —O—(CH$_2$CH$_2$—O—)$_{n5}$—R$_{1-6V}$ where n$_5$ is 1 thru 4 and where R$_{1-6V}$ is:
    (i) —H,
    (ii) C$_1$–C$_4$ alkyl,
(39) —O—CO—(CH$_2$)$_{n3}$—NR$_{1-6M}$R$_{1-6N}$ where n$_3$, R$_{1-6M}$ and R$_{1-6N}$ are as defined above,
(40) —O—SO$_2$—CH$_3$,
(41) —O—SO$_2$—CH$_2$—CH$_3$,
(42) —O—SO$_2$—CH(CH$_3$)$_2$,
(43) —O—SO$_2$—(CH$_2$)$_{n3}$—N(R$_{1-6M}$)(R$_{1-6N}$) where n3, R$_{1-6M}$ and R$_{1-6N}$ are as defined above,
(44) —O—SO$_2$—(CH$_2$)$_{n4}$—R$_{1-6P}$ where n$_4$ and R$_{1-6P}$ are as defined above,
(45) —O—SO$_2$—CF$_3$,
(46) —NR$_{1-6I}$-prodrug where R$_{1-6I}$ is as defined above and prodrug is:
  (a) —CO—CH$_2$—CO—NH—CH$_2$—SO$_2$—O$^-$ cation$^+$,
  (b) —CO—(CH$_2$)$_{n10}$—R$_{1-6W}$ where n$_{10}$ is 1 thru 7 and R$_{1-6W}$ is:
    (i) —COO$^-$ cation$^+$,
    (ii) —NR$_{1-6X}$R$_{1-6Y}$ where R$_{1-6X}$ and R$_{1-6Y}$ are the same or different and are:
      (A) —H,
      (B) C$_1$–C$_3$ alkyl
    (iii) —N$^+$R$_{1-6X}$R$_{1-6Y}$R$_{1-6Z}$ halide$^-$ where R$_{1-6Z}$ is:
      (A) —H,
      (B) C$_1$–C$_3$ alkyl, where halide is:
      (C) —Cl,
      (D) —Br, and where R$_{1-6X}$ and R$_{1-6Y}$ are as defined above,
  (c) —CO—CH(amino acid)-NH$_2$ where amino acid is:
    (i) —H,
    (ii) —CH$_3$,
    (iii) —CH(CH$_3$)$_2$,
    (iv) —CH$_2$—CH(CH$_3$)$_2$,
    (v) —CH$_2$—OH,
    (vi) —CH(OH)(CH$_3$),
    (vii) —CH$_2$—φ,
    (viii) —CH$_2$-[p-hydroxyphenyl],
    (ix) —CH$_2$-[3-indolyl],
    (x) —CH$_2$—S—S—CH$_2$—CH(NH$_2$)—COOH,
    (xi) —CH$_2$—SH,
    (xii) —CH$_2$CH$_2$—S—CH$_3$,
    (xiii) —CH$_2$—COOH,
    (xiv) —CH$_2$—CO—NH$_2$,
    (xv) —CH$_2$—CH$_2$—COOH,
    (xvi) —CH$_2$—CH$_2$—CO—NH$_2$,
    (xvii) —CH$_2$-[2-histidyl],
    (xviii) —(CH$_2$)$_3$—NH—C(NH)—NH$_2$,
    (xix) —(CH$_2$)$_4$—NH$_2$,
    (xx) —CH$_2$—CH$_2$—CH(OH)—CH$_2$—NH$_2$,
    (xxi) —(CH$_2$)$_3$—NH$_2$,
    (xxii) —(CH$_2$)$_3$—NH—CO—NH$_2$,
    (xxiii) —CH$_2$CH$_2$—OH,
  (d) —CO—CH=CH—CO—O$^-$ cation$^+$,
  (e) —CO—N*—CH=CH—N=CH* where the atoms marked with an asterisk (*) are bonded to each other resulting in the formation of a ring,
  (f) —CO—C*=C[(CH$_2$)$_{n11}$—NH$_2$]—CH=CH—CH=CH* where n$_{11}$ is 1 or 2 and where the atoms marked with an asterisk (*) are bonded to each other resulting in the formation of a ring,
  (g) —CO—C*=CH—CH=C(—NR$_{1-6X}$)—CH=CH* where R$_{1-6X}$ is as defined above and where the atoms marked with an asterisk (*) are bonded to each other resulting in the formation of a ring,
  (h) —CO—(CH$_2$)$_{n10}$—CO—O—[C$_6$H$_{12}$O$_6$ sugars] where n$_{10}$ is as defined above,
  (i) —CO—O—CH(CH$_2$—O—CO—R$_{1-6AA}$)$_2$ where the R$_{1-6AA}$'s are the same or different and are:
  (j) C$_1$–C$_{18}$ alkyl,
  (k) —CO—(CH$_2$)$_6$—CO—N(CH$_3$)—CH$_2$—CH$_2$—SO$_3^-$ cation$^+$,
  (l) —CH$_2$—O—CO—(CH$_2$)$_{n10}$—NR$_{1-6X}$R$_{1-6Y}$ where n$_{10}$, R$_{1-6X}$ and R$_{1-6Y}$ are as defined above,
  (m) —CO—NH—C$_6$H$_4$—R$_{1-6BB}$ where R$_{1-6BB}$ is:
    (i) —H,
    (ii) C$_1$–C$_3$ alkyl,
    (iii) —NO$_2$,
  (n) —NR$_{1-6X}$R$_{1-6Y}$ where R$_{1-6X}$ and R$_{1-6Y}$ are as defined above, with the proviso that only one of R$_{1-5}$ or R$_{1-6}$ is —NR$_{1-5I}$-prodrug or —NR$_{1-6I}$-prodrug;

(C)

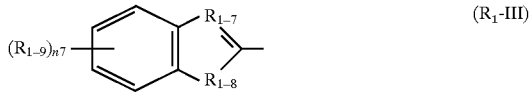
(R$_1$-III)

where R$_{1-7}$ is:
  (1) —N= provided R$_2$ is not —CH$_2$—,
  (2) —CR$_{1-7A}$ where R$_{1-7A}$ is:
    (a) —CO—O—R$_{1-7B}$ where R$_{1-7B}$ is:
      (i) —H,
      (ii) C$_1$–C$_4$ alkyl,
    (b) —CO—N(R$_{1-7C}$)(R$_{1-7D}$) where R$_{1-7C}$ and R$_{1-7D}$ are the same or different and are:
      (i) —H,
      (ii) C$_1$–C$_4$ alkyl and where R$_{1-7C}$ and R$_{1-7D}$ are taken together with the attached nitrogen atom to form a heterocyclic ring selected from the group consisting of:
      (iii) 1-pyrrolidinyl,
      (iv) 1-piperidinyl,
      (v) 1-piperazinyl,
      (vi) N-morpholinyl,
    (c) —CO—COO—R$_{1-7B}$ where R$_{1-7B}$ is as defined above,
    (d) C$_1$–C$_3$ alkyl,
    (e) —CO—φ,
    (f) —CO—R$_{1-7B}$ where R$_{1-7B}$ is as defined above,
    (g) —CO—CO—N(R$_{1-7C}$)(R$_{1-7D}$) where R$_{1-7C}$ and R$_{1-7D}$ are as defined above,
    (h) —(CH$_2$)$_{n6}$—OH where n$_6$ is 1 or 2;
where R$_{1-8}$ is:
  (1) —NR$_{1-8A}$— where R$_{1-8A}$ is:
    (a) —H,
    (b) —SO$_2$—φ,
    (c) —SO$_2$—CH$_3$,
    (d) —CO—R$_{1-8B}$ where R$_{1-8B}$ is:
      (i) C$_1$–C$_4$ alkyl,
      (ii) —CF$_3$,
      (iii) —φ;
where R$_{1-9}$ is:
  (1) —H,
  (2) —F, (3) —Cl,
(4) —Br,
(5) $C_1$–$C_6$ alkyl,
(6) —CHO,
(7) $C_1$–$C_3$ alkoxy,
(8) —CO—$OR_{1-9A}$ where $R_{1-9A}$ is:
 (a) —H,
 (b) $C_1$–$C_4$ alkyl,
 (c) —φ,
 (d) —$CH_2$—φ,
(9) —C≡N,
(10) —$(CH_2)_{n8}$—OH where $n_8$ is 1 thru 5,
(11) —$(CH_2)_{n8}$—$N(R_{1-9B})(R_{1-9C})$ where $R_{1-9B}$ and $R_{1-9C}$ are the same or different and are:
 (a) —H,
 (b) $C_1$–$C_4$ alkyl and where $R_{1-9B}$ and $R_{1-9C}$ are taken together with the attached nitrogen atom to form a heterocyclic ring selected from the group consisting of:
 (c) 1-pyrrolidinyl,
 (d) 1-piperidinyl,
 (e) 1-piperazinyl,
 (f) N-morpholinyl and where $n_8$ is as defined above,
(12) —$NO_2$,
(13) —$N_3$,
(14) —$NR_{1-9D}R_{1-9E}$ where $R_{1-9D}$ and $R_{1-9E}$ are the same or different and are:
 (a) —H,
 (b) $C_1$–$C_5$ alkyl and where $R_{1-9D}$ and $R_{1-9E}$ are taken together with the attached nitrogen atom to form a heterocyclic ring selected from the group consisting of:
 (c) 1-pyrrolidinyl,
 (d) 1-piperidinyl,
 (e) 1-piperazinyl,
 (f) N-morpholinyl,
 (g) 1-aziridinyl,
(15) —$N(R_{1-9F})(CH_2)_{n9}$—$N(R_{1-9G})(R_{1-9H})$ where $n_9$ is 2 thru 5, where $R_{1-9F}$ is:
 (a) —H,
 (b) $C_{1-4}$ alkyl, where $R_{1-9G}$ and $R_{1-9H}$ are the same or different and are:
 (c) —H,
 (d) $C_{1-4}$ alkyl and where $R_{1-9G}$ and $R_{1-9H}$ are taken together with the attached nitrogen atom to form a heterocyclic ring selected from the group consisting of:
 (e) 1-pyrrolidinyl,
 (f) 1-piperidinyl,
 (g) 1-piperazinyl,
 (h) N-morpholinyl,
 (i) 1-aziridinyl,
(16) —NH—$SO_2$—$R_{1-9I}$ where $R_{1-9I}$ is:
 (a) $C_1$–$C_4$ alkyl,
 (b) $C_3$–$C_7$ cycloalkyl,
 (c) —φ,
 (d) —$CH_2$—φ,
(17) —N=$C(R_{1-9J})$—$N(R_{1-9K})(R_{1-9L})$ where
 (a) $R_{1-9J}$ is
  (i) —H,
  (ii) $C_1$–$C_4$ alkyl, where $R_{1-9K}$ and $R_{1-9L}$ are the same or different and are
  (iii) $C_1$–$C_6$ alkyl,
  (iv) $C_3$–$C_7$ cycloalkyl,
  (v) —φ,
 (b) $R_{1-9K}$ and $R_{1-9L}$ are taken together with the attached nitrogen atom to form a heterocyclic ring selected from the group consisting of
  (i) 1-pyrrolidinyl,
  (ii) 1-piperidinyl,
  (iii) 1-piperazinyl,
  (iv) N-morpholinyl,
 (c) $R_{1-9J}$ and $R_{1-9K}$ are taken together with the attached nitrogen atom to form a heterocyclic ring selected from the group consisting of
  (i) 1-pyrrolidinyl,
  (ii) 1-piperidinyl,
(18) —$NR_{1-9F}$—CO—$R_{1-9M}$ where $R_{1-6M}$ is:
 (a) —H,
 (b) $C_1$–$C_4$ alkyl,
 (c) —φ and where $R_{1-9F}$ is as defined above,
(19) —OH,
(20) —O—$CH_2$—φ,
(21) —O—$CF_3$,
(22) —O—$CH_2$—$COOR_{1-9A}$ where $R_{1-9A}$ is as defined above,
(23) —O—CO—$R_{1-9M}$ where $R_{1-9M}$ is as defined above,
(24) —O—$SO_2$—($C_1$–$C_4$ alkyl),
(25) —O—CO—$(CH_2)_{n9}$—COOH, where $n_9$ is as defined above,
(26) —O—$(CH_2)_{n9}$—$N(R_{1-9G})(R_{1-9H})$ where $n_9$, $R_{1-9G}$ and $R_{1-9H}$ are as defined above,
(27) —O-prodrug where prodrug is
 (a) —$PO_2$—$O^-$ cation$^+$ and as defined above,
(28) $C_1$–$C_3$ alkylthio,
where $n_7$ is 1 thru 3, and
 (1) when $n_7$ is 2 or 3, the $R_{1-9}$'s can be the same or different and
 (2) when $n_7$ is 2 and the two $R_{1-9}$ groups are ortho to each other they can be taken together to form —O—$CH_2$—O—, with the proviso that if $n_7$ is 2 or 3, only one of the $R_{1-9}$ groups can be a prodrug;

(D)

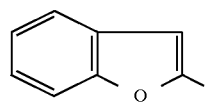

($R_1$-IV)

(E)

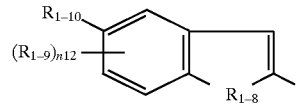

($R_1$-V)

where $n_{12}$ is 0 thru 2 and where $R_{1-8}$ and $R_{1-9}$ are as defined above,
where $R_{1-10}$ is:
 (1) —H,
 (2) —F,
 (3) —Cl,
 (4) —Br,
 (5) $C_1$–$C_6$ alkyl,
 (6) —C≡N,
 (7) —CHO,
 (8) —$(CH_2)_{n13}$—OH where $n_{13}$ is 1 thru 5,
 (9) —$(CH_2)_{n13}$—$N(R_{1-10A})(R_{1-10B})$ where $n_{13}$ is as defined above and $R_{10-A}$ and $R_{10-B}$ are the same or different and are:

(a) —H,
(b) $C_1$–$C_4$ alkyl and where $R_{1-10A}$ and $R_{1-10B}$ are taken together with the attached nitrogen atom to form a heterocyclic ring selected from the group consisting of
(c) 1-pyrrolidinyl,
(d) 1-piperidinyl,
(e) 1-piperazinyl,
(f) N-morpholinyl,
(10) —CO—O—$R_{1-10C}$ where $R_{1-10C}$ is
(a) $C_1$–$C_6$ alkyl,
(b) $C_3$–$C_7$ cycloalkyl,
(c) —φ,
(11) —CO—N($R_{1-10D}$)($R_{1-10E}$) where $R_{1-10D}$ and $R_{1-10E}$ are the same or different and are
(a) $C_1$–$C_6$ alkyl,
(b) $C_3$–$C_7$ cycloalkyl,
(c) —φ, and where $R_{1-10D}$ and $R_{1-10E}$ are taken together with the attached nitrogen atom to form a heterocyclic ring selected from the group consisting of
(d) 1-pyrrolidinyl,
(e) 1-piperidinyl,
(f) 1-piperazinyl,
(g) N-morpholinyl,
(12) —$NO_2$,
(13) —$NH_2$,
(14) —$N_3$,
(15) —NH—$CH_2$—φ,
(16) —NH—$SO_2$—$R_{1-10F}$ where $R_{1-10F}$ is
(a) $C_1$–$C_6$ alkyl,
(b) $C_3$–$C_7$ cycloalkyl,
(c) —φ,
(17) —$NR_{1-10G}(CH_2)_{n14}$—N($R_{1-10A}$)($R_{1-10B}$) where $n_{14}$ is 2 thru 5, where $R_{1-10G}$ is
(a) —H,
(b) $C_{1-4}$ alkyl, where $R_{1-10A}$ and $R_{1-10B}$ are as defined above,
(18) —N($R_{1-10A}$)($R_{1-10B}$) where $R_{1-10A}$ and $R_{1-10B}$ are as defined above,
(19) —N=C($R_{1-10H}$)—N($R_{1-10I}$)($R_{1-10J}$) where
(a) $R_{1-10H}$ is
(i) —H,
(ii) $C_1$–$C_4$ alkyl, where $R_{1-10I}$ and $R_{1-10J}$ are
(i) $C_1$–$C_6$ alkyl,
(ii) $C_3$–$C_7$ cycloalkyl,
(iii) —φ, and where
(b) $R_{1-10I}$ and $R_{1-10J}$ are taken together with the attached nitrogen atom to form a heterocyclic ring selected from the group consisting of
(i) 1-pyrrolidinyl,
(ii) 1-piperidinyl,
(iii) 1-piperazinyl,
(iv) N-morpholinyl,
(c) $R_{1-10H}$ and $R_{1-10J}$ are taken together with the attached nitrogen atom to form a heterocyclic ring selected from the group consisting of
(v) 1-pyrrolidinyl,
(vi) 1-piperidinyl,
(20) —N($R_{1-10G}$)—CO—$R_{1-10K}$ where $R_{1-10K}$ is
(a) —H,
(b) $C_1$–$C_4$ alkyl,
(c) —φ and where $R_{1-10G}$ is defined above,
(21) —N($R_{1-10G}$)-prodrug, where $R_{1-10G}$ and prodrug is as defined above,
(22) —O—$CH_2$—φ,
(23) —O—$CF_3$,
(24) —O—$CH_2$—$COOR_{1-10L}$ where $R_{1-10L}$ is
(a) —H,
(b) $C_1$–$C_4$ alkyl,
(c) —φ,
(d) —$CH_2$—φ,
(25) —O—$SO_2$—($C_1$–$C_4$ alkyl);

(F)

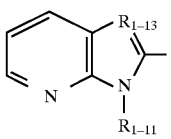

($R_1$-VI)

where $R_{1-11}$
(1) —H,
and $R_{1-13}$ is
(1) —CH=,
(2) —$CR_{1-13A}$ where $R_{1-13A}$ is:
(a) $C_1$–$C_3$ alkyl,
(b) —$(CH_2)_{n15}$—OH where $n_{15}$ is 1 or 2;

(G)

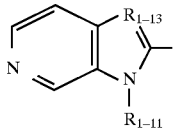

($R_1$-VII)

where $R_{1-11}$ and $R_{1-13}$ are as defined above;

(H)

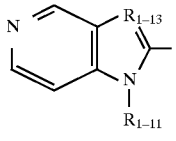

($R_1$-VIII)

where $R_{1-11}$ and $R_{1-13}$ are as defined above;

(I)

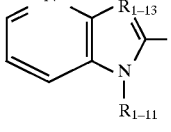

($R_1$-IX)

where $R_{1-11}$ and $R_{1-13}$ are as defined above;

(J)

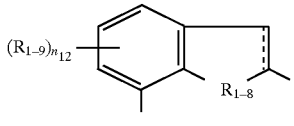

($R_1$-X)

where $R_{1-8}$, $R_{1-9}$ and $n_{12}$ are as defined above;
where (II) $R_2$ is:
(A) —CO—,
(B) —$CH_2$—;

where (III) $R_3$ is:

(B)

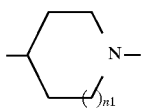 (R₃-II)

where $n_1$ is 1, (C)

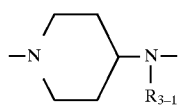 (R₃-III)

where $R_{3-1}$ is:
(1) $C_1$–$C_6$ alkyl,
(2) $C_3$–$C_7$ cycloalkyl;

(D)

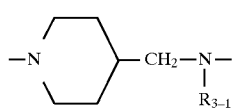

where $R_{3-1}$ is as defined above;
where (IV) $R_4$ is:
(A) —N=,
(B) —CH=,
(C) —CF=,
(D) —C(CF₃)=,
(E) —C(CN)=,
(F) —CCl=;
where (V) $R_5$ is:
(A) —N=,
(B) —CH=,
(C) —CF=,
(D) —CCl=,
(E) —C(CF₃)=,
(F) —C(CN)=;
where (VI) $R_6$ is:
(A) —N=,
(B) —CH=,
(C) —CF=,
(D) —CCl=,
(E) —C(CF₃)=,
(F) —C(CN)=;
where (VII) $R_7$ is:
(A) —N=,
(B) —CH=,
where (VIII) $R_8$ is:
(A) $C_1$–$C_6$ alkyl,
(B) $C_3$–$C_5$ cycloalkyl,
(C) —CH₂—O—$R_{8-1}$ where $R_{8-1}$ is $C_1$–$C_3$ alkyl,
(D) —(CH₂)ₙ₂—Si(CH₃)₃ where $n_2$ is 0 thru 2,
(E) —CH₂—CH₂—CF₃,
(F) —CH₂—CH₂—O—CH₃,
(G) —CH₂—S—$R_{8-1}$ where $R_{8-1}$ is as defined above,
(H) —CH₂—CH₂—CO—O—$R_{8-2}$ where $R_{8-2}$ is $C_1$–$C_2$ alkyl,
(I) —CH₂—CH₂—C≡N;
(J) —CH=CR₈₋₂R₈₋₃ where $R_{8-2}$ and $R_{8-3}$ are the same or different and are:
(1) —H,
(2) $C_1$–$C_2$ alkyl,
with the proviso that at least one but not more than two of $R_4$, $R_5$, $R_6$ and $R_7$ are —N=; and pharmaceutically acceptable salts thereof.

2. Anti-AIDS compounds (I) according to claim 1 where $R_1$ is (A)

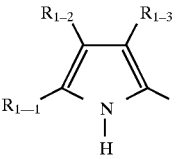 (R₁-I)

3. Anti-AIDS compounds (I) according to claim 2 where $R_{1-1}$, $R_{1-2}$ and $R_{1-3}$ are —H.

4. Anti-AIDS compounds (I) according to claim 1 where $R_1$ is (B)

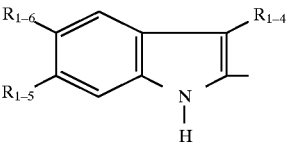 (R₁-II)

5. Anti-AIDS compounds (I) according to claim 4 where $R_{1-4}$ is —H.

6. Anti-AIDS compounds (I) according to claim 4 where $R_{1-5}$ is —H.

7. Anti-AIDS compounds (I) according to claim 4 where $R_{1-6}$ is —H, —NH—SO₂—CH₃, —O—$R_{1-5A}$ and —F.

8. Anti-AIDS compounds (I) according to claim 1 where $R_2$ is —CO—.

9. Anti-AIDS compounds (I) according to claim 1 where $R_3$ is (C)

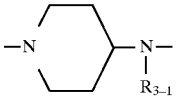 (R₃-III)

10. Anti-AIDS compounds (I) according to claim 9 where $R_{3-1}$ is $C_1$–$C_3$ alkyl.

11. Anti-AIDS compounds (I) according to claim 1 where $R_4$, $R_5$ and $R_6$ are —CH=.

12. Anti-AIDS compounds (I) according to claim 1 where $R_7$ is —N=.

13. Anti-AIDS compounds (I) according to claim 1 where $R_8$ is $C_2$–$C_5$ alkyl, —CH₂—O—$R_{8-1}$, —(CH₂)ₙ₂—Si(CH₃)₃.

14. Anti-AIDS compounds (I) according to claim 13 where $R_8$ is $C_3$–$C_4$ alkyl.

15. Anti-AIDS compounds (I) according to claim 1 which is selected from the group consisting of
1-[5-(methanesulfonamido)indolyl-2-carbonyl]-4-[N-methyl-N-(3-propyl-2-pyridinyl)amino]piperidine,
1-[5-(methanesulfonamido)indolyl-2-carbonyl]-4-[N-ethyl-N-(3-(2-methylpropyl)-2-pyridinyl)amino]piperidine,
1-[pyrrole-2-carbonyl]-4-(N-ethyl-N-(3-(2-methylpropyl)-2-pyridinyl)amino)piperidine, 1-[pyrrole-2-carbonyl]-4-[N-ethyl-N-(3-(propyl)-2-pyridinyl) amino]piperidine, 1-[5-(methanesulfonamido)indolyl-2-carbonyl]-4-[N-ethyl-N-(3-propyl-2-pyridinyl)amino]piperidine, 1-[pyrrole-2-carbonyl]-4-[N-methyl-N-(3-(propyl)-2-pyridinyl)amino]piperidine, 1-[pyrrole-2-carbonyl]-4-[N-methyl-N-(3-(2-methylpropyl)-2-pyridinyl)amino]piperidine, 1-[(5-methanesulfonamido)indolyl-2-carbonyl]-4-[N-methyl-N-(3-(2-methylpropyl)-2-pyridinyl)amino]piperidine, 1-[5-(methoxy)indolyl-2-carbonyl]-4-[N-ethyl-N-(3-propyl-2-pyridinyl)amino]piperidine, 1-[indolyl-2-carbonyl]-4-[N-ethyl-N-(3-propyl)-2-pyridinyl)amino]piperidine, 1-[5-(methanesulfonamido)indolyl-2-carbonyl]-4-[N-ethyl-N-(3-(2'-trimethylsilylethyl)-2-pyridinyl)amino]piperidine, 1-(5-(methanesulfonamido)indolyl-2-carbonyl)-4-(N-methyl-N-(3-methoxymethyl-2-pyridyl)amino)piperidine, 1-(5-(methanesulfonamido)indolyl-2-carbonyl)-4-(N-ethyl-N-(3-methoxymethyl-2-pyridyl)amino)piperidine, 1-(5-(methanesulfonamido)indolyl-2-carbonyl)-4-(N-methyl-N-(3-ethyl-2-pyridyl)amino)piperidine, 1-(5-(methanesulfonamido)indolyl-2-carbonyl)-4-(N-ethyl-N-(3-ethyl-2-pyridyl)amino)piperidine and 1-(5-(methanesulfonamido)indolyl-2-carbonyl)-4-(N-propyl-N-(3-ethyl-2-pyridyl)amino)piperidine.

* * * * *